US009365866B2

(12) United States Patent
Nakanishi et al.

(10) Patent No.: US 9,365,866 B2
(45) Date of Patent: Jun. 14, 2016

(54) VECTORS FOR GENERATING PLURIPOTENT STEM CELLS AND METHODS OF PRODUCING PLURIPOTENT STEM CELLS USING THE SAME

(75) Inventors: Mahito Nakanishi, Tsukuba (JP); Ken Nishimura, Tsukuba (JP); Masayuki Sano, Tsukuba (JP); Manami Ohtaka, Tokyo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 75 days.

(21) Appl. No.: 13/292,953

(22) Filed: Nov. 9, 2011

(65) Prior Publication Data

US 2012/0214240 A1 Aug. 23, 2012

Related U.S. Application Data

(63) Continuation-in-part of application No. 12/792,580, filed on Jun. 2, 2010, now Pat. No. 8,496,941.

(60) Provisional application No. 61/183,724, filed on Jun. 3, 2009.

(30) Foreign Application Priority Data

May 18, 2010 (WO) .................. PCT/JP2010/058368
Nov. 9, 2010 (JP) ................................. 2010-250993

(51) Int. Cl.

| | |
|---|---|
| ***C12N 15/63*** | (2006.01) |
| ***C12N 7/01*** | (2006.01) |
| ***C12N 15/864*** | (2006.01) |
| ***C12N 5/0789*** | (2010.01) |
| ***C12N 15/86*** | (2006.01) |
| ***C12N 5/074*** | (2010.01) |
| ***C12N 15/113*** | (2010.01) |
| ***C12N 15/877*** | (2010.01) |

(52) U.S. Cl.

CPC .............. *C12N 15/86* (2013.01); *C12N 5/0696* (2013.01); *C12N 15/1131* (2013.01); *C12N 15/8775* (2013.01); *C12N 15/8776* (2013.01); *C12N 2310/14* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2760/18843* (2013.01)

(58) Field of Classification Search

None

See application file for complete search history.

(56) References Cited

U.S. PATENT DOCUMENTS

2010/0196993 A1 8/2010 Nishimura et al.
2011/0217274 A1* 9/2011 Reld .......................... 424/93.21

FOREIGN PATENT DOCUMENTS

| | | | |
|---|---|---|---|
| EP | 2322611 | | 5/2011 |
| EP | 2434012 | | 3/2012 |
| EP | 2559757 | | 2/2013 |
| EP | 2612911 | | 7/2013 |
| JP | 2006325531 | | 12/2006 |
| WO | 2006084746 | | 8/2006 |
| WO | 2007/069666 | A1 | 6/2007 |
| WO | 2008129971 | | 10/2008 |
| WO | 2010008054 | | 1/2010 |
| WO | 2010030003 | | 3/2010 |

OTHER PUBLICATIONS

Nishimura et al, Persistent and Stable Gene Expression by a Cytoplasmic RNA Replicon Based on a Noncytopathic Variant Sendai Virus, 2007, vol. 282, No. 37, pp. 27383-27391.*

Takahashi et al. Induction of Pluripotent Stem Cells from Adult Human Fibroblast Cultures by Defined Factors. Cell 2007, vol. 131, p. 861-872.*

Nishimura et al, supplemental table, Persistent and Stable Gene Expression by a Cytoplasmic RNA Replicon Based on a Noncytopathic Variant Sendai Virus, 2007, vol. 282, No. 37, pp. 27383-27391.*

Keisuke et al., "Virus-Free induction of pluripotency and subsequent excision of reprogramming factors", Nature 458(7239):771-775 (2009).

Inoue et al., "Recombinant sendai virus vectors deleted in both the matrix and the fusion genes: Efficient gene transfer with preferable properties", J. of Gene Medicine, 6(10):1069-1081 (2004).

Chivukula et al., "Abate and Switch: miR-145 in Stem Cell Differentiation", Cell, 137(4):606-608 (2009).

Carey et al., "Reprogramming of murine and human somatic cells using a single polycistronic vector", Proceedings of the National Academy of Sciences, 106(1):157-162 (2009).

Yoshizaki et al., "Naked Sendai virus vector lacking all of the envelop-related genes: reduced cytopathogenicity and immunogenicity", J. of Gene Medicine, 8(9):1151-1159 (2006).

Fusaki et al., "Efficient induction of transgene-free human pluripotent stem cells using a vector based on Sendai virus, an RNA virus that does not integrate into the host genome", Proceedings of the Japan Academy, Series B, Physical and Biological Sciences, Tokyo, JP, 85(8):348-362 (2009).

(Continued)

*Primary Examiner* — Maria Marvich

(74) *Attorney, Agent, or Firm* — Sughrue Mion, PLLC

(57) ABSTRACT

A reprogramming gene-loaded Sendai viral vector comprising Sendai virus genes and reprogramming genes, wherein the Sendai virus genes include an NP gene, P/C gene, M gene, F gene, HN gene and L gene, wherein each of the M gene, the F gene and the FIN gene is from a Sendai virus strain Cl.151-derived gene and wherein at least one of the M gene, the F gene and the HN gene is functionally deleted and the L gene encodes the amino-acid sequence of the L protein in which the amino-acid residue at position 1618 is valine and a method of producing the same.

12 Claims, 42 Drawing Sheets
(26 of 42 Drawing Sheet(s) Filed in Color)

(56) References Cited

OTHER PUBLICATIONS

Nishimura et al., "Development of Defective and persistent Sendai virus vector: a unique gene delivery/expression system ideal for cell reprogramming", J. of Biological Chemistry (Feb. 11, 2011), 286(6):4760-4771.

Ban et al., "Efficient generation of transgene-free human induced pluripotent stem cells (iPSCs) by temperature-sensitive Sendai virus vectors", Proceedings of the National Academy of Sciences, 108(34):14234-14239 (2011).

Su et al., "Efficient Generation of Integration-free iPS Cells from human adult peripheral blood using BCL-XL together with Yamanaka Factors", Plos One, 8(5):e64496-e64496 (pp. 1-10) (2013).

Nishimura et al., "Persistent and Stable Gene Expression by a Cytoplasmic RNA Replicon Based on Noncytopathic Variant Sendai Virus", J. of Biological Chemistry, 282(37):27383-27391 (2007).

Seki et al., "Generation of Induced Pluripotent Stem Cells from Human Terminally Differentiated Circulating T Cells", Cell Stem Cell, 7:11-14 (2010).

Loh et al,, "Reprogramming of T Cells from Human Peripheral Blood", Cell Stem Cell, 7:15-19 (2010).

Stadtfeld et al., "A reprogrammable mouse strain from gene-targeted embryonic stem cells", Nature Methods, 7(1):53-55 (2010) (Abstract only).

Yu, et al., Induced Pluripotent Stem Cell Lines Derived from Human Somatic Cells, Science, Reports, Dec. 21, 2007, pp. 1917-1920, vol. 318.

Si-Tayeb et al., "Generation of human induced pluripotent stem cells by simple transient transfection of plasmid DNA encoding reprogramming factors", BMC Developmental Biology, 10:81 (2010).

Fusaki et al., "Efficient induction of transgene-free human pluripotent stem cells using a vector based on Sendai virus, an RNA virus that does not integrate into the host genome", Proceeding of the Japan Academy, Series B, Physical and Biological Sciences, 85(8):348-362 (2009).

* cited by examiner

FIG.3
FIG.3A
(4th day)
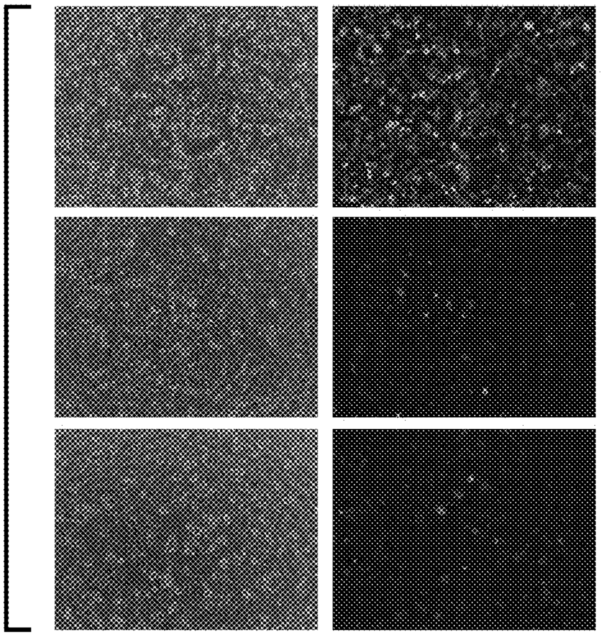
FIG.3B
(10th day)
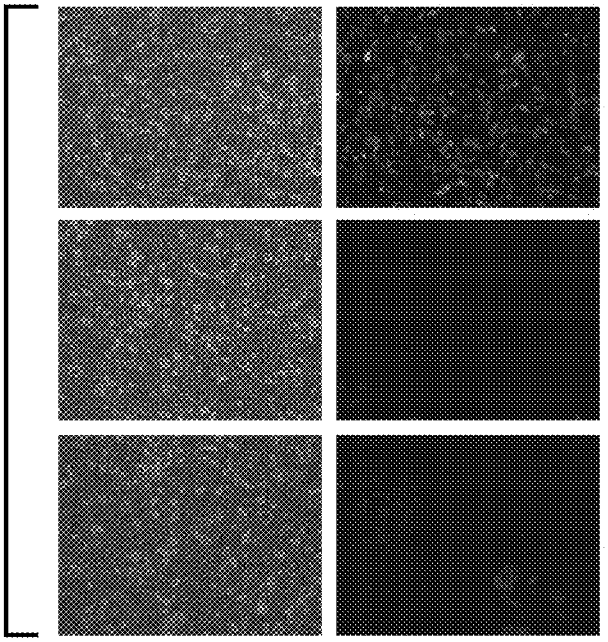

0 d.p.i.

2 d.p.i.

4 d.p.i.

6 d.p.i.

7 d.p.i.

8 d.p.i.

9 d.p.i.

12 d.p.i.

FIG.8
FIG. 8A
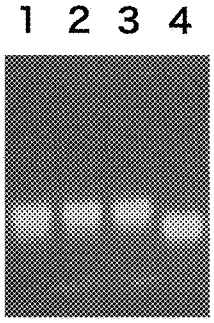
FIG. 8B
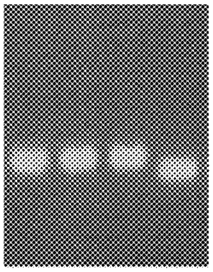
FIG. 8C
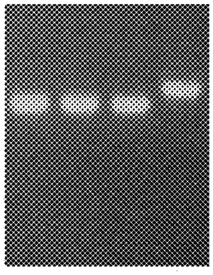

6 d.p.i.

8 d.p.i.

10 d.p.i.

FIG.13
FIG.13A
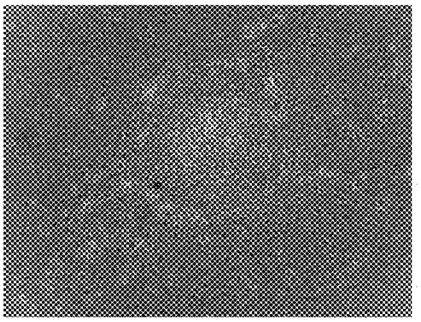
FIG.13B
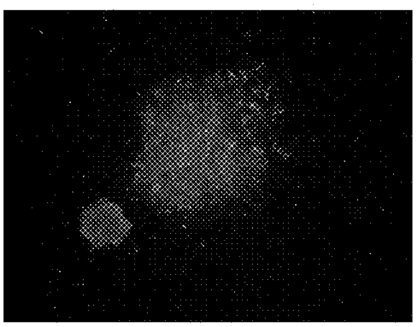

FIG.19
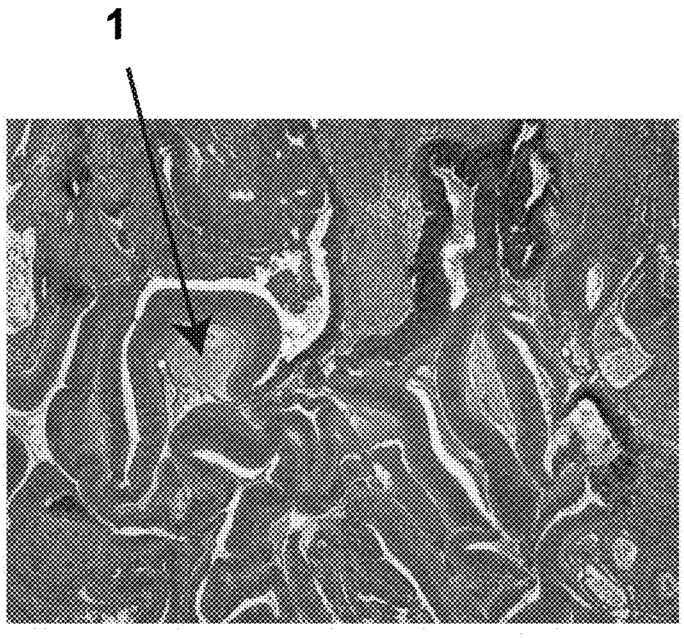
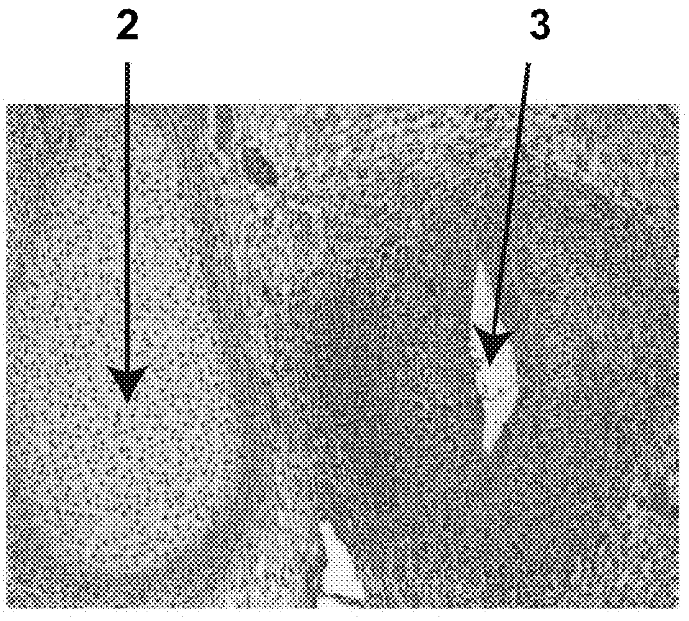

FIG.22
FIG.22A
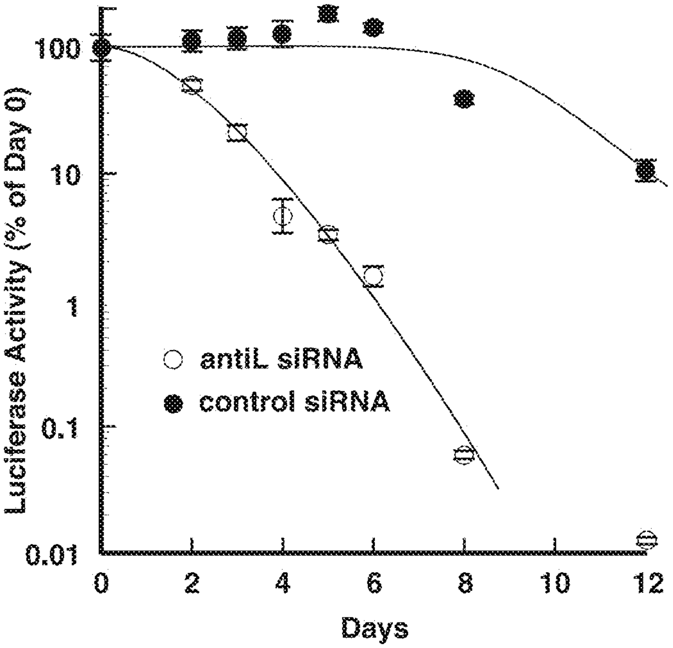
FIG.22B
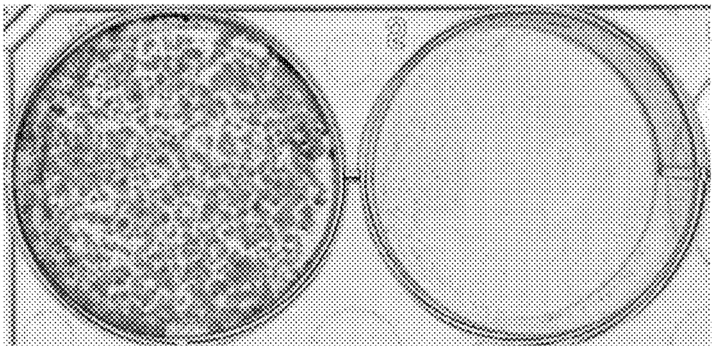

FIG.25
FIG.25A
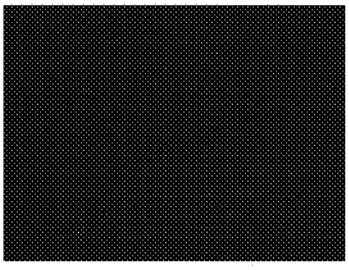
FIG.25B
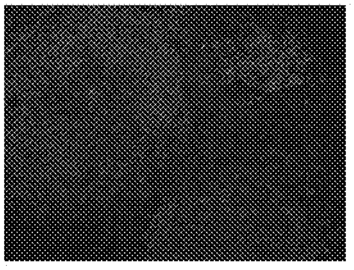

FIG.26
FIG.26A
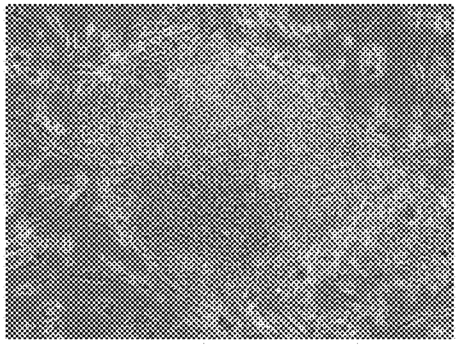
FIG.26B
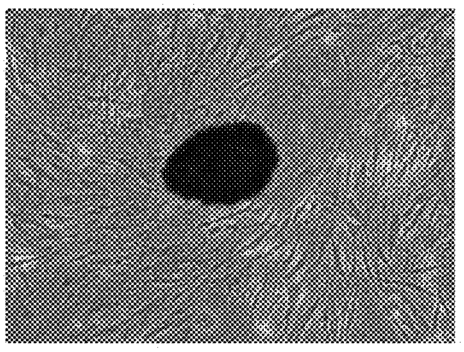

FIG.27
FIG.27A
| | | | | |
|---|---|---|---|---|
| #19 | 1.000 | | | |
| #56 | 0.995 | 1.000 | | |
| #74 | 0.989 | 0.990 | 1.000 | |
| #106 | 0.988 | 0.989 | 0.998 | 1.000 |
| | #19 | #56 | #74 | #106 |
FIG.27B
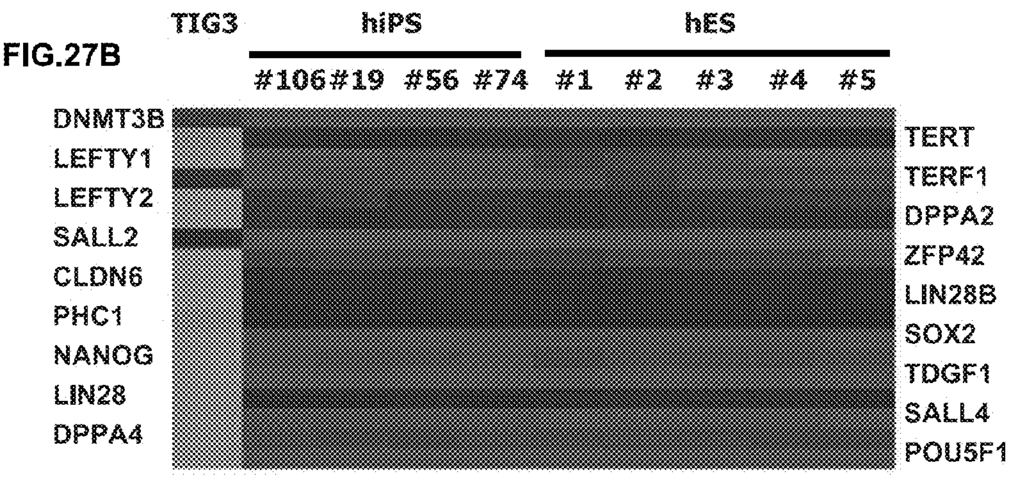
FIG.27C
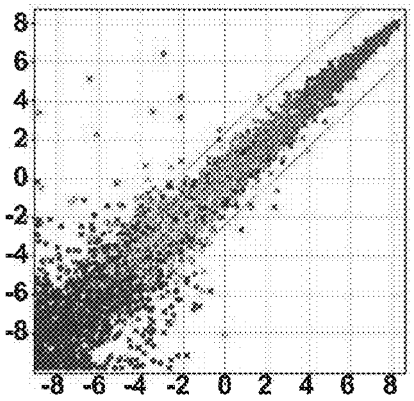

FIG. 31
A
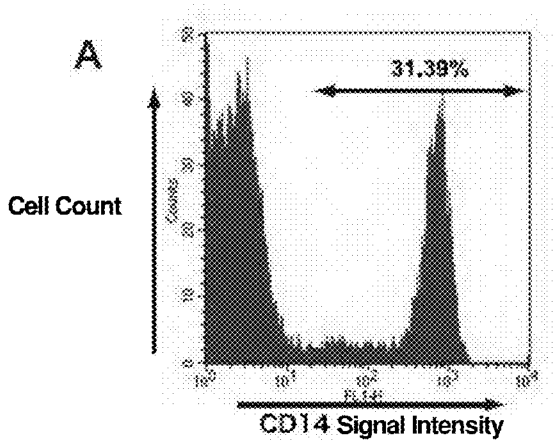
Expression of CD14 antigen in cells purified with Ficoll-Paque PREMIUM 1.073
B
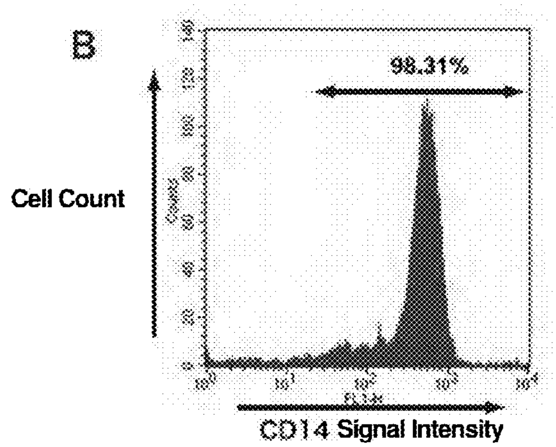
Expression of CD14 antigen in cells purified with Ficoll-Paque PREMIUM 1.073 and then with anti-CD14 antibody-bound magnetic beads
C
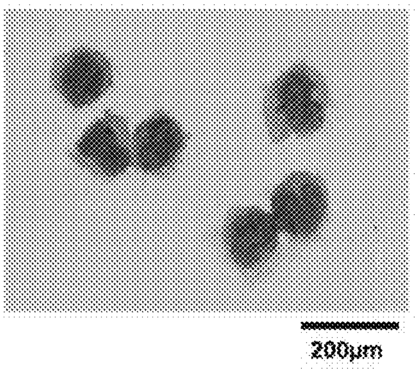
Stained image of cells purified with Ficoll-Paque PREMIUM 1.073 and then with anti-CD14 antibody-bound magnetic beads.

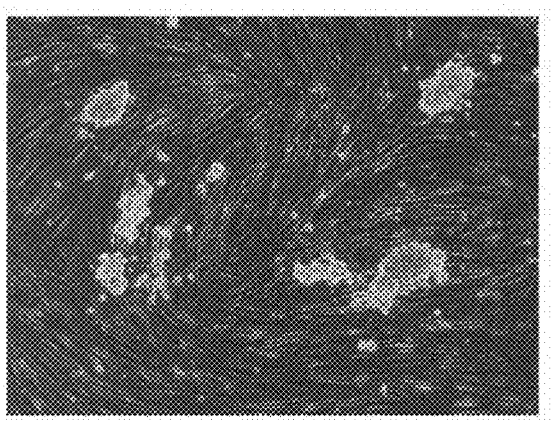

Phase-contrast microscopy image of colonies appearing from monocytes on day 8 of their infection with hOct4/hSox2/hKlf4/hc-Myc sustained expression-inducing Sendai viral vector version 2.

B

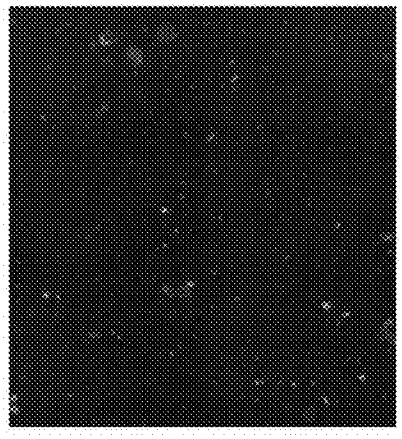

Fluorescence microscopy image (low magnification) of human ES/iPS cell marker-expressing colonies appearing from monocytes on day 8 of their infection with hOct4/hSox2/hKlf4/hc-Myc sustained expression-inducing Sendai viral vector version 3.
Blue: DNA (DAPI staining)
Green: SSEA-4 antigen
Red: TRA-1-60 antigen
(Cells expressing two antigens simultaneously are stained yellow.)

C

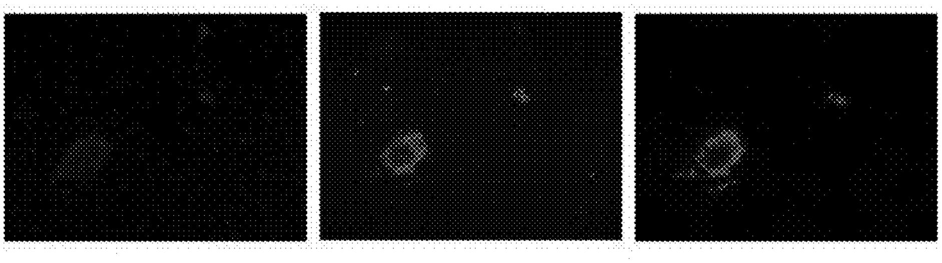

Blue: DNA (DAPI staining) Green: SSEA-4 antigen Red: TRA-1-60 antigen

Fluorescence microscopy image (high magnification) of human ES/iPS cell marker-expressing colonies appearing from monocytes on day 8 of their infection with hOct4/hSox2/hKlf4/hc-Myc sustained expression-inducing Sendai viral vector version 3.

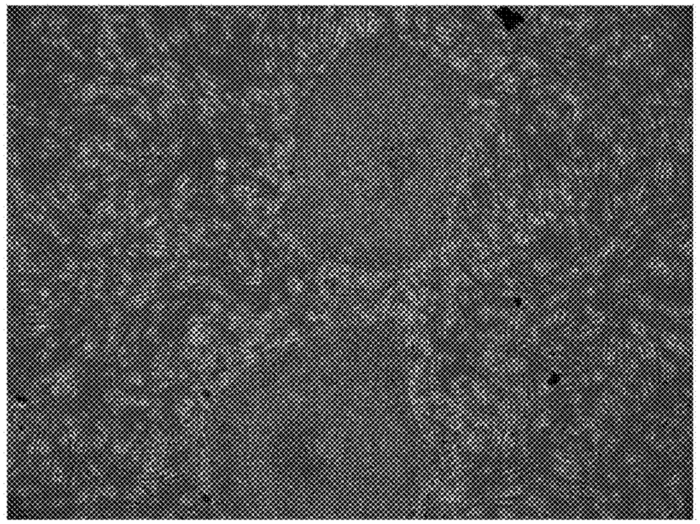

Phase-contrast microscopy image of human iPS cell-like colonies appearing from monocytes infected with hOct4/hSox2/hKlf4/hc-Myc sustained expression-inducing Sendai viral vector version 3.
The photograph was taken on day 31 of infection after three passages.

B

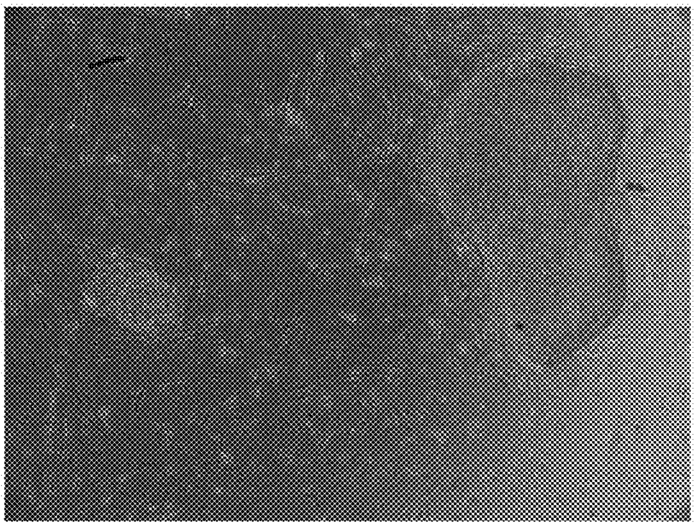

Phase-contrast microscopy image of human iPS cell-like colonies appearing from monocytes infected with hOct4/hSox2/hKlf4/hc-Myc sustained expression-inducing Sendai viral vector version 4.
The photograph was taken on day 31 of infection after three passages.

FIG. 34

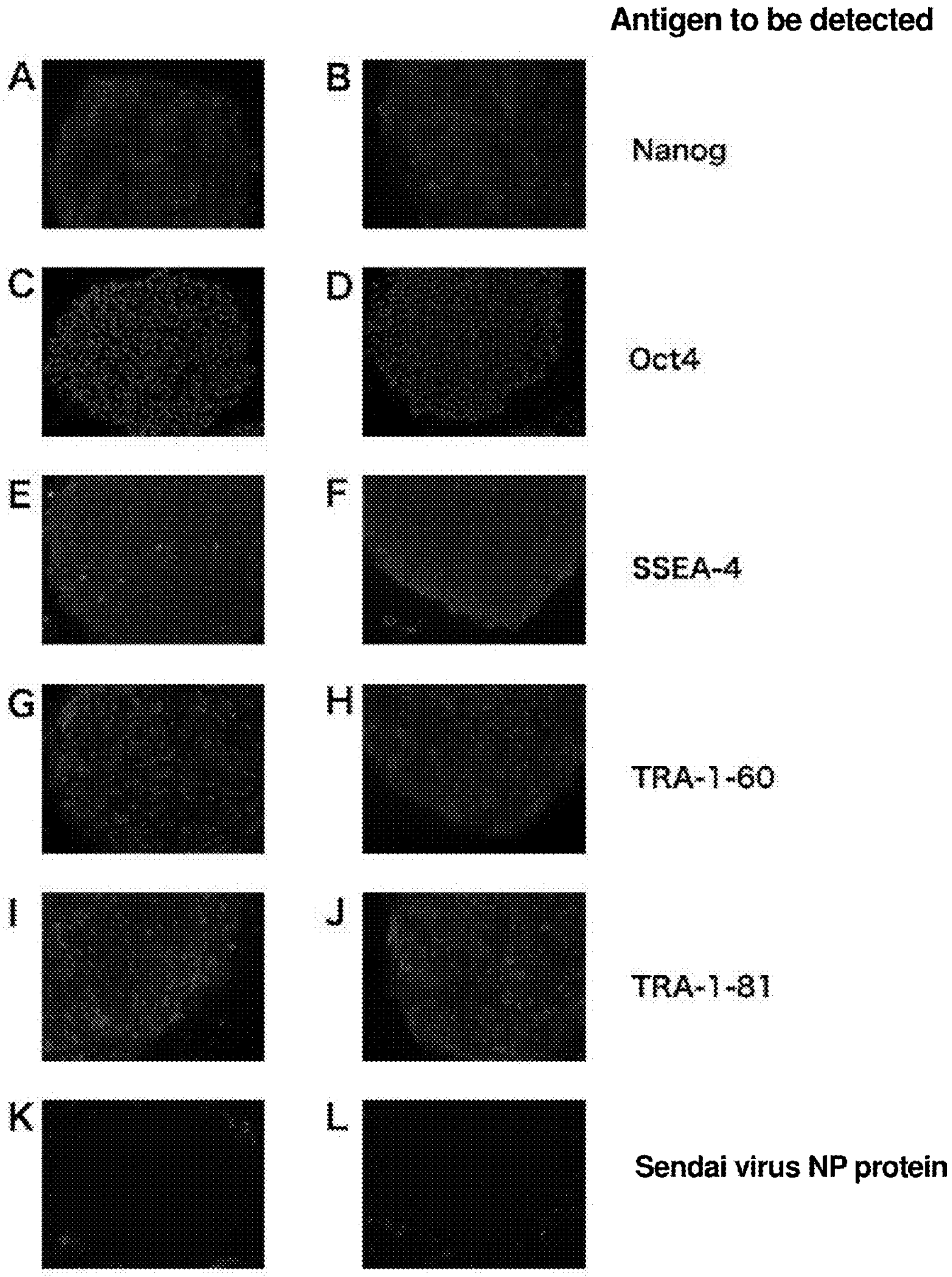

Panels on the left side (A, C, E, G, I and K) are analyses of iPS cells appearing from monocytes infected with hOct4/hSox2/hKlf4/hc-Myc sustained expression-inducing Sendai viral vector version 3; and panels on the right side (B, D, F, H, J and L) are analyses of iPS cells appearing from monocytes infected with hOct4/hSox2/hKlf4/hc-Myc sustained expression-inducing Sendai viral vector version 4.

FIG. 35

Rearrangement Analysis of T Cell Receptor β Chain

A

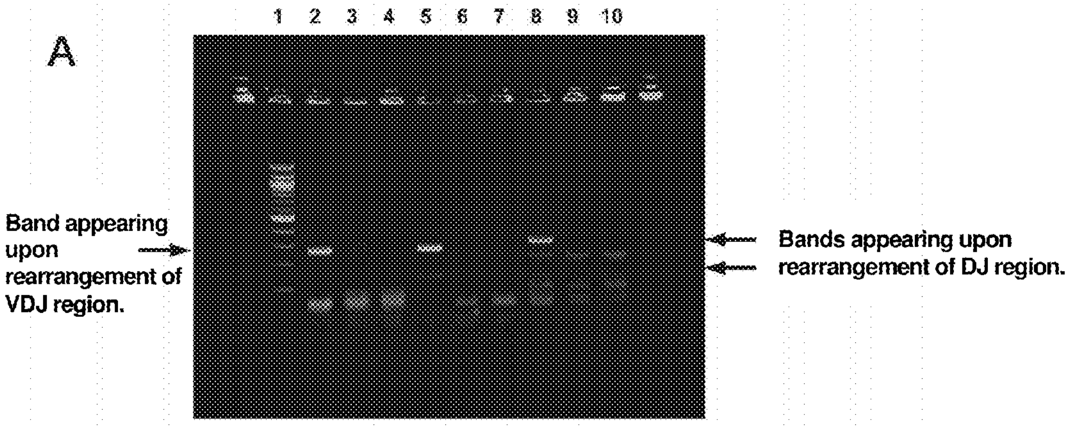

1: Molecular marker (100 bp ladder)
2-4: Rearrangement analysis of VDJ region (A)
5-7: Rearrangement analysis of VDJ region (B)
8-10: Rearrangement analysis of DJ region 3,6,9: Human iPS cells prepared with hOct4/hSox2/hKlf4/hc-Myc sustained expression-inducing Sendai viral vector version 3
4,7,10: Human iPS cells prepared with hOct4/hSox2/hKlf4/hc-Myc sustained expression-inducing Sendai viral vector version 4
2,5,8: Positive control cells Rearrangement Analysis of T Cell Receptor γ Chain

B

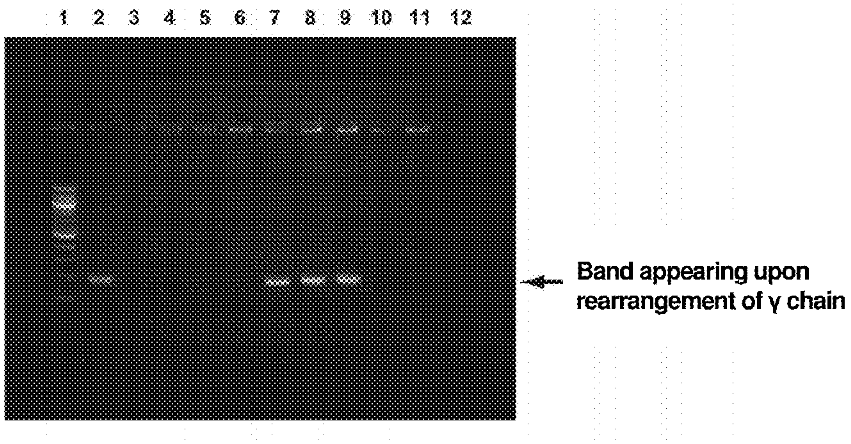

1: Molecular marker (100 bp ladder)
2,7-9,11,12: Rearrangement analysis of γ chain 11: Human iPS cell prepared with hOct4/hSox2/hKlf4/hc-Myc sustained expression-inducing Sendai viral vector version 3
12: Human iPS cell prepared with hOct4/hSox2/hKlf4/hc-Myc sustained expression-inducing Sendai viral vector version 4
3,7,8,9: Positive control cells

FIG. 38

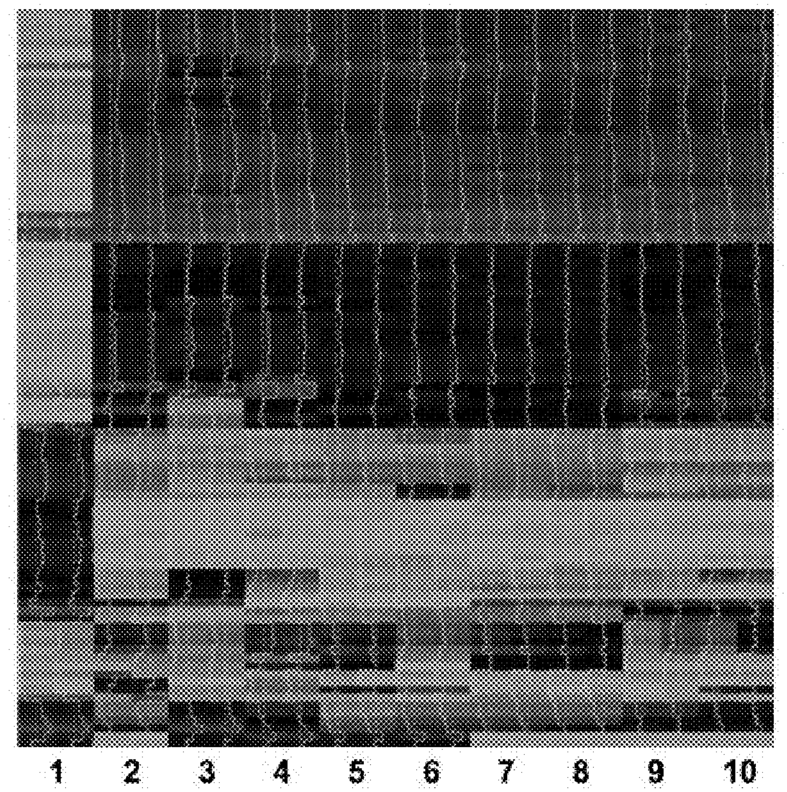

1 : Human fibroblast cell
2 : Human fibroblast cell-derived iPS cell #1
3 : Human ES cell (from Kyoto University)
4 : Human fibroblast cell-derived standard iPS cell strain #201B 7 (from Kyoto University)
5 : Human peripheral blood monocyte-derived iPS cell #1
6 : Human peripheral blood monocyte-derived iPS cell #2
7 : Human fibroblast cell-derived iPS cell #27
8 : Human fibroblast cell-derived iPS cell #26
9 : Human fibroblast cell-derived iPS cell #15
1 0 : Human fibroblast cell-derived iPS cell #13

TCRG tube A: Vγf and Vγ10 primers + Jγ1.1/2.1 and Jγ1.3/2.3

TCRG tube B: Vγ9 and Vγ11 primers + Jγ1.1/2.1 and Jγ1.3/2.3

VECTORS FOR GENERATING PLURIPOTENT STEM CELLS AND METHODS OF PRODUCING PLURIPOTENT STEM CELLS USING THE SAME

RELATED APPLICATION

The present application is a continuation-in-part application of pending U.S. patent application Ser. No. 12/792,580, now U.S. Pat. No. 8,496,941, issued on Jul. 30, 2013, and claims priority of Japanese Patent Application No. 2010-250993 filed on Nov. 9, 2010. U.S. patent application Ser. No. 12/792,580 claims the benefit of U.S. Provisional patent application No. 61/183,724 filed on Jun. 3, 2009 and the International PCT application PCT/JP2010/058368 filed on May 18, 2010. The teachings of both of these priority documents are hereby incorporated herein by reference in their entirety.

BACKGROUND OF THE INVENTION

1. Field of the Invention

The present invention relates to novel recombinant Sendai virus vector constructs for the reprogramming of differentiated somatic cells into induced pluripotent stem (iPS) cells 2. Description of the Related Art Along with the progression toward an aging society, diseases caused by tissue degeneration and damage are increasing rapidly. For example, diseases that increase in frequency with age include metabolic syndromes, such as cerebral infarction, cardiac infarction and renal failure, as well as diseases caused by age-related tissue degeneration, such as Alzheimer's disease, Parkinson's disease and osteoporosis. In addition, type I diabetes, multiple sclerosis, chronic rheumatoid arthritis, thermal burn, spinal damage from injury, and genetic diseases caused by congenital abnormalities in the genetic code, are all diseases caused by tissue degeneration and damage. A number of regeneration therapies are being developed as a means for treating these diseases.

Regeneration therapies can be tentatively classified into two groups: (1) guided regeneration therapies that target the activation of tissue stem cells residing in a patient's tissue, and (2) cell replacement therapies requiring the transplantation of exo-vivo generated stem cells or stem-cell-derived somatic cells or tissues, into a patient. The regeneration potential of tissue stem cells is however often limited. Development of more effective cell replacement therapies is therefore essential to the practical application of regeneration therapies. In particular, with regard to genetic diseases, cell replacement therapies are contemplated where a patient's cells are genetically engineered ex-vivo to repair or replace defective genes prior to transplantation back into the patient.

Treatment of diseases caused by tissue degeneration/damage, also requires the preparation of large amounts of stem cells or stem cell-induced somatic tissues. Thus, pluripotent stem cells capable of self-renewal over long periods of time while maintaining their differentiation potential into various tissue types are essential requirements for the development of effective cell replacement therapies. To date only a few pluripotent stem cells have been characterized that meet these requirements and include embryo-stem cells (ES cells) derived from the epiblast of early mammalian embryos, and ES cells derived from primordial germ cells. These heterogenic cells cannot be used in cell replacement therapies however because their genetic information is different from that of a patient's hence transplantation of the cells into a patient would inevitably lead to tissue rejection.

Cell replacement therapies therefore require the generation of isogenic pluripotent stem cells that are genetically identical to a somatic cell of a patient in order to avoid immunological rejection after transplantation into a patient. To obtain such cells, the invention contemplates the isolation and modification of a patient's own tissue cells to generate isogenic pluripotent stem cells to be practical and efficient, the procedure ideally will require only minimal surgical intervention to harvest a small sample of tissue cells. For example, the procedure contemplates the collection of easily accessible cells requiring minimal surgical intervention, e.g., skin fibroblast cells, oral mucosal cells or hair follicle epithelial cells. To avoid undue stress and discomfort to the patient, the procedure further contemplates the collection of no more than approximately $10^4$ cells for the generation of isogenic pluripotent stem cells.

It is known from research on human ES cells that extensive culture of pluripotent stem cells over long periods of time inevitably leads to the appearance within the cell population of chromosomal abnormalities, such as chromosomal deletions, amplifications and translocations. If established pluripotent stem cells are heterogeneous with respect to chromosomal stability, they would require continuous selection for cell lines with minimal chromosomal rearrangements which would be time consuming, expensive and inefficient. Thus, the method of generating pluripotent stem cells of the invention should reproducibly select not only for pluripotency but also for chromosomal stability within a selected homogeneous clonal population. One method of determining uniformity within a selected clonal population would be to determine an index comprising a correlation coefficient between respective gene expression patterns of the selected cell lines. Using such a selection criteria, only clones of pluripotent cells approaching a coefficient of 1, preferably equal to or greater than 0.98 would be deemed to be sufficiently stable for use in cell replacement therapies.

After the isolation of stable clonal populations derived from a patient's somatic cells, the pluripotency potential and ability to differentiate into various tissues is then determined. Pluripotency can be verified by assessing the potential for differentiation in vitro or by determining the degree of differentiation in vivo after transplantation of the candidate pluripotent stem cells into an immunodeficient animal. Another caveat to this approach is the propensity of pluripotent cells to form malignant teratocarcinomas after transplantation. Thus, in view of the need to verify that a candidate pluripotent stem cell line is not only pluripotent but also safe and suitable for use in regeneration therapies, verification based on differentiation within malignant teratocarcinomas is inappropriate (see Nakanishi, Regenerative Medicine, 9, 216-221, 2010)

One way to distinguish between a pluripotent stem cell which is less likely to become a malignant tumor in vivo and thereby safe for human therapy, from a teratocarcinoma which is a malignant tumor with differentiation capability, is to analyze germ-line (germinal) transmission in a laboratory animal such as a mouse i.e., to analyze the transmission of genetic information derived from the pluripotent stem cell to the germ line within a chimeric animal created from pluripotent cells. Using this method, germ-line transmission is only observed with pluripotent stem cells that are less likely to become a malignant tumor after transplantation in vivo and are thereby safe for human therapies. Germ line transmission is not observed with pluripotent cells that form a teratocarcinoma after transplantation. However, this verification obviously cannot be performed in a human.

To establish reproducible protocols for the isolation and selection of pluripotent stem cells which are safe for human therapy trials, it is first necessary to identify appropriate pluripotent stem cells from a laboratory animal using the germ line transmission method. In other words, protocols for establishing therapeutically safe pluripotent stem cells first need to be developed using non-human animals, preferably, the mouse for which reproductive technologies are well established. The procedures required for efficient germ line transmission of pluripotent stem cells in mice can then be extrapolated to human therapeutic applications.

From the above discussion, a method of reproducibly generating human pluripotent stem cells applicable to regeneration therapies needs to meet the following requirements: 1) an established human pluripotent stem cell must be genetically identical to that of a patient's cell; 2) a human pluripotent stem cell must be established from $10^4$ somatic cells or less; 3) established pluripotent stem cells must be clonal and genetically stable; and 4) the germ-line transmission must be verifiable using a chimeric animal derived from pluripotent stem cells and establishing that the pluripotent stem cells contribute to the germ line.

A pluripotent stem cell having genetic information identical to that of a patient, can be generated by introducing a specific combination of pluripotentency-inducing genes into human somatic cells using retroviral vectors. Ectopic expression of these genes results in the generation of a human induced pluripotent stem cell (human iPS cell) closely resembling a human ES cell. For example, the introduction and the expression of Oct3/4, Sox2, Klf4 and c-Myc in human skin fibroblast cells using a retroviral or lentiviral vector results in the transformation of a somatic cell into a human iPS cell (see Takahashi, et al., Cell, 131, 861-872, 2007). Similarly, the introduction and expression of Oct3/4, Sox2, Nanog and LIN28 in human skin-derived fibroblast cells using lentiviral vectors results in the generation of human iPS cells (see Yu, et al., Science, 318, 1917-1920, 2007).

Furthermore, a human iPS cell can also be produced using a modified technique in which one or two of the above four types of genes are substituted by a low-molecular-weight compound. For example, one publication reports that the introduction and expression of two genes, Oct3/4 and Sox2, into normal human skin-derived fibroblast cells cultured in the presence of a histone deacetylase inhibitor results in the transformation of the fibroblast cells into human iPS cells (see Huangfu, et al., Nature Biotechnology, 26, 1269-1275, 2008).

However, in each of the above methods, the genes introduced into a somatic cell are known to be inserted randomly in the iPS cell's host DNA. Genetic information within the iPS cell is therefore different from that of the original skin fibroblast cell. This means that an iPS cell produced by the above techniques fails to meet the requirement that "therapeutically safe pluripotent stem cells have genetic information that is identical to that of a patient's cell."

In terms of ensuring the safety of cell replacement therapy, the above gene insertion protocol causes the following problem. If exogenous genes are inserted into the chromosomes at random, they are likely to abnormally activate genes adjacent to the insertion sites and possibly cause unpredictable side effects, even promote the expression of genes involved in the initiation of tumor. For example, it is known that, if genes are inserted at non-specific positions on chromosomes of a human bone marrow stem cell that is capable of maintaining a self-renewal ability over a long period of time, the expression of tumorigenic genes, that is normally inhibited in these cells, can become transcriptionally active due to the proximal insertion of foreign genes, which can ultimately lead to a high frequency of tumor initiation in these cells (see Hacein-Bey-Abina, et al., Science, 302, 415-419, 2003).

This gene insertion phenomenon further causes the following problem in terms of ensuring the safety of the cell replacement therapy. In an iPS cell produced by inserting foreign genes into chromosomes, although expression of the foreign genes may be inhibited during the period where a cell is kept in an undifferentiated state, the expression of the foreign genes may be induced when the cell has differentiated into a somatic cell, and the resulting cell is likely to become cancerous. For example, it is known that, in an iPS cell-derived transgenic mouse produced by the introduction of Oct3/4, Sox2, Klf4 and c-Myc into a skin-derived normal fibroblast cell using retroviral vectors, cancer develops at high frequencies due to reactivation of the externally introduced c-Myc gene (see Okita, et al., Nature, 448, 313-317, 2007). Further, it is noted that expression of the Klf4 or Oct3/4 gene also has the potential to lead to the initiation of cancer (see Jaenisch and Young, Cell, 132, 562-582, 2008).

With a view to solving the above problems caused by random gene integration into the chromosomal DNA of the host somatic cell, researchers have attempted to introduce plasmid DNA into a somatic cell that is capable of only transient expression of the iPS-inducing genes. For example, one report describes lipofection of Oct3/4, Sox2, Klf4 and c-Myc, into a mouse skin-derived fibroblast cell that results in the transient expression of these genes sufficient to generate an iPS cell but without the concomitant insertion of the foreign genes into chromosomes of the host fibroblast cell (see Okita, et al., Science, 322, 949-953, 2008). However, close analysis of this method shows that the introduced genes were found to be inserted into chromosomes in 75% of the mouse iPS cells generated. Thus, this method does not necessarily prevent insertion of foreign genes into the genome of the iPS cell. Moreover, there is no report thus far indicating that a human iPS cell can be produced using this approach without insertion of foreign iPS-inducing genes into the genome of the host somatic cell.

In other efforts to mitigate the problems caused by gene insertion into the host cell's genome, transient expression of iPS-inducing genes (Oct3/4, Sox2, Klf4 and c-Myc) using adenoviral vectors was shown to transform a somatic cell into an iPS. For example, it has been reported that a mouse iPS cell can be produced by cloning Oct3/4, Sox2, Klf4 and c-Myc into adenoviral vectors and co-transducing the recombinant adenoviral vectors into a mouse liver-derived normal liver cell (see Stadfeld, et al., Science, 322, 945-949, 2008). However, here again, the introduction of adenoviral vectors into the host cell inevitably leads to the random insertion of the vectors into the genome of the host cell at significant frequencies (see Ohbayashi, et al., Proc. Natl. Acad. Sci. USA, 102, 13628-13633, 2005). Thus, this method fails to prevent random insertion of foreign genes into the genome of the iPS cell. Once again, there is no report indicating that a human iPS cell can be produced from a human-derived somatic cell, without insertion of foreign genes into the genome of the host cell.

It has also been reported that, after producing an iPS cell by randomly inserting Oct3/4, Sox2, Klf4 and c-Myc, into chromosomes, the inserted genes can then be excised from the host genome using recombinase (see Kaji, et al., Nature, 458, 771-775, 2009). For example, Cre recombinase has been shown to remove Oct3/4, Sox2, Klf4 and c-Myc genes from the host genome following induction of iPS cells (see Kaji, et al., Nature, 458, 771-775, 2009). However, at least in these reports, promoter regions necessary for inducing expression of the reprogramming genes remained in the host cell's genome. Genetic information of the produced iPS cell is therefore not identical to that of a parent cell, and interference with gene expression in proximity to the insertion site remains possible.

In other reports, the iPS inducing genes were introduced into the host somatic cells using a transposon. After transient expression of the iPS inducing genes, the transposon was removed by expression of transposase that excises the transposon and the covalently linked iPS inducing genes from the host cell's genome. (see Woltjen, et al., Nature, 458, 766-770, 2009). This method is, however, inefficient, because the probability of successful removal is only about 0.001% of the total number of produced iPS cells, and no examples using a human cell were given. According to a report by Woltjen, et al., even after removal of the transposable element by transposase, a residual four bases remain at the integration site. In this case, it cannot be denied that the potential for insertional mutagenesis remains possible. Moreover, the transposase used for removing the transposon is an enzyme having both an excision activity resulting in the removal of the transposon and an integrase activity that directs the insertion of transposons into the genome of the host cell. Thus, at least in theory, transposons excised from a particular insertion site may be re-inserted at a different location in the genome. Therefore, it would be necessary to check each iPS cell clone to verify that re-insertion has not reoccurred at a different location.

Yu, et al., have reported that simultaneous expression of Oct3/4, Sox2, Klf4, c-Myc, Nanog, LIN28 and SV40 T antigen in a human normal fibroblast cell, using an extrachromosomally-replicable circular DNA vector (EBV vector) having a replication origin of Epstem-Barr virus (EBV) and EBNA1 gene, transforms the fibroblast cell into an iPS cell. All foreign DNA in the iPS cell can then be eliminated by removal of the episome (see Yu, et al., Science, 324, 797-801, 2009). As of now, this is the only report describing the generation human iPS cells that are genetically identical to that of the parent somatic cell. However, the iPS cell production efficiency is only in the range of about 0.0003 to 0.0006%. Hence, at least $3\times10^5$ cells would be required to establish a single iPS cell. Moreover, EBV DNA is not only episomal but can also be inserted into the host cell's DNA at high frequency (see Hurley, et al., J. Virol, 65, 1245-1254, 1991). Thus, this method is also flawed because it does not prevent integration of foreign genes into the genome of the iPS cell. To verify the absence of integration of any foreign DNA again would require the screening of each iPS clone.

A number of different experimental strategies have been devised to generate a iPS cell having genetic information that is identical to that of the parent somatic cell. In one such attempt, a tissue cell nucleus was introduced into an enucleated oocyte (see Wakayama, et al., Science, 292, 740-743, 2001). In another attempt, a peptide capable of crossing cell membranes was fused to the N terminus of each of Oct3/4, Sox2, Klf4 and c-Myc, and scraped-loaded into somatic host cells (see Zhou, et al., Cell Stem Cell, 4, 381-384, 2009). However, there is currently no report indicating that a human iPS cell could be produced using any of these methods.

Recently, Fusaki, et al., (see Fusaki, et al., Proc. Jpn. Acad. Ser. B85, 348-362, 2009) reported a method designed to direct the expression of Oct3/4, Sox2, Klf4 and c-Myc genes in a human skin-derived fibroblast cell and generate pluripotent stem cells, using as a vector a Sendai virus that does not integrate into the host cell's genome (see Fusaki, et al., Proc. Jpn. Acad. Ser. B85, 348-362, 2009 and PCT/JP 2009/062911). In this report, iPS cells were established at a maximum efficiency rate of 1% by loading four types of reprogramming genes on individual vectors, mixing the vectors together and infecting a cell with the mixed vectors. However, this report makes no mention of the genetic stability and the clonality of the iPS cells. According to a semi-qualitative RT-PCR (Reverse Transcription-Polymerase Chain Reaction) analysis of the gene expression, it is immediately apparent that the established iPS cell lines were not entirely clonal i.e. they did not have identical characteristics with respect to chromosomal stability and gene expression profiles. Moreover, only a human iPS cell line is shown in the examples. The report therefore fails to demonstrate that this technique is broadly applicable to different animal species, and that germline transmission can be verified using a chimeric animal model derived from a iPS cell. To date, no method has been described for the generation of human iPS cells that are therapeutically safe for human regeneration therapies. There is therefore an unmet need for therapeutically safe iPS cells that fulfill the following four requirements: 1) the established human pluripotent stem cells have identical genetic information to that of the patient; 2) the human iPS cells can be generated from just $10^4$ cells or less; 3) the established human iPS cells are clonal and genetically stable; and 4) the germline transmission can be demonstrated using a chimeric animal derived from a iPS cell.

Further, it has been reported that by using the above-described foreign genes, human iPS cells can be prepared from various tissue cells including skin-derived fibroblast cells (Takahashi, et al., Cell, 131, 861-872, 2007; Yu, et al., Science, 318, 1917-1920, 2007), hair root-derived keratinocytes (Aasen, et al., Nature Biotechnology, 26, 1276-1284, 2008), bone marrow-derived mesenchymal stem cells (Park, et al., Cell, 134, 877-886, 2008), neural stem cells (Kim, et al., Nature, 461, 649-653, 2009), adipose tissue-derived mesenchymal stem cells (Sun, et al., Proc. Natl. Acad. Sci. USA, 106 15720-15725, 2009), mesenteric cells (Li, et al., Cell Reprogram., 12 237-247, 2010), dental pulp cells (Oda, et al., J. Biol. Chem., 285, 29270-29278, 2010), tooth root cells (Egusa, et al., PLos One, 5, e12743, 2010), peripheral blood-derived mononuclear cells (Loh, et al, Cell Stem Cell, 7, 15-19, 2010; Staerk, et al., Cell Stem Cell, 7, 20-24, 2010), peripheral blood-derived T cells (Loh, et al, Cell Stem Cell, 7, 15-19, 2010; Staerk, et al., Cell Stem Cell, 7, 20-24, 2010; Seki, et al., Cell Stem Cell, 7, 11-14, 2010), and hematopoietic progenitor cells (Loh, et al., Blood, 113 5476-5479, 2009).

It is desirable that living human tissue cells as a raw material for human iPS cells are capable of being collected by a method which does not give a strong invasion into the human body and is free from the risk of contamination with microorganisms (bacteria and viruses). Among the above-listed human tissue cells, skin-derived fibroblast cells, bone marrow-derived mesenchymal stem cells, neural stem cells, adipose tissue-derived mesenchymal stem cells, mesenteric cells, dental pulp cells and dental root cells must respectively be collected by incision of the skin, perforation of the bone marrow, craniotomy, liposuction, surgical operation, tooth extraction and gingivectomy, all being strongly invasive methods. Therefore, these cells are not desirable as a raw material for human iPS cells. Hematopoietic progenitor cells can be collected not only by perforation of the bone marrow but also from peripheral blood after pretreatment such as administration of granulocyte colony-stimulating factor (G-CSF). However, such pretreatment involves compulsive proliferation of hematopoietic stem cells and thus may increase the risk of leukemia. Such pretreatment is undesirable from the viewpoint of safety. Further, the skin, hair root and dental root are directly exposed to the air and cells derived from these tissues are most likely to have been contaminated with environmental microorganisms, so they are not desirable as a raw material for human iPS cells.

Further, it is desirable that a living human tissue cell as a raw material for human iPS cells has the lowest possible levels of mutations resulting from damage added to genome information. This is a condition that need to be satisfied to avoid the risk of carcinogenesis, especially when human iPS cells are to be used for medical purposes. Among the above-listed human tissue cells, skin-derived fibroblast cells and hair root-derived keratinocytes are known to repeatedly undergo damage to the genome by UV rays and repair thereof (Ikehata, Environ. Mol. Mutagen., 41, 280-292, 2003). Thus, it is believed that these cells have a higher risk of mutation than other tissue cells and are not desirable as a raw material for human iPS cells.

Considering the above-described conditions, a living human tissue cell as a raw material for human iPS cells is desirably a cell contained in pheripheral blood which does not require a strongly invasive collection method or a risky pre-treatment and which can be easily obtained by blood collection of only about 10 mL as usually carried out at clinical sites. Examples of cells contained in the peripheral blood of healthy adults include, but are not limited to, lymphocytes (T cells, B cells and NK cells), granulocytes (neutrophils, basophils and eosinophils), monocytes, erythrocytes and platelets.

A living human tissue cell as a raw material for human iPS cells must be a cell that has genetic information necessary for maintaining iPS cells (nuclear genes and mitocondrial genes) and organelles (mitocondria, endoplasmic reticula, etc.). In view of this, erythrocytes and platelets which lack nucleus, and granulocytes (neutrophils, basophils and eosinophils) which almost lack mitocondria and endoplasmic reticula/Golgi apparatuses are not appropriate as a raw material for human iPS cells.

Further, in order to secure complete pluripotency, it is desirable that a living human tissue cell as a raw material for human iPS cells is a cell which has complete genetic information identical to that of a fertilized egg and which does not have irreversible recombinations, mutations and gene deletions in its genetic information in association with cell differentiation. Specific examples of cells which have irreversible recombinations, mutations and gene deletions in their genetic information include peripheral blood-derived T cells in which rereversible recombinations have occurred in T cell receptor genes and peripheral blood-derived B cells in which irreversible recombinations have occurred in antibody genes. This means that, in principle, only one type of T cell receptor or antibody can be produced from iPS cells prepared from peripheral blood-derived T cells or B cells; such iPS cells are unable to differentiate to hematopoietic stem cells which are required to have the capacity to produce a wide variety of T cells and B cells. Therefore, among the above-listed cells, peripheral blood-derived T cells and peripheral blood-derived B cells are undesirable as a raw material for human iPS cells.

Further, since human iPS cells are prepared on mouse or nonself human-derived feeder cells, it is desirable that a living human tissue cell as a raw material for human iPS cells does not have cytotoxicity to heterologous cells and allogeneic nonself cells. Therefore, among the above-listed cells, NK cells which recognize non-autologous cells and show non-specific cytotoxicity are undesirable as a raw material for human iPS cells.

On the other hand, among the above-listed cells, monocytes have an intact nucleus and mitocondria/organelles and retain complete genomic information that has not undergone irreversible changes such as recombination and deletion. Besides, methods for purification of monocytes have been established; they are Ficoll centrifugation in which blood cells are fractionated by difference in specific gravity and a purification method using anti-CD14 antibody bound magnetic beads. By combining these techniques, it is possible to recover a cell population of very high purity (98% or more) in a short period of time and in an aseptic manner. Thus, monocytes are the only human tissue cell that satisfies all of the above-described conditions as a raw material for superior human iPS cells. Therefore, establishing a method of preparing human iPS cells using monocytes as a raw material has critical significance in the attempt of putting pluripotent stem cells into practical use.

On the other hand, any of the cells currently used as a raw material for preparing human iPS cells proliferates through cell division under laboratory culture conditions, and it is believed that the ability to proliferate through cell division is necessary for preparation of human iPS cells (Hanna, et al., Nature, 462, 595-601, 2009). In contrast, monocytes are cells at the terminal stage of differentiation from hematopoietic stem cells and do not have proliferative capacity. Conditions to cause cell division in monocytes in vitro are not known. Therefore, at present, it is believed that preparation of iPS cells from monocytes is not easy to accomplish.

Peripheral blood-derived mononuclear cells obtained by partially purifying peripheral blood by Ficoll centrifugation are composed of lymphocytes (about 80%) and monocytes (about 20%). Therefore, the human iPS cells prepared from peripheral blood mononuclear cells according to the methods described in Loh, et al, Cell Stem Cell, 7, 15-19, 2010 and Staerk, et al., Cell Stem Cell, 7, 20-24, 2010 may probably contain monocytes-derived cells. In fact, the human iPS cells reported in Loh, et al, Cell Stem Cell, 7, 15-19, 2010 and Staerk, et al., Cell Stem Cell, 7, 20-24, 2010 contained iPS cells free from DNA recombination in T cell receptor or antibody gene, suggesting that these cells are derived from mononuclear cells other than T cells and B cells. However, it is unknown from what cell are derived the iPS cells that are believed to be non-T cells. No report has been published to date that shows the preparation of human iPS cells using purified monocytes.

It is known that the nature and safety of self-derived human iPS cells for use in cell replacement therapy are greatly affected by the method of preparation of such iPS cells. In the methods reported in Takahashi, et al., Cell, 131, 861-872, 2007 and Yu, et al., Science, 318, 1917-1920, 2007 that perform gene expression using a retroviral vector or lentiviral vector, the genes used in the preparation of human iPS cells are inserted into the chromosomes and remain therein This means that human iPS cells prepared by these techniques do not satisfy the condition of "pluripotent stem cells having genetic information identical to that of a patient" as a requirement for cell replacement therapy. In the human iPS cells prepared from peripheral blood mononuclear cells by a method using a lentiviral vector as described in Loh, et al., Cell Stem Cell, 7, 15-19, 2010 and Staerk, et al., Cell Stem Cell, 7, 20-24, 2010, genes used in the preparation of human iPS cells are also inserted into the chromosomes and remain therein. Therefore, the thus prepared human iPS cells do not satisfy the condition of "pluripotent stem cells having genetic information identical to that of a patient" as a requirement for in cell replacement therapy.

Further, this phenomenon of gene insertion evokes the following problems in terms of ensuring safety in cell replacement therapy. Briefly, when a foreign gene is inserted at non-specific positions on chromosomes, genes in the vicinity of the insertion site may be abnormally activated to cause adverse effects such as oncogenic transformation of cells. For example, it is known that when genes are inserted with a retroviral vector at non-specific positions on chromosomes of a human bone marrow stem cell that maintains replication competence over a long period of time, oncogenes whose transcription is inhibited in normal cells are abnormally activated due to the effect of inserted foreign genes, causing oncogenic transformation of cells to occur at high frequency (Hacein-Bey-Abina, et al., Science, 302, 415-419, 2003).

This phenomenon of gene insertion further evokes the following problems in terms of ensuring safety in cell replacement therapy. Briefly, in iPS cells prepared by inserting foreign genes into chromosomes, expression of the foreign genes is inhibited as long as the undifferentiated state is maintained. However, as the iPS cell differentiates to a tissue cell, expression of the foreign genes is induced and the tissue cell may turn cancerous. For example, the mouse individual derived from mouse iPS cells prepared by introducing four genes, Oct3/4, Sox2, Klf4 and c-Myc, into skin-derived normal fibroblast cells with a retroviral vector is known to develop cancer at high frequency as a result of reactivation of the foreign c-Myc gene introduced thereinto (see Takahashi and Yamanaka, Cell, 126, 663-676, 2006). In addition to expression of c-Myc gene, it has been pointed out that expression of Klf4 and Oct3/4 genes may also lead to oncogenic transformation of cells (Jaenishi and Young, Cell, 132, 567-582, 2008).

In order to solve the various problems resulting from gene insertion into chromosomes, human iPS cells must be prepared by a method that will not leave foreign genes on chromosomes. As one example of such technology, it has been reported that after preparing human iPS cells with four genes, Oct3/4, Sox2, Klf4 and c-Myc, being inserted at random into chromosomes, the inserted genes can be removed by introducing Cre recombinase (Woltjen, et al., Nature, 458, 766-770, 2009). This technology is also used in the preparation of iPS cells from peripheral blood mononuclear cells as disclosed in Staerk, et al., Cell Stem Cell, 7, 20-24, 2010. (However, removal of the reprogramming genes is not reported in Staerk, et al., Cell Stem Cell, 7, 20-24, 2010). According to the above technology, promoter regions necessary for expressing the reprogramming genes still remain on chromosomes. Therefore, the genetic information of the prepared iPS cells is not completely identical to the genetic information of a corresponding normal cell, and insertion mutation might possibly occur.

Yu et al. reported that seven genes, Oct3/4, Sox2, Klf4, c-Myc, Nanog, LIN28 and SV40 T antigen, were expressed simultaneously in human normal fibroblast cells using a circular DNA vector (EBV vector) having the replication origin of Epstein-Barr virus (EBV) and EBNA1 gene and being capable of extrachromosomal replication, and that foreign gene-free human iPS cells could be prepared utilizing spontaneous dropping off of the vector (see Yu, et al., Science, 324, 797-801, 2009). Recently, Fusaki et al. reported a method in which Oct3/4, Sox2, Klf4 and c-Myc genes were expressed in human skin-derived fibroblast cells or peripheral blood-derived T cells using Sendai virus as a vector capable of expressing foreign genes without inserting them into chromosomes, to thereby prepare pluripotent stem cells (Fusaki, et al., Proc. Jpn. Acad. Ser. B85, 348-362, 2009; Seki, et al., Cell Stem Cell, 7, 11-14, 2010; WO 2010/008054). In this method, four reprogramming genes were loaded on separate vectors, and mixed infection was carried out. It was reported that pluripotent stem cells were prepared at a maximum efficiency of 1%. Another method was reported in which synthetic mRNAs encoding Oct3/4, Sox2, Klf4 and c-Myc proteins were introduced into human fibroblast cells to thereby prepare foreign gene-free human iPS cells at a maximum efficiency of 2% at the highest (Warren, et al., Cell Stem Cell, 7, 1-13, 2010). However, neither of these methods is known to be capable of preparing human iPS cells from monocytes.

Accordingly, there has been reported no method that can be used to prepare human pluripotent stem cells required for cell replacement therapies or the like and which satisfies the following two conditions: 1) using, as a raw material, human peripheral blood-derived monocytes that retain complete genetic information and are yet obtainable by blood collection which is less invasive and has a smaller risk of contamination with microorganisms; and 2) being a technology that enables preparation of human pluripotent stem cells where no externally introduced reprogramming genes are left in order to secure safety.

SUMMARY OF THE INVENTION

The invention discloses methods for establishing an induced pluripotent stem cell (hereinafter referred to as "iPS cell") from a normal human tissue cell at an efficiency rate of 0.01% or more, in such a manner as to have genetic information that is identical to that of a patient's cell and properties similar to those of an ES cell, so as to avoid the possibility of immunological rejection of a transplanted cell and tumorigenic transformation due to integration of foreign genes into the genome of host cell.

This goal can be achieved by using a gene expression system free of activity that could alter the host cell's genome by causing, for example, recombinations, insertions or erroneous DNA repair. The inventors found that a differentiated animal cell can be efficiently reprogrammed by transfecting it with a sustained expression-type Sendai virus containing the human Oct3/4, Sox2, Klf4 and c-Myc reprogramming genes cloned into a Sendai virus (hemagglutinating virus of Japan (HVJ)) vector (JP 4478788B and PCT/JP 2008/057212). The inventors further found that the reprogramming gene-loaded recombinant Sendai viral vector can be introduced into the host cell without the risk of incorporation of the foreign genes into the host cell's genome, and, after reprogramming, the vector can be removed easily and quickly using an siRNA. The induced pluripotent stem cells (iPS cell) generated by this procedure are genetically identical to the parental somatic cell and therefore safe for human therapeutic applications.

Another problem to be solved by the present invention is to ensure that induced pluripotent stem cells (hereinafter, sometimes referred to as "iPS cells") which have genetic information identical to that of a patient and yet have nature close to that of ES cells can be prepared from human peripheral blood monocytes without leaving foreign genes within the resultant cells after use for their preparation. If this problem is solved, pluripotent stem cells which are capable of avoiding immunological rejection of transplanted cells and possibilities of tumorigenesis resulting from insertion of foreign genes into chromosomes and gene damage can be prepared from a cell material obtained by blood collection which is a common medical practice that can be performed with minimum invasion.

The above-described problem can be solved by using a gene expression system that does not have activities for altering human genome through interactions such as recombination, insertion, repair, etc. and which yet is applicable to monocytes. The present inventors have found that ES/iPS cell markers are expressed efficiently by loading genes encoding the human gene products of reprogramming genes Oct3/4, Sox2, Klf4 and c-Myc on a sustained expression-inducing Sendai viral vector (Japanese Patent No. 4478788 and WO 2008/129971) and by then introducing the resultant vector into monocytes highly purified from human peripheral blood. The above-described reprogramming gene-loaded vector has no foreign genes integrated into chromosomes and yet can be easily and swiftly removed after reprogramming if siRNA is used. The present inventors have found that by introducing this vector into purified monocytes, it is possible to prepare highly safe, induced pluripotent stem cells (iPS cells) having genetic information identical to that of the individual who supplied the monocytes. Thus, the present invention has been achieved.

The present invention is specifically described as follows.

(1) A reprogramming gene-loaded Sendai viral vector comprising Sendai virus genes and reprogramming genes, wherein the Sendai virus genes comprise an NP gene, P/C gene, M gene, F gene, HN gene and L gene, wherein each of the M gene, the F gene and the HN gene is from a Sendai virus strain Cl.151-derived gene and wherein at least one of the M gene, the F gene and the HN gene is functionally deleted and the L gene encodes the amino-acid sequence of the L protein in which the amino-acid residue at position 1618 is valine.

(2) In the Sendai viral vector set forth in (1), all of the M gene, the F gene and the HN gene may be functionally deleted.

(3) The Sendai viral vector set forth in (1) or (2) may be a virus particle.

(4) In the Sendai viral vector set forth in any one of (1) to (3), the functional deletion in one or more of the M gene, the F gene and the HN gene may be based on insertion or substitution of a reprogramming gene and/or a marker gene, into or for one or more of the M gene, the F gene and the HN gene.

(5) In the Sendai viral vector set forth in any one of (1) to (4), the reprogramming gene may comprise a combination of Oct3/4, Sox2 and Klf4, or a combination of Oct3/4, Sox2, Klf4 and c-Myc.

(6) There is provided a reprogramming gene-loaded Sendai virus for producing an induced pluripotent stem cell, which comprises the Sendai viral vector set forth in any one of (1) to (5).

(7) The Sendai viral vector may comprise a target sequence for a microRNA. For example, the microRNA may be one that is expressed in induced pluripotent stem cells.

(8) There is also provided a template vector for preparing a reprogramming gene-loaded Sendai virus, which comprises a cloning vector with Sendai virus genes and reprogramming genes, wherein the Sendai virus genes include an NP gene, P/C gene, M gene, F gene, HN gene and L gene, and wherein: each of the M gene, the F gene and the HN gene is a Sendai virus strain Cl.151-derived gene; at least one of the M gene, the F gene and the HN gene is functionally deleted; and the L gene encodes the L protein amino-acid sequence in which the amino-acid residue at position 1618 is valine.

(9) In the template vector set forth in (8), all of the M gene, the F gene and the HN gene may be functionally deleted.

(10) In the template vector set forth in (8) or (9), the functional deletion in one or more of the M gene, the F gene and the HN gene may be based on insertion or substitution of a reprogramming gene and/or a marker gene, into or for one or more of the M gene, the F gene and the HN gene.

(11) In the template vector set forth in any one of (8) to (10), the cloning vector may be a phage vector.

(12) In the template vector set forth in (11), the phage vector may be a λ phage vector.

(13) In the template vector set forth in (8) to (12), the reprogramming gene may comprise a combination of Oct3/4, Sox2 and Klf4, or a combination of Oct3/4, Sox2, Klf4 and c-Myc.

(14) The template vector set forth in (8) to (13) may comprise DNA.

(15) The template vector set forth in (14) has a sequence complementary to a target sequence for an expressed microRNA of a differentiated cell for use in producing an induced pluripotent stem cell.

(16) There is provided a cell, wherein the template vector set forth in (8) to (15) is introduced therein.

(17) In the cell set forth in (16), at least the functionally deleted one of the M gene, the F gene and the HN gene may be introduced thereinto by itself or in combination with an NP gene, a P gene and an L gene.

(18) In the cell set forth in (17), T7 RNA polymerase may be expressed therein.

(19) There is provided a method for producing a reprogramming gene-loaded Sendai virus, which comprises: cultivating the cell as defined in any one of (16) to (18), in culture medium, to form therein a Sendai virus particle which comprises, as its genome, Sendai virus genes and reprogramming genes, wherein the Sendai virus genes include NP gene, P/C gene, M gene, F gene, HN gene and L gene, and wherein: each of the M gene, the F gene and the HN gene is a Sendai virus strain Cl.151-derived gene; at least one of the M gene, the F gene and the HN gene is functionally deleted; and the L gene encodes for an amino-acid sequence of an L protein in which the 1618-th amino-acid residue is valine.

(20) There is provided a method of producing an induced pluripotent stem cell, which comprises: infecting a differentiated cell with the reprogramming gene-loaded Sendai virus set forth in (6) to reprogram the differentiated cell; and then allowing siRNA to act on the vector so as to remove the reprogramming gene-loaded Sendai viral vector from the cell.

(21) In the method set forth in (20), the siRNA may have a sequence for targeting an L protein of a Sendai virus.

(22) There is provided siRNA, which comprises a sequence for targeting an L protein of a Sendai virus.

(23) There is provided a reagent for removing a reprogramming gene-loaded Sendai viral vector after reprogramming a differentiated cell, which comprises the siRNA set forth in (22).

(24) There is provided a method of producing an induced pluripotent stem cell, which comprises: infecting a differentiated cell with the reprogramming gene-loaded Sendai virus set forth in (7) to reprogram the differentiated cell; and then removing the reprogramming gene-loaded Sendai viral vector, after forming an induced pluripotent stem cell, wherein the differentiated cell is a microRNA-expressing cell.

(25) There is provided a method of producing an induced pluripotent stem cell, which comprises: infecting a differentiated cell with the reprogramming gene-loaded Sendai virus set forth in (6) or (7) to reprogram the differentiated cell; and then culturing the cell under high-temperature conditions to promote removal of the reprogramming gene-loaded Sendai viral vector from the cell.

As above, in the Sendai viral vector of the present invention, a plurality of reprogramming genes can be cloned into a single common vector, and expressed simultaneously in the same cell, the reprogramming of a differentiated cell is significantly facilitated. In addition, the reprogramming gene-loaded Sendai viral vector of the present invention can express reprogramming genes while being present in the cytoplasm in a sustained and stable manner, which makes it possible to eliminate the risk of foreign genes being inserted into the host cell's genome, and thus ensures a significantly higher level of safety and a reduced risk of inducing cancer. Furthermore, based on the use of the vector of the present invention, an induced pluripotent stem cell (hereinafter referred to as "iPS cell") that is genetically identical to that of a patient's cell and pluripotency similar to that of an ES cell can be established at a pluripotent stem cell-establishment efficiency rate of from at least 0.01% to over 1%, even from a human normal cell and even if the number of the cells is equal to or less than $10^4$. In addition, the established induced pluripotent stem cells are significantly uniform in cellular properties such as genetic stability and clonality, as evidenced by the fact that the correlation coefficient between the respective gene expression patterns of the cells is 0.98 or more, so that it becomes possible to avoid tumorigenic transformation, which would occur due to prolonged culture of induced pluripotent stem cells. As for the pluripotent stem cell obtained using the Sendai viral vector of the present invention, germline transmission has been confirmed in the mouse. Thus, the pluripotent stem cell is less likely to become a malignant tumor and hence it is safe to use in human therapies. In view of the above points, the pluripotent stem cell is expected to be effective for human therapies.

Since the Sendai viral vector of the present invention is installed with a plurality of reprogramming genes simultaneously and is capable of expressing those genes at a time in the same cell, operations for reprogramming a differentiated cell are extremely simple, efficient and highly reproducible. This is a remarkable characteristic which is not seen in a method in which a plurality of vectors are separately loaded with different reprogramming genes and in mixed for use. The reprogramming gene-loaded Sendai viral vector of the present invention expresses reprogramming genes persistently as it is retained continuously and stably in the cytoplasm. Therefore, the vector has no potential to insert foreign genes into the chromosome and thus will not cause malignant transformation of cells. The viral vector of the present invention is extremely safe. By using this vector, induced pluripotent stem cells (hereinafter, sometimes referred to as iPS cells) which have genetic information identical to that of a patient and yet have pluripotency close to that of ES cells can be prepared from $10^4$ or less human monocytes that can be collected with minimum invasion.

After inducing expression of the reprogramming gene in the cell cytoplasm, the reprogramming gene-loaded Sendai viral vector can be easily removed from the cell using siRNA that targets a preselected sequence that is incorporated into the Sendai virus genome. This makes it possible to obtain an iPS cell that is genetically identical to that of the differentiated parent cell and that is safe for human therapeutic use. In other instances, the vector can be removed by means of culture at high-temperatures. Alternatively, the vector can be removed more easily from the cell using the function of endogenous microRNA (miRNA). As a result, even greater safety is obtained and, at the same time, an iPS cell which has genetic information completely identical to that of the individual who supplied the differentiated cell can be obtained. Considering these points, the obtained iPS cells have great potential for application to humans.

Moreover, the wide host cell specificity/cellular specificity of the Sendai virus means that iPS cells can be established from a wide variety of human tissue cells other than fibroblast cells (i.e. blood cells). This makes it possible to confirm the function of the iPS cells using a nonhuman animal.

Compared with adenoviral vectors, EBV vectors, conventional Sendai viral vectors as well as other more conventional DNA vectors, for generating iPS cells, the present invention permits the generation of iPS cells in a simple and efficient manner with excellent reproducibility, while drastically enhancing the safety of the produced iPS cell. This should contribute greatly to the implementation of iPS technology to a wide range of therapeutic applications, such as regeneration therapies (particularly, cell replacement therapy and gene therapy) as well as promote research on the development of new drugs using patient-derived iPS cell having various genetic backgrounds. The availability of genetically defined human pluripotent stem cells also promises to facilitate research on various stem cell-related diseases, for example, the etiology of cancer stem cells and their role in metastasis.

Further, according to the present invention, human iPS cells that have complete genetic information and which yet are highly safe in the absence of foreign reprogramming genes can be prepared from human peripheral blood monocytes obtained by blood collection—a method that is less invasive and has a smaller risk of contamination with microorganisms—in an extremely efficient and simple manner with high reproducibility. This is a great advance that has been impossible to achieve by those methods that use DNA vectors (such as adenoviral or EBV vector) or conventional Sendai viral vectors, which have been used in iPS cell preparation. With this advance it has become possible to prepare human iPS cells easily from peripheral blood even in general medical institutions, which greatly contributes to progress in a wide range of technical fields including regenerative therapy (especially, cell replacement therapy and gene therapy), research in drug development using iPS cells from patients with various genetic backgrounds, manufacturing of biopharmaceuticals using human cells, elucidation of causes of cancer and intractable diseases and development of effective treatments, and so on.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 3A (at day 4) and 3B (at day 10) are photographs showing the result of removal of a sustained expression-type Sendai viral vector from a cell by use of siRNA.

6A), endogenous mouse Oct4 gene (FIG. 6B) and endogenous mouse Nanog gene (FIG. 6C) in a mouse embryonic fibroblast cell on the 14th day after infection with the hOct4/hSox2hKlf4/hc-Myc sustained expression-inducing Sendai viral vector. Lane 1: non-infection with vector (negative control). Lane 2: $14^{th}$ day post infection with vector. Lane 3: $40^{th}$ day post infection with vector.

Figure 7:
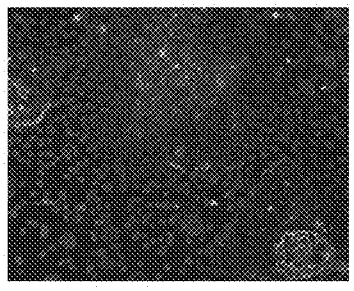

FIG. 7 is a photograph showing expression of SSEA-1 antigen in a mouse embryonic fibroblast cell on the 14th day after infection with the hOct4/hSox2/hKlf4/hc-Myc sustained expression-inducing Sendai viral vector using a fluorescent antibody method. Green: mouse pluripotent cell-specific antigen SSEA-1. Blue: DNA (DAPI staining).

FIG. 8 depicts electrophoresis photographs showing a genome PCR-based gene-type analysis result of a mouse iPS marker-expressing cell prepared using a sustained expression-type Sendai viral vector (FIG. 8A: D18Mit4; FIG. 8B: D7Mit4; FIG. 8C: D4Mir15). Lane 1: C57/BL mouse derived fibroblast cell. Lane 2: C57/BL mouse-derived colony #1. Lane 3: C57/BL mouse-derived colony #2. Lane 4: 129 mouse derived ES cell.

Figures 9, 9A, 9B:
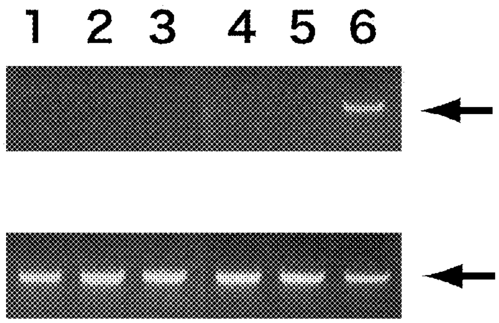

FIG. 9 depicts an electrophoresis photograph showing expression (indicated by the arrows) of Sendai virus NP gene (FIG. 9A) and endogenous mouse Nanog gene (FIG. 9B) in a mouse iPS marker-expressing cell after removal of a sustained expression-inducing Sendai viral vector using an siRNA. Lane 1: mouse iPS cell MEF/MKOS #3. Lane 2: mouse iPS cell MEF/MKOS #4. Lane 3: mouse iPS cell MEF/MKOS #6. Lane 4: mouse iPS cell MEF/MKOS #21. Lane 5: mouse iPS cell MEF/MKOS #1. Lane 6: cell before removal of vector.

Figure 10:
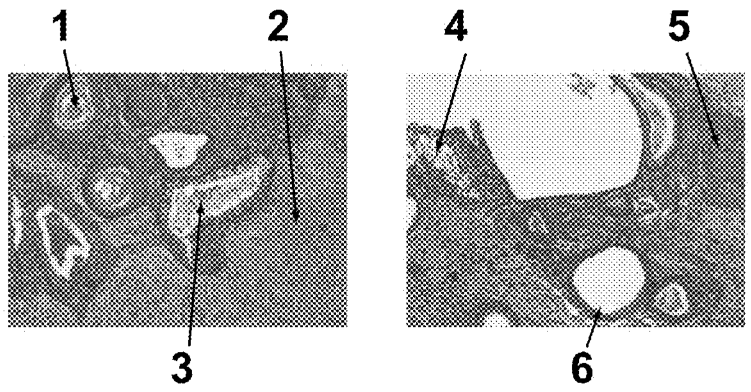

FIG. 10 depicts photographs showing HE stained histological sections of teratoma derived from a mouse iPS marker-expressing cell after removal of a sustained expression-inducing Sendai viral vector by use of siRNA. 1: Skin (derived from ectoderm); 2: Nerve (derived from ectoderm); 3: Digestive tract (derived from endoderm); 4: Adipocyte (derived from mesoderm); 5: Muscle (derived from mesoderm); 6: Thyroid grand (derived from endoderm).

Figure 11:
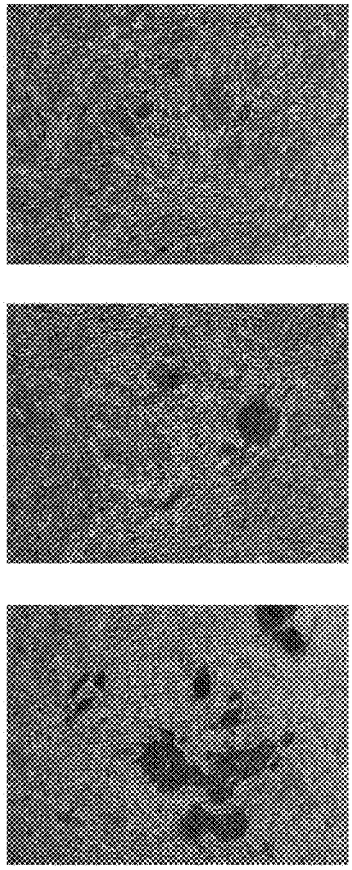

FIG. 11 is a series of time-lapse photographs using a phase contrast microscope (from 6 to 10 days post infection) showing expression of alkaline phosphatase in a human embryonic fibroblast cell infected with the hOct4/hSox2/hKlf4/hc-Myc sustained expression-inducing Sendai viral vector. Red: alkaline phosphatase. D.p.i.: days post infection.

Figure 12:
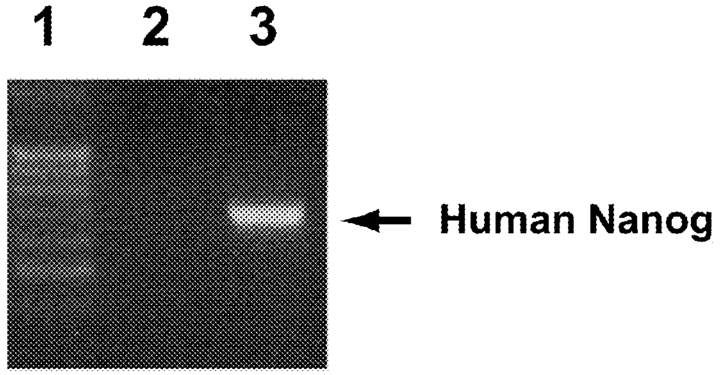

FIG. 12 depicts a photograph showing expression of endogenous human Nanog gene in a human embryonic fibroblast cell on the 14th day after infection with the hOct4/hSox2/hKlf4/hc-Myc sustained expression-inducing Sendai viral vector. Lane 1: molecular weight marker. Lane 2: normal human fibroblast not infected with vector. Lane 3: human iPS cell-like colony.

FIG. 13 depicts a photograph showing expression of SSEA-4 antigen in a human embryonic fibroblast cell on the 25th day after infection with the hOct4/hSox2/hKlf4/hc-Myc sustained expression-inducing Sendai viral vector. Green: human pluripotent stem cell-specific antigen SSEA-4. FIG. 13A: phase contrast microscopic observation. FIG. 13B: Fluorescent microscopic observation.

Figures 14, 14A, 14B:
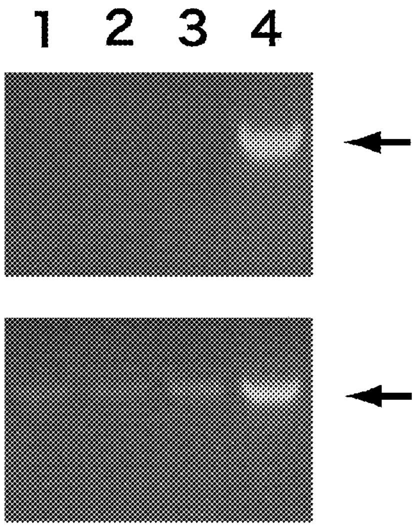

FIG. 14 depicts two photographs showing expression (indicated by the arrows) of Sendai virus NP gene (FIG. 14A) and endogenous human Nanog gene (FIG. 14 B) in a human iPS marker-expressing cell after removal of a sustained expression-inducing Sendai viral vector using an siRNA. Lane 1: human iPS cell (TIG/MKOS #19). Lane 2: human iPS cell (TIG/MKOS #32). Lane 3: human iPS cell (TIG/MKOS #30). Lane 4: iPS cell-like colony before removal of vector.

Figure 15:
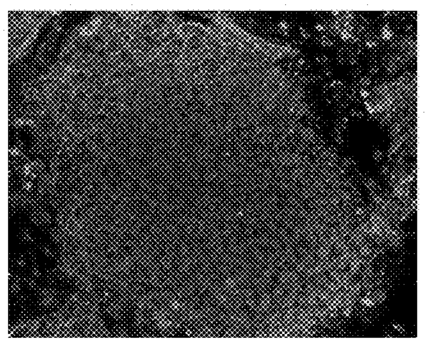

FIG. 15 depicts a photograph showing expression of SSEA-4 antigen and endogenous human Oct4 protein in a human iPS marker-expressing cell after removal of a sustained expression-inducing Sendai viral vector using an siRNA. Green: human pluripotent stem cell-specific antigen SSEA-4. Red: human pluripotent stem cell-specific antigen Oct4.

Figures 16, 16A, 16B, 16C:
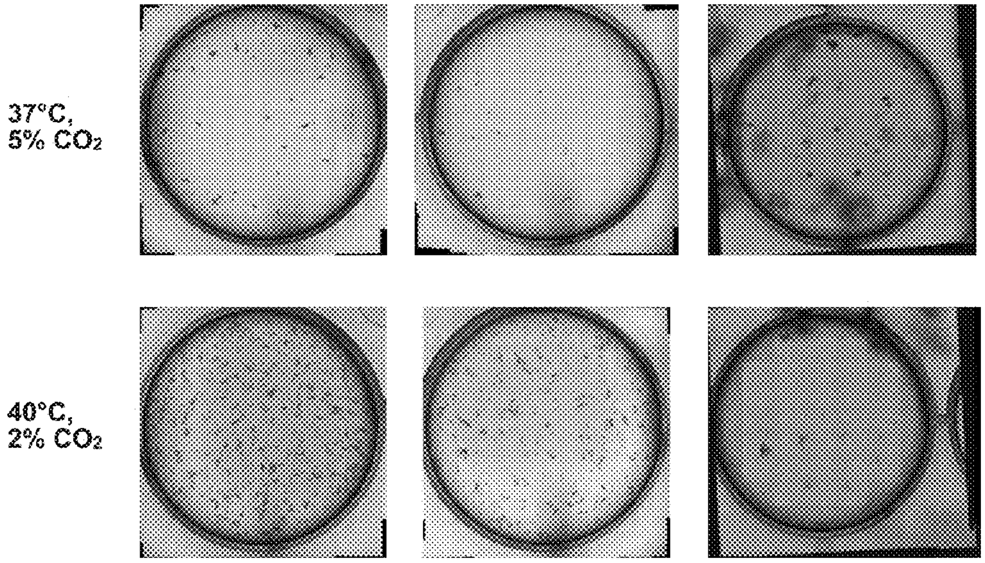
Figure 17:
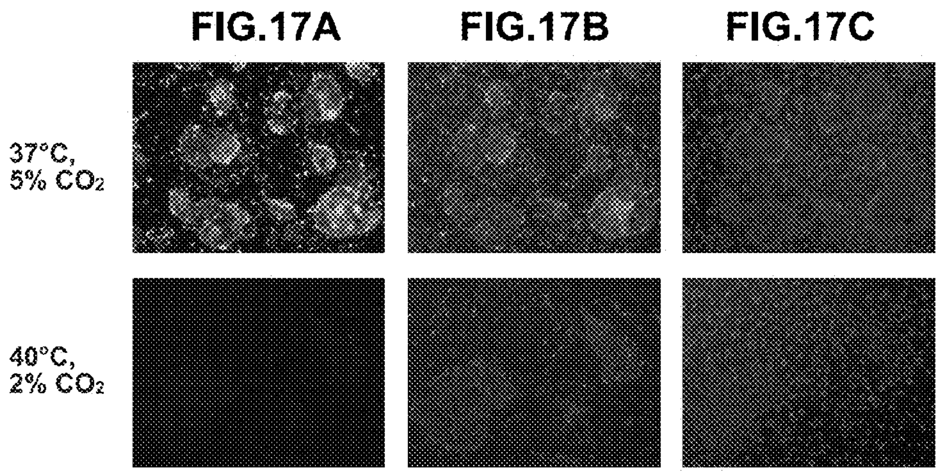

FIG. 16 depicts a series of photographs showing respective emergence efficiencies of a human iPS marker (i.e., alkaline phosphatase)-expressing cell colony, under normal culture conditions (37° C., 5% $CO_2$) and under high-temperature culture conditions (40° C., 2% $CO_2$). The cells infected with Sendai viral vector and with the retroviral vector were stained for alkaline phosphatase, respectively, on the $10^{th}$ and $20^{th}$ day after infection. Red: alkaline phosphatase, an iPS cell marker. FIG. 16A: hOct4/hSox2/hKlf4/hc-Myc sustained-expression inducing Sendai vector; FIG. 16B: hOct4/hSox2/hKlf4/hc-Myc sustained-expression inducing Sendai vector Version 2; FIG. 16C: hOct4/hSox2/hKlf4/hc-Myc sustained-expression inducing retroviral vector FIG. 17 depicts a photograph showing respective efficiencies of removal of a Sendai viral vector from a human iPS marker-expressing cell (measured by the reduced detection of Sendai virus antigen using a fluorescent antibody method), under normal culture conditions (37° C., 5% $CO_2$) and under high-temperature culture conditions (40° C., 2% $CO_2$), each for 7 days. FIG. 17A shows the detection of Sendai virus NP antigen; FIG. 17B shows the detection of SSEA-4, an iPS/ES cell marker; FIG. 17C shows DAPI staining (detection of DNA).

Figure 18:
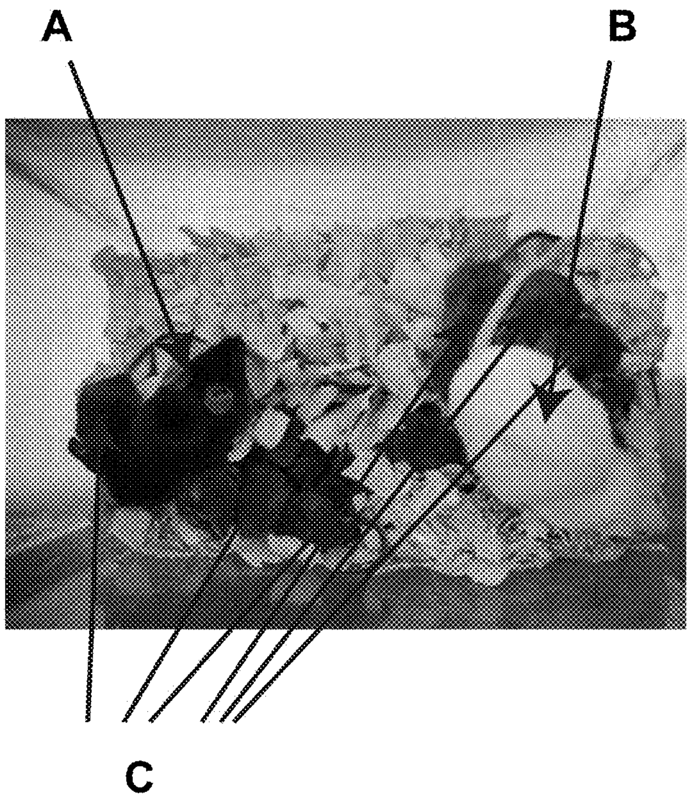

FIG. 18 depicts a photograph showing a mouse iPS cell-derived chimeric mouse prepared using a hOct4/hSox2/hKlf4/hc-Myc sustained expression-inducing Sendai viral vector Version 2, and germ-line transmission from the mouse. A: Mouse A (iPS cell-KOSM #24-derived chimeric mouse male); B: Mouse B (ICR mouse, female); C: Baby mice from mouse A and mouse B.

FIG. 19 depicts a photograph of a tissue slice of a teratoma derived from a human iPS marker-expressing cell after removal of a hOct4/hSox2/hKlf4/hc-Myc sustained expression-inducing Sendai viral vector therefrom. 1: Intestinal canal (derived from endoderm); 2: Cartilage (derived from mesoderm); 3: Neural tube (derived from ectoderm).

Figure 20:
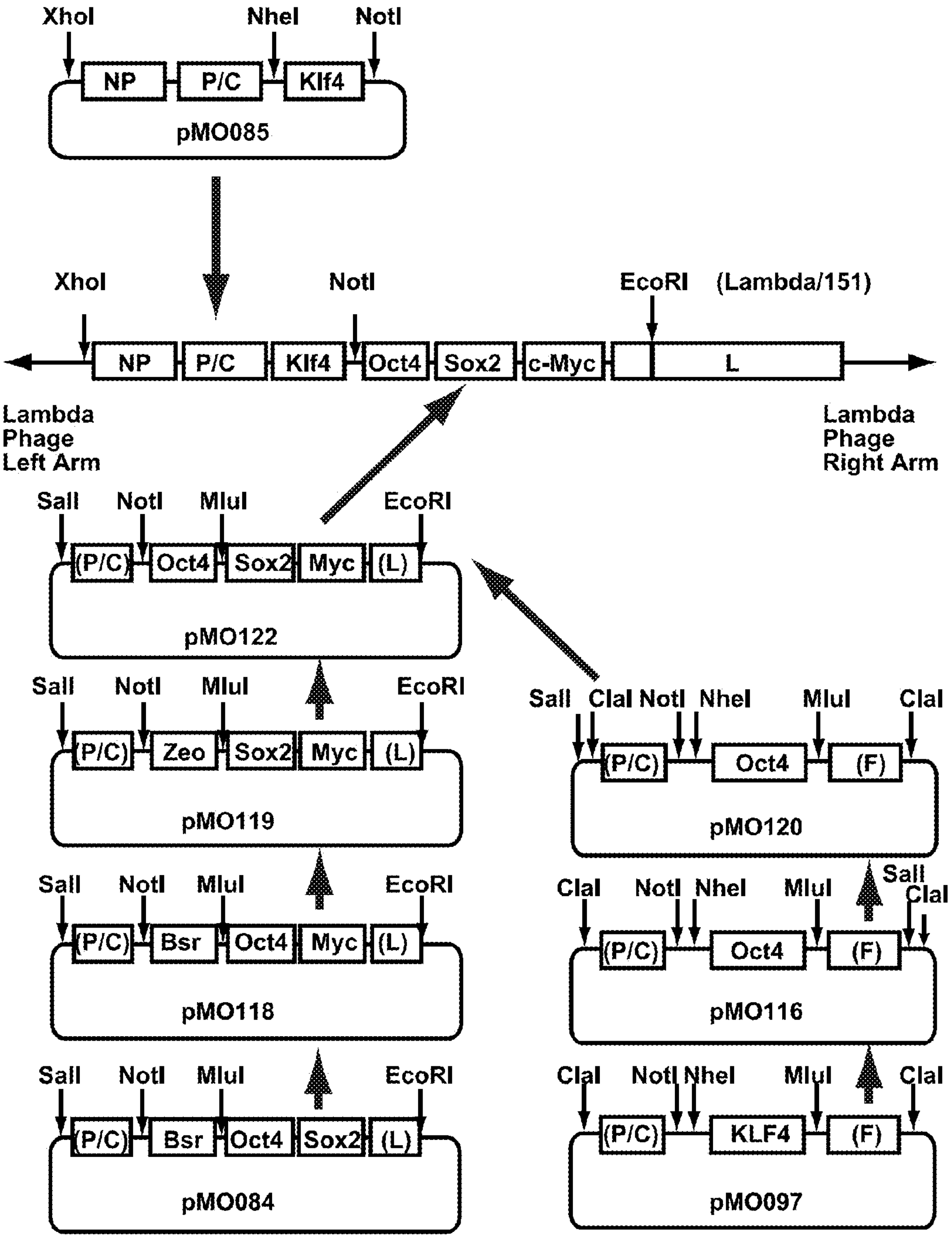

FIG. 20 is a diagram showing the preparation of a template cDNA for producing the hOct4/hSox2/hKlf4/hc-Myc sustained expression-inducing Sendai viral vector Version 2.

Figure 21:
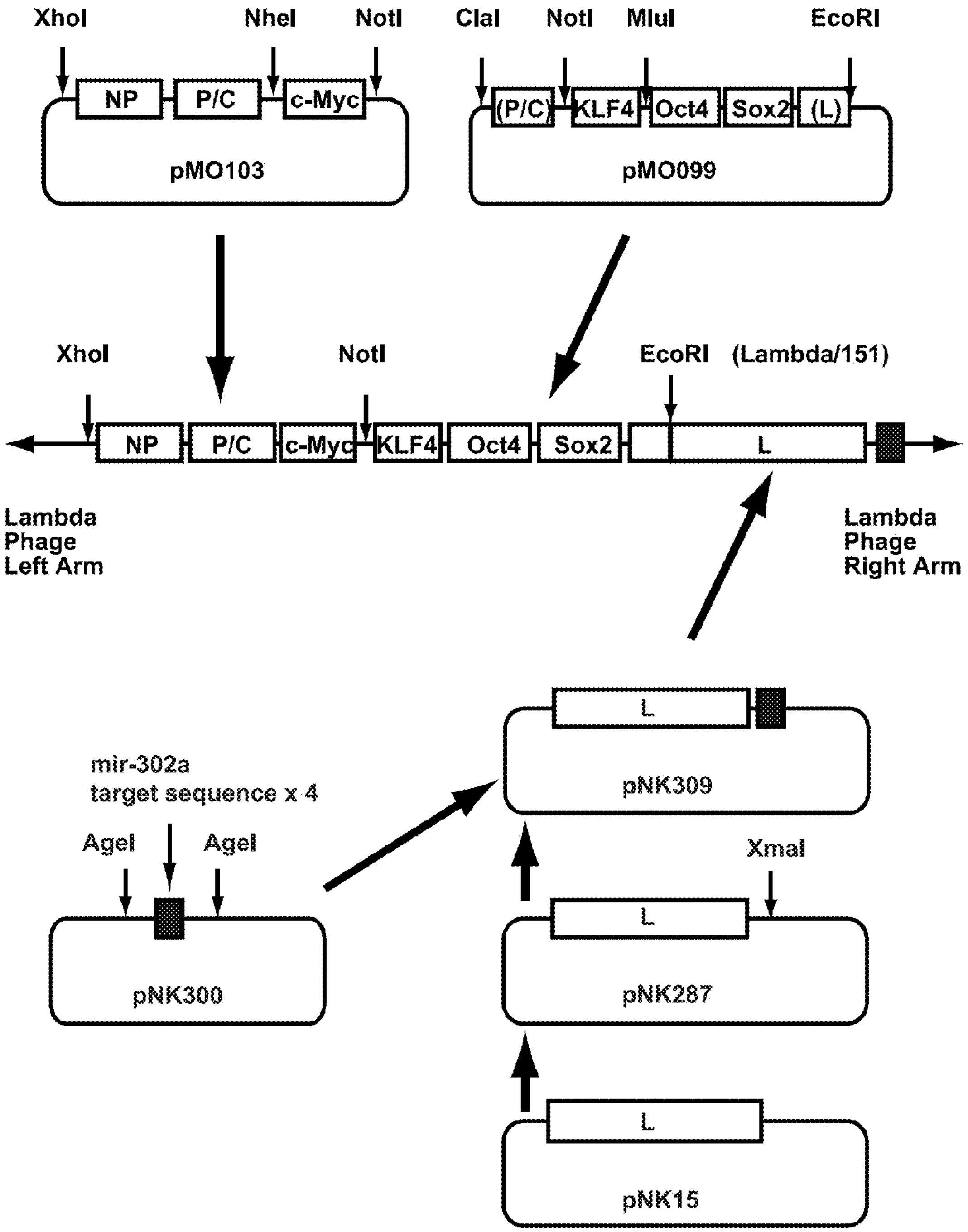

FIG. 21 is a diagram showing the preparation of a template cDNA for producing a hOct4/hSox2/hKlf4/hc-Myc sustained expression-inducing Sendai viral vector Version 3.

FIG. 22 is a graph obtained by quantitatively measuring a temporal change in removal of a sustained expression-type Sendai viral vector from a cell, using siRNA. FIG. 22A shows the selective removal of KO/Hyg/EGFP/Luc2CP-loaded sustained expression-type Sendai viral vector using siRNA. FIG. 22B shows hygromycin resistance in cells after removal of KO/Hyg/EGFP/Luc2CP-loaded sustained expression-type Sendai viral vector, using siRNA (right) and before removal of the vector (left).

Figure 23:
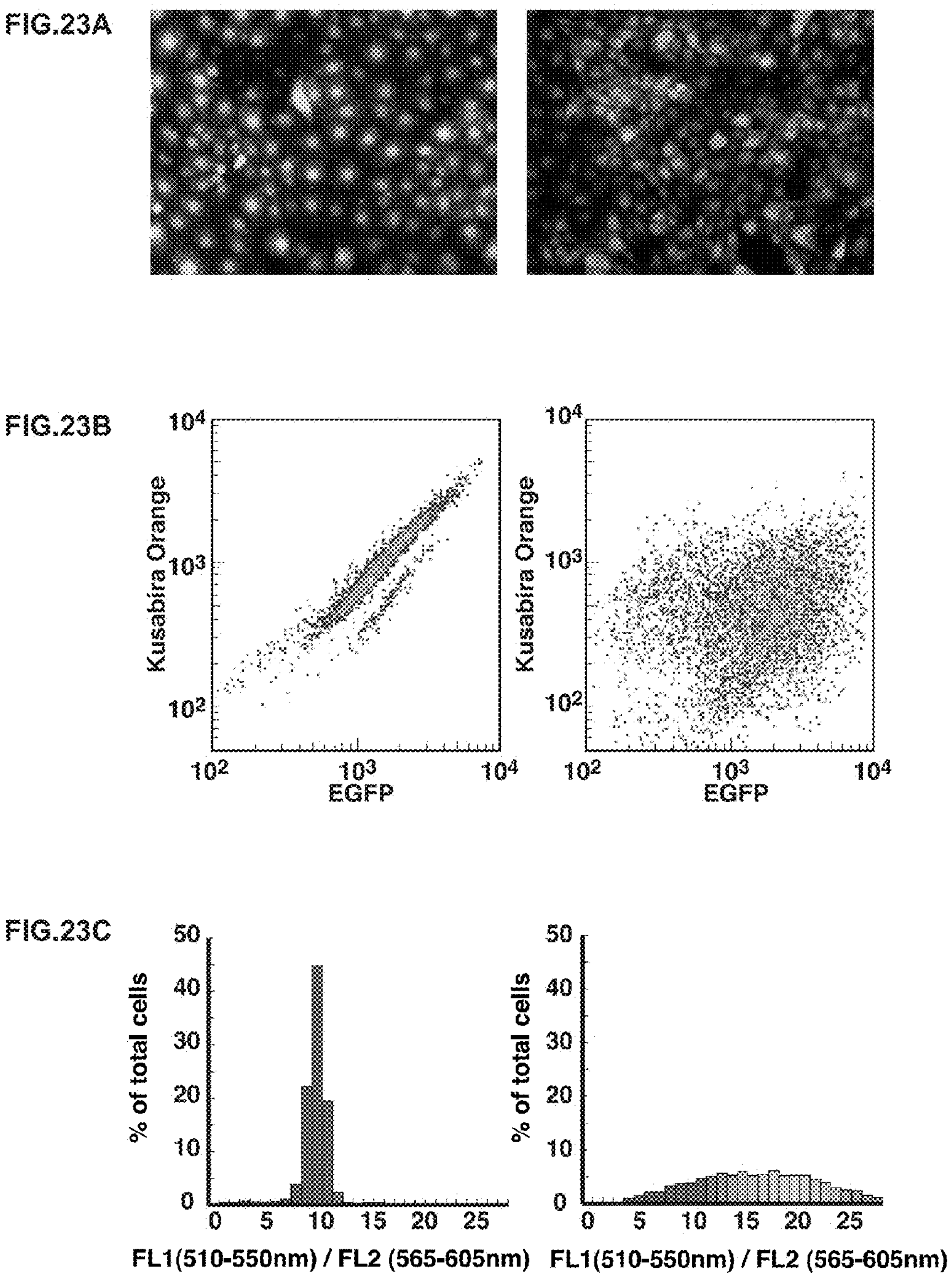

FIG. 23 depicts a photograph and a graph showing a comparison between the gene expression patterns of recombinant exogenous genes cloned into a single common sustained expression-type Sendai viral vector versus where each exogenous gene is cloned into an individual sustained expression-type Sendai viral vector. FIG. 23A shows a fluorescent microscopic observation of $LLCMK_2$ (SeVdp/KO/HygB/EGFP/Luc2CP) cells (Left) and $LLCMK_2$ (SeVdp/Zeo/KO/CLuc+SEVdp/Bsr/EGFP/91phox) cells (Right). FIG. 23B shows FACSalibur analysis of $LLCMK_2$ (SeVdp/KO/HygB/EGFP/Luc2CP) cells (Left) and $LLCMK_2$ (SeVdp/Zeo/KO/CLuc+SeVdp/Bsr/EGFP/91phox) cells (Right). FIG. 23C shows data obtained by reanalyzing results of the FACSalibur analysis of $LLCMK_2$ (SeVdp/KO/HygB/EGFP/Luc2CP) cells (Left) and $LLCMK_2$ (SEVdp/Zeo/KO/CLuc+SeVdp/Bsr/EGFP/91phox) cells (Right) in terms of ratio between KO and EGFP.

Figure 24:
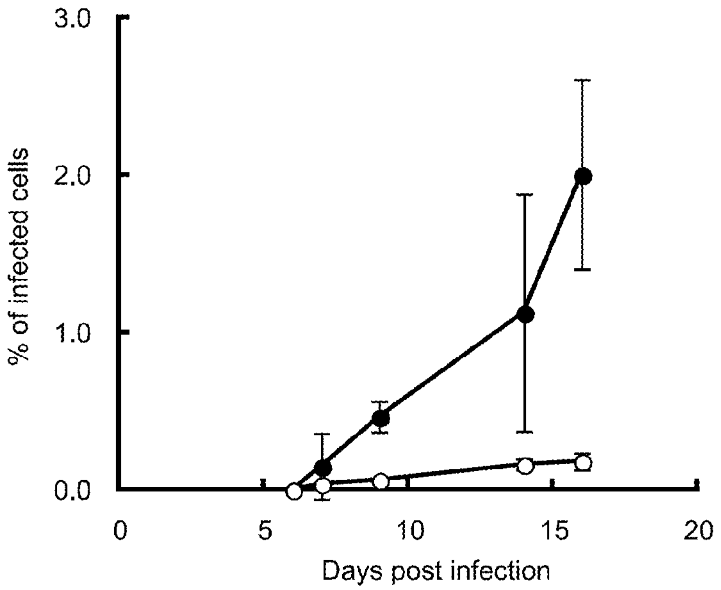

FIG. 24 depicts a graph showing the temporal change in emergence efficiency of a mouse iPS marker-expressing cell, after transfection with either a single common sustained expression-type Sendai viral vector comprising four types of reprogramming genes or after transfection with individual sustained expression-type Sendai viral vectors each comprising a different reprogramming gene. Filled circles: hOct4/hSox2/hKlf4/hc-Myc sustained expression-inducing Sendai viral vector. Open circles: a mixture of hOct4/hSox2/hKlf4 sustained expression-inducing Sendai viral vector and Zeo/KO/hc-Myc sustained expression-inducing Sendai viral vector.

FIG. 25 depicts photographs showing the establishment of a human iPS marker-expressing cell using the hOct4/hSox2/hKlf4/hc-Myc sustained expression-inducing Sendai viral vector Version 3. FIG. 25A: Detection of Sendai virus-NP antigen; FIG. 25B: Detection of SSEA-4 antigen, an iPS/ES cell marker. On the $24^{th}$ day after infection with the vector (the cells were subcultured twice during this period), the vector was removed without any treatment with siRNA, etc and NP antigen becomes undetectable.

FIG. 26 depicts a photograph of a human iPS marker-expressing cell established from adult human peripheral blood mononuclear cells using a hOct4/hSox2/hKlf4/hc-Myc sustained expression-inducing Sendai viral vector. FIG. 26A: phase contrast microscope image; FIG. 26B: alkaline phosphatase stain image FIG. 27 depicts a diagram showing a comparison between gene expression patterns of a plurality of types of human iPS marker-expressing cells established using a hOct4/hSox2/hKlf4/hc-Myc sustained expression-inducing Sendai viral vector. FIG. 27A shows the correlation coefficients of four human iPS marker-expressing cell lines established using hOct4/hSox2/hKlf4/hc-Myc sustained expression-inducing Sendai viral vector. FIG. 27B shows a comparison of human ES marker gene expression between four human iPS marker-expressing cell lines established using hOct4/hSox2/hKlf4/hc-Myc sustained expression-inducing Sendai viral vector, and five human ES cell lines. Stronger reddish color indicates higher intensity of expression. FIG. 27C shows the correlation of gene expression between human iPS marker-expressing cells established using the hOct4/hSox2/hKlf4/hc-Myc sustained expression-inducing Sendai viral vector (#56 cell line, X-axis) and human ES cells (Kyoto Univ. #4 cell line, Y-axis).

Figure 28:
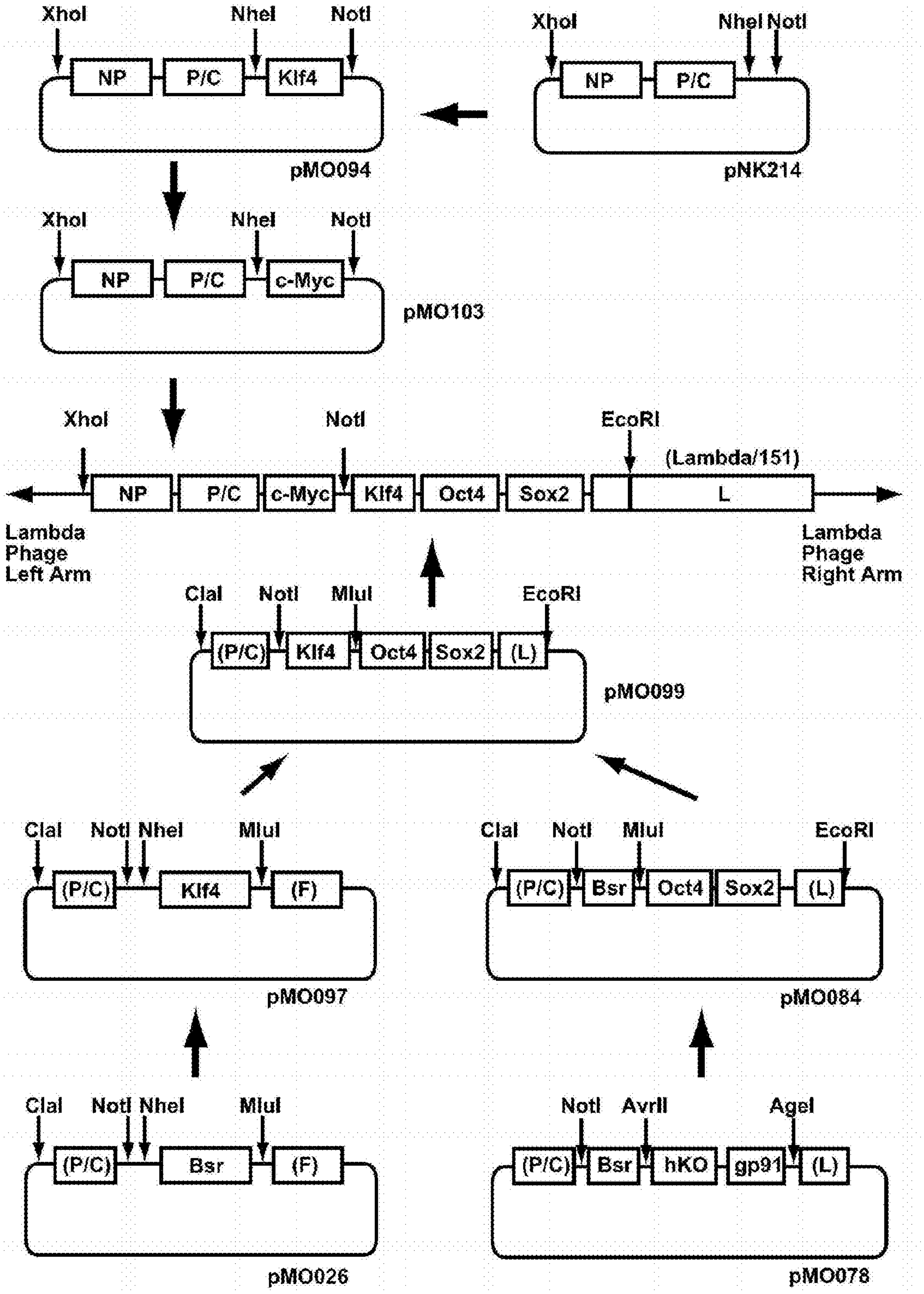

FIG. 28 shows an outline for preparing a template cDNA for producing hOct4/hSox2/hKlf4/hc-Myc sustained expression-inducing Sendai viral vector version 1.

Figure 29:
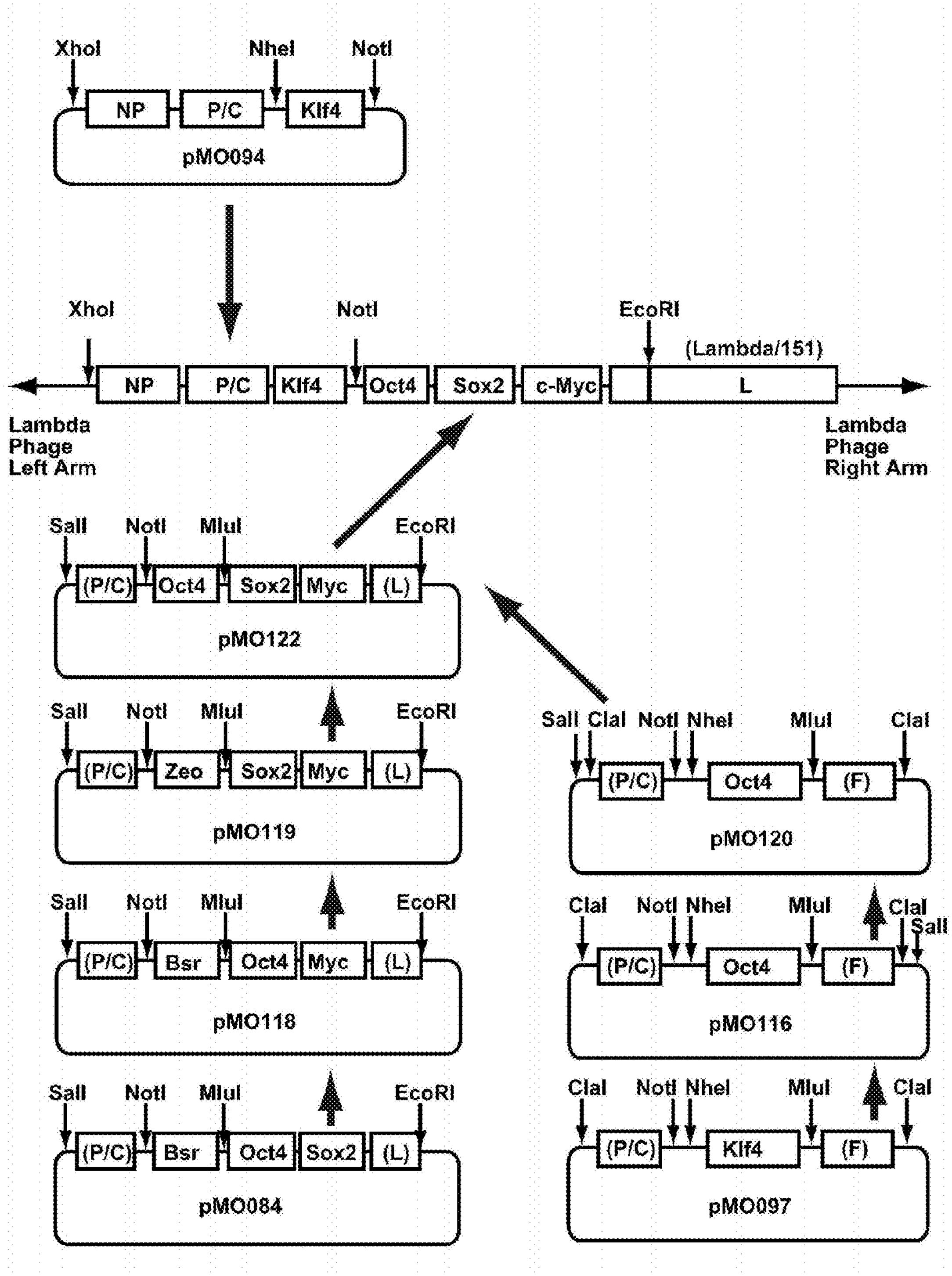

FIG. 29 shows an outline for preparing a template cDNA for producing hOct4/hSox2/hKlf4/hc-Myc sustained expression-inducing Sendai viral vector version 2.1.

Figure 30:
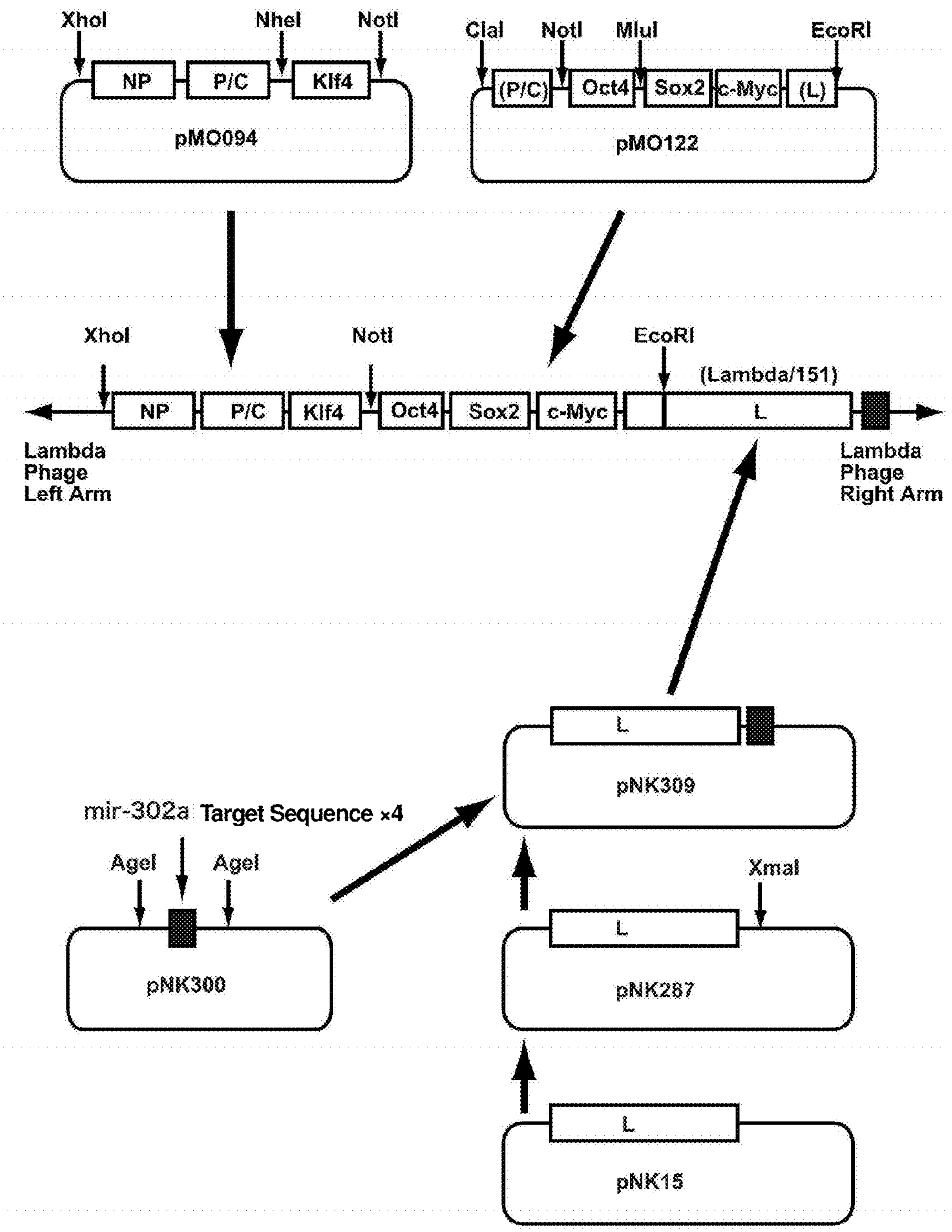

FIG. 30 shows an outline for preparing a template cDNA for producing hOct4/hSox2/hKlf4/hc-Myc sustained expression-inducing Sendai viral vector version 4.

FIG. 31 shows the purity of purified human peripheral blood-derived monocytes.

FIG. 32 shows the expression of human iPS/ES cell markers in human peripheral blood-derived monocytes on day 8 of their infection with hOct4/hSox2/hKlf4/hc-Myc sustained expression-inducing Sendai viral vectors.

FIG. 33 shows photographs of phase-contrast microscopy images of human iPS cells prepared from human peripheral blood-derived monocytes using hOct4/hSox2/hKlf4/hc-Myc sustained expression-inducing Sendai viral vectors.

FIG. 34 shows the expression of human iPS/ES cell markers in human iPS cells prepared from human peripheral blood-derived monocytes using hOct4/hSox2/hKlf4/hc-Myc sustained expression-inducing Sendai viral vectors.

FIG. 35 shows the analysis of T cell receptor genes in the genome DNA of human iPS cells prepared from human peripheral blood-derived monocytes using hOct4/hSox2/hKlf4/hc-Myc sustained expression-inducing Sendai viral vectors.

Figure 36:
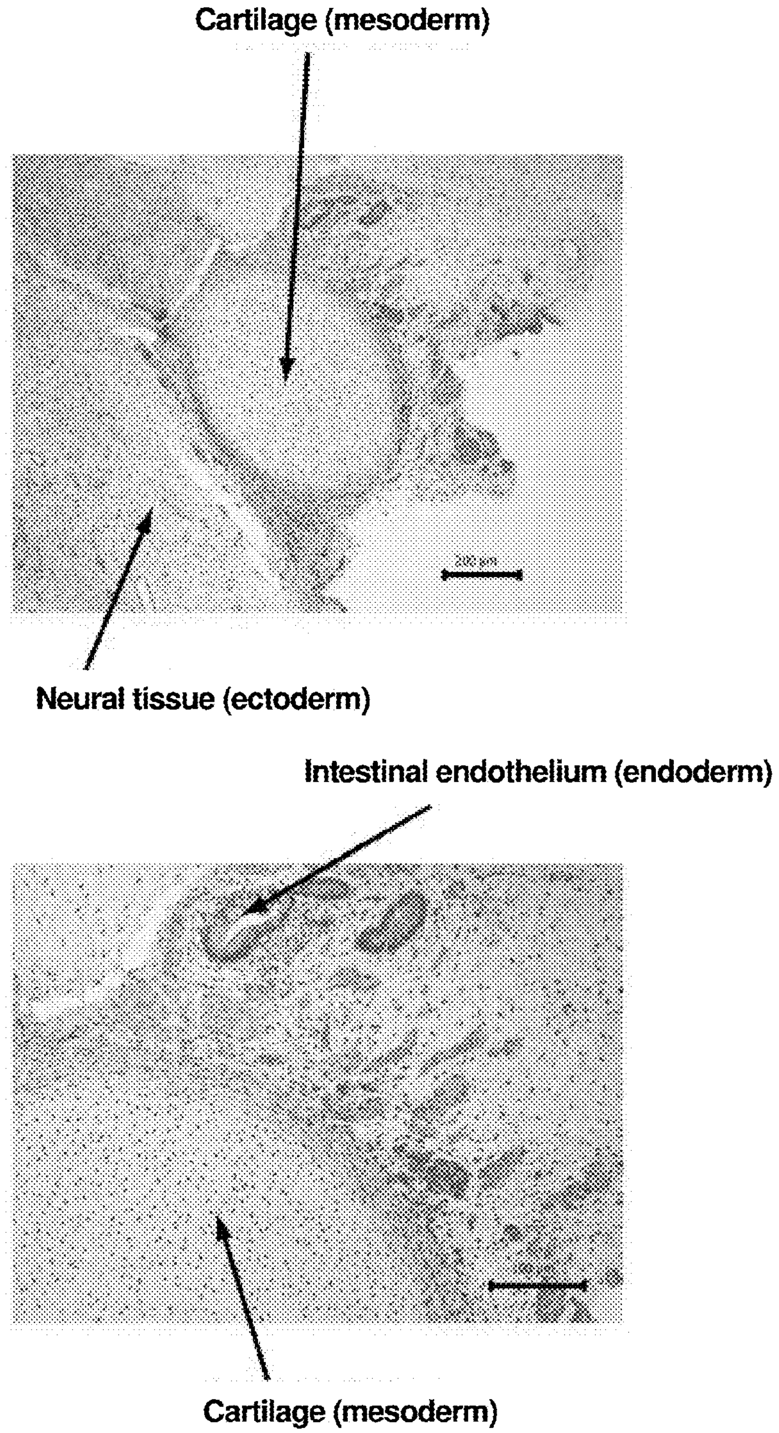

FIG. 36 shows the results of observation of teratoma tissue sections derived from human peripheral blood monocytes-derived iPS cells that had been freed of hOct4/hSox2/hKlf4/hc-Myc sustained expression-inducing Sendai viral vectors.

Figure 37:
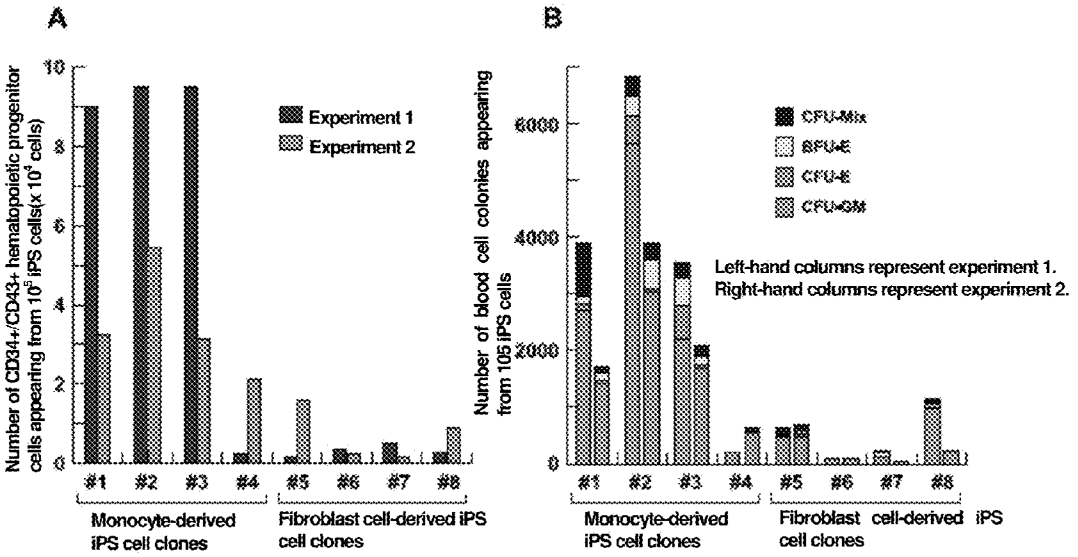

FIG. 37 shows the results of analysis of the capacity of redifferentiation into blood cells of human peripheral blood monocytes-derived iPS cells that had been freed of hOct4/hSox2/hKlf4/hc-Myc sustained expression-inducing Sendai viral vectors.

FIG. 38 shows the results of gene expression in human peripheral blood monocytes-derived iPS cells established with hOct4/hSox2/hKlf4/hc-Myc sustained expression-inducing Sendai viral vectors, as compared with gene expressions in human fibroblast cell-derived iPS cells and human ES cells.

Figure 39:
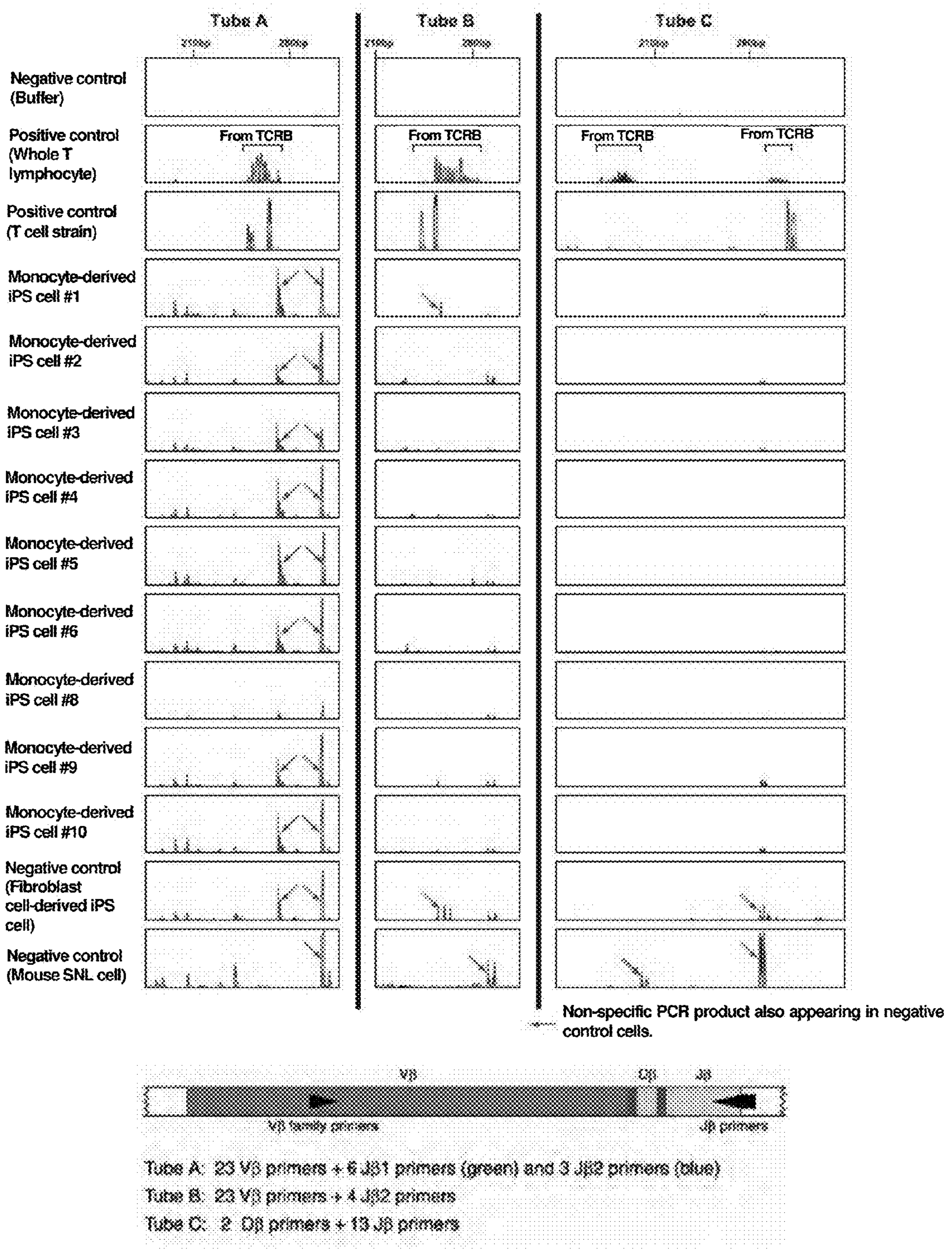

FIG. 39 shows the results of examination of the rearrangement of T cell receptor β chain (TCRB) gene in the genome of human peripheral blood monocytes-derived iPS cells established with hOct4/hSox2/hKlf4/hc-Myc sustained expression-inducing Sendai viral vectors.

Figure 40:
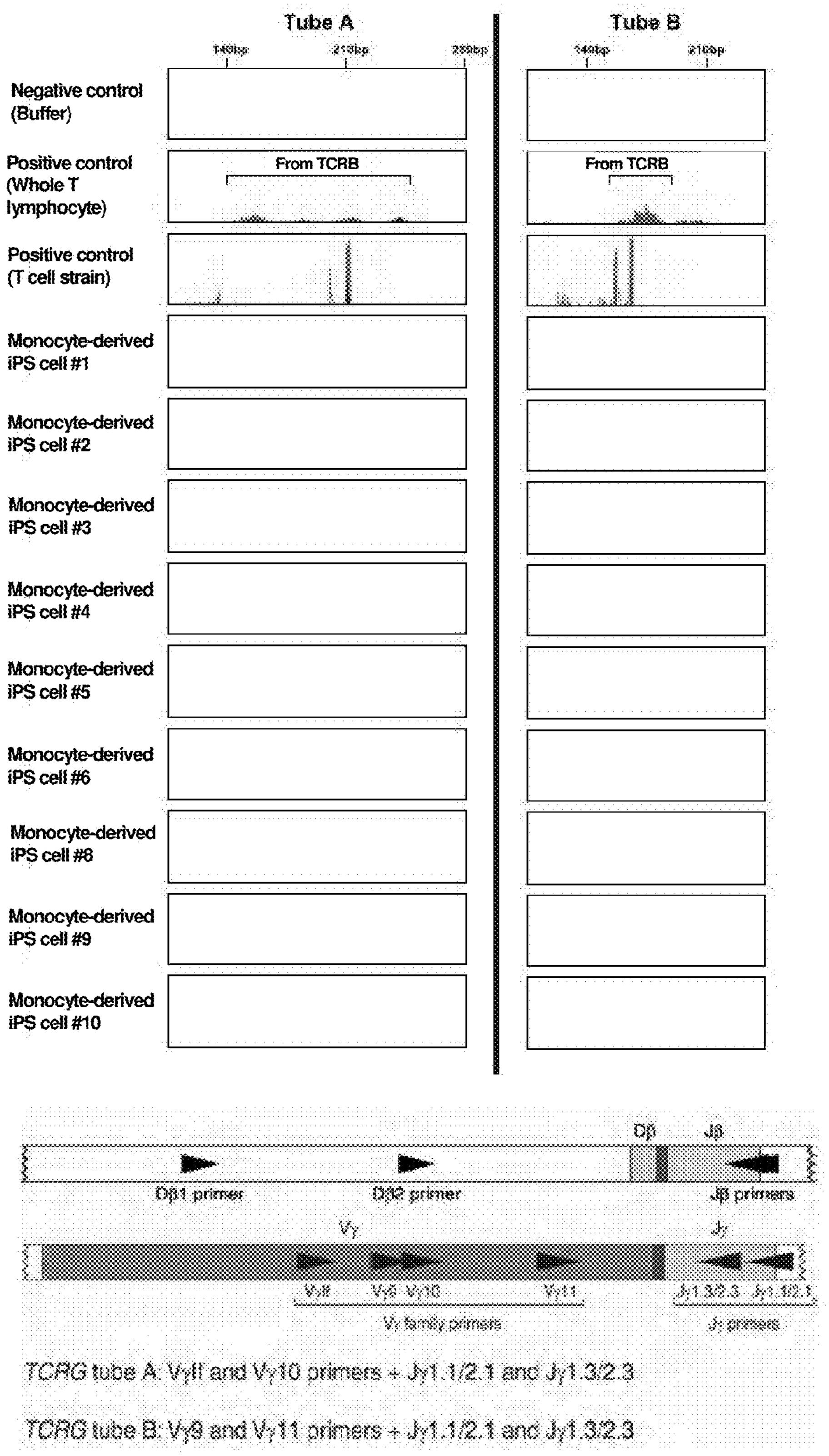

FIG. 40 shows the results of examination of the rearrangement of T cell receptor γ chain (TCRG) gene in the genome of human peripheral blood monocytes-derived iPS cells established with hOct4/hSox2/hKlf4/hc-Myc sustained expression-inducing Sendai viral vectors.

Figure 41:
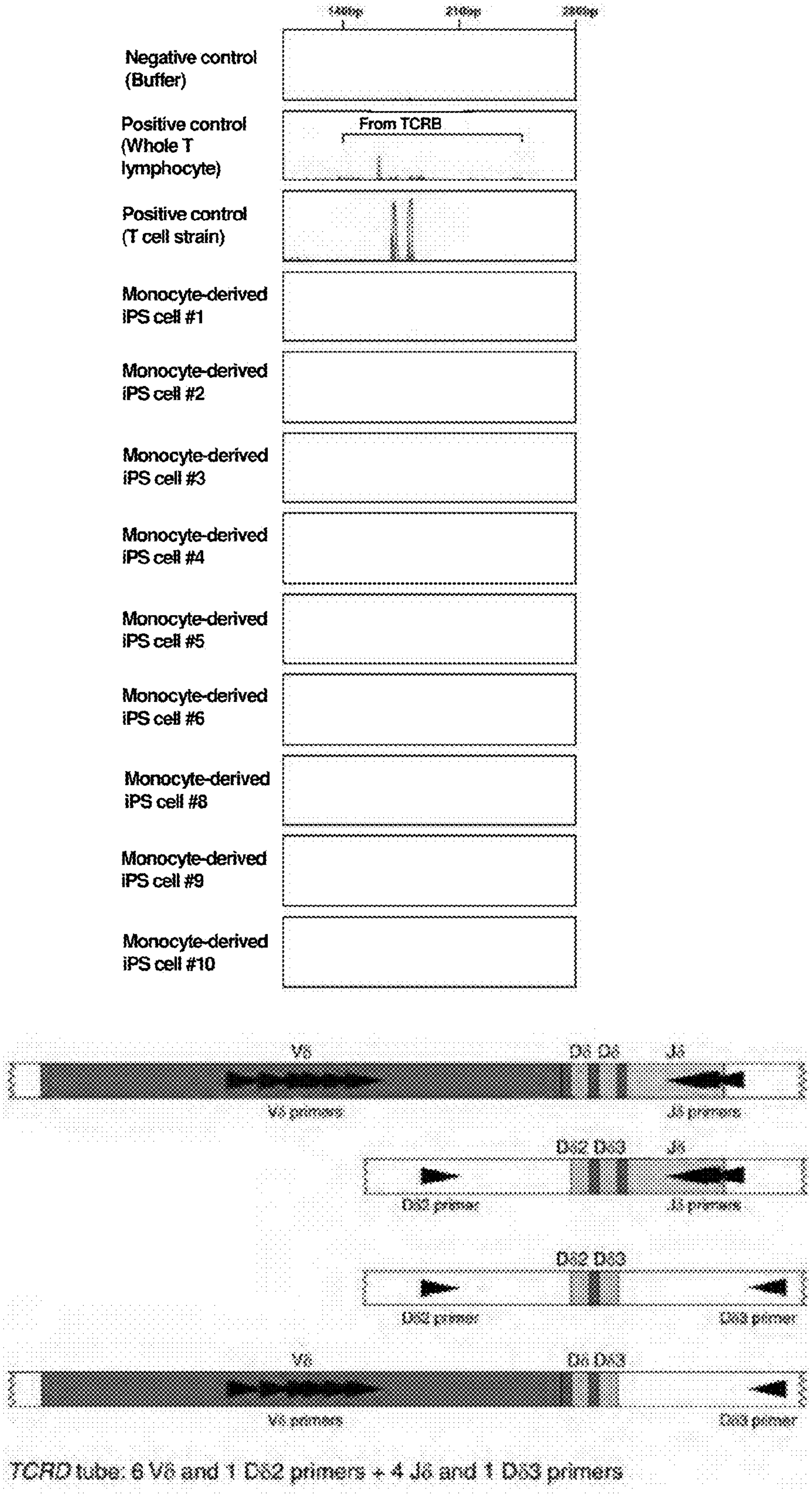

FIG. 41 shows the results of examination of the rearrangement of T cell receptor δ chain (TCRD) gene in the genome of human peripheral blood monocytes-derived iPS cells established with hOct4/hSox2/hKlf4/hc-Myc sustained expression-inducing Sendai viral vectors.

Figure 42:
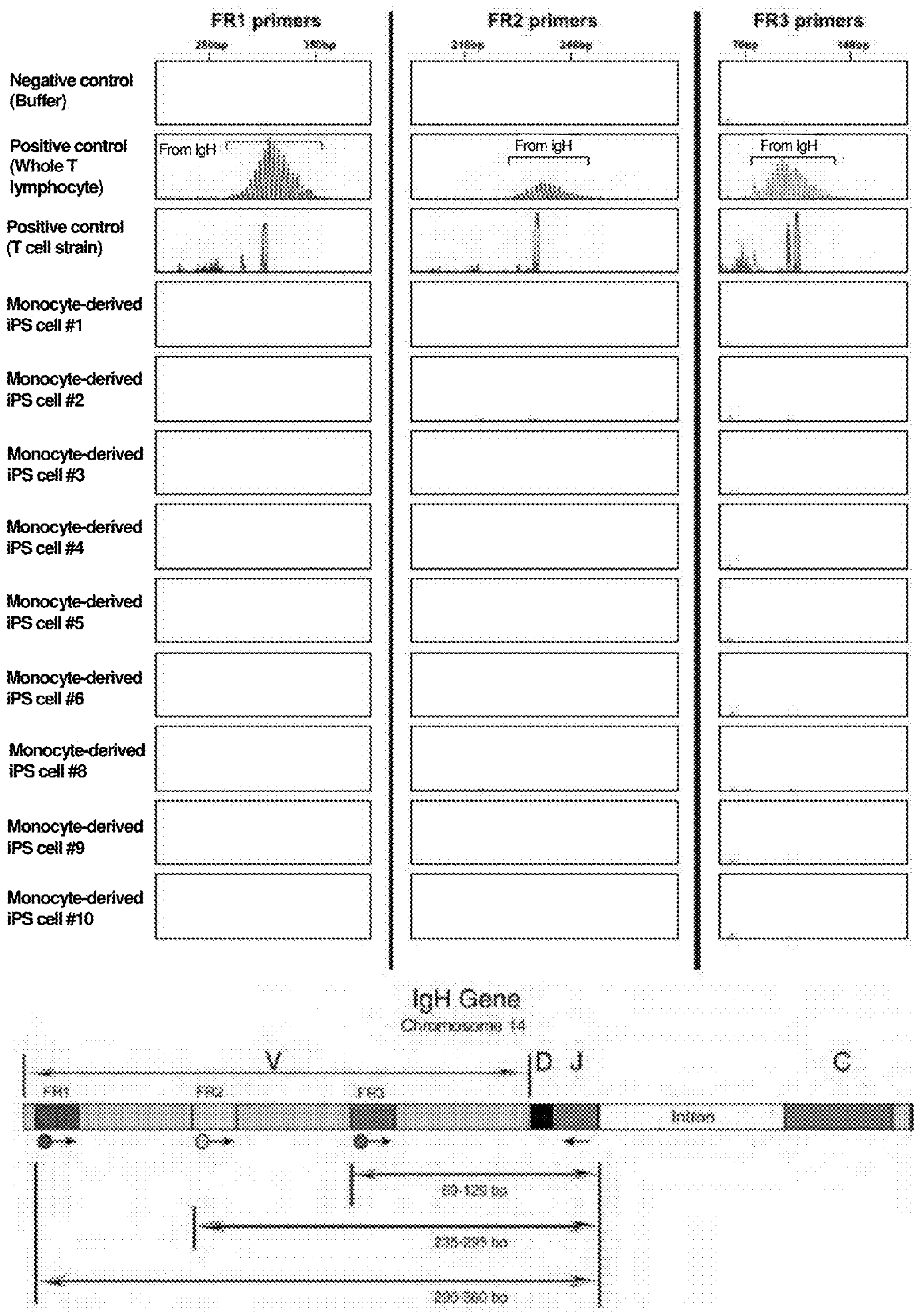

FIG. 42 shows the results of examination of the rearrangement of immunoglobulin heavy chain (IGH) gene in the genome of human peripheral blood monocytes-derived iPS cells established with hOct4/hSox2/hKlf4/hc-Myc sustained expression-inducing Sendai viral vectors.

DESCRIPTION OF THE EXEMPLARY EMBODIMENTS

A vector loaded with a reprogramming gene for use in producing an induced pluripotent stem cell in the present invention is a Sendai virus particle which has an NP gene, a P/C gene and an L gene each derived from a Sendai virus, and at least one of F, M and HN genes of the Sendai virus is functionally deleted (this vector will hereinafter be referred to as "Sendai viral vector"). As used in this specification, the term "gene" or "gene material" encompasses negative-strand RNA or cDNA and positive-strand RNA or cDNA complementary thereto. In other words, any vector capable of synthesizing either one of such genes or gene materials by means of transcription or reverse transcription should be construed as being included in the present invention.

As used herein, the term "functionally deleted" means a gene is rendered non-functional by deletion of the complete gene sequence or a portion thereof sufficient to abolish the activity of the gene by, for example, inhibiting the expression of the gene through deletion of key regulatory sequences or by deletion of parts of the gene's coding region or by the disruption of the gene's open reading frame.

As used in this specification, the term "induced pluripotent stem cell (iPS cell)" means a cell which expresses a morphology similar to an embryonic stem cell (ES cell), and an embryonic stem cell-specific marker, and has a self-renewal ability in vitro. iPS cells also have the potential to differentiate into any of the three germ layers in vivo and in vitro. For example, Nanog, Oct4, alkaline phosphatase, SSEA-1 and SSEA-4 antigens are well known markers of embryonic stem cells and can be readily detected in iPS cells.

[Constituent Materials of Sendai Viral Vector]

The Sendai viral vector is a recombinant transfection/expression vector in which a gene of a Sendai virus can be replaced with any exogenous gene thus enabling the expression of the exogenous gene in any transfected cell. Sendai viruses have an NP gene, a P/C gene, an F gene, an M gene, an HN gene and an L gene, which are required for the transcription and replication of the Sendai virus. The F, M and HN genes also have a role in formation of a virus particle. Recombinant Sendai viral vectors lacking the F, M and HN genes are therefore incapable of forming new virus particles and hence further propagation after transfection into a cell.

The Sendai viral vector of the present invention comprises an L gene which encodes an L protein where the 1618-th amino acid is replaced by a valine. This mutation was found in the amino-acid sequence of an L protein derived from the Sendai virus strain Cl.151, which exhibits temperature-sensitive growth, where almost no virus particle is produced at 38° C., but at 32° C., the replication cycle becomes active and permits the production of virus particles. Sendai virus strain Cl.151 was first reported by Tetsuya Yoshida, PhD, in 1979 (Yoshida, et al., (1979), Virology, 92, 139-154).

Sendai virus strains Cl.151 have L proteins harboring a mutated amino acid residue at position 1618 together with a reduced ability to induce interferon activity in transfected cells. This strain can therefore sustain infectious ability without cytotoxicity, so that, when a foreign gene is incorporated into the Senda virus genome, expression of the gene will be maintained in the cell for a long period of time. For example, the leucine residue at position 1618 of the L gene of the Sendai virus strain Nagoya, can be mutated to a valine. As described herein, an L protein where the 1618-th residue is valine will be referred to as a "mutated-L protein", and the gene, which encodes the mutated-L protein will be referred to as "mutated-L gene."

Thus, the NP, C/P and L genes as constituent genes of the Sendai viral vector of the present invention may have a base sequence derived from wild-type cytopathic Sendai virus strains, such as a Sendai virus strain Nagoya or Z, as long as the L gene has the above mutation.

A transcriptional termination sequence of a Sendai virus may be artificially inserted into the 3'-terminal end of the genomic RNA. The copy number of anti-genomic RNAs can then be further reduced to lower the interferon-inducing ability within the transfected cell.

As a prerequisite to Sendai virus infection of an animal cell, it is essential that the Sendai virus have the mutated-L gene, in addition to F, M and HN genes derived from the Sendai virus strain Cl.151. Thus, the Sendai viral vector having the mutated-L gene and the Sendai virus strain Cl.151-derived F, M and HN genes together can have a sustained infectious ability without cytotoxicity, so that, when a foreign gene is inserted into the Sendai virus vector, the expression of the gene will be maintained in the cell over a long period of time. In Sendai viral vectors based on the strain Cl.151, one or more (including "all") of the strain Cl.151-derived F, M and HN genes may be functionally deleted, without interfering with the ability of the recombinant vector to drive the expression of the exogenous gene. In this case, even if only one of the three genes is functionally deleted, the transmissibility of the vector can be significantly suppressed. In view of fully suppressing transmissibility, it is preferable to functionally delete all of the F, M and HN genes. The functional deletion of one or more of the F, M and HN genes may be based on simple deletion of a part or all of the three genes, or insertion or replacement with an exogenous gene of interest.

A full-length cDNA of the Sendai virus strain Cl.151 has already been registered in the GenBank (Accession Number AB275416).

[Reprogramming Gene]

A reprogramming gene is inserted into the Sendai viral vector of the present invention. Reprogramming genes may include the combination of mammalian Oct3/4, Sox2 and Klf4 genes together with a mammalian (e.g human or mouse) c-Myc gene and, one or more of Nanog, LIN28, Esrrb, UTFI and TERT (telomerase catalytic subunit), or a gene encoding large T antigen of SV40.

[Template Vector for Preparing Reprogramming Gene-Loaded Sendai Viral Vector]

In the present invention, the NP, P/C and mutated-L genes as constituent materials of the Sendai viral vector are inserted into a cloning vector, such as phage, together with the reprogramming genes. In this process, all of the reprogramming genes can be inserted into the cloning vector together. This allows for the generation of reprogramming gene-loaded Sendai viral vector that contains all the genes required for reprogramming. Reprogramming is therefore efficiently performed without the need for introducing each reprogramming gene into a different vector.

The recombinant vector obtained in the above manner can then serve as a template for preparing reprogramming gene-loaded Sendai virus of the present invention, i.e., a Sendai virus particle carrying all the required reprogramming genes. This recombinant vector will hereinafter be referred to as "template vector".

The template vector is prepared by incorporating the NP, P/C and mutated-L genes, and the reprogramming genes into a vector such as phage, in the following order: NP→P/C→reprogramming genes (a marker gene may further be introduced therein as described later)→mutated L.

The reprogramming genes or the marker gene may be used to functionally delete at least one of the F, M and HN genes of the Sendai viral vector, by replacement of at least one of the F, M and HN genes with the reprogramming genes or marker gene.

A marker gene, such as a drug-resistance gene, can be inserted into the template vector. This makes it possible to facilitate screening of a target cell containing the template vector or the Sendai viral vector.

More specifically, the template vector is prepared by combining the constituent materials of the Sendai viral vector comprising the above genes, the reprogramming gene cDNAs, and the marker gene cDNA, together in the above order, to form a (+) strand genomic RNA. For example, the constituent material cDNA is incorporated into a cloning vector, such as λ DASH II. A T7 promoter sequence and three guanidine residues are then cloned into the upstream side of the incorporated full-length cDNA (i.e. at the 3'-terminal end of the genomic RNA), and a hairpin ribozyme sequence of a tobacco ringspot virus and a termination sequence of T7 RNA polymerase are then inserted on the downstream side of the full-length cDNA (i.e. at the 5'-terminal end of the genomic RNA).

The T7 promoter sequence is added to allow a (+) strand genome RNA to be synthesized from the 3'-terminal end of the genomic RNA by T7 RNA polymerase, and three guanidine residues are added to enhance the efficiency of RNA transcription by the T7 RNA polymerase (S. Leyrer, et al., (1998) J. Virol. Methods, 75; 47-58). The hairpin ribozyme sequence of the tobacco ringspot virus is added to allow the transcript (+) strand genome RNA to be accurately cut at one end, and the termination sequence of T7 RNA polymerase is added to allow the RNA transcription by the T7 RNA polymerase to terminate at a discrete location.

[Preparation of Reprogramming Gene-Loaded Sendai Viral Vector]

The template vector harboring the reprogramming genes can then be introduced into a viral vector-producing cell in order to prepare a reprogramming gene-loaded Sendai virus.

In order to transcribe (+) strand anti-genomic RNA from the template vector in a virus-producing cell, it is necessary to supply exogenous T7 RNA polymerase. For example, the viral vector-producing cell line can be infected with T7 RNA polymerase-expression vaccinia virus, or may be a cell strain in which T7 RNA polymerase is constitutively expressed.

The cell strain (BHK/T7 cell) is just such a cell line because it expresses a humanized T7 RNA polymerase gene that permits significantly higher levels of T7 RNA polymerase gene expression as compared with a cell strain (BSR-T7-5 cell) that expresses a conventional bacterial T7 RNA polymerase gene. As a result of production of recombinant viruses using the BHK/T7 cell line, large amounts of recombinant viruses can be efficiently generated and collected.

The presence of T7 RNA polymerase within the viral vector-producing cell drives transcription of the template vector from the T7 promoter sequence. Downstream sequences are then cleaved off by the hairpin ribozyme sequence, so that a (+) strand anti-genomic RNA molecule is generated corresponding to a DNA portion including the NP gene, the P/C gene, the reprogramming genes and the mutated-L gene in the template vector that may further include a marker gene as needed.

An expression vector for producing NP, P and L gene products may be additionally introduced into the viral vector-producing cell having the (+) strand anti-genomic RNA transcribed from the template vector by the T7 RNA polymerase. In this case, the NP, P and L gene products are bound to the (+) strand anti-genomic RNA to form an RNP complex (nucleocapsid). Then, using the RNP complex as a template, a (−) strand genomic RNA is transcribed from the (+) strand anti-genomic RNA by the RNA polymerase in the viral vector-producing cell. The (−) strand genome RNA is bound to NP, P and mutated-L gene products in the viral vector-producing cell to form a RNP complex including the (−) strand genomic RNA.

In the template vector used in the above manner, one or more of the strain Cl.151-derived M, F and HN genes are functionally deleted thereby suppressing the ability to form infectious virus particles. To propagate virus, the missing gene products are transfected into the viral vector-producing cell comprising the RNP complex (nucleocapsid) with the (−) strand genomic RNA. The transfected cell is then incubated at the permissive temperature of 32° C.

Consequently, the RNP complex (nucleocapsid) including the (−) strand genome RNA is incorporated into viral vector particles to generate reprogramming gene-loaded Sendai virus. As described above, in the present invention, an expression vector containing the missing gene either the F, M and HN genes, is separately introduced into the viral vector-producing cell to form virus particles. This makes it possible to harvest the virus particle from a culture supernatant of the viral vector-producing cell. In cases where two or more of the F, M and HN genes are absent, the expression vector may contain one or more of the missing genes or alternatively each of the missing genes can be cloned into a single expression vector that is then co-transfected into the viral vector-producing cell.

In the above virus-particle production process, virus production can be further enhanced by introducing supplemental expression vectors for an NP gene, a P/C gene and an L gene.

In addition, a drug-resistance gene may be inserted into the target viral vector-producing cell as discussed above. In this case, it becomes possible to select viral vector-producing cells through incubation in culture medium containing the appropriate drug. Alternatively, a target viral vector-producing cell may be isolated using a marker gene, such as the EGFP gene.

The reprogramming gene-loaded Sendai virus obtained in the above manner is in the form of a virus particle that is capable of infecting a differentiated cell. However, as one or more of the F, M and HN genes of the vector are functionally deleted, the formation of a viral vector from the infected cells is suppressed. In addition, the L gene of the vector is mutated such that the leucine at position 1618 of the encoded L protein is replaced with valine. This modification inhibits the induction of interferon in the transfected cells, and permits the sustained expression of the reprogramming genes within the infected cells.

[Reprogramming of Differentiated Cell]

The recombinant Sendai virus particle containing the reprogramming genes is then used to infect a differentiated cell derived from a normal human or a patient with a disease of interest. Differentiated cells may be, for example, fibroblast cells, oral mucosal cells, blood cells, hair follicle epithelial cells, or cells obtained by surgical intervention or tissue biopsies, such as liver cells, large intestinal mucosa cells, small intestinal mucosa cells and lung epithelial cells. Human peripheral blood-derived monocytes were used in Examples 24 to 26 described later. Differentiated cells are not limited to human cells, but include differentiated cells of an animal, such as mouse, rat, hamster, guinea pig, rabbit, dog, cat, monkey, bovine, pig, sheep, goat or chicken, which are permissive to Sendai virus infection. Sendai viruses can infect a wide variety of animal cells, equine-derived cells and B-lymphocytes of various animal species are rare exceptions that Sendai virus cannot infect. This feature is a significant advantage over other viral vector systems that exhibit a narrow host range, such as a retroviral vector, a lentiviral vector or an adenoviral vector; or other gene expression systems usable only in human cells, such as an EBV vector; or even plasmid expression vectors, transposon and EBV vectors that have to be introduced into the cells using a physical delivery system. For example, although the adenoviral vector can be used to reprogram a mature mouse liver cell, the reprogramming efficiency rate is only 0.0005% at best. Moreover, adenoviral vectors are incapable of reprogramming a mouse or human fibroblast cell.

On the contrary, the reprogramming gene-loaded Sendai viral vector of the present invention can reprogram a mouse fibroblast cell (see Example 5), a human blood mononuclear cell (see Example 18), as well as a human fibroblast cell. In addition, a chimeric mouse derived from a mouse iPS cell produced using the reprogramming gene-loaded Sendai viral vector of the present invention contributes to the germ-line. Cell lines produced by the present invention are therefore more likely to be normal pluripotent stem cells that are therapeutically safe (see Example 10).

In the reprogramming gene-loaded Sendai viral vector of the present invention, an L gene is mutated to inhibit interferon induction, and M, F and HN genes in a wild-type Sendai virus are functionally deleted. Thus, the vector exhibits a sustained infectious ability without cytotoxicity, and, after infection of a differentiated cell, it persists in the cytoplasm of the infected cell. Even after cell division, this state is maintained. This feature is not observed in other types of Sendai viral vectors without a mutated-L gene or with at least one of the M, F and HN genes of the wild-type Sendai virus. Thus, the use of the Sendai viral vector of the present invention makes it possible to maintain expression of the reprogramming genes for 10 to 20 days, which is required for the completion of the reprogramming process. Reprogramming can therefore be completed using a single gene delivery. This advantage is not available with adenoviral vectors or plasmid vectors that are only capable of inducing transient gene expression. For example, in cases where Oct3/4, Sox2, Klf4 and c-Myc are loaded on the reprogramming gene-loaded Sendai viral vector of the present invention, even if a cell is infected with the vector only once, the cell can maintain expression of the exogenous reprogramming genes, and expression of endogenous reprogramming genes as well as alkaline phosphatase, a marker of an embryo-stem cell (ES cell), starts to be detectable after 7 to 14 days post-transfection.

Once inside the cell, Sendai viral vectors of the present invention remain episomal and do not insert themselves into the host genome unlike other vector systems. Thus, iPS cells generated with modified Sendai virus of the invention are significantly safer for human therapeutic applications because the lack of genomic integration minimizes the risk of oncogene activation within the host genome. In this regard, the Sendai viral vector of the present invention is significantly superior to other systems, such as retroviral vectors, lentiviral vectors, adenoviral vectors, transposon vectors and plasmid vectors in general (such as the EBV vector) all of which have the propensity to integrate into the host genome. The possibility of integration and the subsequent uncontrolled long-term expression of some reprogramming genes such as c-Myc, Oct4 or LIN28 is particularly undesirable because the long term expression of these genes is known to induce cancer or pre-cancerous states such as cell dysplasia.

As noted above, strategies for the reprogramming of somatic cells must also favor genomic stability and reproducibly generate clonal cell populations having identical properties. Ideally, the viral vector should be capable of accepting multiple reprogramming genes permitting the simultaneous transfer of all genes into the same cell while at the same time directing the expression of all the genes in unison. Reprogramming genes may be transferred into a somatic cell by infection with viral particles containing a single common Sendai viral vector having all the reprogramming genes in cis, as shown in the Examples of the present invention. Alternatively each reprogramming gene can be cloned into its own Sendai virus vector. Viral particles, each containing a viral vector comprising at least one reprogramming gene are then mixed together prior to infection of the somatic cells, as disclosed in Fusaki, et al., Proc. Jpn. Acad. Ser. B85, 348-362, 2009 and PCT/JP 2009/062911. To determine if there is a difference in gene expression between genes cloned in cis on a single viral vector and the same genes cloned on individual viral vectors, the Enhanced Green Fluorescent Protein (EGFP) gene and the Kusabira-Orange (KO) gene were cloned into a single common vector or into individual viral vectors. The results show that optimal gene expression is obtained when the reprogramming genes are present on a single common vector (see Example 15). Moreover, the simultaneous transfer of the reprogramming genes on a single vector into a somatic cell also promotes iPS cell generation with enhanced efficiency (see Example 16).

In the reprogramming gene-loaded Sendai viral vector of the present invention, all of the reprogramming genes are loaded on a single common vector, so that, when the vector of the present invention is used, emergence efficiency of an iPS cell (reprogramming efficiency) is extremely high. For example, in cases where Oct3/4, Sox2, Klf4 and c-Myc are loaded thereon, the efficiency rate increases up to 16.8% (see Examples 5 and 8). In contrast, a reprogramming efficiency rate in a mature mouse liver cell using adenoviral vectors is only 0.0005% or less. Even with EBV vectors, the reprogramming efficiency rate is only in the range of about 0.0003 to 0.0006%.

The presence of all reprogramming genes on a single common vector ensures their coordinated expression which results in the generation of iPS cells with significantly more uniform properties. For example, in an analysis of iPS cells established using the procedures described herein, gene expression of the iPS candidates was analyzed by a DNA chip method and the correlation coefficient between four different cell lines was determined to be 0.98 or more (see Example 19). This contrasts with the fact that the gene expression pattern in pluripotent stem cells established using a retroviral vector is generally non-uniform, and the correlation coefficient between cell lines is 0.95 or less in many cases (Reference: Chin, et al., Cell Stem Cells, 5, 111-123, 2009).

As above, it became evident that, based on the use of the reprogramming gene-loaded Sendai viral vector of the present invention where four types of reprogramming genes are cloned into a single common vector, pluripotent stem cells having uniform properties can be established with significantly high efficiency while constantly ensuring excellent reproducibility.

[Removal of Reprogramming Genes]

The reprogramming gene-loaded Sendai virus of the present invention infects a differentiated cell, and the reprogramming genes are expressed sustainably in the cytoplasm of the cell to reprogram it. In order to make the genetic information of the reprogrammed cell identical to that of the original or pre-programming cell, the reprogramming genes need to be removed from the cell. In the present invention, the entire reprogramming gene-loaded Sendai viral vector is removed using a siRNA. The siRNA is designed to target the L gene of the Sendai viral vector. According to experimental results by the inventors, the reprogramming gene-loaded Sendai viral vector can be completely removed by targeting the L gene, although the reprogramming gene-loaded Sendai viral vector can also be removed to some extent by targeting the NP gene or the P gene. For example, a target region of the L gene can be the segment allocated between 527-th or 1913-th nucleotide of the L protein gene. The target region may be any other suitable region. The siRNA is introduced into the cell 5 to 20 days after the reprogramming gene-loaded Sendai virus infected the differentiated cell.

Instead of siRNA, microRNA (miRNA) may be used to remove the viral vector from the cell. miRNA is a small RNA transcribed from the genome of an animal cell, and capable of interacting with a transcript to adjust the function thereof. In an interaction with mRNA, there exists a mechanism where the miRNA binds to a target sequence on the mRNA to induce decomposition of the mRNA or suppress translation of the mRNA. Target sequences for a specific miRNA can be artificially inserted into a protein-noncoding region of a mRNA. Expression of the miRNA then inhibits the expression of the gene. Thus, the reprogramming gene-loaded Sendai viral vector can be removed in the same manner as that used in the siRNA approach by adding a target sequence for miRNA to an L, NP or P gene-noncoding region of the Sendai viral vector. Expression of miRNA in the cell then suppresses expression of the L, NP or P gene. The miRNA to be used for the above purpose may include, but is not limited to, mir-302a that is specifically expressed, for example, in human or mouse ES cells. For example, the technique of removing the reprogramming gene-loaded Sendai viral vector using miRNA has the advantage of being able to automatically remove the Sendai viral vector without the need for externally introducing siRNA because the mir-302a is expressed as soon as a differentiated cells is reprogrammed into an iPS cell. Further, in a human cell, the removal of the vector can also be promoted by means of culture at a high temperature (40° C.).

The reprogramming gene-loaded Sendai viral vector can therefore be removed using either a siRNA that targets the L gene, by culture at a high-non-permissive temperature, or by introducing a target sequence for miRNA into the non-coding regions of the L, NP or P gene-in the Sendai virus vector.

Consequently, the induced iPS cell is genetically identical to that of the parental differentiated cell used to generate the iPS stem cell. By the end of the procedure the cell does not contain any foreign exogenous DNA and its potential for self renewal is enhanced, Various examples of the present invention are described below. It is understood that the present invention is not limited to the following examples.

EXAMPLES

Example 1

Preparation of Cells for Constructing Sustained Expression-Type Sendai Viral Vectors A cDNA (SEQ ID NO: 1 in the following Sequence Table) encoding T7 RNA polymerase where codons are optimized to improve expression in an animal cell, was cloned into a plasmid pCX4SRalpha-neo vector for preparing a retroviral vector. A cDNA encoding Sendai virus strain Cl.151 M protein was first cloned into a plasmid pCX4SRalpha-puro vector for preparing a retroviral vector. The plasmid DNAs were then introduced into respective PLATE packaging cells using Lipofectamine 2000, and retroviruses (T7 RNA polymerase recombinant retrovirus and 151M recombinant retrovirus) obtained from a culture supernatant. The T7 RNA polymerase recombinant retrovirus was transfected into BHK-21 cells. The infected BHK-21 cells were then transferred to a Dulbecco's Modified Minimal Essential Medium (DMEM) containing 800 μg/ml of G418 and 10% of fetal bovine serum (FCS), and G418-resistant cells (BHK/T7 (SE)) which stably express T7 RNA polymerase were isolated. Subsequently, the 151M recombinant retrovirus was transfected into BHK/T7 (SE) cells and the infected BHK/T7 (SE) cells were transferred to a DMEM containing 800 μg/ml of G418, 15 μg/ml of puromycin and 10% of FCS. G418+puromycin-resistant cells (BHK/T7/151M (SE)) which stably express T7 RNA polymerase and an M protein were isolated.

Example 2

Figure 1:
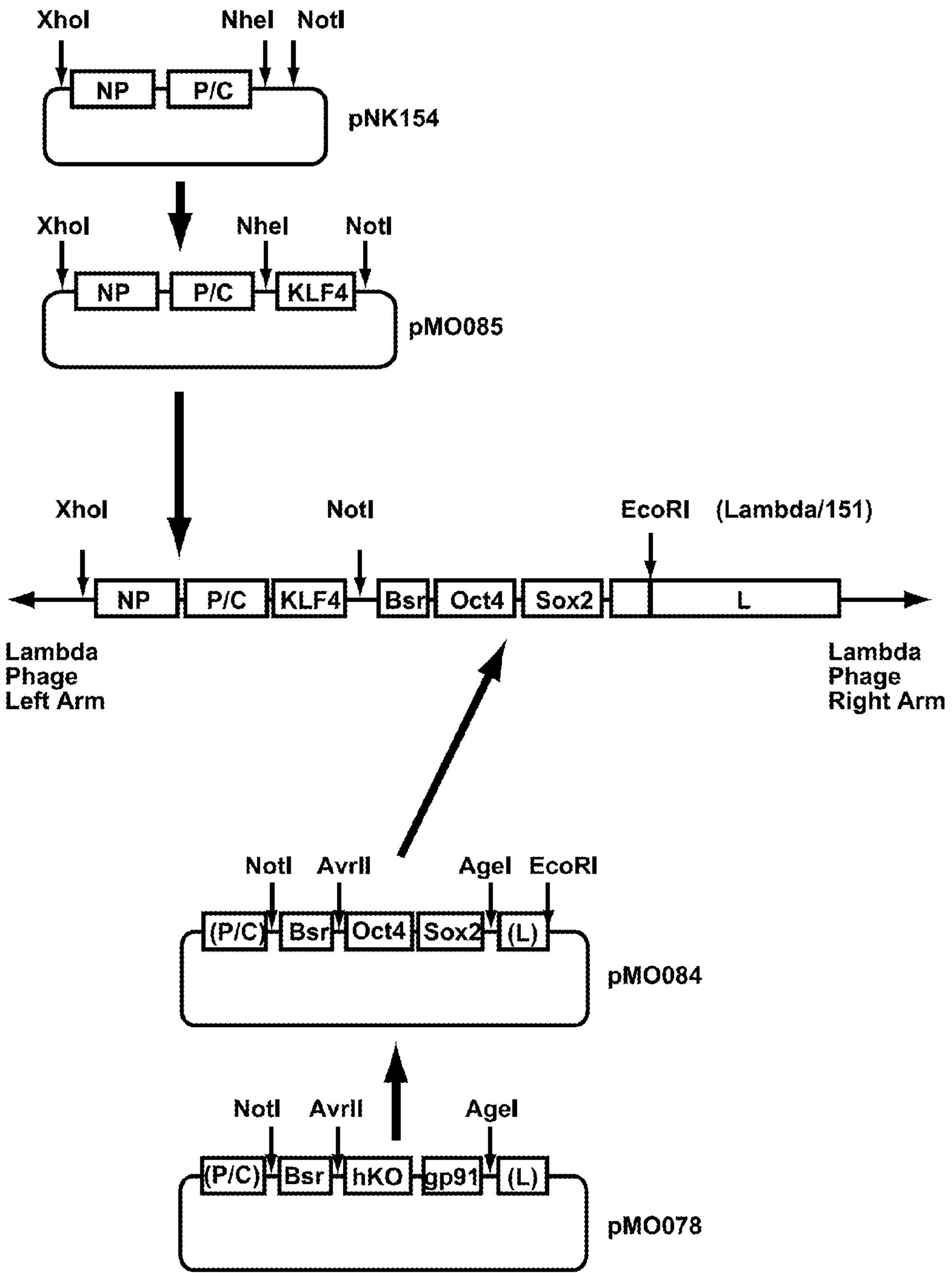
FIG. 1 is a diagram of the preparation of a template cDNA for producing a hOct4/hSox2/hKlf4 sustained expression-inducing Sendai viral vector.

Preparation of hOct4/hSox2/hKlf4 Sustained Expression-Inducing Sendai Viral Vector (1) Construction of Template cDNA for Preparing Recombinant Sendai Virus A double-stranded DNA (SEQ ID NO: 2 in the Sequence Table) including Avr II recognition sequence, human Oct4 ORF, Sendai virus (SeV) genome cDNA (bases 6617 to 6666), human Sox2 ORF and Age I recognition sequence in this order was synthesized, and then cloned into the plasmid vector pUC57 (the cloning was achieved using GenScript Inc.) (pUC57-OctSox). A DNA sequence cut from the pUC57-OctSox at Avr II and Age I sites was inserted between Arv II and Age I sites of a plasmid vector pMO078 (SEQ ID NO: 3 in the Sequence Table) where Cla I recognition sequence, SeV strain Cl.151 genome cDNA (bases 2871 to 3650), Not I recognition sequence, a blasticidin S-resistance gene, Mlu I recognition sequence, SeV strain Cl.151 genome cDNA (bases 4728 to 4828), Avr II recognition sequence, humanized Kusabira-Orange gene, an SeV strain Cl.151 genome cDNA (bases 6617 to 6666), gp91phox gene, Age I recognition sequence and SeV strain Cl.151 genome cDNA (bases 8442 to 10479) were inserted into a plasmid pBluescript II SK(+) (Agilent Technologies Inc.)) in this order. In this manner, a plasmid pMO084 was constructed (FIG. 1).

A double-stranded DNA (SEQ ID NO: 4 in the Sequence Table) including Nhe I recognition sequence, human Klf4 ORF, Sendai virus transcription termination sequence, Sendai virus transcription initiation sequence and Not I recognition sequence in this order was synthesized, and then cloned in a plasmid vector pUC57 (the cloning was achieved using GenScript Inc.) (pUC57-KLF4). A DNA sequence cut from the pUC57-KLF4 at Nhe I and Not I sites was inserted between Nhe I and Not I sites of a plasmid vector pNK154 (SEQ ID NO: 5 in the Sequence Table) where SeV strain Nagoya genome cDNA (bases 1 to 2871), SeV strain Cl.151 genome cDNA (bases 2872 to 3656), Nhe I recognition sequence and Not I recognition sequence are inserted into pBluescript II SK(+) (Agilent Technologies Inc.)) in this order. In this manner, a plasmid pMO085 was obtained (FIG. 1).

A DNA fragment (including a T7 promoter sequence, a SeV genome cDNA (bases 1 to 3655) and a human Klf4 cDNA) cut from the pMO085 at restriction endonucleases Xho I and Not I, a DNA fragment (including human Oct4 and human Sox2 cDNAs) cut from the pMO084 at restriction endonucleases Not I and EcoR I, and a DNA fragment (including a cDNA complementary to bases 10480 to 15384 in the SeV genome, and a right arm in a λ DASH II) cut from a phage genome DNA of λ/151 (lambda phage vector cloned with a full-length SeV strain Cl.151 genome cDNA: Nishimura, et al., J. Biol. Chem., 282, 27383-27391, 2007) at EcoR I site, were then combined together, and cloned into a lambda phage vector λDASH II to prepare λ/SeVp (Mp+Klf4, ΔM:: Bsr, ΔF:: Oct4, ΔHN:: Sox2) (FIG. 1) (a cDNA complementary to a full-length genome of a hOct4/hSox2/hKlf4 sustained expression-inducing Sendai viral vector described as SEQ ID NO: 6 in the Sequence Table).

(2) Preparation of hOct4/hSox2/hKlf4 Sustained Expression-Inducing Sendai Virus

BHK/T7/151M (SE) cells were seeded on a 6-well plate at a density of $5\times10^5$ cells/well, and washed after cultivation for 24 hours. A λ/SeVp (Mp+Klf4, ΔM:: Bsr, ΔF:: Oct4, ΔHN:: Sox2) phage DNA, an NP protein-expression plasmid pGEM/NP, a P protein-expression plasmid pGEM/P, an L protein-expression plasmid pGEM/L, an F protein-expression plasmid pSRD-FZmut and an HN protein-expression plasmid pMKIT-NaHN were suspended in 300 μL of Opti-MEM, respectively, at quantitative ratios of 2 μg, 1 μg, 1 μg, 1 μg and 1 μg, and the obtained suspension was mixed with 300 μL of Opti-MEM containing 10 μL of Lipofectamine 2000. After leaving the mixture at room temperatures for 20 minutes, it was added to the cells, and the cells were cultured for 4 hours. Then, the cells were washed, and after adding DMEM containing 10% of FCS, further cultured at 32° C. for 3 days. Then, the cells were transferred to DMEM containing 10% of FCS and 10 μg of blastcidin S. Blastcidin-resistant cells were then isolated as hOct4/hSox2/hKlf4 sustained expression-inducing Sendai viral vector-producing cells (BHK/T7/151M/KBOS). The occurrence of reconstruction of a vector genome was confirmed by a fluorescent antibody method using antibody to Sendai virus NP protein and antibodies to hOct4/hSox2/hKlf4 gene products.

2 μg each of pMKIT-151M, pSRD-ZFmut and pMKIT/NaHN as defective gene-expression plasmids were introduced into $5.0\times10^5$ BHK/T7/151M/KBOS cells using Lipofectamine 2000. After 4 hours, the cells were washed, and, after adding DMEM containing 10% of FCS thereto, further cultured at 32° C. for 4 days. Culture supernatant containing a hOct4/hSox2/hKlf4 sustained expression-inducing Sendai virus was then harvested. The culture supernatant was filtered through a 0.45 μm filter, and ultracentrifuged as needed to concentrate the vector. The vector suspension was quickly frozen using liquid nitrogen, and cryopreserved at −80° C.

Example 3

Figure 2:
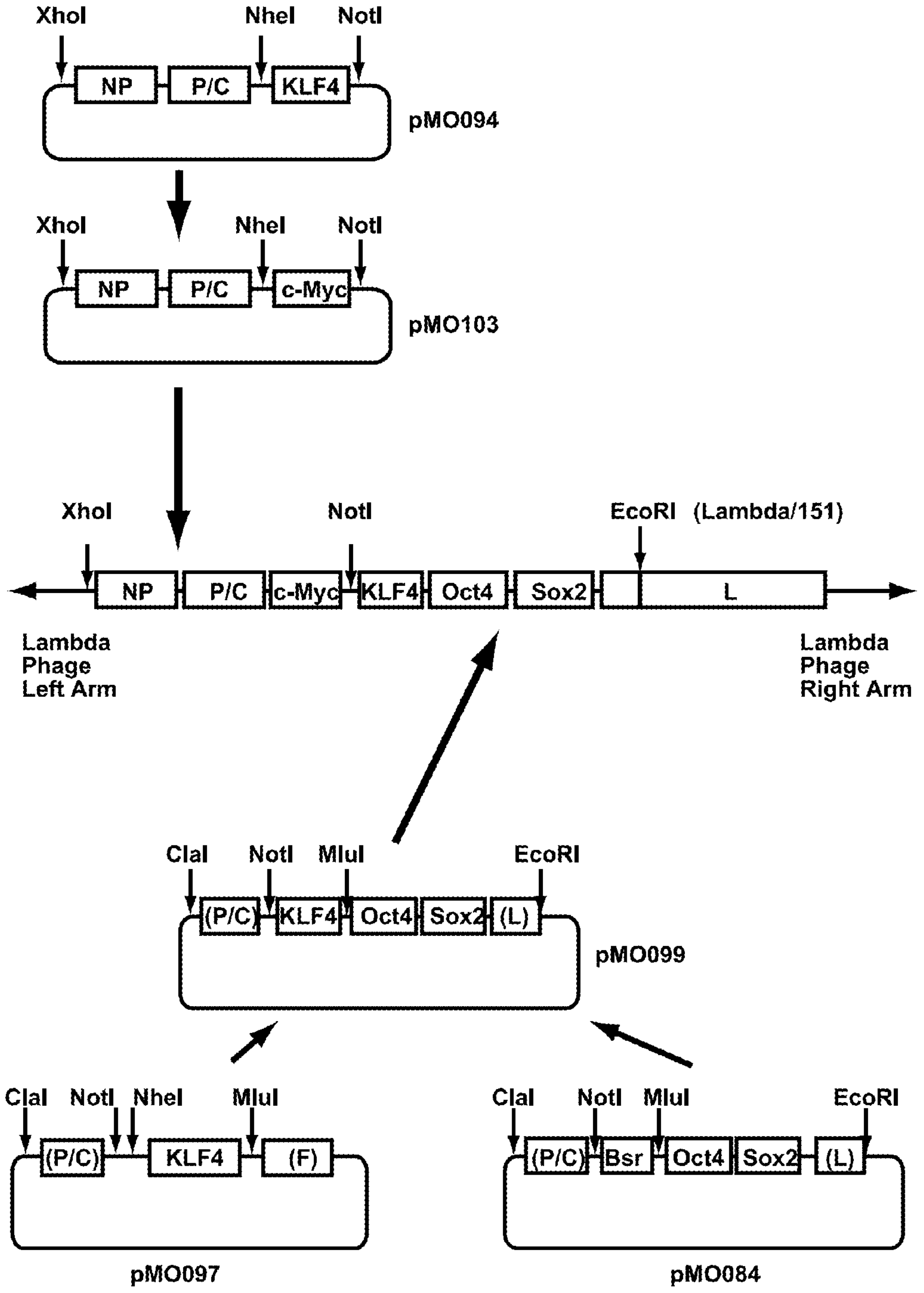
FIG. 2 is a diagram of the preparation of a template cDNA for producing a hOct4/hSox2/hKlf4/hc-Myc sustained expression-inducing Sendai viral vector.

Preparation of hOct4/hSox2/hKlf4/hc-Myc Sustained Expression-Inducing Sendai Viral Vector (1) Preparation of Vector cDNA A human Klf4 gene was amplified from the pUC57-KLF4 by a PCR method using two primers consisting of 5'-ACTAGCTAGCAGTCTGACATGGCTGTCAGCGACGCGCT-3' (SEQ ID NO: 7 in the Sequence Table (N-terminal side)) and 5'-GGTCCACGCGTTTAAAAA TGCCTCTTCATGTG-3' (SEQ ID NO: 8 in the Sequence Table (C-terminal side)) as hKlf4 gene-amplifying primers. The termini of the obtained double-stranded DNA were cut at Nhe I and Mlu I sites, and inserted between Nhe I and Mlu I sites of pMO026 (SEQ ID NO: 9 in the Sequence Table) (a plasmid vector where Cla I recognition sequence, SeV strain C1.151 genome cDNA (bases 2871 to 3650), Not I recognition sequence, Nhe I recognition sequence, blasticidin S-resistance gene, Mlu I recognition sequence and SeV strain C1.151 genome cDNA (bases 4728 to 5335) were inserted into pBluescript II SK(+)). In this manner, pMO097 was obtained. Furthermore, a fragment between Cla I and Mlu I sites of the pMO097 was combined with a fragment between Cla I and Mlu I sites of the pMO084 to obtain pMO099 (FIG. 2).

A human c-Myc gene was amplified from a plasmid pJL1 including a full-length human c-Myc cDNA by a PCR method using two primers consisting of 5'-ACTAGCTAGCTTAGA CGCTGGATTTTTTTCGGGTAGTGG-3' (SEQ ID NO: 10 in the Sequence Table (N-terminal side)) and 5'-GTCCGACGTCCTTACGCACAAGAGTTCCGT-3' (SEQ ID NO: 11 in the Sequence Table (C-terminal side)) as hc-Myc gene-amplifying primers. The termini of the double-stranded DNA were cut at Nhe I and Aat II sites, and inserted between Nhe I and Aat II sites of pMO094 (SEQ ID NO: 12 in the Sequence Table) (a plasmid vector where an SeV strain Nagoya genome cDNA (bases 1 to 43), Sendai virus transcription termination sequence, SeV strain Nagoya genome cDNA (bases 56 to 2870), SeV strain Cl.151 genome cDNA (bases 2871 to 3656), Nhe I recognition sequence, human Klf4 ORF, Aat II recognition sequence, Sendai virus transcription termination sequence, Sendai virus transcription initiation sequence and Not I recognition sequence were inserted into pBluescript II SK(+) (Agilent Technologies Inc.)). In this manner, pMO103 was obtained (FIG. 2).

Based on the plasmids obtained as described above, the T7 promoter sequence and DNA fragment SeV (1 to 3655 with c-Myc), and DNA fragment SeV (3655 to 10480 with KLF4/Oct4/Sox2), were cut out from pMO103 and pMO099, respectively, and combined with a DNA fragment of SeV (10480 to 15384)+the right arm of the λ DASH II obtained by cutting the λ/151 at the EcoR I site. Then, the combination was cloned to prepare λ/SeVp (Mp+myc, ΔM:: Klf4, ΔF:: Oct4, ΔHN:: Sox2) (FIG. 2) (a cDNA complementary to a full-length genome of a hc-Myc/hOct4/hSox2/hKlf4 sustained expression-inducing Sendai viral vector is described as SEQ ID NO: 13 in the Sequence Table).

(2) Preparation of hOct4/hSox2/hKlf4/hc-Myc Sustained Expression-Inducing Sendai Virus The BHK/T7/151M (SE) cells were seeded on a 6-well plate at a density of $5\times10^5$ cells/well, and, after culture for 24 hours, the cells were washed. A λ/SeVp (Mp+myc, ΔM:: Klf4, ΔF:: Oct4, ΔHN:: Sox2) phage DNA, an NP protein-expression plasmid pGEM/NP, a P protein-expression plasmid pGEM/P, an L protein-expression plasmid pGEM/L, an F protein-expression plasmid pSRD-FZmut and an HN protein-expression plasmid pMKIT-NaHN were suspended in 300 μL of Opti-MEM, respectively, at quantitative ratios of 2 μg, 1 μg, 1 μg, 1 μg, 1 μg and 1 μg, and the obtained suspension was mixed with 300 μL of Opti-MEM containing 10 μL of Lipofectamine 2000. After leaving the culture medium at room temperatures for 20 minutes, the culture medium was added to the cells, and the cells were cultured for 4 hours. The cells were washed and, after adding DMEM containing 10% of FCS, further cultured at 32° C. for 3 days and 37° C. for another 3 days. Cells were then stained using the fluorescent antibody method (see Example 20) using antibody directed to Sendai virus NP protein and antibodies to the hOct4/hSox2/hKlf4 gene products, to confirm the reconstruction of the vector genome in the cells. The cell population was used as hOct4/hSox2/hKlf4/hc-Myc sustained expression-inducing Sendai virus producing cells without further cloning.

2 μg each of pMKIT-151M, pSRD-ZFmut and pMKIT/NaHN as defective gene-expression plasmids were introduced into $5.0\times10^5$ hOct4/hSox2/hKlf4/hc-Myc sustained expression-inducing Sendai virus-producing cells using Lipofectamine 2000. After 4 hours, the cells were washed, and, after adding DMEM containing 10% of FCS, further cultured at 32° C. for 4 to 9 days. The culture supernatant containing hOct4/hSox2/hKlf4/hc-Myc sustained expression-inducing Sendai virus was then harvested, filtered through a 0.45 μm filter and ultracentrifuged, to concentrate the vector, as needed. The virus suspension was frozen using liquid nitrogen, and cryopreserved at −80° C.

Example 4

Removal of the Sustained Expression-Type Sendai Viral vector from Cells Using siRNA In order to remove the vector sequences from the cells stably transduced with the sustained expression-type Sendai viral vector, two types of short interfering RNAs (siRNAs) were designed to suppress expression of the L gene encoding a subunit of RNA-dependent RNA polymerase that is necessary for sustained infection of the vector (#1: sense strand 5'-GGUUCAGCAUCAAAUAUGAAG-3' (SEQ ID NO: 14 in the Sequence Table), antisense strand 5'-UCAUAUUUGAUGCUGAACCAU-3' (SEQ ID NO: 15 in the Sequence Table), #2: sense strand 5'-GGUCCAGACAUGAAUUCAAAG-3' (SEQ ID NO: 16 in the Sequence Table), antisense strand 5'-UUGAAUUCAUGUCUGGACCAU-3' (SEQ ID NO: 17 in the Sequence Table)). In order to check for removal of the viral vector by the siRNA, BHK/T7 cells stably transduced with the sustained expression-type Sendai viral vector containing an *aequorea victoria*-derived EGFP gene (enhanced green fluorescent protein: Clontech Laboratories Inc.) were seeded onto a 48-well plate at a density of $1.0\times10^4$ cells/well. The next day, the siRNA targeting the L gene was added to the cells to a final concentration of 100 nM. After 4 days post transfection, EGFP fluorescence was examined by fluorescence microscopy. The intensity of EGFP fluorescence in the cell having the L gene specific siRNA was greatly reduced, as compared to cells exposed to a negative control siRNA that targets a firefly luciferase gene (FIG. 3A). Moreover, some of the cells treated with the siRNA were re-seeded on a 12-well plate, and cultured for another 6 days. As a result of the L gene-specific siRNA activity, no EGFP fluorescence was detected in most all of the cells. This shows that the reduction in intensity of EGFP fluorescence is not caused by temporary suppression of gene expression, but by removal of the vector sequences from the cells (FIG. 3B).

Example 5

Induction of the Cells Expressing Mouse iPS Marker from Mouse Embryo-Derived Fibroblast Cells (1) Preparation of Mouse Embryo-Derived Fibroblast Cells An embryo was removed from a mouse (C57BL/6J or Nanog-EGFP (Enhanced Green Fluorescent Protein) knock-in mouse (STOCK Tg (Nanog-GFP, Puro) 1Yam) at the 14th day of pregnancy. After removing the head, four limbs and internal organs, the remaining body parts were chopped up, and treated with trypLE Express (Invitrogen Corp.) at 37° C. for 30 minutes. After a brief spin to dispose of non-cellular components, the cells in the supernatant were cultured in Dulbecco's Modified Minimal Essential Medium (DMEM) containing 10% of fetal bovine serum (FCS) to obtain mouse embryo-derived fibroblast cells (MEFs).

(2) Induction of the Cells Expressing Mouse iPS Markers

The MEFs were cultured in a 12-well plate at a density of $1.0\times10^5$ cells/well. The next day, each of the hOct4/hSox2/hKlf4 sustained expression-inducing Sendai virus prepared in Example 2, the hOct4/hSox2/hKlf4/hc-Myc sustained expression-inducing Sendai virus prepared in Example 3 and the hOct4/hSox2/hKlf4/hc-Myc sustained expression-inducing Sendai virus Version 2, described in Example 12 were added to the culture medium to infect the MEFs at room temperature, and then the infected MEFs were cultured at 37° C. overnight.

Mitomycin-treated MEFs were plated on a gelatin-coated dish. After attachment, the vector-infected cells were seeded on top of the quiescent feeder layer. The cells were then cultured in mouse ES medium (DMEM, 15% FCS, 0.1 mM nonessential amino acids, 0.55 mM 2-ME, 1000 U/ml Leukemia Inhibitory Factor (LIF)) or KSR medium (Knockout DMEM, 15% Knockout Serum Replacement (KSR), 2 mM Glutamine, 0.1 mM nonessential amino acids, 0.05 mM 2-ME, 1000 U/ml Leukemia Inhibitory Factor (LIF)).

Figure 4:
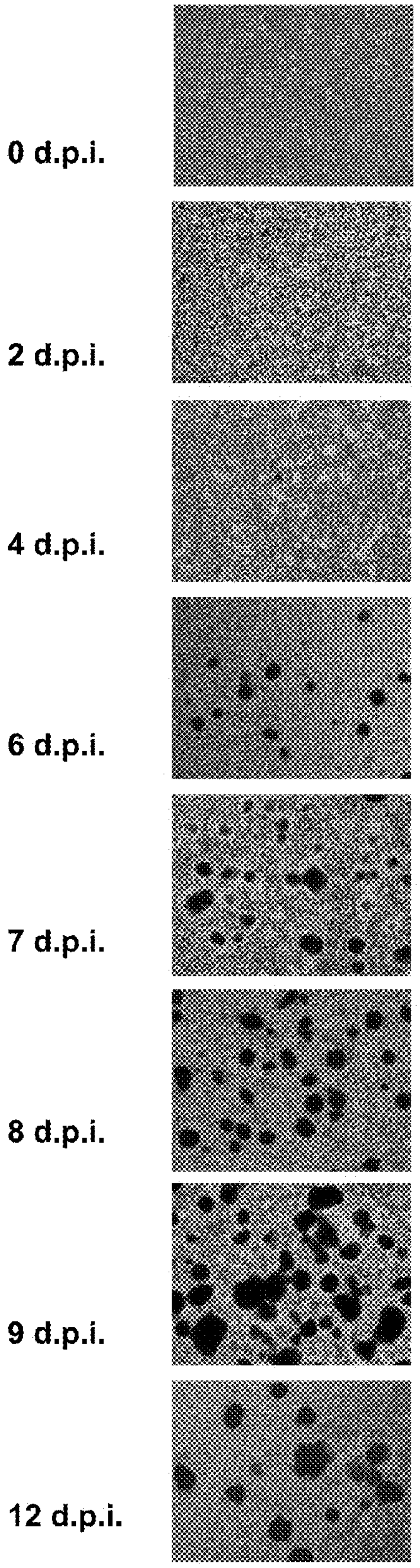
FIG. 4 is a series of time-lapse phase photographs using a phase contrast microscope (from 0 to 12 days post infection) showing the expression of alkaline phosphatase in a mouse embryonic fibroblast cell infected with the hOct4/hSox2/hKlf4/hc-Myc sustained expression-inducing Sendai viral vector.
Figure 5:
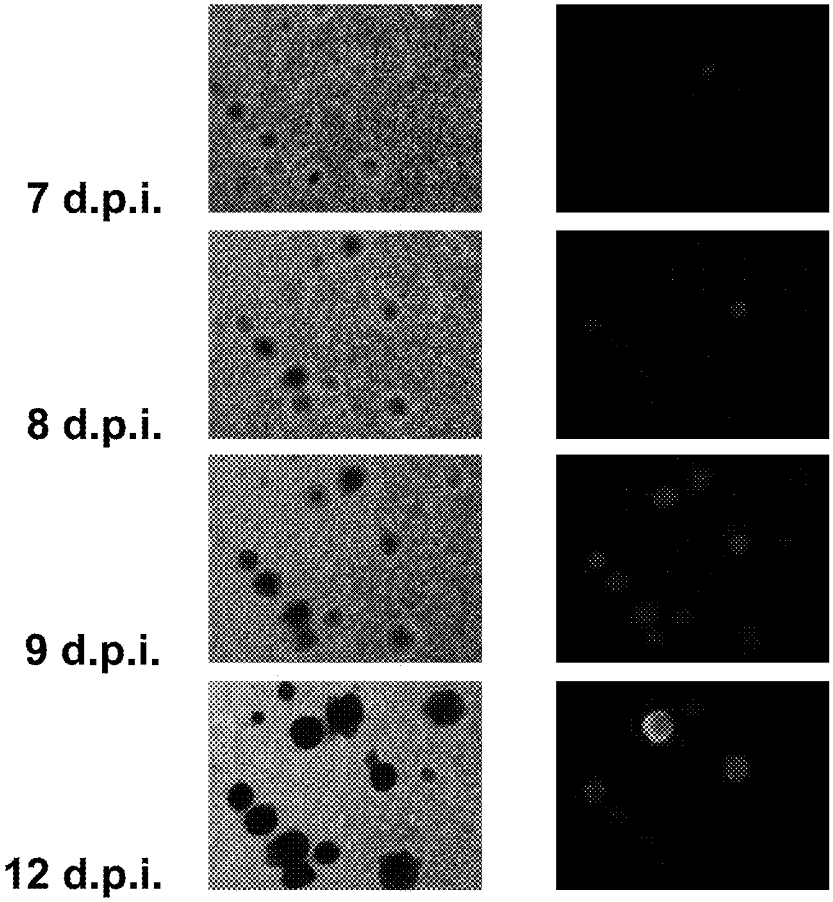
FIG. 5 is a series of time-lapse photographs using a phase contrast and fluorescent microscope (from 7 to 12 days post infection) showing expression of EGFP in a Nanog-EGFP knock-in mouse embryonic fibroblast cell infected with the hOct4/hSox2/hKlf4/hc-Myc sustained expression-inducing Sendai viral vector. Red: alkaline phosphatase. Green: nanog-GFP. D.p.i.: days post infection. Left side: Phase contrast microscopic observation. Right side: Fluorescent microscopic observation.
Figures 6, 6A, 6B, 6C:
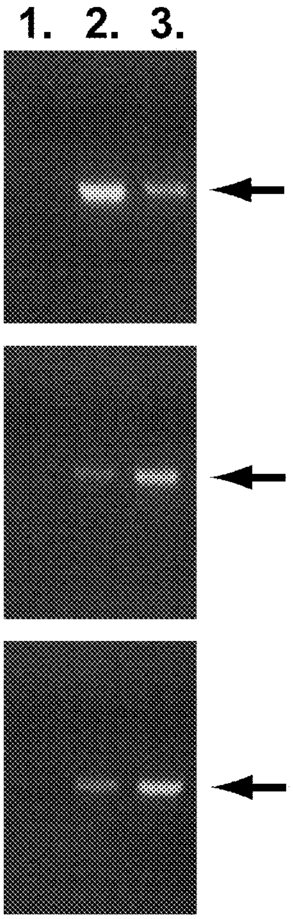
FIG. 6 depicts an RT-PCR analysis showing the expression (indicated by the arrows) of the Sendai virus NP gene (FIG.

6 days after infection with the hOct4/hSox2/hKlf4/hc-Myc sustained expression-inducing Sendai virus, ES-like cell colonies formed that stained positive for alkaline phosphatase activity (FIG. 4). In those MEFS derived from Nanog-EGFP knock-in mice, GFP-positive colonies were detected 8 days post-infection indicating induction of expression from the endogenous Nanog gene (FIG. 5). RT-PCR analysis further showed that (see Example 20 (c)), mouse Nanog (FIG. 6C) and Oct4 (FIG. 6B) (markers of a mouse iPS cell) are induced in cells forming iPS colonies (FIG. 6). Using the fluorescent antibody method (see Example 20 (a)), mouse SSEA-1 was detected in cells within the iPS colonies (FIG. 7). Genotyping (see Example 20 (d)) demonstrated that the genetic make-up of the induced mouse iPS marker-expressing cell is identical to that of the parent MEFs but different from that of a mouse ES cell used as a positive control. Hence, these results demonstrate that mouse iPS marker-expressing cells were generated by introducing hOct4, hSox2, hKlf4, hc-Myc into MEFs (FIG. 8). Substantially the same result was obtained with hOct4/hSox2/hKlf4/hc-Myc sustained expression-inducing Sendai viral vector Version 2.

(3) Test for Induction Efficiency of Mouse iPS Marker-Expressing Cells

The proportion of cells infected with the sustained expression-type Sendai virus was quantitatively measured using a fluorescent antibody method against the NP (see Example 20 (a)), and the number of alkaline phosphatase activity-positive colonies (see Example 20 (b)) was corrected for infection efficiency to calculate the induction efficiency of mouse iPS marker-expressing cells. The results are shown in Table 1.

TABLE 1

Temporal observation of the emergence frequency of alkaline phosphatase-expressing cell in mouse embryo fibroblast cells infected with hOct4, hSox2, hKlf4, and hc-Myc sustained expression-inducing Sendai virus

| Time (days) after infection | Frequency with respect to all cells (%) | Frequency with respect to infected cells (%) |
|---|---|---|
| 6 | 5.3 | 9.1 |
| 7 | 8.6 | 14.9 |
| 9 | 13.1 | 22.5 |
| 12 | 7.1 | 12.3 |

As seen in the results of Table 1, it became evident that the cells expressing mouse iPS marker can be induced with significantly higher efficiency than previous iPS reports in which four genes consisting of hOct4, hSox2, hKlf4 and hc-Myc were introduced into differentiated cells using a retroviral vector or by using other vector systems. Substantially the same result was obtained with the hOct4/hSox2/hKlf4/hc-Myc sustained expression-inducing Sendai viral vector Version 2.

Example 6

Production of Mouse iPS Cells by Removal of the RNA Genome of Sustained Expression-Type Sendai Viral Vector Sequences In order to remove the vector RNA from the cells expressing the mouse iPS markers obtained in Example 5, the siRNA targeting the L gene was introduced into the cells as described in Example 4. At the first and subsequent cell passages, the siRNA was introduced as a mixture with lipofectamin 2000 into the culture medium. After about one week, fluorescent antibody staining (see Example 20 (a)) confirmed that no vector RNA remained in any of the colonies as judged by the inability of the antibody assay to detect Sendai virus NP protein, as described in Example 5. Furthermore, a colony was cloned, and checked by RT-PCR (see Example 20 (c)) for the absence of any NP gene-derived messenger RNA (mRNA). The reprogramming procedure of the invention therefore produced a mouse iPS cell clone devoid of any vector sequences (see FIG. 9A). Moreover, RT-PCR analysis (see Example 20 (c)), confirmed the expression of mouse Nanog and Oct4 gene in the iPS stem cell colonies. The expression of these iPS cell markers was maintained even after the removal of all of the Sendai virus vector sequences (FIG. 9B).

Example 7

Formation of Teratomas after Transplantation of Mouse iPS Cells into Immunocompromised Mice The iPS cells obtained in Example 6 were adjusted to a concentration of $1.0\times10^6$ cells/100 μL PBS, and transplanted under a skin at the root of a leg of a mouse (C. B17/Icr-scidJc1) sedated using isoflurane anesthesia. 2 weeks after the inoculation, a visually identifiable teratoma formed. 30 days after the implantation, the teratoma was excised and fixed in Bouin's fixative solution (75% of saturated picric acid, 12% of formalin, 3% of acetic acid), and dehydrated by treatment with 70% ethanol solution (1 hour), 90% ethanol solution (1 hour), 100% ethanol solution (1 hour, twice), 50% ethanol solution, 50% 2-butanol solution (1 hour) and 100% 2-butanol solution (30 minutes, twice). Samples were then fixed in paraffin, and subjected to HE staining. As can be seen in FIG. 10, the teratomas contained tissues resulting from the differentiation of iPS cells into tissues of all three germ layers.

Example 8

Induction of Cells Expressing Human iPS Marker from Human Embryo-Derived Fibroblast Cells (1) Induction of Human iPS Marker-Expressing Cells TIG3 cells, i.e. human embryo-derived fibroblast cells, were cultured in a 12-well plate at a density of $10\times10^5$ cells/well. After one day, each of the hOct4/hSox2/hKlf4/hc-Myc sustained expression-inducing Sendai virus (prepared in Example 3) and the hOct4/hSox2/hKlf4/hc-Myc sustained expression-inducing Sendai virus Version 2 (prepared in Example 12) were added to the culture medium, and left at room temperature for 2 hours. The cells were then cultured in the presence of the recombinant Sendai viruses overnight at 37° C. The virus-infected cells were then plated on a feeder layer of mitomycin-treated MEFs and cultured in hES medium (DMEM/F12, 20% of Knockout Serum Replacement (KSR), 0.1 mM nonessential amino acids, 0.55 mM 2-ME, 10 ng/ml bFGF) or a primate ES cell culture medium (ReproCELL).

As shown in FIG. 11, 10 days after the start of infection with the hOct4/hSox2/hKlf4/hc-Myc sustained expression-inducing Sendai virus, human ES-like cell colonies formed that expressed alkaline phosphatase (see Example 20 (b)). RT-PCR analysis (see Example 20 (c)), confirmed that human Nanog expression is induced in human iPS cells that are capable of forming colonies (see FIG. 12). Using a fluorescent antibody method (see Example 20 (a)), these colonies were also shown to express SSEA-4 antigen, a marker characteristic of embryonic stem cells and iPS cells (FIG. 13). Substantially the same results were obtained using the hOct4/hSox2/hKlf4/hc-Myc sustained expression-inducing Sendai virus Version 2.

(2) Test for Induction Efficiency of Human iPS Marker-Expressing Cells

The fluorescent antibody method (see Example 20 (a)) was used to determine the amount of NP protein present in cells infected with the sustained expression-type Sendai virus. The amount of NP protein correlates with the infection rate of the recombinant Sendai virus. The number of cells in an alkaline phosphatase activity-positive colony (see Example 20 (b)) was then corrected for the rate of infection which allowed the calculation of the induction efficiency of human iPS marker-expressing cells. The results are shown in Table 2.

TABLE 2

Frequency of alkaline phosphatase-expressing cells in human embryo fibroblast cells infected with the hOct4, hSox2, hKlf4, and hc-Myc sustained expression-inducing Sendai virus as a function of time after the initiation of infection (6-10 days).

| Time (days) after infection | Frequency with respect to all cells (%) | Frequency with respect to infected cells (%) |
|---|---|---|
| 6 | 2.7 | 10.2 |
| 8 | 3.7 | 13.9 |
| 10 | 4.4 | 16.8 |

As can be seen from the results in Table 2, it became evident that the cells expressing human iPS markers can be induced with significantly higher efficiency than previous reports of iPS cell generation in which hOct4, hSox2, hKlf4 and hc-Myc were introduced into the host cell using a retroviral vector or by using other vector systems. Substantially the same results were obtained after infection with hOct4/hSox2/hKlf4/hc-Myc sustained expression-inducing Sendai virus Version 2.

(3) Change in Induction Efficiency of Human iPS Marker-Expressing Cells Due to Difference in Culture Conditions The efficiency with which human embryo-derived fibroblast cells infected with the recombinant Sendai virus are reprogrammed to become iPS cells can be significantly enhanced up to 10 fold by culturing the infected cells at 40° C. and in 2% $CO_2$, instead of the normal cell culture conditions of 37° C. in 5% $CO_2$. While this phenomenon was commonly observed after infection with the hOct4/hSox2/hKlf4/hc-Myc sustained expression-inducing Sendai virus (FIG. 16A) and the hOct4/hSox2/hKlf4/hc-Myc sustained expression-inducing Sendai virus Version 2 (FIG. 16B), it was not observed after infection with hOct4/hSox2/hKlf4/hc-Myc recombinant retrovirus (FIG. 16C).

Example 9

Production of Human iPS Cells by Removing the RNA Genome of Sustained Expression-Type Sendai Viral Vector The human iPS marker-expressing cells obtained in Example 8 were successfully cultured for long periods of time. One month after infection with the vector, fluorescent antibody staining of Sendai virus NP protein confirmed that no vector RNA genome remained in the cells as described in Example 5. RT-PCR analysis of NP gene expression as described in Example 7 further confirmed the absence of viral vector sequences in these cells (FIG. 14A). In addition, RT-PCR analysis of Nanog mRNA (see Example 20 (c)), demonstrated that endogenous Nanog expression persists in iPS cells even after the cells no longer contain any detectable viral vector sequences (FIG. 14B). The same is true for the stem cell markers human SSEA-4 and Oct-4 (see FIG. 15) detected using appropriate fluorescent antibodies (see Example 20 (a)) further indicating that these endogenous stem cell markers do not require the persistent expression of the reprogramming genes in order to maintain the stem cell phenotype.

Removal of the viral vector sequences can be enhanced by subjecting the newly formed human iPS marker-expressing cells to subculture conditions at 40° C., 2% $CO_2$, instead of the normal conditions 37° C., 5% $CO_2$ (FIG. 17). The sustained expression-type Sendai viral vector used in this test has the property that gene expression deteriorates rapidly at high temperature (40° C.), which facilitates the removal of the vector from the host cell.

Example 10

Preparation of Chimeric Mouse from Mouse iPS Cells

The iPS cell line KOSM #24 was established from MEFs derived from a Nanog-EGFP (Enhanced Green Fluorescent Protein) knock-in mouse (STOCK Tg (Nanog-GFP, Puro) 1Yam), as described in Examples 5 and 6 using the hOct4/hSox2/hKlf4/hc-Myc sustained expression-inducing Sendai viral vector Version 2. A chimeric mouse was prepared according to a method described in the following Reference (Manipulating the Mouse Embryo, A Laboratory Manual, Third Edition (Nagy, A., et al, Cold Spring Harbor Laboratory Press, 2003)).

An eight-cell embryo was collected from the uterus of an ICR mouse (female, 6 to 8 week-old) on the 2.5th day of pregnancy and washed in M2 Medium. The embryo was then cultured in KSOM (Potassium Simplex Optimized Medium) for 1 to 2 hours, and then subjected to a microinjection. Mouse iPS cells were first dispersed with trypsin, and 10 to 15 iPS cells were introduced into the embryo from a small hole formed in a zona pellucida. Subsequently, the embryo was cultured in KSOM for additional 24 hours, and then transplanted into the uterus of a female ICR mouse (surrogate parent mouse) crossed with a male mouse with bound ductus deferens. The chimaerism of the mouse after childbirth and germ-line transmission to progeny was determined by checking hair color and by detecting the presence of genes unique to the iPS cells. High levels of chimaerism, and germ-line transmission were observed (FIG. 18).

Example 11

Formation of Teratoma from Human iPS Cells

The human iPS cells obtained in Example 9 were adjusted to a concentration of $1.0\times10^6$ cells/40 μL Hepes Buffered Saline Solution (HBSS)/mouse. A testis of a mouse (C.B17/Icr-scidJc1) anesthesized with Nembutal and isoflurane, was inoculated with iPS cells. After about 8 weeks, a visually identifiable teratoma formed. After 60 days post-inoculation, the teratoma was excised and fixed in Bouin's fixative solution (75% of saturated picric acid, 12% of formalin, 3% of acetic acid), and dehydrated by a treatment with 70% ethanol solution (1 hour), 90% ethanol solution (1 hour), 100% ethanol solution (1 hour, twice), 50% ethanol solution, 50% 2-butanol solution (1 hour) and 100% 2-butanol solution (30 minutes, twice). The specimen was then fixed in paraffin. Sections of 6 μm thickness were then prepared using a microtome, the section were deparaffinized, and subjected to HE staining. Differentiation to all of three germ layers was observed within each teratocarcinoma analyzed (FIG. 19).

Example 12

Preparation of hOct4/hSox2/hKlf4/hc-Myc Sustained Expression-Inducing Sendai Viral Vector Version 2

(1) Human c-Myc gene was amplified from a plasmid pJL1 including a full-length human c-Myc cDNA by a PCR method using two primers consisting of 5'-ACTAGCTAGCTTAGA CGCTGGATTTTTTTCGGGTAGTGG-3' (SEQ ID NO: 32 in the Sequence Table (N-terminal side)) and 5'-GTCCACCGGTCTTACGCACAAGAGTTCCGT-3' (SEQ ID NO: 33 in the Sequence Table (C-terminal side)) as hc-Myc gene-amplifying primers. The termini of the double-stranded PCR DNA fragment were then cleaved at the Nhe I and Age I sites, and cloned between the Nhe I and Age I sites of the pMO084 prepared in Example 2 to generate plasmid pMO118 (see FIG. 20).

Human Sox2 gene was amplified from pUC57-Sox2 by a PCR method using two primers hSox2 gene-amplifying primers consisting of 5'-AGTACCTAGGCGCATGTACAACATGATGGAGACGG-3' (SEQ ID NO: 34 in the Sequence Table (N-terminal side)) and 5'-GTCCGACGTCCTCACATGTGTGAGAGG GGCAGT-3' (SEQ ID NO: 35 in the Sequence Table (C-terminal side)). The termini of the double-stranded PCR DNA fragment were cleaved at Avr II and Aat II sites, and cloned between the Avr II and Aat II sites of the pMO118 plasmid to form pMO119 (FIG. 20).

Human Oct4 gene was amplified from pUC57-Oct4 by a PCR method using two hOct4 gene-amplifying primers consisting of 5'-ACTAGCTAGCGGTTCCCCATGGCGGGACACCTGGCTTCGG-3' (SEQ ID NO: 36 in the Sequence Table (N-terminal side)) and 5'-GGTCCACGCGTTCAGTTTGAATGC ATGGGAGAGCC-3' (SEQ ID NO: 37 in the Sequence Table (C-terminal side)). The termini of the double-stranded PCR DNA fragment was then cleaved at Nhe I and Mlu I sites, and inserted between the Nhe I and Mlu I sites of the pMO097 to generate the plasmid pMO116. The orientation of a Cla I-Cla I fragment of the pMO116 was reversed to obtain pMO120. Next, a Sal I and Mlu I fragment of pMO119 was combined with a fragment between Sal I and Mlu I sites of pMO120 to generate pMO122 (FIG. 20).

Based on the plasmids obtained thus far, a T7 promoter sequence to SeV (1 to 3655 with Klf4), and SeV (3655 to 10480 with Oct4/Sox2/c-Myc), were cut out from pMO085 and pMO122 respectively and combined with a DNA fragment of SeV (10480 to 15384)+the right arm of the λ DASH II obtained by cutting the λ/151 at EcoR I site. The combination was then cloned to prepare λ/SeVp (Mp+Klf4, ΔM:: Oct4, ΔF:: Sox2, ΔHN:: c-Myc) (FIG. 20) (a cDNA complementary to a full-length genome of a hOct4/hSox2/hKlf4/hc-Myc sustained expression-inducing Sendai viral vector Version 2 described as SEQ ID NO: 38 in the Sequence Table).

(2) Preparation of hOct4/hSox2/hKlf4/hc-Myc Sustained Expression-Inducing Sendai Viral Vector Version 2

In accordance with the protocol described in Example 3, a hOct4/hSox2/hKlf4/hc-Myc sustained expression-inducing Sendai viral vector Version 2 was prepared from the cDNA complementary to a full-length genome of the hOct4/hSox2/hKlf4/hc-Myc sustained expression-inducing Sendai viral vector Version 2.

Example 13

Preparation of hOct4/hSox2/hKlf4/hc-Myc Sustained Expression-Inducing Sendai Viral Vector Version 3 Capable of being Automatically Removed from iPS Cell (1) In order to clone a sequence formed by connecting four target sequences for mir-302a which is ES cell-specific of miRNA, two sets of oligo DNAs consisting of a set of 5'-CCGGTTATCACCAAAACATGGAAGCACT-TACGATTCACCAAAACATGGAAGCACTT AGGTACC-3' (SEQ ID NO: 39 in the Sequence Table) and 5'-TAAGT-GCTTCCATGT TTTGGTGAATCGTAAGTGCTTCCAT-GTTTTGGTGATAA-3' (SEQ ID NO: 40 in the Sequence Table) and a set of 5'-TCACCAAAACATGGAAGCACT-TACGATTCACCAAAA CATGGAAGCACTTAA-3' (SEQ ID NO: 41 in the Sequence Table) and 5'-CCGGTTAAGT GCTTCCATGTTTTGGTGAATCGTAAGT-GCTTCCATGTTTTGGTGAGGTACC-3' (SEQ ID NO: 42 in the Sequence Table) were annealed, and then ligated together. Ligated DNA was cloned into pGL4.12 (Promega Corp.) cut at Age I site to obtain pNK300.

A plasmid vector pNK15 (SEQ ID NO: 43 in the Sequence Table) was prepared by inserting the SeV strain Cl.151 genome cDNA (bases 9014 to 15384), a hairpin ribozyme sequence of a tobacco ringspot virus and a termination sequence of T7 RNA polymerase into pBluescript II SK(+) (Agilent Technologies, Inc.)). Then, using 5'-GA-CAGCTCGTAATCCC GGGTCCCTATCGTGC-3' (SEQ ID NO: 44 in the Sequence Table (sense strand)) and 5'-GCAC-GATAGGGACCCGGGATTACGAGCTGTC-3' (SEQ ID NO: 45 in the Sequence Table (antisense strand)) as an Xma I-recognition sequence insertion site-forming primer, an Xma I-recognition sequence was inserted into the plasmid vector pNK15 at a site just after SeV (15244) by a Quickchange Site-directed Mutagenesis II kit (Agilent Technologies, Inc.), to obtain pNK287. A fragment obtained by cutting the pNK300 at Age I site was inserted into the Xma I site of the pNK287 to generate pNK309 (FIG. 21).

T7 promoter sequence to SeV (1 to 3655 with c-Myc), and SeV (3655 to 10480 with Klf4/Oct4/Sox2), was cut out from pMO103 and pMO099 as described in Example 3, and the connected SeV (9014 to 15384)-hairpin ribozyme sequence-T7 RNA polymerase termination sequence was cut out from the pNK309. Then, these fragments were combined with a DNA fragment consisting of right and left arms of the λ DASH II, and the obtained combination was cloned to create λ/SeVp (Mp+myc, ΔM:: Klf4, ΔF:: Oct4, ΔHN:: Sox2, L+mir302T4) (FIG. 21) (a cDNA complementary to a full-length genome of a hOct4/hSox2/hKlf4/hc-Myc sustained expression-inducing Sendai viral vector Version 3 is described as SEQ ID NO: 46 in the Sequence Table).

(2) Preparation of hOct4/hSox2/hKlf4/hc-Myc Sustained Expression-Inducing Sendai Viral Vector Version 3

In accordance with the process described in the Example 3, a hOct4/hSox2/hKlf4/hc-Myc sustained expression-inducing Sendai viral vector Version 3 was prepared from the cDNA complementary to a full-length genome of the hOct4/hSox2/hKlf4/hc-Myc sustained expression-inducing Sendai viral vector Version 3.

Example 14

Evaluation on Temporal Change in Removal of RNA Genome of Sustained Expression-Type Sendai Viral Vector from Cell Using siRNA As for the technique of removing the vector genome from a cell stably transfected with the RNA genome of the sustained expression-type Sendai viral vector, using siRNA, as described in the Example 4, an additional evaluation was carried out to quantitatively analyze temporal change in the removal and confirm that no vector genome remained in the cell after siRNA treatment, as follows.

As a marker of gene expression by the sustained expression-type Sendai viral vector, unstable firefly luciferase gene (Luc2CP, Promega Corp.) and *Escherichia coli* hygromycin B-resistant gene (HygB) were used. A luciferase activity reflects the copy number of the recombinant Sendai viral RNAs, and the number of hygromycin B-resistant cells reflects the number of cells transfected with the sustained expression-type Sendai viral vector.

A KO/HygB/EGFP/Luc2CP-loaded sustained expression-type Sendai viral vector containing a Luc2CP gene and a HygB gene was prepared by substituting the hOct4 gene, the hSox2 gene, the hKlf4 gene and the hc-Myc gene with the Kusabira Orange (KO) gene (Medical & Biological Laboratories, Co. Ltd.), HygB gene, Enhanced Green Fluorescent Protein (EGFP) gene, and Luc2CP gene, respectively, using the same methodology as that described for the cloning of hOct4/hSox2/hKlf4/hc-Myc sustained expression-inducing Sendai viral vector (see Example 3). Two types of short interfering RNAs (siRNAs) (same as Example 4) were used for suppressing expression of L gene (#1: sense strand 5'-GG-UUCAGCAUCAAAUAUGAAG-3' (SEQ ID NO: 14 in the Sequence Table) and antisense strand 5'-UCAUAU-UUGAUGCUGAACCAU-3' (SEQ ID NO: 15 in the Sequence Table). siRNA complimentary to sea-firefly luciferase gene (Rluc, Promega Corp.) served as negative control because it did not have any homologous with the Sendai viral vector genome.

In order to check for the removal of the viral genome by the siRNA, a HeLa cell stably transduced with the genome of the sustained expression-type Sendai viral vector containing a Luc2CP gene and HygB gene was seeded into a 24-well plate at a concentration of $3\times10^4$ cells/0.4 mL medium (MEM, 10% fetal bovine serum)/well. The siRNA was diluted with Opti-MEM to a final concentration of 40 nM, and 1 μl, of Lipofectamine RNAiMAX (Lifetechnologies, Inc.) was added the cell medium at room temperature for 20 minutes. Then, the siRNA was added to the above cells. Subsequently, the cells were collected at different times after transfection. On the 3rd and 6th days, the cells were subcultured under the above conditions, and the siRNA was added again using the above conditions. As a result, the luciferase activity as an index of an amount of the vector in the cell was lowered with time. On and after the 8th day, luciferase activity was no longer detectable (see FIG. 22A).

Cells transfected with siRNA were passaged 3 times over a 4 week period in the absence of siRNA. Cells were then cultured in the presence of selective medium containing 200 μg/mL of hygromycin B, and further cultured another week. As a result of the selection, no hygromycin B-resistance clone emerged, which demonstrates that none of the cells contained the sustained expression-type Sendai viral vector containing with the HygB gene (FIG. 22B).

Example 15

Evaluation of the Gene Expression Patterns of Two Foreign Genes Incorporated into the Sustained Expression-Type Sendai Viral Vector Previous experiments show that all four types of reprogramming genes need to be expressed simultaneously in a common cell, in order to produce an iPS cell. If the balance of expression intensity between the reprogramming genes is changed, the reprogramming efficiency decreases (Reference: Papapetrou, et al., Proc. Natl. Acad. Sci. USA, 106, 12759-12764, 2009), and a low-quality cell line having a similar configuration to an iPS cell but without pluripotency is likely to emerge (Reference: Chan, et al., Nat. Biotech., 27, 1034-1037, 2009). Thus, the method of producing iPS cells with high efficiency and excellent reproducibility needs to meet the following two requirements: 1) the four types of reprogramming genes must be introduced simultaneously into a common cell; and 2) the transduced reprogramming genes must be expressed simultaneously within each cell. To introduce the four types of reprogramming genes into a cell using the sustained expression-type Sendai viral vector, all of the reprogramming genes were cloned into a single vector, as shown in the Examples of the present invention. To determine if this cis configuration was more efficient at inducing iPS colonies than a trans configuration, each of the reprogramming genes was cloned into individual Sendai vectors. Virus produced from each of these vectors were then mixed and used to infect differentiated cells, as disclosed in the PCT/JP2009/062911 and Fusaki, et al., Proc. Jpn. Acad. Ser. B85, 348-362, 2009). Differences between the expression patterns of a foreign gene in the cis or trans configuration was then evaluated, by comparing expression patterns of two types of genes: the Kusabira Orange (KO) gene and Enhanced Green Fluorescent Protein (EGFP) gene present on each of the Sendai viral vectors.

The KO/HygB/EGFP/Luc2CP-loaded sustained expression-type Sendai viral vector described in Example 14 contains both the KO and EGFP genes. Further, for use as a vector loaded with only KO gene, a Zeo/KO/CLuc-loaded sustained expression-type Sendai viral vector was prepared by removing the hKlf4 gene from the hOct4/hSox2/hKlf4 sustained expression-inducing Sendai viral vector as described in the Example 2, and substituting the Bsr gene, the Oct4 gene and Sox2 gene with zeocin-resistant (Zeo) gene, the KO gene and secreted luciferase (CLuc) gene, respectively. For use as a vector loaded with only the EGFP gene, a Bsr/EGFP/gp91phox-loaded sustained expression-type Sendai viral vector was prepared by removing the hKlf4 gene from the hOct4/hSox2/hKlf4 sustained expression-inducing Sendai viral vector as described in the Example 2, and substituting the Oct4 gene and Sox2 gene with EGFP gene and chronic granulomatous disease-caused gene (gp91phox), respectively.

The monkey $LLCMK_2$ cell line was infected with the KO/HygB/EGFP/Luc2CP-loaded vector at a multiplicity of infection (m.o.i) of 5 vector particles/cell, and the resulting cells were selected with hygromycin B, to establish a cell pool $LLCMK_2$ (SeVdp/KO/HygB/EGFP/Luc2) containing the KO/HygB/EGFP/Luc2CP-loaded vector. In the same manner, the Zeo/KO/CLuc-loaded vector and the Bsr/EGFP/91phox-loaded vectors were mixed at a vector particle ratio of 1:1, and $LLCMK_2$ cells were infected with the mixed vectors at a m.o.i of 5 vector particles/cell, and the resulting cells were simultaneously selected with blasticidin S and Zeocin, to establish a cell pool $LLCMK_2$ (SeVdp/Zeo/KO/CLuc+SeVdp/Bsr/EGFP/91phox) having both vectors in each of the cells.

The two types of cell lines were then observed by fluorescent microscopy (Zeiss), and two images thereof were superimposed on each other, while assigning a red pseudocolor and a green pseudocolor to fluorescence generated by KO and fluorescence generated by EGFP, respectively. The image of $LLCMK_2$ (SeVdp/KO/HygB/EGFP/Luc2) cells became yellow which indicates that KO and EGPF are simultaneously expressed, whereas the image of the $LLCMK_2$ (SeVdp/Zeo/KO/CLuc+SeVdp/Bsr/EGFP/gp91phox) cells indicated a mixture of red/yellow/green-colored cells, which shows that a balance between the expression of KO and EGFP is significantly different in each cell (FIG. 23A).

In order to quantitatively analyze the balance between the expressions of KO and EGFP, the above cells were analyzed by a Fluorescent-activated Cell Analyzer (BD FACSCalibur, Becton, Dickinson and Company). $10^4$ $LLCMK_2$ (SeVdp/KO/HygB/EGFP/Luc2) cells and $10^4$ $LLCMK_2$ (SeVdp/Zeo/KO/CLuc+SeVdp/Bsr/EGFP/91phox) cells were suspended in 2 mL of buffer to measure the fluorescence intensity (FL1) of EGFP and a fluorescence intensity (FL2) of KO. The analysis shows that the ratio between the fluorescence intensities of EGFP and KO in the $LLCMK_2$ (SeVdp/KO/HygB/EGFP/Luc2) is constant, whereas the ratio in the $LLCMK_2$ (SeVdp/Zeo/KO/CLuc+SeVdp/Bsr/EGFP/91phox) cells fluctuates significantly (FIG. 23B). In an analysis of the ratio between FL1 and FL2, 50% or more of the $LLCMK_2$ (SeVdp/KO/HygB/EGFP/Luc2) cells had the same ratio, whereas the ratio in the $LLCMK_2$ (SeVdp/Zeo/KO/CLuc+SeVdp/Bsr/EGFP/gp91phox) was widely distributed in a broad range from 0 to 100% (FIG. 23C).

The above results show that the function of simultaneously introducing two or more types of genes into each cell to induce gene expression at the same ratio can be achieved by the process of cloning the four types of reprogramming genes on a single common vector, as shown in the Examples of the present invention, but cannot be readily achieved when each of the four types of reprogramming genes are cloned into individual vectors that are mixed together prior to infection as disclosed in the PCT/JP2009/062911 and the Fusaki, et al., Proc. Jpn. Acad. Ser. B85, 348-362, 2009.

Example 16

Induction of iPS Cells Using Sustained Expression-Type Sendai Viral Vectors Each Loaded with a Reprogramming Gene iPS cell production efficiency with Sendai vector comprising all four types of reprogramming genes on a single common vector to produce iPS cells, as shown in the Examples of the present invention, was then compared to iPS induction by infection with Sendai virus containing only one of the reprogramming genes, as disclosed in PCT/JP2009/062911 and the Fusaki, et al., Proc. Jpn. Acad. Ser. B85, 348-362, 2009.

The hOct4/hSox2/hKlf4/hc-Myc sustained expression-inducing Sendai viral vector containing all four types of reprogramming genes was compared with the hOct4/hSox2/hKlf4 sustained expression-inducing Sendai viral vector comprising three reprogramming genes (as shown in the Example 2), and a Zeo/KO/hc-Myc sustained expression-inducing Sendai viral vector containing just c-Myc. The Zeo/KO/hc-Myc sustained expression-inducing Sendai viral vector was prepared by substituting the Oct4 gene, the Sox2 gene and the Klf4 gene of the hOct4/hSox2/hKlf4 sustained expression-inducing Sendai viral vector with the Zeo gene, KO gene and c-Myc gene, respectively.

According to the Example 5, cells were infected with the hOct4/hSox2/hKlf4/hc-Myc sustained expression-inducing Sendai virus or a mixture of hOct4/hSox2/hKlf4 sustained expression-inducing Sendai virus with the Zeo/KO/hc-Myc sustained expression-inducing Sendai virus at a vector particle ratio of 1:1. Emergence of iPS cell colonies was checked by an index based on emergence of an alkaline phosphatase-positive cell colony. As a result, it could be shown that cloning the four types of reprogramming genes on the single common vector produces iPS cells with a cell production efficiency far greater than that obtained by mixing viruses each having only one of the reprogramming gene (FIG. 24).

Example 17

Induction of iPS Cells Using hOct4/hSox2/hKlf4/hc-Myc Sustained Expression-Inducing Sendai Virus Version 3

TIG3 cells was seeded on a 12-well plate at a density of $1.0\times10^5$ cells/well. On the next day, the hOct4/hSox2/hKlf4/hc-Myc sustained expression-inducing Sendai viral vector prepared in Example 3, or the hOct4/hSox2/hKlf4/hc-Myc sustained expression-inducing Sendai viral vector Version 3 prepared in Example 13, was added to the medium to induce human iPS cells according to Example 8. Colonies was subcultured twice. Then, on the 24th day after infection, colonies were fluorescently stained using an antibody against NP protein As shown in FIG. 25A, colonies induced with hOct4/hSox2/hKlf4/hc-Myc sustained expression-inducing Sendai viral vector Version 3 did not contain any vector (FIG. 25) whereas expressed iPS/ES marker SSEA-4 antigen (FIG. 25B).

The above result clearly shows that, when human iPS cells are induced with the hOct4/hSox2/hKlf4/hc-Myc sustained expression-inducing Sendai virus Version 3, the vector is automatically removed by the microRNA, mir-302a, expressed in the induced iPS cell.

Example 18

Establishment of iPS Cells from Human Peripheral-Blood Mononuclear Cells 20 mL of adult blood was diluted with 20 mL of PBS (−), and layered on 6 mL of Lymphoprep. The blood was then centrifuged at 1.800 r.p.m. for 30 minutes to separate an upper layer of platelets, an intermediate layer including mononuclear cells and a lower layer including red blood cells. The intermediate layer was washed with PBS (−) to obtain human peripheral-blood mononuclear cells. In accordance with the technique described in Example 8, the cells were infected with hOct4/hSox2/hKlf4/hc-Myc sustained expression-inducing Sendai virus, and then cultured. iPS cells positive for alkaline phosphatase and having a morphology similar to that of a human ES cell formed (FIG. 26). Cell colonies were not detected in a negative control comprising cells that were not infected with the Sendai vector.

Example 19

Comparison Between Gene Expression Patterns in Human iPS Cells Produced with Sustained Expression-Type Recombinant Sendai Virus (1) Preparation of Target RNA to be Analyzed iPS cells produced using the hOct4/hSox2/hKlf4/hc-Myc sustained expression-inducing Sendai virus according to the process in Example 8 were cultured on matrigel (Becton, Dickinson and Company) in MEF conditioned medium without any feeder cells. $1.0\times10^6$ cells were then collected and whole cell RNA was extracted using ISOGEN (Nippon Gene Co. Ltd.). As a control, five human ES cell lines established at the Institute for Frontier Medical Sciences, Kyoto University, were cultured in the absence of feeder cells, and whole cell RNA was extracted, in the same manner.

(2) Analysis of Gene Expression 0.5 µg of whole cell RNA was labeled with Cy3, using Quick Amp Labeling Kit (Agilent Technologies, Inc.). The labeled RNA was hybridized with Whole Human Genome (4×44 k) DNA array (Agilent Technologies, Inc.), using a Gene Expression Hybridization Kit (Agilent Technologies, Inc.), and a signal was acquired using Agilent DNA Microarray Scanner. The acquired signal was analyzed using GeneSpringGX10 software (Agilent Technologies, Inc.) to obtain a correlation coefficient between respective gene expression patterns of cell clones (FIG. 27A). The gene expression patterns of human iPS cells produced using the hOct4/hSox2/hKlf4/hc-Myc sustained expression-inducing Sendai virus were significantly similar to each other, as evidenced by a correlation coefficient of 0.98 or more. This shows that iPS cells having with significantly uniform properties can be established by the method of the present invention. In addition, each of the iPS cells subjected to this analysis expressed a marker gene which was strongly expressed in human ES cells and at the same expression level as that observed in ES cells (FIG. 27B). This means that the gene expression of iPS cells has high correlativity with that of human ES cells (FIG. 27C).

Example 20

Preparation of hOct4/hSox2/hKlf4/hc-Myc Sustained Expression-Inducing Sendai Viral Vector Version 1

Preparation of Vector cDNA

A double-stranded DNA (SEQ ID NO: 2 in the Sequence Table) including Avr II recognition sequence, human Oct4 ORF, Sendai virus (SeV) genome cDNA (bases 6617 to 6666), human Sox2 ORF and Age I recognition sequence in this order was synthesized, and then cloned into the plasmid vector pUC57 (the cloning was entrusted to GenScript Inc.) (pUC57-OctSox). A DNA sequence cut from the pUC57-OctSox with Avr II and Age I was inserted between Arv II and Age I sites of a plasmid vector pMO078 (SEQ ID NO: 3 in the Sequence Table) where Cla I recognition sequence, SeV strain Cl.151 genome cDNA (bases 2871 to 3650), Not I recognition sequence, a blasticidin S-resistance gene, Mlu I recognition sequence, SeV strain Cl.151 genome cDNA (bases 4728 to 4828), Avr II recognition sequence, humanized Kusabira-Orange gene, SeV strain Cl.151 genome cDNA (bases 6617 to 6666), gp91phox gene, Age I recognition sequence and SeV strain Cl.151 genome cDNA (bases 8442 to 10479) had been inserted into a plasmid pBluescript II SK(+) (Agilent Technologies Inc.) in this order. In this manner, a plasmid pMO084 was obtained (FIG. 28).

A double-stranded DNA (SEQ ID NO: 4 in the Sequence Table) including Nhe I recognition sequence, human Klf4 ORF, Sendai virus transcription termination sequence, Sendai virus transcription initiation sequence and Not I recognition sequence in this order was synthesized, and then cloned into a plasmid vector pUC57 (the cloning was entrusted to GenScript Inc.) (pUC57-KLF4). Human Klf4 gene was amplified by PCR from pUC57-KLF4 using the following two primers: 5'-ACTAGCTAGCAGTCTGACATGGCTGT-CAGCGACGCGCT-3' (SEQ ID NO: 7 in the Sequence Table; N-terminal side) and 5'-GGTCCACGCGTT-TAAAAATGCCTCTTCATGTG-3' (SEQ ID NO: 8 in the Sequence Table; C-terminal side). The ends of the resultant double-stranded DNA were cut with Nhe I and Mlu I, and then the DNA was inserted between Nhe I and Mlu I sites of pMO026 [a plasmid vector in which Cla I recognition sequence, SeV strain Cl.151 genome cDNA (bases 2871 to 3650), Not I recognition sequence, Nhe I recognition sequence, blasticidin S resistance gene, Mlu I recognition sequence and SeV strain Cl.151 genome cDNA (bases 4728 to 5335) had been inserted into pBluescript II SK(+) in this order] (SEQ ID NO: 9 in the Sequence Table) to thereby obtain pMO097. Subsequently, Cla I-Mlu I fragment from pMO097 was linked to Cla I-Mlu I fragment from pMO084 to thereby obtain pMO099 (FIG. 28).

A DNA sequence cut from the pUC57-KLF4 with Nhe I and Not I was inserted between Nhe I and Not I sites of a plasmid vector pNK214 (SEQ ID NO: 5 in the Sequence Table) in which SeV strain Nagoya genome cDNA (bases 1 to 43), Sendai virus transcription termination sequence, SeV strain Nagoya genome cDNA (bases 56 to 2870), SeV strain Cl.151 genome cDNA (bases 2871 to 3656), Nhe I recognition sequence and Not I recognition sequence had been inserted into pBluescript II SK(+) (Agilent Technologies Inc.) in this order. In this manner, plasmid pMO094 (SEQ ID NO: 12 in the Sequence Table) was obtained (FIG. 28). Human c-Myc gene was amplified by PCR from plasmid pJL1 comprising full-length human c-Myc cDNA using the following primers: 5'-ACTAGCTAGCTTAGACGCTG-GATTTTTTTCGGGTAGTGG-3' (SEQ ID NO: 10 in the Sequence Table; N-terminal side) and 5'-GTCCGACGTC-CTTACGCACAAGAGTTCCGT-3' (SEQ ID NO: 11 in the Sequence Table; C-terminal side). The ends of the resultant double-stranded DNA were cut with Nhe I and Aat II, and then the DNA was inserted between Nhe I-Aat II sites of pMO094 to thereby obtain pMO103 (FIG. 28).

After obtaining these plasmids, a DNA fragment containing T7 promoter sequence through SeV: 1-3655 was cut out from pMO103 and a DNA fragment containing SeV: 3655-10480 was cut out from pMO099. These fragments were combined with a DNA fragment containing SeV: 10480-1538+λDASHII right arm obtained by digesting λ/151 (Nishimura, et al., JBC, 282, 27383-27391, 2007) with EcoR I and cloned together to thereby prepare λ/SeVp (Mp+myc, ΔM::Klf4, ΔF::Oct4, ΔHN::Sox2) (FIG. 28) (cDNA complementary to the full-length genome of h-cMyc/hOct4/hSox2/hKlf4 sustained expression-inducing Sendai viral vector version 1 is shown in SEQ ID NO: 13 in the Sequence Table).

(2) Preparation of hOct4/hSox2/hKlf4/hc-Myc Sustained Expression-Inducing Sendai Viral Vector Version 1

BHK/T7/151M (SE) cells were seeded on 6-well plates at a density of $5\times10^5$ cells/well, and washed after 24 hr cultivation. λ/SeVp (Mp+myc, ΔM::Klf4, ΔF::Oct4, ΔHN::Sox2) phage DNA, NP protein expression plasmid pGEM/NP, P protein expression plasmid pGEM/P, L protein expression plasmid pGEM/L (pGEM/NP, pGEM/P and pGEM/L are described in Garcin, et al., EMBO J., 14, 6087-6094, 1995), F protein expression plasmid pSRD-FZmut and HN protein expression plasmid pMKIT-NaHN (pSRD-FZmut and pMKIT-NaHN are described in Taira, et al., Arch. Virol., 140, 187-194, 1995) were suspended in 300 μL of Opti-MEM at quantitative ratios of 2 μg, 1 μg, 1 μg, 1 μg, 1 μg and 1 μg, respectively. The thus obtained suspension was mixed with 300 μL of Opti-MEM (Life Technologies) containing 10 μL of Lipofectamine 2000. The mixture was left at room temperature for 20 minutes and added to the cells, which were then cultured for 4 hours. Then, the cells were washed again, and after addition of 10% FCS-containing DMEM, cultured further at 32° C. for 3 days. Then, the cells were cultured further at 37° C. for 3 days. The resultant cells were stained by the fluorescence antibody technique using antibodies to Sendai virus NP protein and antibodies to hOct4, hSox2 and hKlf4 gene products to thereby confirm that reconstruction of the vector genome had occurred in the transfected cells. This cell population was used as hOct4/hSox2/hKlf4/hc-Myc sustained expression-inducing Sendai viral vector version 1 producing cells without further cloning.

2 μg each of three defective gene-expression plasmids, pMKIT-151M (Taira, et al., Arch. Virol., 140, 187-194, 1995), pSRD-ZFmut and pMKIT/NaHN, was introduced into $5.0\times10^5$ hOct4/hSox2/hKlf4/hc-Myc sustained expression-inducing Sendai viral vector version 1 producing cells using Lipofectamine 2000. After 4 hours, the cells were washed, and, after addition of 10% FCS-containing DMEM thereto, cultured further at 32° C. for 4 to 9 days. Subsequently, the culture supernatant containing the hOct4/hSox2/hKlf4 sustained expression-inducing Sendai viral vector was harvested, filtered through a 0.45 μm filter and, if necessary, ultracentrifuged to concentrate the vector. The vector suspension was quickly frozen using liquid nitrogen, and cryopreserved at −80° C.

Example 21

Preparation of hOct4/hSox2/hKlf4/hc-Myc Sustained Expression-Inducing Sendai Viral Vector Version 2.1

(1) Preparation of Vector cDNA

Human c-Myc gene was amplified by PCR from plasmid pJL1 comprising full-length human c-Myc cDNA using the following primers: 5'-ACTAGCTAGCTTAGACGCTG-GATTTTTTTCGGGTAGTGG-3' (SEQ ID NO: 32 in the Sequence Table; N-terminal side) and 5'-GTCCACCG-GTCTTACGCACAAGAGTTCCGT-3' (SEQ ID NO: 33 in the Sequence Table; C-terminal side). The ends of the resultant double-stranded DNA were cut with Nhe I and Age I. The thus obtained DNA was inserted between Nhe I-Age I sites of pMO084 prepared in Example 20 to thereby obtain plasmid pMO118 (FIG. 29).

Human Sox2 gene was amplified by PCR from pUC57-Sox2 using the following primers: 5'-AGTACCTAGGCG-CATGTACAACATGATGGAGACGG-3' (SEQ ID NO: 34 in the Sequence Table; N-terminal side) and 5'-GTC-CGACGTCCTCACATGTGTGAGAGGGGCAGT-3' (SEQ ID NO: 35 in the Sequence Table; C-terminal side). The ends of the resultant double-stranded DNA were cut with Avr II and Aat II. The thus obtained DNA was inserted between Avr II-Aat II sites of pMO118 to thereby obtain pMO119 (FIG. 29).

Human Oct4 gene was amplified by PCR from pUC57-Oct4 using the following primers: 5'-ACTAGCTAGCGGT-TCCCCATGGCGGGACACCTGGCTTCGG-3' (SEQ ID NO: in the Sequence Table; N-terminal side) and 5'-GGTC-CACGCGTTCAGTTTGAATGCATGGGAGAGCC-3' (SEQ ID NO: 37 in the Sequence Table; C-terminal side). The ends of the resultant double-stranded DNA were cut with Nhe I and Mlu I. The thus obtained DNA was inserted between Nhe I-Mlu I sites of pMO097 to thereby obtain pMO116. Subsequently, the orientation of the Cla I-Cla I fragment of pMO116 was reversed to thereby obtain pMO120. Then, the Sal I-Mlu I fragment of pMO119 was linked to the Sal I-Mlu I fragment of pMO120 to thereby obtain pMO122 (FIG. 29).

After obtaining these plasmids, a DNA fragment containing T7 promoter sequence through SeV: 1-3655 was cut out from pMO094 (Example 20, FIG. 28) and a DNA fragment containing SeV: 3655-10480 was cut out from pMO122. These fragments were combined with a DNA fragment containing SeV: 10480-1538+λDASHII right arm obtained by digesting λ/151 with EcoR I and cloned together to thereby prepare λ/SeVp (Mp+Klf4, ΔM::Oct4, ΔF::Sox2, ΔHN::c-Myc) (FIG. 29) (cDNA complementary to the full-length genome of hOct4/hSox2/hKlf4/hc-Myc sustained expression-inducing Sendai viral vector version 2.1 is shown in SEQ ID NO: 38 in the Sequence Table).

(2) Preparation of hOct4/hSox2/hKlf4/hc-Myc Sustained Expression-Inducing Sendai Viral Vector Version 2.1 hOct4/hSox2/hKlf4/hc-Myc sustained expression-inducing Sendai viral vector version 2.1 was prepared from the above-described cDNA complementary to the full-length genome of hOct4/hSox2/hKlf4/hc-Myc sustained expression-inducing Sendai viral vector version 2.1 in the same manner as described in (2) in Example 20.

Example 22

Preparation of hOct4/hSox2/hKlf4/hc-Myc Sustained Expression-Inducing Sendai Viral Vector Version 4 to be Automatically Removed from iPS Cells (1) Preparation of Vector cDNA A DNA fragment containing T7 promoter sequence through SeV: 1-3655 was cut out from pMO094 prepared in Example 21; a DNA fragment containing SeV: 3655-10480 was cut out from pMO122; and a DNA fragment containing SeV: 9014-15384-hairpin ribozyme sequence—T7 RNA polymerase termination sequence was cut out from pNK309 prepared in Example 13. These fragments were combined with DNA fragments of λDASHII right arm and left arm, and cloned together to thereby prepare λ/SeVp (Mp+Klf4, ΔM::Oct4, ΔF::Sox2, ΔHN::c-Myc, L+mir302T4) (FIG. 30) (cDNA complementary to the full-length genome of hOct4/hSox2/hKlf4/hc-Myc sustained expression-inducing Sendai viral vector version 4 is described in SEQ ID NO: 47 in the Sequence Table).

(2) Preparation of hOct4/hSox2/hKlf4/hc-Myc Sustained Expression-Inducing Sendai Viral Vector Version 4 hOct4/hSox2/hKlf4/hc-Myc sustained expression-inducing Sendai viral vector version 4 was prepared from the above-described cDNA complementary to the full-length genome of hOct4/hSox2/hKlf4/hc-Myc sustained expression-inducing Sendai viral vector version 4 in the same manner as described in (2) in Example 20.

Example 23

Purification of Monocytes from Human Peripheral Blood

Peripheral blood (38 mL) from an adult (age 54, male) was diluted with PBS(−) (42 mL) to make a total volume of 80 mL. 8 mL of the diluted peripheral blood was layered over 7 mL of Ficoli-Paque PREMIUM 1.073 (GE Healthcare) and centrifuged at 1800 r.p.m. for 30 minutes. Mononuclear cells comprising monocytes were recovered from the intermediate layer between Ficoll layer and the upper layer. To 2.5 mL of this fraction, 12 mL of PBS(−), 2% fetal bovine serum and 1 mM EDTA were added. The resultant mixture was centrifuged at 1000 r.p.m. for 10 minutes to remove platelets, and mononuclear cells were recovered as pellet. Further, CD14 (monocyte specific antigen) positive cells were purified from the resultant mononuclear cells magnetically using anti-CD14 antibody-bound magnetic beads (Miltenyi Biotec). The thus purified cells were stained with anti-CD14-FITC (DAKO) and subjected to flowcytometry to assay their purity. The purity after purification with Ficoli-Paque was 31% (FIG. 31A). The purity increased to 98% or more after further purification with anti-CD14 antibody-bound magnetic beads (FIG. 31B). When the finally purified cells were observed with Wright's stain, almost all of the cells retained the typical monocytic shape (FIG. 31C). Through the above-described tests, a total of $6\times10^6$ monocytes with 98% or more purity were recovered.

Example 24

Induction of iPS Marker-Expressing Cells from Human Peripheral Blood-Derived Monocytes (1) Induction of Human iPS Marker-Expressing Cells To $3\times10^5$ human monocytes isolated in Example 23, the hOct4/hSox2/hKlf4/hc-Myc sustained expression-inducing Sendai viral vector (version 1, 2.1, 3 or 4) prepared in Example 13, 20, 21 or 22 was added to give a total volume of 200 μL and allowed to infect at room temperature for 2 hours. As a comparison control, a sustained expression-inducing Sendai viral vector not loaded with reprogramming genes was used. After the infection, 500 μL of medium (RPMI 1640, 10% bovine serum) was added thereto, followed by low speed centrifugation to remove the vector. The infected monocytes were suspended in a medium for human ES cells (ReproCELL) and seeded at $1\times10^5$ cells/well/500 μL on 12-well plates in which feeder cells (mouse embryo-derived fibroblast cells pre-treated with mitomycin C) had been cultured at a density of $1.8\times10^5$ cells/well. Then, the cells were cultured at 37° C. under 5% $CO_2$ gas. Culture medium was exchanged every other day.

In human monocytes infected with the hOct4/hSox2/hKlf4/hc-Myc sustained expression-inducing Sendai viral vector, colonies of aggregating and growing cells were observed from day 5 to day 8 of culture (FIG. 32A). Such cell clusters did not appear in monocytes infected with the comparison control (i.e., sustained expression-inducing Sendai viral vector not loaded with reprogramming genes). Cells constituting these cell clusters were expressing SSEA-4 antigen and TRA-1-60 antigen, both being human iPS cell markers (FIGS. 32B and 32C).

(2) Assay of Efficiency of Colony Induction from Human Peripheral Blood-Derived Monocytes On day 8 of infection with the hOct4/hSox2/hKlf4/hc-Myc sustained expression-inducing Sendai viral vector (version 1, 2.1, 3 or 4), the number of colonies which had the shape shown in FIG. 32A were measured and divided by the number of cells seeded ($1\times10^5$) to thereby calculate the colony induction efficiency. The results are shown in Table 3.

TABLE 3

Observation of Colony Appearance Frequency in Human Peripheral Blood-Derived Monocytes Infected with hOct4/hSox2/hKlf4/hc-Myc Sustained Expression-Inducing Sendai Viral Vector (Version 1, 2.1, 3 or 4)

| Type of hOct4/hSox2/hKlf4/hc-Myc sustained expression-inducing Sendai viral vector | Number of colonies | Colony induction efficiency (%) |
|---|---|---|
| Version 1 | 381 | 0.381 |
| Version 2.1 | 342 | 0.342 |
| Version 3 | 636 | 0.636 |
| Version 4 | 85 | 0.085 |

From the results shown in Table 3, it was believed that approximately 0.1 to 0.6% of the cells (with some difference depending on the vector used) formed colonies which may potentially become iPS cells in the future.

Example 25

Preparation of Human iPS Cells by Removal of the RNA Genome of Sustained Expression-Inducing Sendai Viral Vector The human iPS marker-expressing cells that appeared in Example 24 were dissociated with trypsin and subcultured under the same culture conditions. At the same time, anti-L gene siRNA was added to the medium 3 times in total in the same manner as shown in Example 14 to thereby remove the Sendai viral vector. On day 15 of infection, the cells were subcultured using a dissociation solution for human ES cells and subjected to an additional two treatments with siRNA. On day 31 of infection, colonies with a flat shape similar to the shape of typical human ES/iPS cells appeared (FIGS. 33A and 33B). These colonies expressed Nanog (FIGS. 34A and 34B), Oct4 (FIGS. 34C and 34D), SSEA-4 antigen (FIGS. 34E and 34F), TRA-1-60 antigen (FIGS. 34G and 34H) and TRA-1-81 antigen (FIGS. 34I and 34J), all being human iPS cell markers, but they did not express the NP antigen of Sendai virus (FIGS. 34K and 34L). Thus, these colonies were confirmed to be Sendai viral vector-free human iPS cells.

Example 26

Rearrangement Analysis of T Cell Receptor Gene in Human Monocyte-Derived iPS Cells In the preparation of human peripheral blood monocyte-derived iPS cells described in Examples 23 to 25, the monocytes used for the preparation had a purity of 98% or more, suggesting an extremely high possibility that the iPS cells shown in Example 25 were derived from monocytes. However, mononuclear cells before purification with anti-CD14 antibody bound magnetic beads contain lymphocytes (T cells and B cells). In particular, it is already known that iPS cells can be prepared from T cells (Loh, et al, Cell Stem Cell, 7, 15-19, 2010; Staerk, et al., Cell Stem Cell, 7, 20-24, 2010; Seki, et al., Cell Stem Cell, 7, 11-14, 2010), so it was examined whether the iPS cells shown in Example 25 was derived from T cells or B cells that the cell material used contained at a probability of 2% or less.

First, it is known that human peripheral blood B cells is not capable of being infected with Sendai virus (Nakanishi, et al., J. Cont. Rel., 54, 61-68, 1998) and this denies the possibility that the iPS cells shown in Example 25 was derived from B cells. In order to examine whether the iPS cells shown in Example 25 were derived from T cells, rearrangement of T cell receptor gene was investigated. This technique has been established in the clinical field as a method to diagnose whether a leukemia cell of interest is derived from T cells.

The genome DNA of human iPS cells was purified with DNeasy Blood & Tissue kit (QIAGEN), and 40 ng (FIG. 35A) or 20 ng (FIG. 35B) of the purified DNA was used for the analysis. The rearrangement of T cell receptor β chain gene was analyzed by PCR according to the method described in van Dongen, et al., Leukemia, 17, 2257-2317, 2003. The rearrangement of T cell receptor γ chain gene was analyzed by PCR according to the method described in Benhattar, et al, Diagn. Mol. Pathol., 4, 108-112, 1995. The results are shown in FIG. 35.

When rearrangement has occurred in T cell receptor β chain gene, a distinct DNA band is detected at approximately 300 bp or 180 bp. In the genome DNA of the T cell-derived iPS cells used as a comparison control, rearrangement occurred and a distinct band was detected. On the other hand, no corresponding band was detected in the genome DNA of the two samples of iPS cells shown in Example 25 (FIG. 35A). Likewise, when rearrangement has occurred in T cell receptor γ chain gene, a distinct DNA band is detected at approximately 200 bp. In the genome DNA of the T cell-derived iPS cells used as a comparison control, rearrangement occurred and a distinct band was detected. On the other hand, no corresponding band was detected in the genome DNA of the two samples of iPS cells shown in Example 25 (FIG. 35B).

These results demonstrated that the iPS cells shown in Example 25 were not derived from either T cells or B cells, but derived from monocytes.

Example 27

Formation of Teratoma from Human Peripheral Blood Monocyte-Derived iPS Cells

The human peripheral blood monocyte-derived iPS cells obtained in Example 25 were adjusted to a concentration of $1.0 \times 10^6$ cells/40 µL Hepes Buffered Saline Solution (HBSS)/mouse. The testis of a mouse (C.B17/Icr-scidJc1) anesthetized with Nembutal and isoflurane was exposed, inoculated with the adjusted iPS cells, and sutured. About 8 weeks after the inoculation, a visually identifiable teratoma formed, and 60 days after inoculation, the teratoma was excised and fixed in Bouin's fixative solution (75% of saturated picric acid, 12% formalin, 3% acetic acid), and dehydrated by treating with 70% ethanol (1 hour), 90% ethanol (1 hour), 100% ethanol (1 hour, twice), 50% ethanol:50% 2-butanol solution (1 hour) and 100% 2-butanol (30 minutes, twice). The specimen was fixed in paraffin and 6 µm-thick sections were then prepared using a microtome. The sections were deparaffinized and subjected to HE staining. As a result, differentiation to all of three germ layers was observed. Thus, that human peripheral blood monocyte-derived iPS cells were confirmed to have pluripotency (FIG. 36).

Example 28

Examination of the Capacity of Human Peripheral Blood Monocyte-Derived iPS Cells to Redifferentiate to Blood Cells It is known that human iPS cells, often retaining the epigenetic characters of the somatic cell used for their preparation, tend to easily redifferentiate to cells of the same tissue as that of the original somatic cell. If human peripheral blood monocyte-derived iPS cells have a tendency to easily redifferentiate to hematopoietic progenitor cells with intact genome, such iPS cells are extremely useful in regenerative therapies, in vitro preparation of platelets, and so on. Then, using a system allowing ES cells to differentiate to blood cells in vitro (Takayama, et al., Blood, 111, 5298-5306 (2008)), human peripheral blood monocyte-derived iPS cells and human fibroblast cell-derived iPS cells were compared with respect to their tendency to differentiate to blood cells.

The human peripheral blood monocyte-derived iPS cells obtained in Example 25 and the human fibroblast cell-derived iPS cells obtained in Example 9 were allowed to redifferentiate to blood cells according to the method described in Takayama, et al., Blood, 111, 5298-5306 (2008). Briefly, iPS cells prepared in small clusters of about 100 cells were overlayered on mouse mesenchymal stem cell strain C3H10T1/2 (obtained from RIKEN BioResource Center) (in a 100 mm dish) that had been irradiated with γ rays (50 Gy) immediately before use to be deprived of proliferative capacity. The cells were cultured in a differentiation medium (Iscove modified DMEM, 10 μg/mL human insulin, 5.5 μg/mL human transferring, 5 ng/mL sodium selenite, 2 mM L-glutamine, 0.45 mM monothioglycerol, 50 μg/mL ascorbic acid, 15% FCS, VEGF 20 ng/mL) for two weeks. After two weeks, bag-like structures called iPS-sac were isolated, and the number of CD34/CD43 positive (hematopoietic progenitor cell marker positive) cells contained therein was counted by flowcytometry (FIG. 37A). The results are shown in terms of the number of CD34/CD43 positive cells appearing per $10^5$ human iPS cells.

Of the four human peripheral blood monocyte-derived iPS cell clones, three clones showed a significantly higher capacity of differentiation to hematopoietic progenitor cells than human fibroblast cell-derived iPS cells and one clone showed a comparable differentiation capacity to that of human fibroblast cell-derived iPS cells. These results revealed that human peripheral blood monocyte-derived iPS cells redifferentiated to human hematopoietic progenitor cells more easily than human fibroblast cell-derived iPS cells, although both types of iPS cells were similarly prepared using the hOct4/hSox2/hKlf4/hc-Myc sustained expression-inducing Sendai viral vector.

Further, $2\times10^4$ cells contained in the iPS-sac were re-seeded on γ ray-irradiated C3H10T1/2 cells (in a 6-well plate) and cultured in a differentiation medium containing cytokine cocktail (containing human IL-6, IL-11 and SCF; Pharmacia & Upjohn) for 3 weeks. The medium was exchanged once every 3 days. After 3 weeks, colonies of blood cells appearing therein were identified by their shapes, and the numbers of those colonies were quantitatively determined (FIG. 37B). The results are shown in terms of the numbers of colony forming unit-granulocyte/macrophage (CFU-GM), colony forming unit-erythroid (CFU-E), burst forming unit-erythroid (BFU-E) and colony forming unit-mix (CFU-Mix) appearing per $10^5$ human iPS cells, and the total of their numbers. Of the four human peripheral blood monocyte-derived iPS cell clones, three had a higher activity for producing differentiated blood cell colonies than human fibroblast cell-derived iPS cells and one clone showed a comparable activity to that of human fibroblast cell-derived iPS cells. From these results, it was confirmed that human hematopoietic progenitor cells derived from human peripheral blood monocyte-derived iPS cells have a normal capacity to differentiate to macrophages, granulocytes and erythroids.

Example 29

Gene Expression in Human Peripheral Blood Monocyte-Derived iPS Cells Established with hOct4/hSox2/hKlf4/hc-Myc Sustained Expression-Inducing Sendai Viral Vector as Compared with Gene Expression in Human Fibroblast Cell-Derived iPS Cells and Human ES Cells (1) Preparation of RNA Samples for Analysis The human peripheral blood monocyte-derived iPS cells obtained in Example 25 and the human fibroblast cell-derived iPS cells obtained in Example 9 were cultured in MEF conditioned medium on Matrigel (Becton, Dickinson and Company) without using feeder cells, and each type of cells was recovered in an amount of $1.0\times10^6$ cells. From the thus recovered cells, total cellular RNA was extracted with ISOGEN (Nippon Gene Co., Ltd.). As comparison controls, human normal fibroblast cells, human ES cells and standard human iPS cell strain 201B7 (provided by Dr. Shinya Yamanaka, Kyoto University; as prepared by introducing hOct4, hSox2, hKlf4 and hc-Myc genes with a retrovirus vector) were cultured and RNA extracted in the same manner.

(2) Analysis of Gene Expression

Total cellular RNA (0.5 μg) was labeled with Cy3 using Quick Amp Labeling Kit (Agilent Technologies, Inc.). The labeled RNA was hybridized to Whole Human Genome (4×44 k) DNA array (Agilent Technologies, Inc.) using Gene Expression Hybridization Kit (Agilent Technologies, Inc.), and signals were obtained with an Agilent DNA microarray scanner. The thus obtained signals were analyzed with GeneSpringGX10 software (Agilent Technologies, Inc.), and gene expressions in individual cell clones were analyzed by a display method called Heat Map in which the intensity of gene expression is indicated by a gradient from red to green (FIG. 38). As a result, human peripheral blood monocyte-derived iPS cells established with the hOct4/hSox2/hKlf4/hc-Myc sustained expression-inducing Sendai viral vector showed a gene expression pattern almost comparable to the corresponding patterns for human fibroblast cell-derived iPS cells prepared in the same manner, standard human iPS cell strain 201B7, and human ES cells.

Example 30

Analysis of Rearrangement of T Cell Receptor Gene in the Genome DNA of Human Peripheral Blood Monocyte-Derived iPS Cells Established with hOct4/hSox2/hKlf4/hc-Myc Sustained Expression-Inducing Sendai Viral Vector In order to confirm that the human peripheral blood monocyte-derived iPS cells obtained in Example 25 was not derived from T lymphocytes present in a small amount in the monocyte fraction used for their preparation, rearrangement of T cell receptor gene was examined. In differentiated T cells, rearrangement of T cell receptor gene has necessarily occurred and such T cells have either T cell receptor consisting of α/β chains or T cell receptor consisting of γ/δ chains. In T cells having T cell receptor consisting of α/β chains, rearrangement of β chain gene is necessarily the first to occur. Therefore, this gene was analyzed. In T cells having T cell receptor consisting of γ/δ chains, both γ chain gene and δ chain gene have been rearranged. Therefore, both genes were analyzed.

The genome DNA of human iPS cells was purified with DNeasy Blood & Tissue kit (QIAGEN), and 0.5 μg of the purified DNA was used for analysis. As positive controls, the peripheral blood whole T cell-derived genome DNA attached to the analysis kit and the genome DNA derived from a cell strain of T cells in which occurrence of rearrangement of each T cell receptor gene had been confirmed were used. As negative controls, the genome DNA of fibroblast-derived human iPS cells and the genome DNA of mouse feeder cells were used. Rearrangement of β chain gene and γ chain gene was detected with TCRB+TCRG T-Cell Clonality Assay for ABI Fluorescence Detection (InvivoScribe Technologies); and rearrangement of δ chain gene was detected with TCRD Clonality Assay for ABI Fluorescence Detection (InvivoScribe Technologies). The sizes of PCR products were analyzed with 3130 Genetic Analyzer (Applied Biosystem). In any of the genome DNAs, a specific PCR product can be detected if rearrangement has occurred in T cell receptor gene contained in the genome DNA. The results of rearrangement of β chain gene are shown in FIG. 39; the results of rearrangement of γ chain gene are shown in FIG. 40; and the results of rearrangement of δ chain gene are shown in FIG. 41. In any of the above results, no PCR product specific to rearrangement of T cell receptor gene was recognized in the genome DNA of human peripheral blood monocyte-derived iPS cells. Thus, it was confirmed that these iPS cells were not derived from T lymphocytes present in a small amount in the monocyte fraction used for their preparation.

Example 31

Analysis of Rearrangement of Immunoglobulin Heavy Chain Gene in the Genome DNA of Human Peripheral Blood Monocyte-Derived iPS Cells Established with hOct4/hSox2/hKlf4/hc-Myc Sustained Expression-Inducing Sendai Viral Vector In order to confirm that the human peripheral blood monocyte-derived iPS cells obtained in Example 25 was not derived from B lymphocytes present in a small amount in the monocyte fraction used for their preparation, the characteristic occurrence of examination was performed to check for rearrangement of immunoglobulin heavy chain gene in differentiated B cells.

The genome DNA of human iPS cells was purified with DNeasy Blood & Tissue kit (QIAGEN), and 0.5 μg of the purified DNA was used for analysis. As positive controls, the peripheral blood whole B cell-derived genome DNA attached to the analysis kit and the genome DNA derived from a cell strain of B cells in which occurrence of rearrangement had been confirmed were used. As negative controls, the genome DNA of fibroblast-derived human iPS cells and the genome DNA of mouse feeder cells were used. Rearrangement of immunoglobulin heavy chain gene was detected with IGH Gene Rearrangement Assay for ABI Fluorescence Detection (InvivoScribe Technologies). The sizes of PCR products were analyzed with 3130 Genetic Analyzer (Applied Biosystem). In any of the genome DNAs, a specific PCR product can be detected when rearrangement has occurred in immunoglobulin heavy chain gene contained in the genome DNA. The results of analysis are shown in FIG. 42. No PCR product specific to rearrangement of immunoglobulin heavy chain gene was observed in any of the samples of the genome DNA of human peripheral blood monocyte-derived iPS cells. Thus, it was confirmed that these iPS cells were not derived from B lymphocytes present in the monocyte fraction used for their preparation.

Example 32

Quantitation of Gene Expression Found in Examples 5 to 11

(a) Verification of Gene Expression by Indirect Fluorescent Antibody Method

Expressions of human Oct4, human Sox2, human Klf4, human c-Myc, mouse SSEA-1, human SSEA-4 and Sendai virus NP gene in each cell were verified using antibodies to each of the antigens. A primary antibody and a dilution rate used herein are as follows. The human Oct4: rabbit anti-Oct4 polyclonal antibody (Abcam Inc.) [×100]; the human Sox2: rabbit anti-Sox2 polyclonal antibody (Abcam Inc.) [×100]; the human Klf4: rabbit anti-Klf4 polyclonal antibody (CeMines Inc.) [×100]; the human c-Myc: rabbit anti-c-myc polyclonal antibody (Santa Cruz Biotechnology Inc.) [×100]; the SSEA-1: mouse anti-SSEA-1 monoclonal antibody (Santa Cruz Biotechnology Inc.) [×200]; the SSEA-4: mouse anti-SSEA-4 monoclonal antibody (Santa Cruz Biotechnology Inc.) [×200]; and the Sendai virus NP: mouse anti-NP monoclonal antibody [×200] or rabbit anti-NP polyclonal antibody [×1000].

(b) Alkaline Phosphatase Staining

Culture medium was first removed, and the cells were washed with PBS. Then, Vector Red Alkaline Phosphatase Kit I (Vector Laboratories Inc.) was added to the cells, and left to react at room temperatures for 20 to 30 minutes. Cells having alkaline phosphatase activity stained red.

(c) Verification of the Expression of Mouse Nanog, Mouse Oct4, Human Nanog and Sendai Virus NP Gene by Reverse Transcription-Polymerase Chain Reaction (RT-PCR) Method.

Total RNA was extracted from iPS cells using ISOGEN (Nippon Gene Co. Ltd.). cDNA was synthesized using random primer according to instructions in the SuperScript III First strand synthesis system (Life technologies, Inc.). Target cDNA was then amplified by PCR using the following primers. The mouse Nanog: 5'-GGAAGCATCGAATTCTGGGA-3' (SEQ ID NO: 18 in the Sequence Table (sense strand)), 5'-CGGAGCAGCATTCCAAGGCT-3' (SEQ ID NO: 19 in the Sequence Table (antisense strand)); the mouse Oct4: 5'-TGAGCCGTCTTTCCACCAGG-3' (SEQ ID NO: 20 in the Sequence Table (sense strand)); 5'-ACATGGTCTCCAGACTCCAC-3' (SEQ ID NO: 21 in the Sequence Table (antisense strand)); the human Nanog: 5'-AGCATCCGACTGTAAA GAAT-3' (SEQ ID NO: 22 in the Sequence Table (sense strand)), 5'-CCTCTCCACA GTTATAGAAG-3' (SEQ ID NO: 23 in the Sequence Table (antisense strand)); SeV NP: 5'-AGACCCTAAGAGGACGAAGA-3' (SEQ ID NO: 24 in the Sequence Table (sense strand)), 5'-ACTCCCATGGCGTAACTCCATAGTG-3' (SEQ ID NO: 25 in the Sequence Table (antisense strand)).

(d) Genotyping of Mouse Cell

Genomic DNA was extracted using DNeasy Tissue Kit (QIAGEN Inc.). The extracted DNA was subjected to PCR using the following primer to determine a genotype. D18Mit4: 5'-ACTGTTGCTGG GGAATGG-3' (SEQ ID NO: 26 in the Sequence Table (sense strand)), 5'-CCAAGTTCA AAGCTGCTGG-3' (SEQ ID NO: 27 in the Sequence Table (antisense strand)); D7Mit44: 5'-TTCTGGCCTCTGTGAAGTAGTG-3' (SEQ ID NO: 28 in the Sequence Table (sense strand)), 5-GTGAAACCATGGTGCAGATG-3' (SEQ ID NO: 29 in the Sequence Table (antisense strand)); and D4Mit15: 5'-AGGAATACTGAATGTGGACTTTCC-3' (SEQ ID NO: 30 in the Sequence Table (sense strand)), 5'-TCCCTTGATTAACAGAAGACCTG-3' (SEQ ID NO: 31 in the Sequence Table (antisense strand)).

While the present invention has been particularly shown and described with reference to the methods disclosed herein and as illustrated in the drawings, it is not confined to the details set forth and this invention is intended to cover any modifications and changes as may come within the scope and spirit of the following claims.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A method for producing an induced pluripotent stem cell comprising the steps of: infecting a differentiated cell with a Sendai viral vector comprising a Sendai virus NP gene, P/C gene, and L gene, wherein the L gene encodes a Sendai virus L protein in which the amino-acid residue at position 1618 is valine, and wherein said Sendai viral vector further comprises one or more genes, selected from the group consisting of: the M gene from a Sendai virus strain Cl.151; the F gene from a Sendai virus strain Cl.151; and the HN gene from a Sendai virus strain Cl.151, wherein the one or more genes are functionally-deleted by insertion or substitution with reprogramming genes, wherein the reprogramming genes comprise a combination of Oct3/4, Sox2 and Klf4, or a combination of Oct3/4, Sox2, Klf4 and c-Myc; and culturing the infected cell to induce reprogramming of the infected cell to the pluripotent stem cell, wherein the viral vector further comprises a target sequence for a microRNA, such that when a microRNA interacts with said target sequence, the viral vector is removed from the stem cell.

2. The method of claim 1, wherein the microRNA is expressed in the induced pluripotent stem cells.

3. The method of claim 1, wherein the differentiated cell is a fibroblast cell, an oral mucosal cell, a blood cell or a hair follicle epithelial cell.

4. The method of claim 3, wherein the blood cell is a peripheral blood obtained mononuclear cell.

5. The method of claim 4, wherein the peripheral blood obtained mononuclear cell is a monocyte.

6. The method of claim 4, wherein the peripheral blood-derived mononuclear cell is obtained from a human.

7. The method of claim 1, wherein the microRNA is mir-302a.

8. A method for producing an induced pluripotent stem cell comprising the steps of: infecting a differentiated cell with a reprogramming gene loaded Sendai viral vector comprising a Sendai virus NP gene, P/C gene, and L gene, wherein the L gene encodes a Sendai virus L protein in which the amino-acid residue at position 1618 is valine, and wherein said Sendai viral vector further comprises one or more genes, selected from the group consisting of: the M gene from a Sendai virus strain Cl.151; the F gene from a Sendai virus strain Cl.151; and the HN gene from a Sendai virus strain Cl.151, wherein the one or more genes are functionally-deleted by insertion or substitution with reprogramming genes, wherein the reprogramming genes comprise a combination of Oct3/4, Sox2 and Klf4, or a combination of Oct3/4, Sox2, Klf4 and c-Myc; culturing the infected cell to induce reprogramming of the infected cell to the pluripotent stem cell; and introducing an siRNA molecule into the induced pluripotent stem cell, wherein the siRNA comprises a sequence that targets said L gene in said vector, and wherein the introduction of said siRNA molecule into said induced pluripotent stem cell leads to the removal of said vector from said induced pluripotent stem cell.

9. The method of claim 8, wherein the differentiated cell is a fibroblast cell, an oral mucosal cell, a blood cell or a hair follicle epithelial cell.

10. The method of claim 9, wherein the blood cell is a peripheral blood-derived mononuclear cell.

11. The method of claim 10, wherein the peripheral blood-derived mononuclear cell is a monocyte.

12. The method of claim 10, wherein the peripheral blood-derived mononuclear cell is obtained from a human.

* * * * *

SEQUENCE LISTING

<160> NUMBER OF SEQ ID NOS: 47

<210> SEQ ID NO 1
<211> LENGTH: 2652
<212> TYPE: DNA
<213> ORGANISM: Artificial
<220> FEATURE:
<223> OTHER INFORMATION: Synthetic construct (Codon-optimaized T7 RNA polymerase)

<400> SEQUENCE: 1
atgaacacca tcaacattgc caaaaacgat ttcagcgaca ttgagctggc cgccatcccc 60
ttcaataccc tggccgatca ctacggggag cggctggcca gggagcagct ggccctggag 120
cacgagtctt acgagatggg cgaggcccgg ttccggaaaa tgtttgaacg ccagctgaaa 180
gccggagaag tggccgataa cgccgccgcc aagcctctga ttaccaccct gctgcccaag 240
atgattgccc ggattaacga ttggttcgaa gaggtgaaag ccaagagggg caagagacct 300
accgcctttc agtttctgca ggaaatcaaa cctgaagccg tggcctacat caccattaag 360
accacactgg cctgcctgac cagcgccgac aacaccacag tgcaggccgt ggccagcgcc 420
atcggcagag ccatcgagga cgaagccagg ttcgggagga tcagggatct ggaggccaag 480
cacttcaaga aaaatgtgga agagcagctg aataagcggg tgggccacgt gtacaagaag 540
gccttcatgc aggtggtgga agccgatatg ctgagcaaag gcctgctggg cggagaagcc 600
tggagctctt ggcacaagga agatagcatt cacgtgggcg tgagatgtat tgaaatgctg 660
attgagagca cagggatggt gtccctgcac cggcagaacg ccggagtggt gggccaggat 720
agcgagacca tcgagctggc cccgaatat gccgaggcca ttgccacaag agccggggcc 780
ctggccggga tctctccaat gttccagcca tgcgtggtgc ctccaaagcc atggacaggc 840
atcaccggag ggggctactg ggccaatggg cgcaggcctc tggccctggt gaggacccac 900
agcaaaaagg ccctgatgcg ctacgaggac gtgtacatgc ctgaggtgta caaagccatc 960
aacattgccc agaacaccgc ctggaagatc aacaagaaag tgctggccgt ggccaatgtg 1020
attaccaagt ggaagcactg tccagtggaa gacatccctg ccatcgagcg cgaggaactg 1080
cctatgaagc ccgaggacat tgatatgaac cccgaagccc tgacagcctg gaagagagcc 1140
gccgccgccg tgtaccgcaa agatcgcgcc cggaagtcta ggagaatttc cctggagttc 1200
atgctggagc aggccaataa gttcgccaac cacaaggcca tctggttccc ctacaatatg 1260
gattggcgcg gccgggtgta tgccgtgtcc atgttcaatc cccagggcaa cgacatgacc 1320
aaaggcctgc tgacactggc caagggcaag cccatcggca aggaaggata ttattggctg 1380
aagatccacg gcgccaattg tgccggggtg gacaaagtgc cttttcctga aaggatcaag 1440
ttcatcgagg agaaccacga gaacatcatg gcctgtgcca aatctcccct ggagaacacc 1500
tggtgggccg aacaggactc tcctttctgc tttctggcct tttgtttcga gtacgccggg 1560
gtgcagcacc acggcctgtc ctacaattgc tctctgcctc tggcctttga cggctcttgc 1620
tccgggattc agcactttag cgccatgctg cgggacgaag tgggcggaag ggccgtgaat 1680
ctgctgccct ccgaaaccgt gcaggatatc tacggcatcg tggccaagaa agtgaatgaa 1740
atcctgcagg ccgatgccat caacgggaca gataacgaag tggtgaccgt gacagacgag 1800
aatacaggcg agattagcga aaaagtgaaa ctggggacca aggccctggc cggccagtgg 1860
ctggcccacg gcgtgacaag gtctgtgacc aagcgcagcg tgatgaccct ggcctacggc 1920
tccaaagagt tcgggttcag acagcaggtg ctggaagaca caatccagcc tgccatcgac 1980

-continued

```
agcggaaagg ggcccatgtt cacccagcca aaccaggccg ccggctatat ggccaagctg   2040

atctgggaaa gcgtgtctgt gacagtggtg gccgccgtgg aggccatgaa ttggctgaag   2100

agcgccgcca agctgctggc cgccgaagtg aaagacaaga agacaggaga gattctgagg   2160

aagaggtgcg ccgtgcactg ggtgaccccca gatggattcc ccgtgtggca ggagtacaag   2220

aaaccaatcc agaccaggct gaatctgatg ttcctgggcc agtttcgcct gcagccaaca   2280

attaacacca acaaggattc cgagattgat gcccacaagc aggaatctgg catcgccccc   2340

aactttgtgc actctcagga tgggtctcac ctgaggaaga ccgtggtgtg ggcccacgaa   2400

aaatatggaa ttgagtcctt tgccctgatt cacgattcct ttggcacaat ccctgccgac   2460

gccgccaacc tgttcaaggc cgtgagagaa accatggtgg atacctacga atcttgcgat   2520

gtgctggccg atttctacga ccagttcgcc gatcagctgc acgagtccca gctggacaag   2580

atgcccgccc tgcccgccaa aggcaacctg aacctgcggg atattctgga gagcgatttt   2640

gccttcgcct aa                                                        2652
```

```
<210> SEQ ID NO 2
<211> LENGTH: 2129
<212> TYPE: DNA
<213> ORGANISM: Artificial
<220> FEATURE:
<223> OTHER INFORMATION: Synthetic construct of optimized human
      Oct4,human Sox2 and a part of Sendai virus genome cDNA

<400> SEQUENCE: 2
```

```
cctaggttcc ccatggcggg acacctggct tcggatttcg ccttctcgcc ccctccaggt     60

ggtggaggtg atgggccagg ggggccggag ccgggctggg ttgatcctcg gacctggcta    120

agcttccaag gccctcctgg agggccagga atcgggccgg gggttgggcc aggctctgag    180

gtgtggggga ttcccccatg ccccccgccg tatgagttct gtggggggat ggcgtactgt    240

gggccccagg ttggagtggg gctagtgccc caaggcggct tggagacctc tcagcctgag    300

ggcgaagcag gagtcggggt ggagagcaac tccgatgggg cctccccgga gccctgcacc    360

gtcacccctg gtgccgtgaa gctggagaag gagaagctgg agcaaaaccc ggaggagtcc    420

caggacatca aagctctgca gaaagaactc gagcaatttg ccaagctcct gaagcagaag    480

aggatcaccc tgggatatac acaggccgat gtggggctca ccctgggggt tctatttggg    540

aaggtattca gccaaacgac catctgccgc tttgaggctc tgcagcttag cttcaagaac    600

atgtgtaagc tgcggccctt gctgcagaag tgggtggagg aagctgacaa caatgaaaat    660

cttcaggaga tatgcaaagc agaaaccctc gtgcaggccc gaaagagaaa gcgaaccagt    720

atcgagaacc gagtgagagg caacctggag aatttgttcc tgcagtgccc gaaacccaca    780

ctgcagcaga tcagccacat cgcccagcag cttgggctcg agaaggatgt ggtccgagtg    840

tggttctgta accggcgcca gaagggcaag cgatcaagca gcgactatgc acaacgagag    900

gattttgagg ctgctgggtc tcctttctca gggggaccag tgtcctttcc tctggcccca    960

gggccccatt ttggtacccc aggctatggg agccctcact tcactgcact gtactcctcg   1020

gtccctttcc ctgaggggga agcctttccc cctgtctccg tcaccactct gggctctccc   1080

atgcattcaa actgaggacg tcagatctgt atataataag aaaaacttag ggtgaaagtg   1140

aggttgcgcg gtattttagc tagcccgcat gtacaacatg atggagacgg agctgaagcc   1200

gccgggcccg cagcaaactt cgggggggcgg cggcggcaac tccaccgcgg cggcggccgg   1260

cggcaaccag aaaaacagcc cggaccgcgt caagcggccc atgaatgcct tcatggtgtg   1320
```

-continued

```
gtcccgcggg cagcggcgca agatggccca ggagaacccc aagatgcaca actcggagat   1380

cagcaagcgc ctgggcgccg agtggaaact tttgtcggag acggagaagc ggccgttcat   1440

cgacgaggct aagcggctgc gagcgctgca catgaaggag cacccggatt ataaataccg   1500

gccccggcgg aaaaccaaga cgctcatgaa gaaggataag tacacgctgc ccggcgggct   1560

gctggccccc ggcggcaata gcatggcgag cggggtcggg gtgggcgccg gcctgggcgc   1620

gggcgtgaac cagcgcatgg acagttacgc gcacatgaac ggctggagca acggcagcta   1680

cagcatgatg caggaccagc tgggctaccc gcagcacccg ggcctcaatg cgcacggcgc   1740

agcgcagatg cagcccatgc accgctacga cgtgagcgcc ctgcagtaca actccatgac   1800

cagctcgcag acctacatga acggctcgcc cacctacagc atgtcctact cgcagcaggg   1860

cacccctggc atggctcttg gctccatggg ttcggtggtc aagtccgagg ccagctccag   1920

ccccccctgtg gttacctctt cctcccactc cagggcgccc tgccaggccg gggacctccg   1980

ggacatgatc agcatgtatc tccccggcgc cgaggtgccg gaacccgccg cccccagcag   2040

acttcacatg tcccagcact accagagcgg cccggtgccc ggcacggcca ttaacggcac   2100

actgcccctc tcacacatgt gagaccggt                                     2129
```

```
<210> SEQ ID NO 3
<211> LENGTH: 5851
<212> TYPE: DNA
<213> ORGANISM: Artificial
<220> FEATURE:
<223> OTHER INFORMATION: Synthetic construct of pMO078

<400> SEQUENCE: 3

gaattcgagt catcccgaga cgcgagttat gtgtttgcaa gacgtgccct aaagtctgca     60

aactatgcag agatgacatt caatgtatgc ggcctgatcc tttctgccga gaaatcttcc    120

gctcgtaagg tagatgagaa caaacaactg ctcaaacaga tccaagagag cgtggaatca    180

ttccgggata tttacaagag attctctgag tatcagaaag aacagaactc attgctgatg    240

tccaacctat ctacacttca tatcatcaca gatagaggtg gcaagactga caacacagac    300

tcccttacaa ggtccccctc cgtttttgca aaatcaaaag agaacaagac taaggctacc    360

aggtttgacc catctatgga gaccttagaa gatatgaagt acaaaccgga cctaatccga    420

gaggatgaat ttagagatga gatccgcaac ccggtgtacc aagagaggga cacagaaccc    480

agggcctcaa acgcatcacg tctcttcccc tccaaagaga agcacacaat gcactctctc    540

aggctcgtca tagagagcag tcccctaagc agagctgaga aagcagcata tgtgaaatca    600

ttatccaagt gcaagacaga ccaagaggtt aaggcagtca tggaactcgt agaagaggac    660

atagagtcac tgaccaacta gatcccgggt gaggcatccc accatcctca gtcacagaga    720

gacccaatct accatcagca tcagccagta aagattaaga aaaacttagg gtgaaagaaa    780

tgcggccgct tggcgccaga atatatgaaa acatttaaca tttctcaaca agatctagaa    840

ttagtagaag tagcgacaga gaagattaca atgctttatg aggataataa acatcatgtg    900

ggagcggcaa ttcgtacgaa aacaggagaa atcatttcgg cagtacatat tgaagcgtat    960

ataggacgag taactgtttg tgcagaagcc attgccattg gtagtgcagt ttcgaatgga   1020

caaaaggatt ttgacacgat tgtagctgtt agacaccctt attctgacga agtagataga   1080

agtattcgag tggtaagtcc ttgtggtatg tgtagggagt tgatttcaga ctatgcacca   1140

gattgttttg tgttaataga aatgaatggc aagttagtca aaactacgat tgaagaactc   1200

attccactca aatatacccg aaattaaaac gcgtcagaga cctgcaacaa tgtctcaagc   1260
```

agacaccacc tggcagtcgg agccaccggg tcactccttg tcttaaataa gaaaaactta 1320
gggataaagt cccttagatc tagcctaggg ggaccatggt gagcgtgatc aagcccgaga 1380
tgaagatgaa gtacttcatg gacggcagcg tgaacggcca cgagttcacc gtggagggcg 1440
agggcaccgg caagccctac gagggccacc aggagatgac cctgagggtg acaatggcca 1500
agggcggccc catgcccttc agcttcgacc tggtgagcca caccttctgc tacggccaca 1560
ggcccttcac caagtacccc gaggagatcc ccgactactt caagcaggcc ttccccgagg 1620
gcctgagctg ggagaggagc ctccagttcg aggacggcgg cttcgccgcc gtgagcgccc 1680
acatcagcct gaggggcaac tgcttcgagc acaagagcaa gttcgtgggc gtgaacttcc 1740
ccgccgacgg ccccgtgatg cagaaccaga gcagcgactg ggagcccagc accgagaaga 1800
tcaccacctg cgacggcgtg ctgaagggcg acgtgaccat gtacctgaag ctggccggcg 1860
gcggcaacca caagtgccag ttcaagacca cctacaaggc cgccaagaag atcctgaaga 1920
tgccccagag ccacttcatc ggccacaggc tggtgaggaa gaccgagggc aacatcaccg 1980
agctggtgga ggacgccgtg gcccactgct gaagacgtca gatctgtata taataagaaa 2040
aacttagggt gaaagtgagg ttgcgcggta ttttagctag ctgccaccat ggggaactgg 2100
gctgtgaatg aggggctctc catttttgtc attctggttt ggctggggtt gaacgtcttc 2160
ctctttgtct ggtattaccg ggtttatgat attccaccta agttctttta cacaagaaaa 2220
cttcttgggt cagcactggc actggccagg gcccctgcag cctgcctgaa tttcaactgc 2280
atgctgattc tcttgccagt ctgtcgaaat ctgctgtcct tcctcagggg ttccagtgcg 2340
tgctgctcaa caagagttcg aagacaactg gacaggaatc tcacctttca taaaatggtg 2400
gcatggatga ttgcacttca ctctgcgatt cacaccattg cacatctatt taatgtggaa 2460
tggtgtgtga atgcccgagt caataattct gatccttatt cagtagcact ctctgaactt 2520
ggagacaggc aaaatgaaag ttatctcaat tttgctcgaa agagaataaa gaaccctgaa 2580
ggaggcctgt acctggctgt gaccctgttg gcaggcatca ctggagttgt catcacgctg 2640
tgcctcatat taattatcac ttcctccacc aaaaccatcc ggaggtctta ctttgaagtc 2700
ttttggtaca cacatcatct ctttgtgatc ttcttcattg gccttgccat ccatggagct 2760
gaacgaattg tacgtgggca gaccgcagag agtttggctg tgcataatat aacagtttgt 2820
gaacaaaaaa tctcagaatg ggaaaaaata aaggaatgcc caatccctca gtttgctgga 2880
aaccctccta tgacttggaa atggatagtg ggtcccatgt ttctgtatct ctgtgagagg 2940
ttggtgcggt tttggcgatc tcaacagaag gtggtcatca ccaaggtggt cactcaccct 3000
ttcaaaacca tcgagctaca gatgaagaag aaggggttca aaatggaagt gggacaatac 3060
atttttgtca agtgcccaaa ggtgtccaag ctggagtggc accctttttac actgacatcc 3120 gcccctgagg aagacttctt tagtatccat atccgcatcg ttggggactg gacagagggg 3180
ctgttcaatg cttgtggctg tgataagcag gagtttcaag atgcgtggaa actacctaag 3240
atagcggttg atgggccctt tggcactgcc agtgaagatg tgttcagcta tgaggtggtg 3300
atgttagtgg gagcagggat tggggtcaca ccccttcgcat ccattctcaa gtcagtctgg 3360
tacaaatatt gcaataacgc caccaatctg aagctcaaaa agatctactt ctactggctg 3420
tgccgggaca cacatgcctt tgagtggttt gcagatctgc tgcaactgct ggagagccag 3480
atgcaggaaa ggaacaatgc cggcttcctc agctacaaca tctacctcac tggctgggat 3540
gagtctcagg ccaatcactt tgctgtgcac catgatgagg agaaagatgt gatcacaggc 3600

-continued

```
ctgaaacaaa agactttgta tggacggccc aactgggata atgaattcaa gacaattgca   3660

agtcaacacc ctaataccag aataggagtt ttcctctgtg gacctgaagc cttggctgaa   3720

accctgagta aacaaagcat ctccaactct gagtctggcc ctcggggagt gcatttcatt   3780

ttcaacaagg aaaacttcta acaccggtgt cggctttgct gacactagag tcatctccga   3840

acatccacaa tatctctcag tctcttacgt ctctcacagt attaagaaaa acccagggtg   3900

aatgggaagc ttgccatagg tcatggatgg gcaggagtcc tcccaaaacc cttctgacat   3960

actctatcca gaatgccacc tgaactctcc catagtcagg gggaagatag cacagttgca   4020

cgtcttgtta gatgtgaacc agccctacag actaaaggac gacagcataa taaatattac   4080

aaagcacaaa attaggaacg gaggattgtc ccctcgtcaa attaagatca ggtctctggg   4140

taaggctctt caacgcacaa taaaggattt agaccgatac acctttgaac cgtacccaac   4200

ctactctcag gaattactta ggcttgatat accagagata tgtgacaaaa tccgatccgt   4260

cttcgcggtc tcggatcggc tgaccaggga gttatctagt gggttccagg atctttggtt   4320

gaatatcttc aagcaactag gcaatataga aggaagagag gggtacgatc cgttgcagga   4380

tatcggcacc atcccggaga taactgataa atacagcagg aatagatggt ataggccatt   4440

cctaacttgg ttcagcatca aatatgacat gcggtggatg cagaagacca gaccgggggg   4500

acccctcgat acctctaatt cacataacct cctagaatgc aaatcataca ctctagtaac   4560

atacggagat cttatcatga tactgaacaa gttgacattg acagggtata tcctaacccc   4620

tgagctggtc ttgatgtatt gtgatgttgt agagggaagg tggaatatgt ctgctgcagg   4680

gcatctagat aagaagtcca ttgggataac aagcaaaggt gaggaattat gggaactagt   4740

ggattccctc ttctcaagtc ttggagagga aatatacaat gtcatcgcac tattggagcc   4800

cctatcactt gctctcatac aactaaatga tccagttata cctctacgtg gggcatttat   4860

gaggcatgtg ttgacagagc tacaggctgt tttaacaagt agggacgtgt acacagatgc   4920

tgaagcagac actattgtgg agtcgttact cgccattttc catggaacct ctattgatga   4980

gaaagcagag atcttttcct tctttaggac atttggccac cccagcttag aggctgtcac   5040

tgccgccgac aaggtaaggg cccatatgta tgcacaaaag gcaataaagc ttaagaccct   5100

atacgagtgt catgcagttt tttgcactat catcataaat gggtatagag agaggcatgg   5160

cggacagtgg cccccctgtg acttccctga tcacgtgtgt ctagaactaa ggaacgctca   5220

agggtccaat acggcaatct cttatgaatg tgctgtagac aactatacaa gtttcatagg   5280

cttcaagttt cggaagttta tagaaccaca actagatgaa gatctcacaa tatatatgaa   5340

agacaaagca ctatcccccca ggaaggaggc atgggactct gtatacccgg atagtaatct   5400

gtactataaa gccccagaat ctgaagagac ccggcggctt attgaagtgt tcataaatga   5460

tgagaatttc aacccagaag aaattatcaa ttatgtggag tcaggagatt ggttgaaaga   5520

cgagaagttc aacatctcgt acagtctcaa agagaaagag atcaagcaag agggtcgtct   5580

attcgcaaaa atgacttata agatgcgagc cgtacaggtg ctggcagaga cactactggc   5640

taaaggaata ggagagctgt tcagcgaaaa tgggatggtt aaaggagaga tagacctact   5700

taaaagattg actactcttt ctgtctcagg agtccccagg actgattcag tgtacaataa   5760

ctctaaatca tcagagaaga gaaacgaagg catgaaaaag aagaactctg gggggtactg   5820

ggacgaaaag aagaggtcca gacatgaatt c                                 5851
```

<210> SEQ ID NO 4
<211> LENGTH: 1478

<212> TYPE: DNA
<213> ORGANISM: Artificial
<220> FEATURE:
<223> OTHER INFORMATION: Synthetic construct of optimized human Klf4 and a part of Sendai virus genome cDNA

<400> SEQUENCE: 4

```
gctagcacct aggtctgaca tggctgtcag cgacgcgctg ctcccatctt tctccacgtt     60

cgcgtctggc ccggcgggaa gggagaagac actgcgtcaa gcaggtgccc cgaataaccg    120

ctggcgggag gagctctccc acatgaagcg acttccccca gtgcttcccg gccgccccta    180

tgacctggcg gcggcgaccg tggccacaga cctggagagc ggcggagccg gtgcggcttg    240

cggcggtagc aacctggcgc ccctacctcg gagagagacc gaggagttca acgatctcct    300

ggacctggac tttattctct ccaattcgct gacccatcct ccggagtcag tggccgccac    360

cgtgtcctcg tcagcgtcag cctcctcttc gtcgtcgccg tcgagcagcg gccctgccag    420

cgcgccctcc acctgcagct tcacctatcc gatccgggcc gggaacgacc cgggcgtggc    480

gccgggcggc acgggcggag gcctcctcta tggcagggag tccgctcccc ctccgacggc    540

tcccttcaac ctggcggaca tcaacgacgt gagcccctcg ggcggcttcg tggccgagct    600

cctgcggcca gaattggacc cggtgtacat tccgccgcag cagccgcagc cgccaggtgg    660

cgggctgatg ggcaagttcg tgctgaaggc gtcgctgagc gcccctggca gcgagtacgg    720

cagcccgtcg gtcatcagcg tcagcaaagg cagccctgac ggcagccacc cggtggtggt    780

ggcgccctac aacggcgggc cgccgcgcac gtgccccaag atcaagcagg aggcggtctc    840

ttcgtgcacc cacttgggcg ctggaccccc tctcagcaat ggccaccggc cggctgcaca    900

cgacttcccc ctggggcggc agctccccag caggactacc ccgaccctgg gtcttgagga    960

agtgctgagc agcagggact gtcaccctgc cctgccgctt cctcccggct tccatcccca   1020

cccggggccc aattacccat ccttcctgcc cgatcagatg cagccgcaag tcccgccgct   1080

ccattaccaa gagctcatgc cacccggttc ctgcatgcca gaggagccca agccaaagag   1140

gggaagacga tcgtggcccc ggaaaaggac cgccacccac acttgtgatt acgcgggctg   1200

cggcaaaacc tacacaaaga gttcccatct caaggcacac ctgcgaaccc acacaggtga   1260

gaaaccttac cactgtgact gggacggctg tggatggaaa ttcgcccgct cagatgaact   1320

gaccaggcac taccgtaaac acacggggca ccgcccgttc cagtgccaaa aatgcgaccg   1380

agcattttcc aggtcggacc acctcgcctt acacatgaag aggcattttt aaagacgtcg   1440

attaagaaaa acttagggtg aaagttcatc gcggccgc                           1478
```

<210> SEQ ID NO 5
<211> LENGTH: 3696
<212> TYPE: DNA
<213> ORGANISM: Artificial
<220> FEATURE:
<223> OTHER INFORMATION: Synthetic construct (A part of Sendai virus genome cDNA : XhoI-T7pro-SevcDNA-NheI-Not1)

<400> SEQUENCE: 5

```
ctcgagtaat acgactcact atagggacca aacaagagaa gaaacatgta tggaatatat     60

aatgaagtta gacaggattt tagggtcaaa gtatccaccc tgaggagcag gttccagatc    120

cttttctttg ctgccaaagt tcacgatggc cgggttgttg agcaccttcg atacatttag    180

ctctaggagg agcgaaagta ttaataagtc gggaggaggt gctgttatcc ccggccagag    240

gagcacagtc tcagtgttca tactaggccc aagtgtgact gatgatgcag acaagttatt    300
```

-continued

```
cattgcaaca accttcctag ctcactcatt ggacacagat aagcagcact ctcagagagg    360
agggttcctc gtctctctgc ttgccatggc ttacagtagt ccagaattgt acttgacaac    420
aaacggagta aacgccgatg tcaaatatgt gatctacaac atagagaaag accctaagag    480
gacgaagaca gacggattca ttgtgaagac gagagatatg gaatatgaga ggaccacaga    540
atggctgttt ggacctatgg tcaacaagag cccactcttc cagggtcaac gggatgctgc    600
agaccctgac acactccttc aaatctatgg gtatcctgca tgcctaggag caataattgt    660
ccaagtctgg attgtgctgg tgaaggccat cacaagcagc gccggcttaa ggaaagggtt    720
cttcaacagg ttagaggcgt tcagacaaga cggcaccgtg aaaggtgcct tagttttcac    780
tggggagaca gttgagggga taggctcggt tatgagatct cagcaaagcc ttgtatctct    840
catggttgag acccttgtga ctatgaatac tgcaagatct gatctcacca cattagagaa    900
gaacatccag atcgttggga actacatccg agatgcaggg ctggcttcct tcatgaacac    960
tattaaatat ggggtggaga caaagatggc agctctaacg ttgtcaaacc tgaggcccga   1020
tattaataag cttagaagcc tcatagacac ctacctgtca aaaggcccca gagctccctt   1080
tatctgtatc ctcaaggacc ctgttcatgg tgaatttgct ccaggcaatt atcctgcact   1140
atggagttac gccatgggag tcgccgtcgt acagaacaag tcaatgcagc agtacgtcac   1200
agggaggaca taccttgata tggaaatgtt cttactagga caagccgtgg caaaggatgc   1260
tgaatcgaag atcagcagtg ccttggaaga tgagttagga gtgacggata cagccaagga   1320
gaggctcaga catcatctgg caaacttgtc cggtggggat ggtgcttacc acaaaccaac   1380
aggcggtggt gcaattgagg tagctctaga caatgccgat atcgacctgg aaacagaagc   1440
tcatgcggac caggacgcta ggggttgggg tggagatagt ggtgaaagat gggcacgtca   1500
ggtgagtggt ggccactttg tcacactaca tggggctgaa cggttagagg aggaaaccaa   1560
tgatgaggat gtatcagaca tagagagaag aatagccatg agactcgcag agagacggca   1620
agaggattct gcaacccatg gagatgaagg ccgcaataac ggtgttgatc acgaagaaga   1680
tgacgatgcc gcagcagcag ctgggatagg aggaatctag gatcatacga ggcctcaagg   1740
tacttgatcc gcagtaagaa aaacttaggg tgaaagttca tccaccgatc ggctcaggca   1800
aggccacacc caaccccacc gaccacaccc agcagtcgag acagccacgg cttcggctac   1860
acttaccgca tggatcaaga tgccttcatt cttaaagaag attctgaagt tgagaggaag   1920
gcgccaggag gacgagagtc gctctcggat gttatcggat tcctcgatgc tgtcctgtcg   1980
aatgaaccaa ctgacatcgg aggggacaga agctggctcc acaacaccat caacactccc   2040
caaggaccag gctctgctca tagagccaaa agtgagggcg aaggagaagt ctcaacaccg   2100
tcgacccaag ataatcgatc aggtgaggag agtagagtct ctgggagaac aagcaagcca   2160
gaggcagaag cacatgctgg aaaccttgat aaacaaaata tacactgggc ctttagggga   2220
agaactggta caaactctgt atctcaggat ctggacgatg gaggagactc cggaatcctt   2280
gaaaatcctc caaatgagag aggatatccg agatcaggta ttgaagatga aaacagagag   2340
atggctgcgc accctgataa gaggggagaa gaccaagctg aaggacttcc agaagaggta   2400
cgaggaggta catccctacc tgatgaagga gaaggtggag caagtaataa tggaagaagc   2460
atggagcctg gcagctcaca tagtgcaaga gtaactgggg tcctggtgat tcctagcccc   2520
gaacttgaag aggctgtgct acggaggaac aaaagaagac ctaccaacag tgggtccaaa   2580
cctcttactc cagcaaccgt gcctggcacc cggtccccac cgctgaatcg ttacaacagc   2640
acagggtcac caccaggaaa acccccatct acacaggatg agcacatcaa ctctggggac   2700
```

```
acccccgccg tcagggtcaa agaccggaaa ccatcaatag ggactcgctc tgtctcagat   2760

tgtccagcca acggccgccc aatccatccg ggtatagaga ccgactcaac aaaaaagggc   2820

ataggagaga acacatcatc tatgaaagat atggctacat tgttgacgag tcttggtgta   2880

atccagtctg ctcaagaatt cgagtcatcc cgagacgcga gttatgtgtt tgcaagacgt   2940

gccctaaagt ctgcaaacta tgcagagatg acattcaatg tatgcggcct gatcctttct   3000

gccgagaaat cttccgctcg taaggtagat gagaacaaac aactgctcaa acagatccaa   3060

gagagcgtgg aatcattccg ggatatttac aagagattct ctgagtatca gaaagaacag   3120

aactcattgc tgatgtccaa cctatctaca cttcatatca tcacagatag aggtggcaag   3180

actgacaaca cagactccct tacaaggtcc ccctccgttt ttgcaaaatc aaaagagaac   3240

aagactaagg ctaccaggtt tgacccatct atggagacct tagaagatat gaagtacaaa   3300

ccggacctaa tccgagagga tgaatttaga gatgagatcc gcaacccggt gtaccaagag   3360

agggacacag aacccagggc ctcaaacgca tcacgtctct tcccctccaa agagaagccc   3420

acaatgcact ctctcaggct cgtcatagag agcagtcccc taagcagagc tgagaaagca   3480

gcatatgtga aatcattatc caagtgcaag acagaccaag aggttaaggc agtcatggaa   3540

ctcgtagaag aggacataga gtcactgacc aactagatcc cgggtgaggc atcccaccat   3600

cctcagtcac agagagaccc aatctaccat cagcatcagc cagtaaagat taagaaaaac   3660

ttagggtgaa agaaatttca ccgctagcgc ggccgc                             3696
```

<210> SEQ ID NO 6
<211> LENGTH: 14760
<212> TYPE: DNA
<213> ORGANISM: Artificial
<220> FEATURE:
<223> OTHER INFORMATION: Synthetic construct of template cDNA for
SeVp(Mp+Klf4,delta-M::Bsr,delta-F::Oct4,delta-HN::Sox2)

<400> SEQUENCE: 6

```
accaaacaag agaagaaaca tgtatggaat atataatgaa gttagacagg attttagggt     60

caaagtatcc accctgagga gcaggttcca gatccttttc tttgctgcca aagttcacga    120

tggccgggtt gttgagcacc ttcgatacat ttagctctag gaggagcgaa agtattaata    180

agtcgggagg aggtgctgtt atccccggcc agaggagcac agtctcagtg ttcatactag    240

gcccaagtgt gactgatgat gcagacaagt tattcattgc aacaaccttc ctagctcact    300

cattggacac agataagcag cactctcaga gaggagggtt cctcgtctct ctgcttgcca    360

tggcttacag tagtccagaa ttgtacttga caacaaacgg agtaaacgcc gatgtcaaat    420

atgtgatcta caacatagag aaagacccta agaggacgaa gacagacgga ttcattgtga    480

agacgagaga tatggaatat gagaggacca cagaatggct gtttggacct atggtcaaca    540

agagcccact cttccagggt caacgggatg ctgcagaccc tgacacactc cttcaaatct    600

atgggtatcc tgcatgccta ggagcaataa ttgtccaagt ctggattgtg ctggtgaagg    660

ccatcacaag cagcgccggc ttaaggaaag ggttcttcaa caggttagag gcgttcagac    720

aagacggcac cgtgaaaggt gccttagttt tcactgggga gacagttgag gggataggct    780

cggttatgag atctcagcaa agccttgtat ctctcatggt tgagaccctt gtgactatga    840

atactgcaag atctgatctc accacattag agaagaacat ccagatcgtt gggaactaca    900

tccgagatgc agggctggct tccttcatga acactattaa atatggggtg gagacaaaga    960

tggcagctct aacgttgtca aacctgaggc ccgatattaa taagcttaga agcctcatag   1020
```

-continued acacctacct gtcaaaaggc cccagagctc cctttatctg tatcctcaag gaccctgttc 1080
atggtgaatt tgctccaggc aattatcctg cactatggag ttacgccatg ggagtcgccg 1140
tcgtacagaa caagtcaatg cagcagtacg tcacagggag gacatacctt gatatggaaa 1200
tgttcttact aggacaagcc gtggcaaagg atgctgaatc gaagatcagc agtgccttgg 1260
aagatgagtt aggagtgacg gatacagcca aggagaggct cagacatcat ctggcaaact 1320
tgtccggtgg ggatggtgct taccacaaac caacaggcgg tggtgcaatt gaggtagctc 1380
tagacaatgc cgatatcgac ctggaaacag aagctcatgc ggaccaggac gctaggggtt 1440
ggggtggaga tagtggtgaa agatgggcac gtcaggtgag tggtggccac tttgtcacac 1500
tacatggggc tgaacggtta gaggaggaaa ccaatgatga ggatgtatca gacatagaga 1560
gaagaatagc catgagactc gcagagagac ggcaagagga ttctgcaacc catggagatg 1620
aaggccgcaa taacggtgtt gatcacgaag aagatgacga tgccgcagca gcagctggga 1680
taggaggaat ctaggatcat acgaggcctc aaggtacttg atccgcagta agaaaaactt 1740
agggtgaaag ttcatccacc gatcggctca ggcaaggcca cacccaaccc caccgaccac 1800
acccagcagt cgagacagcc acggcttcgg ctacacttac cgcatggatc aagatgcctt 1860
cattcttaaa gaagattctg aagttgagag gaaggcgcca ggaggacgag agtcgctctc 1920
ggatgttatc ggattcctcg atgctgtcct gtcgaatgaa ccaactgaca tcggaggggga 1980 cagaagctgg ctccacaaca ccatcaacac tccccaagga ccaggctctg ctcatagagc 2040
caaaagtgag ggcgaaggag aagtctcaac accgtcgacc caagataatc gatcaggtga 2100
ggagagtaga gtctctggga gaacaagcaa gccagaggca gaagcacatg ctggaaacct 2160
tgataaacaa aatatacact gggcctttag ggaagaact ggtacaaact ctgtatctca 2220
ggatctggac gatggaggag actccggaat ccttgaaaat cctccaaatg agagaggata 2280
tccgagatca ggtattgaag atgaaaacag agagatggct gcgcaccctg ataagagggg 2340
agaagaccaa gctgaaggac ttccagaaga ggtacgagga ggtacatccc tacctgatga 2400
aggagaaggt ggagcaagta ataatggaag aagcatggag cctggcagct cacatagtgc 2460
aagagtaact ggggtcctgg tgattcctag ccccgaactt gaagaggctg tgctacggag 2520
gaacaaaaga agacctacca acagtgggtc caaacctctt actccagcaa ccgtgcctgg 2580
cacccggtcc ccaccgctga atcgttacaa cagcacaggg tcaccaccag gaaaaccccc 2640
atctacacag gatgagcaca tcaactctgg ggacaccccc gccgtcaggg tcaaagaccg 2700
gaaaccatca atagggactc gctctgtctc agattgtcca gccaacggcc gcccaatcca 2760
tccgggtata gagaccgact caacaaaaaa gggcatagga gagaacacat catctatgaa 2820
agatatggct acattgttga cgagtcttgg tgtaatccag tctgctcaag aattcgagtc 2880
atcccgagac gcgagttatg tgtttgcaag acgtgcccta aagtctgcaa actatgcaga 2940
gatgacattc aatgtatgcg gcctgatcct ttctgccgag aaatcttccg ctcgtaaggt 3000
agatgagaac aaacaactgc tcaaacagat ccaagagagc gtggaatcat tccgggatat 3060
ttacaagaga ttctctgagt atcagaaaga acagaactca ttgctgatgt ccaacctatc 3120
tacacttcat atcatcacag atagaggtgg caagactgac aacacagact cccttacaag 3180
gtccccctcc gtttttgcaa aatcaaaaga gaacaagact aaggctacca ggtttgaccc 3240
atctatggag accttagaag atatgaagta caaaccggac ctaatccgag aggatgaatt 3300
tagagatgag atccgcaacc cggtgtacca agagagggac acagaaccca gggcctcaaa 3360

```
cgcatcacgt ctcttcccct ccaaagagaa gcccacaatg cactctctca ggctcgtcat   3420
agagagcagt cccctaagca gagctgagaa agcagcatat gtgaaatcat tatccaagtg   3480
caagacagac caagaggtta aggcagtcat ggaactcgta gaagaggaca tagagtcact   3540
gaccaactag atcccgggtg aggcatccca ccatcctcag tcacagagag acccaatcta   3600
ccatcagcat cagccagtaa agattaagaa aaacttaggg tgaaagaaat ttcaccgcta   3660
gcacctaggt ctgacatggc tgtcagcgac gcgctgctcc catctttctc cacgttcgcg   3720
tctggcccgg cgggaaggga gaagacactg cgtcaagcag gtgccccgaa taaccgctgg   3780
cgggaggagc tctcccacat gaagcgactt cccccagtgc ttcccggccg cccctatgac   3840
ctggcggcgg cgaccgtggc cacagacctg gagagcggcg gagccggtgc ggcttgcggc   3900
ggtagcaacc tggcgcccct acctcggaga gagaccgagg agttcaacga tctcctggac   3960
ctggacttta ttctctccaa ttcgctgacc catcctccgg agtcagtggc cgccaccgtg   4020
tcctcgtcag cgtcagcctc ctcttcgtcg tcgccgtcga gcagcggccc tgccagcgcg   4080
ccctccacct gcagcttcac ctatccgatc cgggccggga acgacccggg cgtggcgccg   4140
ggcggcacgg gcggaggcct cctctatggc agggagtccg ctccccctcc gacggctccc   4200
ttcaacctgg cggacatcaa cgacgtgagc cctcgggcgg gcttcgtggc cgagctcctg   4260
cggccagaat tggacccggt gtacattccg ccgcagcagc cgcagccgcc aggtggcggg   4320
ctgatgggca agttcgtgct gaaggcgtcg ctgagcgccc ctggcagcga gtacggcagc   4380
ccgtcggtca tcagcgtcag caaaggcagc cctgacggca gccacccggt ggtggtggcg   4440
ccctacaacg gcgggccgcc gcgcacgtgc cccaagatca agcaggaggc ggtctcttcg   4500
tgcacccact tgggcgctgg acccccctctc agcaatggcc accggccggc tgcacacgac   4560
ttcccccctgg ggcggcagct ccccagcagg actaccccga ccctgggtct tgaggaagtg   4620
ctgagcagca gggactgtca ccctgccctg ccgcttcctc ccggcttcca tccccacccg   4680
gggcccaatt acccatcctt cctgcccgat cagatgcagc cgcaagtccc gccgctccat   4740
taccaagagc tcatgccacc cggttcctgc atgccagagg agcccaagcc aaagagggga   4800
agacgatcgt ggccccggaa aaggaccgcc acccacactt gtgattacgc gggctgcggc   4860
aaaacctaca caaagagttc ccatctcaag gcacacctgc gaacccacac aggtgagaaa   4920
ccttaccact gtgactggga cggctgtgga tggaaattcg cccgctcaga tgaactgacc   4980
aggcactacc gtaaacacac ggggcaccgc ccgttccagt gccaaaaatg cgaccgagca   5040
ttttccaggt cggaccacct cgccttacac atgaagaggc atttttaaag acgtcgatta   5100
agaaaaactt agggtgaaag ttcatcgcgg ccgcttggcg ccagaatata tgaaaacatt   5160
taacatttct caacaagatc tagaattagt agaagtagcg acagagaaga ttacaatgct   5220
ttatgaggat aataaacatc atgtgggagc ggcaattcgt acgaaaacag gagaaatcat   5280
ttcggcagta catattgaag cgtatatagg acgagtaact gtttgtgcag aagccattgc   5340
cattggtagt gcagtttcga atggacaaaa ggattttgac acgattgtag ctgttagaca   5400
ccccttattct gacgaagtag atagaagtat tcgagtggta agtccttgtg gtatgtgtag   5460
ggagttgatt tcagactatg caccagattg ttttgtgtta atagaaatga atggcaagtt   5520
agtcaaaact acgattgaag aactcattcc actcaaatat acccgaaatt aaaacgcgtc   5580
agagacctgc aacaatgtct caagcagaca ccacctggca gtcggagcca ccgggtcact   5640
ccttgtctta aataagaaaa acttagggat aaagtccctt agatctagcc taggttcccc   5700
atggcgggac acctggcttc ggatttcgcc ttctcgcccc ctccaggtgg tggaggtgat   5760
```

-continued

```
gggccagggg ggccggagcc gggctgggtt gatcctcgga cctggctaag cttccaaggc   5820
cctcctggag ggccaggaat cgggccgggg gttgggccag gctctgaggt gtgggggatt   5880
cccccatgcc ccccgccgta tgagttctgt ggggggatgg cgtactgtgg gccccaggtt   5940
ggagtggggc tagtgcccca aggcggcttg gagacctctc agcctgaggg cgaagcagga   6000
gtcggggtgg agagcaactc cgatggggcc tccccggagc cctgcaccgt cacccctggt   6060
gccgtgaagc tggagaagga gaagctggag caaaacccgg aggagtccca ggacatcaaa   6120
gctctgcaga aagaactcga gcaatttgcc aagctcctga agcagaagag gatcaccctg   6180
ggatatacac aggccgatgt ggggctcacc ctgggggttc tatttgggaa ggtattcagc   6240
caaacgacca tctgccgctt tgaggctctg cagcttagct tcaagaacat gtgtaagctg   6300
cggcccttgc tgcagaagtg ggtggaggaa gctgacaaca atgaaaatct tcaggagata   6360
tgcaaagcag aaaccctcgt gcaggcccga aagagaaagc gaaccagtat cgagaaccga   6420
gtgagaggca acctggagaa tttgttcctg cagtgcccga aacccacact gcagcagatc   6480
agccacatcg cccagcagct tgggctcgag aaggatgtgg tccgagtgtg gttctgtaac   6540
cggcgccaga agggcaagcg atcaagcagc gactatgcac aacgagagga ttttgaggct   6600
gctgggtctc ctttctcagg gggaccagtg tcctttcctc tggccccagg gccccatttt   6660
ggtaccccag gctatgggag ccctcacttc actgcactgt actcctcggt ccctttccct   6720
gagggggaag cctttccccc tgtctccgtc accactctgg gctctcccat gcattcaaac   6780
tgaggacgtc agatctgtat ataataagaa aaacttaggg tgaaagtgag gttgcgcggt   6840
attttagcta gcccgcatgt acaacatgat ggagacggag ctgaagccgc cgggcccgca   6900
gcaaacttcg gggggcggcg gcggcaactc caccgcggcg gcggccggcg gcaaccagaa   6960
aaacagcccg gaccgcgtca agcggcccat gaatgccttc atggtgtggt cccgcgggca   7020
gcggcgcaag atggcccagg agaaccccaa gatgcacaac tcggagatca gcaagcgcct   7080
gggcgccgag tggaaacttt tgtcggagac ggagaagcgg ccgttcatcg acgaggctaa   7140
gcggctgcga gcgctgcaca tgaaggagca cccggattat aaataccggc cccggcggaa   7200
aaccaagacg ctcatgaaga aggataagta cacgctgccc ggcgggctgc tggcccccgg   7260
cggcaatagc atggcgagcg gggtcggggt gggcgccggc ctgggcgcgg gcgtgaacca   7320
gcgcatggac agttacgcgc acatgaacgg ctggagcaac ggcagctaca gcatgatgca   7380
ggaccagctg ggctacccgc agcacccggg cctcaatgcg cacggcgcag cgcagatgca   7440
gcccatgcac cgctacgacg tgagcgccct gcagtacaac tccatgacca gctcgcagac   7500
ctacatgaac ggctcgccca cctacagcat gtcctactcg cagcagggca cccctggcat   7560
ggctcttggc tccatgggtt cggtggtcaa gtccgaggcc agctccagcc cccctgtggt   7620
tacctcttcc tcccactcca gggcgccctg ccaggccggg gacctccggg acatgatcag   7680
catgtatctc cccggcgccg aggtgccgga acccgccgcc cccagcagac ttcacatgtc   7740
ccagcactac cagagcggcc cggtgcccgg cacggccatt aacggcacac tgcccctctc   7800
acacatgtga gaccggtgtc ggctttgctg acactagagt catctccgaa catccacaat   7860
atctctcagt ctcttacgtc tctcacagta ttaagaaaaa cccagggtga atgggaagct   7920
tgccataggt catggatggg caggagtcct cccaaaaccc ttctgacata ctctatccag   7980
aatgccacct gaactctccc atagtcaggg ggaagatagc acagttgcac gtcttgttag   8040
atgtgaacca gccctacaga ctaaaggacg acagcataat aaatattaca aagcacaaaa   8100
```

-continued

```
ttaggaacgg aggattgtcc cctcgtcaaa ttaagatcag gtctctgggt aaggctcttc   8160
aacgcacaat aaaggattta gaccgataca cctttgaacc gtacccaacc tactctcagg   8220
aattacttag gcttgatata ccagagatat gtgacaaaat ccgatccgtc ttcgcggtct   8280
cggatcggct gaccagggag ttatctagtg ggttccagga tctttggttg aatatcttca   8340
agcaactagg caatatagaa ggaagagagg ggtacgatcc gttgcaggat atcggcacca   8400
tcccggagat aactgataaa tacagcagga atagatggta taggccattc ctaacttggt   8460
tcagcatcaa atatgacatg cggtggatgc agaagaccag accgggggga cccctcgata   8520
cctctaattc acataacctc ctagaatgca aatcatacac tctagtaaca tacggagatc   8580
ttatcatgat actgaacaag ttgacattga cagggtatat cctaacccct gagctggtct   8640
tgatgtattg tgatgttgta gagggaaggt ggaatatgtc tgctgcaggg catctagata   8700
agaagtccat tgggataaca agcaaaggtg aggaattatg ggaactagtg gattccctct   8760
tctcaagtct tggagaggaa atatacaatg tcatcgcact attggagccc ctatcacttg   8820
ctctcataca actaaatgat ccagttatac ctctacgtgg ggcatttatg aggcatgtgt   8880
tgacagagct acaggctgtt ttaacaagta gggacgtgta cacagatgct gaagcagaca   8940
ctattgtgga gtcgttactc gccattttcc atggaacctc tattgatgag aaagcagaga   9000
tcttttcctt ctttaggaca tttggccacc ccagcttaga ggctgtcact gccgccgaca   9060
aggtaagggc ccatatgtat gcacaaaagg caataaagct taagacccta tacgagtgtc   9120
atgcagtttt ttgcactatc atcataaatg ggtatagaga gaggcatggc ggacagtggc   9180
ccccctgtga cttccctgat cacgtgtgtc tagaactaag gaacgctcaa gggtccaata   9240
cggcaatctc ttatgaatgt gctgtagaca actatacaag tttcataggc ttcaagtttc   9300
ggaagtttat agaaccacaa ctagatgaag atctcacaat atatatgaaa gacaaagcac   9360
tatcccccag gaaggaggca tgggactctg tatacccgga tagtaatctg tactataaag   9420
ccccagaatc tgaagagacc cggcggctta ttgaagtgtt cataaatgat gagaatttca   9480
acccagaaga aattatcaat tatgtggagt caggagattg gttgaaagac gagaagttca   9540
acatctcgta cagtctcaaa gagaaagaga tcaagcaaga gggtcgtcta ttcgcaaaaa   9600
tgacttataa gatgcgagcc gtacaggtgc tggcagagac actactggct aaaggaatag   9660
gagagctgtt cagcgaaaat gggatggtta aaggagagat agacctactt aaaagattga   9720
ctactctttc tgtctcagga gtccccagga ctgattcagt gtacaataac tctaaatcat   9780
cagagaagag aaacgaaggc atgaaaaaga agaactctgg ggggtactgg gacgaaaaga   9840
agaggtccag acatgaattc aaggcaacag attcatcaac agacggctat gaaacgttaa   9900
gttgcttcct cacaacagac ctcaagaaat actgcttaaa ctggagattt gaaagtactg   9960
cattgtttgg tcagagatgc aacgagatat ttggcttcaa gaccttcttt aactggatgc  10020
atccagtcct tgaaaggtgt acaatatatg ttggggatcc ttactgtcca gtcgccgacc  10080
ggatgcatcg acaactccag gatcatgcag actctggcat tttcatacat aatcctaggg  10140
ggggcataga aggttactgc cagaagctgt ggaccttaat ctcaatcagt gcaatccacc  10200
tagcagctgt gagagtgggt gtcagggtct ctgcaatggt tcagggtgac aatcaagcta  10260
tagccgtgac atcaagagta cctgtagctc agacttacaa gcagaagaaa aatcatgtct  10320
ataaggagat caccaaatat tttggtgctc taagacacgt catgtttgat gtagggcacg  10380
agctaaaatt gaacgagacc atcattagta gcaagatgtt tgtctatagt aaaagaatat  10440
actatgatgg gaagatttta ccacagtgcc tgaaagcctt gaccaggtgt gtattctggt  10500
```

ccgagacact ggtagatgaa aacagatctg cttgttcgaa catctcaaca tccatagcaa 10560
aagctatcga aaatgggtat tctcctatac taggctactg cattgcgttg tataagacct 10620
gtcagcaggt gtgcatatca ctagggatga ctataaatcc aactatcagc ccgaccgtaa 10680
gagatcaata ctttaagggt aagaattggc tgagatgtgc agtgttgatt ccagcaaatg 10740
ttggaggatt caactacatg tctacatcta gatgctttgt tagaaatatt ggagaccccg 10800
cagtagcagc cctagctgat ctcaaaagat tcatcagagc ggatctgtta gacaagcagg 10860
tactatacag ggtcatgaat caagaacccg gtgactctag ctttctagat tgggcttcag 10920
acccttattc atgtaacctc ccgcattctc agagtataac tacgattata aagaatatca 10980
ctgctagatc tgtgctgcag gaatccccga atcctctact gtctggtctc ttcaccgaga 11040
ctagtggaga agaggatctc aacctggcct cgttccttat ggaccggaaa gtcatcctgc 11100
cgagagtggc tcatgagatc ctgggtaatt ccttaactgg agttagggag gcgattgcag 11160
ggatgcttga tacgaccaag tctctagtga gatccagcgt taagaaagga ggattatcat 11220
atgggatatt gaggaggctt gtcaattatg atctattgca gtacgagaca ctgactagaa 11280
ctctcaggaa accggtgaaa gacaacatcg aatatgagta tatgtgttca gttgagctag 11340
ctgtcggtct aaggcagaaa atgtggatcc acctaactta cgggagaccc atacatgggc 11400
tagaaacacc agacccttta gagctcttga ggggaacatt tatcgaaggt tcagaggtgt 11460
gcaagctttg caggtctgag ggagcagacc ccatctatac atggttctat ctccctgaca 11520
atatagacct ggacacgctt acaaacggat gtccggctat aagaatcccc tattttggat 11580
cagccactga tgaaaggtcg gaagcccaac tcgggtatgt aagaaatcta agcaaacccg 11640
caaaggctgc catccggata gctatggtgt atacgtgggc ctacgggact gatgagatat 11700
cgtggatgga agccgctctt atagcccaaa caagagctaa tctgagctta gagaatctaa 11760
agctgctgac tcctgtttca acctccacta atctatctca taggttgaaa gatacggcaa 11820
cccagatgaa gttctctagt gcaacactag tccgtgcaag tcggttcata acaatatcaa 11880
atgataacat ggcactcaaa gaagcagggg agtcgaagga tactaatctc gtgtatcagc 11940
agattatgct aactgggcta agcttgttcg agttcaatat gagatataag aaaggttcct 12000
tagggaagcc actgatattg cacttacatc ttaataacgg gtgctgtata atggagtccc 12060
cacaggaggc gaatatcccc ccaaggtcca cattagattt agagattaca caagagaaca 12120
ataaattgat ctatgatcct gatccactca aggatgtgga ccttgagcta tttagcaagg 12180
tcagagatgt tgtacataca gttgacatga cttattggtc agatgatgaa gttatcagag 12240
caaccagtat ctgtactgca atgacgatag ctgatacaat gtctcaatta gatagagaca 12300
acctaaaaga gatgatcgcg ctagtaaatg acgatgatgt caacagcctg attactgagt 12360
ttatggtgat tgatgttcct ttattttgct caacgttcgg gggtattcta gtcaatcagt 12420
ttgcatactc actctacggc ttaaacatca gaggaaggga agaaatatgg ggacatgtag 12480
tccggattct taaagatacc tcccacgcag ttctaaaagt cttatctaat gctctatctc 12540
atcccaaaat cttcaaacga ttctggaatg caggtgtcgt ggaacctgtg tatgggccta 12600
acctctcaaa tcaggacaag atactcttgg ccctctctgt ctgtgaatat tctgtggatc 12660
tattcatgca cgattggcaa gggggtgtac cgcttgagat ctttatctgt gacaatgacc 12720
cagatgtggc cgacatgagg aggtcctctt tcttggcaag acatcttgca tacctatgca 12780
gcgtggcaga gatatctagg gatgggccaa gattagaatc aatgaactct ctagagaggc 12840

```
tcgagtcact aaagagttac ctggaactca catttcttga tgacccggta ctgaggtaca    12900

gtcagttgac tggcctagtc atcaaagtat tcccatctac tttgacctat atccggaagt    12960

catctataaa agtgttaagg acaagaggta taggagtccc tgaagtctta gaagattggg    13020

atcccgaggc agataatgca ctgttagatg gtatcgcggc agaaatacaa cagaatattc    13080

ctttgggaca tcagactaga gccccttttt gggggttgag agtatccaag tcacaggtac    13140

tgcgtctccg ggggtacaag gagatcacaa gaggtgagat aggcagatca ggcgttggtc    13200

tgacgttacc attcgatgga agatatctat ctcaccagct gaggctcttt ggcatcaaca    13260

gtactagctg cttgaaagca cttgaactta cctacctatt gagcccctta gttgacaagg    13320

ataaagatag gctatatttta ggggaaggag ctggggccat gctttcctgt tatgacgcta    13380

ctcttggccc atgcatcaac tattataact caggggtata ctcttgtgat gtcaatgggc    13440

agagagagtt aaatatatat cctgctgagg tggcactggt gggaaagaaa ttaaacaatg    13500

ttactagtct gggtcaaaga gttaaagtgt tattcaacgg gaatcctggc tcgacatgga    13560

ttggaaatga tgagtgtgag gctttgattt ggaatgaatt gcagaatagc tcgataggcc    13620

tagtccactg tgacatggag ggaggagatc ataaggatga tcaagttgta ctgcatgagc    13680

attacagtgt aatccggatc gcgtatctgg tgggggatcg agacgttgtg cttataagca    13740

agattgctcc taggctgggc acggattgga ccaggcagct cagcctatat ctgagatact    13800

gggacgaggt taacctaata gtgcttaaaa catctaaccc tgcttccaca gagatgtatc    13860

tcctatcgag gcatcccaaa tctgacatta tagaggacag caagacggtg ttagctagtc    13920

tcctcccttt gtcaaaagaa gatagcatca agatagaaaa gtggatctta atagagaagg    13980

caaaggctca cgaatgggtt actcgggaat tgagagaagg aagctcttca tcagggatgc    14040

ttagacctta ccatcaagca ctgcagacgt ttggctttga accaaacttg tataaattga    14100

gcagagattt cttgtccacc atgaacatag ctgatacaca caactgcatg atagctttca    14160

acagggtttt gaaggataca atcttcgaat gggctagaat aactgagtca gataaaaggc    14220

ttaaactaac tggtaagtat gacctgtatc ctgtgagaga ttcaggcaaa ttgaagacag    14280

tttctagaag acttgtgcta tcttggatat ctttatctat gtccacaaga ttggtaactg    14340

ggtcattccc tgaccagaag tttgaagcaa gacttcaatt gggaatagtt tcattatcat    14400

cccgtgaaat caggaacctg agggttatca caaaaacttt attagaccgg tttgaggata    14460

ttatacatag tataacgtac agattcctca ccaaagaaat aaagattttg atgaagattt    14520

tagggggcagt caagatgttc ggggccaggc aaaatgaata cacgaccgtg attgatgatg    14580

gatcactggg tgatatcgag ccatatgaca gctcgtaata attagtccct atcgtgcaga    14640

acgatcgaag ctccgcggta cctggaagtc ttggactgat ccatatgaca atagtaagaa    14700

aaacttacaa gaagacaaga aaatttaaaa gaatacatat ctcttaaact cttgtctggt    14760
```

<210> SEQ ID NO 7
<211> LENGTH: 38
<212> TYPE: DNA
<213> ORGANISM: Artificial
<220> FEATURE:
<223> OTHER INFORMATION: Primer

<400> SEQUENCE: 7
actagctagc agtctgacat ggctgtcagc gacgcgct                              38

<210> SEQ ID NO 8
<211> LENGTH: 32

<212> TYPE: DNA
<213> ORGANISM: Artificial
<220> FEATURE:
<223> OTHER INFORMATION: Primer

<400> SEQUENCE: 8
ggtccacgcg tttaaaaatg cctcttcatg tg 32

<210> SEQ ID NO 9
<211> LENGTH: 1845
<212> TYPE: DNA
<213> ORGANISM: Artificial
<220> FEATURE:
<223> OTHER INFORMATION: Synthetic construct of pMO026

<400> SEQUENCE: 9
gaattcgagt catcccgaga cgcgagttat gtgtttgcaa gacgtgccct aaagtctgca 60
aactatgcag agatgacatt caatgtatgc ggcctgatcc tttctgccga gaaatcttcc 120
gctcgtaagg tagatgagaa caaacaactg ctcaaacaga tccaagagag cgtggaatca 180
ttccgggata tttacaagag attctctgag tatcagaaag aacagaactc attgctgatg 240
tccaacctat ctacacttca tatcatcaca gatagaggtg gcaagactga caacacagac 300
tcccttacaa ggtccccctc cgtttttgca aaatcaaaag agaacaagac taaggctacc 360
aggtttgacc catctatgga gaccttagaa gatatgaagt acaaaccgga cctaatccga 420
gaggatgaat ttagagatga gatccgcaac ccggtgtacc aagagaggga cacagaaccc 480
agggcctcaa acgcatcacg tctcttcccc tccaaagaga agcccacaat gcactctctc 540
aggctcgtca tagagagcag tcccctaagc agagctgaga aagcagcata tgtgaaatca 600
ttatccaagt gcaagacaga ccaagaggtt aaggcagtca tggaactcgt agaagaggac 660
atagagtcac tgaccaacta gatcccgggt gaggcatccc accatcctca gtcacagaga 720
gacccaatct accatcagca tcagccagta aagattaaga aaaacttagg gtgaaagaaa 780
tgcggccgct tgctagcaga atatatgaaa acatttaaca tttctcaaca agatctagaa 840
ttagtagaag tagcgacaga gaagattaca atgctttatg aggataataa acatcatgtg 900
ggagcggcaa ttcgtacgaa aacaggagaa atcatttcgg cagtacatat tgaagcgtat 960
ataggacgag taactgtttg tgcagaagcc attgccattg gtagtgcagt ttcgaatgga 1020
caaaaggatt ttgacacgat tgtagctgtt agacaccctt attctgacga agtagataga 1080
agtattcgag tggtaagtcc ttgtggtatg tgtagggagt tgatttcaga ctatgcacca 1140
gattgttttg tgttaataga aatgaatggc aagttagtca aaactacgat tgaagaactc 1200
attccactca aatatacccg aaattaaaac gcgtcagaga cctgcaacaa tgtctcaagc 1260
agacaccacc tggcagtcgg agccaccggg tcactccttg tcttaaataa gaaaaactta 1320
gggataaagt cccttgtgag tgcttggttg caaaactctc cccttgggaa acatgacagc 1380
atatatccgg aggtcacagt gcatctcaac atcactactg gttgttctca ccacattggt 1440
ctcgtgtcag attcccaggg atatgctctc taacataggg gtcatagtcg atgaagggaa 1500
atcactgaag atagctgggt cccacgaatc gaggtacata gtactgagtc tagttccggg 1560
ggtagacctt gagaatggat gcggaacagc tcaggttatc cagtacaaga gcctactgaa 1620
caggctgtta atcccattga gggatgcctt agatcttcag gaggctctga taactgtcac 1680
caatgatacg acacaaaatg ccggtgttcc acagttgaga ttcttcggtg ctgtgattgg 1740
tactatcgca cttggagtgg cgacatcagc acagatcacc acagggattg cactagccga 1800

-continued agcgagggag gccaaaagag acatagcgct catcaaggaa tcgat 1845

<210> SEQ ID NO 10
<211> LENGTH: 39
<212> TYPE: DNA
<213> ORGANISM: Artificial
<220> FEATURE:
<223> OTHER INFORMATION: Primer

<400> SEQUENCE: 10
actagctagc ttagacgctg gatttttttc gggtagtgg 39

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
gtccgacgtc cttacgcaca agagttccgt 30

<210> SEQ ID NO 12
<211> LENGTH: 5160
<212> TYPE: DNA
<213> ORGANISM: Artificial
<220> FEATURE:
<223> OTHER INFORMATION: Synthetic construct of pMO094(+E)Mp;Klf4 XhoI-

<400> SEQUENCE: 12
ctcgagtaat acgactcact atagggacca aacaagagaa gaaacatgta tggaatatat 60
aatgaagttt aagaaaaact tagggtcaaa gtatccaccc tgaggagcag gttccagatc 120
cttttctttg ctgccaaagt tcacgatggc cgggttgttg agcaccttcg atacatttag 180
ctctaggagg agcgaaagta ttaataagtc gggaggaggt gctgttatcc ccggccagag 240
gagcacagtc tcagtgttca tactaggccc aagtgtgact gatgatgcag acaagttatt 300
cattgcaaca accttcctag ctcactcatt ggacacagat aagcagcact ctcagagagg 360
agggttcctc gtctctctgc ttgccatggc ttacagtagt ccagaattgt acttgacaac 420
aaacggagta aacgccgatg tcaaatatgt gatctacaac atagagaaag accctaagag 480
gacgaagaca gacggattca ttgtgaagac gagagatatg gaatatgaga ggaccacaga 540
atggctgttt ggacctatgg tcaacaagag cccactcttc cagggtcaac gggatgctgc 600
agaccctgac acactccttc aaatctatgg gtatcctgca tgcctaggag caataattgt 660
ccaagtctgg attgtgctgg tgaaggccat cacaagcagc gccggcttaa ggaaagggtt 720
cttcaacagg ttagaggcgt tcagacaaga cggcaccgtg aaaggtgcct tagttttcac 780
tggggagaca gttgagggga taggctcggt tatgagatct cagcaaagcc ttgtatctct 840
catggttgag acccttgtga ctatgaatac tgcaagatct gatctcacca cattagagaa 900
gaacatccag atcgttggga actacatccg agatgcaggg ctggcttcct tcatgaacac 960
tattaaatat ggggtggaga caaagatggc agctctaacg ttgtcaaacc tgaggcccga 1020
tattaataag cttagaagcc tcatagacac ctacctgtca aaaggcccca gagctccctt 1080
tatctgtatc ctcaaggacc ctgttcatgg tgaatttgct ccaggcaatt atcctgcact 1140
atggagttac gccatgggag tcgccgtcgt acagaacaag tcaatgcagc agtacgtcac 1200
agggaggaca taccttgata tggaaatgtt cttactagga caagccgtgg caaaggatgc 1260
tgaatcgaag atcagcagtg ccttggaaga tgagttagga gtgacggata cagccaagga 1320

-continued

```
gaggctcaga catcatctgg caaacttgtc cggtggggat ggtgcttacc acaaaccaac   1380
aggcggtggt gcaattgagg tagctctaga caatgccgat atcgacctgg aaacagaagc   1440
tcatgcggac caggacgcta ggggttgggg tggagatagt ggtgaaagat gggcacgtca   1500
ggtgagtggt ggccactttg tcacactaca tggggctgaa cggttagagg aggaaaccaa   1560
tgatgaggat gtatcagaca tagagagaag aatagccatg agactcgcag agagacggca   1620
agaggattct gcaacccatg gagatgaagg ccgcaataac ggtgttgatc acgaagaaga   1680
tgacgatgcc gcagcagcag ctgggatagg aggaatctag gatcatacga ggcctcaagg   1740
tacttgatcc gcagtaagaa aaacttaggg tgaaagttca tccaccgatc ggctcaggca   1800
aggccacacc caaccccacc gaccacaccc agcagtcgag acagccacgg cttcggctac   1860
acttaccgca tggatcaaga tgccttcatt cttaaagaag attctgaagt tgagaggaag   1920
gcgccaggag gacgagagtc gctctcggat gttatcggat tcctcgatgc tgtcctgtcg   1980
aatgaaccaa ctgacatcgg aggggacaga agctggctcc acaacaccat caacactccc   2040
caaggaccag gctctgctca tagagccaaa agtgagggcg aaggagaagt ctcaacaccg   2100
tcgacccaag ataatcgatc aggtgaggag agtagagtct ctgggagaac aagcaagcca   2160
gaggcagaag cacatgctgg aaaccttgat aaacaaaata tacactgggc ctttaggga   2220
agaactggta caaactctgt atctcaggat ctggacgatg gaggagactc cggaatcctt   2280
gaaaatcctc caaatgagag aggatatccg agatcaggta ttgaagatga aaacagagag   2340
atggctgcgc accctgataa gaggggagaa gaccaagctg aaggacttcc agaagaggta   2400
cgaggaggta catccctacc tgatgaagga gaaggtggag caagtaataa tggaagaagc   2460
atggagcctg gcagctcaca tagtgcaaga gtaactgggg tcctggtgat tcctagcccc   2520
gaacttgaag aggctgtgct acggaggaac aaaagaagac ctaccaacag tgggtccaaa   2580
cctcttactc cagcaaccgt gcctggcacc cggtccccac cgctgaatcg ttacaacagc   2640
acagggtcac caccaggaaa acccccatct acacaggatg agcacatcaa ctctggggac   2700
acccccgccg tcagggtcaa agaccggaaa ccatcaatag ggactcgctc tgtctcagat   2760
tgtccagcca acggccgccc aatccatccg ggtatagaga ccgactcaac aaaaaagggc   2820
ataggagaga acacatcatc tatgaaagat atggctacat tgttgacgag tcttggtgta   2880
atccagtctg ctcaagaatt cgagtcatcc cgagacgcga gttatgtgtt tgcaagacgt   2940
gccctaaagt ctgcaaacta tgcagagatg acattcaatg tatgcggcct gatcctttct   3000
gccgagaaat cttccgctcg taaggtagat gagaacaaac aactgctcaa acagatccaa   3060
gagagcgtgg aatcattccg ggatatttac aagagattct ctgagtatca gaaagaacag   3120
aactcattgc tgatgtccaa cctatctaca cttcatatca tcacagatag aggtggcaag   3180
actgacaaca cagactccct tacaaggtcc ccctccgttt ttgcaaaatc aaaagagaac   3240
aagactaagg ctaccaggtt tgacccatct atggagacct tagaagatat gaagtacaaa   3300
ccggacctaa tccgagagga tgaatttaga gatgagatcc gcaacccggt gtaccaagag   3360
agggacacag aacccagggc ctcaaacgca tcacgtctct tcccctccaa agagaagccc   3420
acaatgcact ctctcaggct cgtcatagag agcagtcccc taagcagagc tgagaaagca   3480
gcatatgtga aatcattatc caagtgcaag acagaccaag aggttaaggc agtcatggaa   3540
ctcgtagaag aggacataga gtcactgacc aactagatcc cgggtgaggc atcccaccat   3600
cctcagtcac agagagaccc aatctaccat cagcatcagc cagtaaagat taagaaaaac   3660
```

ttagggtgaa agaaatttca ccgctagcac ctaggtctga catggctgtc agcgacgcgc 3720
tgctcccatc tttctccacg ttcgcgtctg gcccggcggg aagggagaag acactgcgtc 3780
aagcaggtgc cccgaataac cgctggcggg aggagctctc ccacatgaag cgacttcccc 3840
cagtgcttcc cggccgcccc tatgacctgg cggcggcgac cgtggccaca gacctggaga 3900
gcggcggagc cggtgcggct tgcggcggta gcaacctggc gcccctacct cggagagaga 3960
ccgaggagtt caacgatctc ctggacctgg actttattct ctccaattcg ctgacccatc 4020
ctccggagtc agtggccgcc accgtgtcct cgtcagcgtc agcctcctct tcgtcgtcgc 4080
cgtcgagcag cggccctgcc agcgcgccct ccacctgcag cttcacctat ccgatccggg 4140
ccgggaacga cccgggcgtg gcgccgggcg gcacgggcgg aggcctcctc tatggcaggg 4200
agtccgctcc ccctccgacg gctcccttca acctggcgga catcaacgac gtgagcccct 4260
cgggcggctt cgtggccgag ctcctgcggc cagaattgga cccggtgtac attccgccgc 4320
agcagccgca gccgccaggt ggcgggctga tgggcaagtt cgtgctgaag gcgtcgctga 4380
gcgcccctgg cagcgagtac ggcagcccgt cggtcatcag cgtcagcaaa ggcagccctg 4440
acggcagcca cccggtggtg gtggcgccct acaacggcgg gccgccgcgc acgtgcccca 4500
agatcaagca ggaggcggtc tcttcgtgca cccacttggg cgctggaccc cctctcagca 4560
atggccaccg gccggctgca cacgacttcc ccctggggcg gcagctcccc agcaggacta 4620
ccccgaccct gggtcttgag gaagtgctga gcagcaggga ctgtcaccct gccctgccgc 4680
ttcctcccgg cttccatccc cacccggggc ccaattaccc atccttcctg cccgatcaga 4740
tgcagccgca agtcccgccg ctccattacc aagagctcat gccacccggt tcctgcatgc 4800
cagaggagcc caagccaaag aggggaagac gatcgtggcc ccggaaaagg accgccaccc 4860
acacttgtga ttacgcgggc tgcggcaaaa cctacacaaa gagttcccat ctcaaggcac 4920
acctgcgaac ccacacaggt gagaaacctt accactgtga ctgggacggc tgtggatgga 4980
aattcgcccg ctcagatgaa ctgaccaggc actaccgtaa acacacgggg caccgcccgt 5040
tccagtgcca aaaatgcgac cgagcatttt ccaggtcgga ccacctcgcc ttacacatga 5100
agaggcattt ttaaagacgt cgattaagaa aaacttaggg tgaaagttca tcgcggccgc 5160

<210> SEQ ID NO 13
<211> LENGTH: 15696
<212> TYPE: DNA
<213> ORGANISM: Artificial
<220> FEATURE:
<223> OTHER INFORMATION: Synthetic construct of template cDNA for
SeVp(Mp+myc,delta-M::Klf4,delta-F::Oct4,delta-HN::Sox2)

<400> SEQUENCE: 13
accaaacaag agaagaaaca tgtatggaat atataatgaa gtttaagaaa aacttagggt 60
caaagtatcc accctgagga gcaggttcca gatccttttc tttgctgcca aagttcacga 120
tggccgggtt gttgagcacc ttcgatacat ttagctctag gaggagcgaa agtattaata 180
agtcgggagg aggtgctgtt atccccggcc agaggagcac agtctcagtg ttcatactag 240
gcccaagtgt gactgatgat gcagacaagt tattcattgc aacaaccttc ctagctcact 300
cattggacac agataagcag cactctcaga gaggagggtt cctcgtctct ctgcttgcca 360
tggcttacag tagtccagaa ttgtacttga caacaaacgg agtaaacgcc gatgtcaaat 420
atgtgatcta caacatagag aaagacccta agaggacgaa gacagacgga ttcattgtga 480
agacgagaga tatggaatat gagaggacca cagaatggct gtttggacct atggtcaaca 540

-continued

```
agagcccact cttccagggt caacgggatg ctgcagaccc tgacacactc cttcaaatct    600
atgggtatcc tgcatgccta ggagcaataa ttgtccaagt ctggattgtg ctggtgaagg    660
ccatcacaag cagcgccggc ttaaggaaag ggttcttcaa caggttagag gcgttcagac    720
aagacggcac cgtgaaaggt gccttagttt tcactgggga gacagttgag gggataggct    780
cggttatgag atctcagcaa agccttgtat ctctcatggt tgagaccctt gtgactatga    840
atactgcaag atctgatctc accacattag agaagaacat ccagatcgtt gggaactaca    900
tccgagatgc agggctggct tccttcatga acactattaa atatggggtg gagacaaaga    960
tggcagctct aacgttgtca aacctgaggc ccgatattaa taagcttaga agcctcatag   1020
acacctacct gtcaaaaggc cccagagctc cctttatctg tatcctcaag gaccctgttc   1080
atggtgaatt tgctccaggc aattatcctg cactatggag ttacgccatg ggagtcgccg   1140
tcgtacagaa caagtcaatg cagcagtacg tcacagggag gacatacctt gatatggaaa   1200
tgttcttact aggacaagcc gtggcaaagg atgctgaatc gaagatcagc agtgccttgg   1260
aagatgagtt aggagtgacg gatacagcca aggagaggct cagacatcat ctggcaaact   1320
tgtccggtgg ggatggtgct taccacaaac caacaggcgg tggtgcaatt gaggtagctc   1380
tagacaatgc cgatatcgac ctggaaacag aagctcatgc ggaccaggac gctaggggtt   1440
ggggtggaga tagtggtgaa agatgggcac gtcaggtgag tggtggccac tttgtcacac   1500
tacatggggc tgaacggtta gaggaggaaa ccaatgatga ggatgtatca gacatagaga   1560
gaagaatagc catgagactc gcagagagac ggcaagagga ttctgcaacc catggagatg   1620
aaggccgcaa taacggtgtt gatcacgaag aagatgacga tgccgcagca gcagctggga   1680
taggaggaat ctaggatcat acgaggcctc aaggtacttg atccgcagta agaaaaactt   1740
agggtgaaag ttcatccacc gatcggctca ggcaaggcca cacccaaccc caccgaccac   1800
acccagcagt cgagacagcc acggcttcgg ctacacttac cgcatggatc aagatgcctt   1860
cattcttaaa gaagattctg aagttgagag gaaggcgcca ggaggacgag agtcgctctc   1920
ggatgttatc ggattcctcg atgctgtcct gtcgaatgaa ccaactgaca tcggaggga    1980
cagaagctgg ctccacaaca ccatcaacac tccccaagga ccaggctctg ctcatagagc   2040
caaaagtgag ggcgaaggag aagtctcaac accgtcgacc caagataatc gatcaggtga   2100
ggagagtaga gtctctggga gaacaagcaa gccagaggca gaagcacatg ctggaaacct   2160
tgataaacaa aatatacact gggcctttag gggaagaact ggtacaaact ctgtatctca   2220
ggatctggac gatggaggag actccggaat ccttgaaaat cctccaaatg agagaggata   2280
tccgagatca ggtattgaag atgaaaacag agagatggct gcgcaccctg ataagagggg   2340
agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
atctacacag gatgagcaca tcaactctgg ggacaccccc gccgtcaggg tcaaagaccg   2700
gaaaccatca atagggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
```

-continued

```
gatgacattc aatgtatgcg gcctgatcct ttctgccgag aaatcttccg ctcgtaaggt   3000
agatgagaac aaacaactgc tcaaacagat ccaagagagc gtggaatcat tccgggatat   3060
ttacaagaga ttctctgagt atcagaaaga acagaactca ttgctgatgt ccaacctatc   3120
tacacttcat atcatcacag atagaggtgg caagactgac aacacagact cccttacaag   3180
gtccccctcc gtttttgcaa aatcaaaaga gaacaagact aaggctacca ggtttgaccc   3240
atctatggag accttagaag atatgaagta caaaccggac ctaatccgag aggatgaatt   3300
tagagatgag atccgcaacc cggtgtacca agagagggac acagaaccca gggcctcaaa   3360
cgcatcacgt ctcttcccct ccaaagagaa gcccacaatg cactctctca ggctcgtcat   3420
agagagcagt cccctaagca gagctgagaa agcagcatat gtgaaatcat tatccaagtg   3480
caagacagac caagaggtta aggcagtcat ggaactcgta gaagaggaca tagagtcact   3540
gaccaactag atcccgggtg aggcatccca ccatcctcag tcacagagag acccaatcta   3600
ccatcagcat cagccagtaa agattaagaa aaacttaggg tgaaagaaat ttcaccgcta   3660
gcttagacgc tggatttttt tcgggtagtg gaaaaccagc agcctcccgc gacgatgccc   3720
ctcaacgtta gcttcaccaa caggaactat gacctcgact acgactcggt gcagccgtat   3780
ttctactgcg acgaggagga gaacttctac cagcagcagc agcagagcga gctgcagccc   3840
ccggcgccca gcgaggatat ctggaagaaa ttcgagctgc tgcccacccc gcccctgtcc   3900
cctagccgcc gctccgggct ctgctcgccc tcctacgttg cggtcacacc cttctccctt   3960
cggggagaca acgacggcgg tggcgggagc ttctccacgg ccgaccagct ggagatggtg   4020
accgagctgc tgggaggaga catggtgaac cagagtttca tctgcgaccc ggacgacgag   4080
accttcatca aaaacatcat catccaggac tgtatgtgga gcggcttctc ggccgccgcc   4140
aagctcgtct cagagaagct ggcctcctac caggctgcgc gcaaagacag cggcagcccg   4200
aaccccgccc gcggccacag cgtctgctcc acctccagct tgtacctgca ggatctgagc   4260
gccgccgcct cagagtgcat cgacccctcg gtggtcttcc cctaccctct caacgacagc   4320
agctcgccca agtcctgcgc ctcgcaagac tccagcgcct tctctccgtc ctcggattct   4380
ctgctctcct cgacggagtc ctccccgcag ggcagccccg agcccctggt gctccatgag   4440
gagacaccgc ccaccaccag cagcgactct gaggaggaac aagaagatga ggaagaaatc   4500
gatgttgttt ctgtggaaaa gaggcaggct cctggcaaaa ggtcagagtc tggatcacct   4560
tctgctggag gccacagcaa acctcctcac agcccactgg tcctcaagag gtgccacgtc   4620
tccacacatc agcacaacta cgcagcgcct ccctccactc ggaaggacta tcctgctgcc   4680
aagagggtca agttggacag tgtcagagtc ctgagacaga tcagcaacaa ccgaaaatgc   4740
accagcccca ggtcctcgga caccgaggag aatgtcaaga ggcgaacaca caacgtcttg   4800
gagcgccaga ggaggaacga gctaaaacgg agcttttttg ccctgcgtga ccagatcccg   4860
gagttggaaa acaatgaaaa ggcccccaag gtagttatcc ttaaaaaagc cacagcatac   4920
atcctgtccg tccaagcaga ggagcaaaag ctcatttctg aagaggactt gttgcggaaa   4980
cgacgagaac agttgaaaca caaacttgaa cagctacgga actcttgtgc gtaaggacgt   5040
cgattaagaa aaacttaggg tgaaagttca tcgcggccgc ttgctagcag tctgacatgg   5100
ctgtcagcga cgcgctgctc ccatctttct ccacgttcgc gtctggcccg gcgggaaggg   5160
agaagacact gcgtcaagca ggtgccccga ataaccgctg gcgggaggag ctctcccaca   5220
tgaagcgact tcccccagtg cttcccggcc gcccctatga cctggcggcg gcgaccgtgg   5280
```

-continued

```
ccacagacct ggagagcggc ggagccggtg cggcttgcgg cggtagcaac ctggcgcccc   5340

tacctcggag agagaccgag gagttcaacg atctcctgga cctggacttt attctctcca   5400

attcgctgac ccatcctccg gagtcagtgg ccgccaccgt gtcctcgtca gcgtcagcct   5460

cctcttcgtc gtcgccgtcg agcagcggcc ctgccagcgc gccctccacc tgcagcttca   5520

cctatccgat ccgggccggg aacgacccgg gcgtggcgcc gggcggcacg ggcggaggcc   5580

tcctctatgg cagggagtcc gctccccctc cgacggctcc cttcaacctg gcggacatca   5640

acgacgtgag cccctcgggc ggcttcgtgg ccgagctcct gcggccagaa ttggacccgg   5700

tgtacattcc gccgcagcag ccgcagccgc caggtggcgg gctgatgggc aagttcgtgc   5760

tgaaggcgtc gctgagcgcc cctggcagcg agtacggcag cccgtcggtc atcagcgtca   5820

gcaaaggcag ccctgacggc agccacccgg tggtggtggc gccctacaac ggcgggccgc   5880

cgcgcacgtg ccccaagatc aagcaggagg cggtctcttc gtgcacccac ttgggcgctg   5940

gaccccctct cagcaatggc caccggccgg ctgcacacga cttcccccctg gggcggcagc   6000

tccccagcag gactaccccg accctgggtc ttgaggaagt gctgagcagc agggactgtc   6060

accctgccct gccgcttcct cccggcttcc atccccaccc ggggcccaat tacccatcct   6120

tcctgcccga tcagatgcag ccgcaagtcc cgccgctcca ttaccaagag ctcatgccac   6180

ccggttcctg catgccagag gagcccaagc caaagagggg aagacgatcg tggccccgga   6240

aaaggaccgc cacccacact tgtgattacg cgggctgcgg caaaacctac acaaagagtt   6300

cccatctcaa ggcacacctg cgaacccaca caggtgagaa accttaccac tgtgactggg   6360

acggctgtgg atggaaattc gcccgctcag atgaactgac caggcactac cgtaaacaca   6420

cggggcaccg cccgttccag tgccaaaaat gcgaccgagc attttccagg tcggaccacc   6480

tcgccttaca catgaagagg catttttaaa cgcgtcagag acctgcaaca atgtctcaag   6540

cagacaccac ctggcagtcg gagccaccgg gtcactcctt gtcttaaata agaaaaactt   6600

agggataaag tcccttagat ctagcctagg ttccccatgg cgggacacct ggcttcggat   6660

ttcgccttct cgcccccctcc aggtggtgga ggtgatgggc cagggggggcc ggagccgggc   6720

tgggttgatc ctcggacctg gctaagcttc caaggccctc ctggagggcc aggaatcggg   6780

ccgggggttg ggccaggctc tgaggtgtgg gggattcccc catgcccccc gccgtatgag   6840

ttctgtgggg ggatggcgta ctgtgggccc caggttggag tggggctagt gccccaaggc   6900

ggcttggaga cctctcagcc tgagggcgaa gcaggagtcg gggtggagag caactccgat   6960

ggggcctccc cggagccctg caccgtcacc cctggtgccg tgaagctgga gaaggagaag   7020

ctggagcaaa acccggagga gtcccaggac atcaaagctc tgcagaaaga actcgagcaa   7080

tttgccaagc tcctgaagca gaagaggatc accctgggat atacacaggc cgatgtgggg   7140

ctcaccctgg gggttctatt tgggaaggta ttcagccaaa cgaccatctg ccgctttgag   7200

gctctgcagc ttagcttcaa gaacatgtgt aagctgcggc ccttgctgca gaagtgggtg   7260

gaggaagctg acaacaatga aaatcttcag gagatatgca aagcagaaac cctcgtgcag   7320

gcccgaaaga gaaagcgaac cagtatcgag aaccgagtga gaggcaacct ggagaatttg   7380

ttcctgcagt gcccgaaacc cacactgcag cagatcagcc acatcgccca gcagcttggg   7440

ctcgagaagg atgtggtccg agtgtggttc tgtaaccggc gccagaaggg caagcgatca   7500

agcagcgact atgcacaacg agaggatttt gaggctgctg ggtctccttt ctcaggggga   7560

ccagtgtcct ttcctctggc cccagggccc cattttggta ccccaggcta tgggagccct   7620

cacttcactg cactgtactc ctcggtccct ttccctgagg gggaagcctt tccccctgtc   7680
```

-continued

```
tccgtcacca ctctgggctc tcccatgcat tcaaactgag gacgtcagat ctgtatataa   7740
taagaaaaac ttagggtgaa agtgaggttg cgcggtattt tagctagccc gcatgtacaa   7800
catgatggag acggagctga agccgccggg cccgcagcaa acttcggggg gcggcggcgg   7860
caactccacc gcggcggcgg ccggcggcaa ccagaaaaac agcccggacc gcgtcaagcg   7920
gcccatgaat gccttcatgg tgtggtcccg cgggcagcgg cgcaagatgg cccaggagaa   7980
ccccaagatg cacaactcgg agatcagcaa gcgcctgggc gccgagtgga aacttttgtc   8040
ggagacggag aagcggccgt tcatcgacga ggctaagcgg ctgcgagcgc tgcacatgaa   8100
ggagcacccg gattataaat accggccccg gcggaaaacc aagacgctca tgaagaagga   8160
taagtacacg ctgcccggcg ggctgctggc ccccggcggc aatagcatgg cgagcggggt   8220
cggggtgggc gccggcctgg gcgcgggcgt gaaccagcgc atggacagtt acgcgcacat   8280
gaacggctgg agcaacggca gctacagcat gatgcaggac cagctgggct acccgcagca   8340
cccgggcctc aatgcgcacg gcgcagcgca gatgcagccc atgcaccgct acgacgtgag   8400
cgccctgcag tacaactcca tgaccagctc gcagacctac atgaacggct cgcccaccta   8460
cagcatgtcc tactcgcagc agggcacccc tggcatggct cttggctcca tgggttcggt   8520
ggtcaagtcc gaggccagct ccagcccccc tgtggttacc tcttcctccc actccagggc   8580
gccctgccag gccggggacc tccgggacat gatcagcatg tatctccccg gcgccgaggt   8640
gccggaaccc gccgccccca gcagacttca catgtcccag cactaccaga gcggcccggt   8700
gcccggcacg gccattaacg gcacactgcc cctctcacac atgtgagacc ggtgtcggct   8760
ttgctgacac tagagtcatc tccgaacatc cacaatatct ctcagtctct tacgtctctc   8820
acagtattaa gaaaaaccca gggtgaatgg gaagcttgcc ataggtcatg gatgggcagg   8880
agtcctccca aaacccttct gacatactct atccagaatg ccacctgaac tctcccatag   8940
tcagggggaa gatagcacag ttgcacgtct tgttagatgt gaaccagccc tacagactaa   9000
aggacgacag cataataaat attacaaagc acaaaattag gaacggagga ttgtcccctc   9060
gtcaaattaa gatcaggtct ctgggtaagg ctcttcaacg cacaataaag gatttagacc   9120
gatacacctt tgaaccgtac ccaacctact ctcaggaatt acttaggctt gatataccag   9180
agatatgtga caaaatccga tccgtcttcg cggtctcgga tcggctgacc agggagttat   9240
ctagtgggtt ccaggatctt tggttgaata tcttcaagca actaggcaat atagaaggaa   9300
gagaggggta cgatccgttg caggatatcg gcaccatccc ggagataact gataaataca   9360
gcaggaatag atggtatagg ccattcctaa cttggttcag catcaaatat gacatgcggt   9420
ggatgcagaa gaccagaccg gggggacccc tcgatacctc taattcacat aacctcctag   9480
aatgcaaatc atacactcta gtaacatacg gagatcttat catgatactg aacaagttga   9540
cattgacagg gtatatccta acccctgagc tggtcttgat gtattgtgat gttgtagagg   9600
gaaggtggaa tatgtctgct gcagggcatc tagataagaa gtccattggg ataacaagca   9660
aaggtgagga attatgggaa ctagtggatt ccctcttctc aagtcttgga gaggaaatat   9720
acaatgtcat cgcactattg gagcccctat cacttgctct catacaacta aatgatccag   9780
ttatacctct acgtggggca tttatgaggc atgtgttgac agagctacag gctgttttaa   9840
caagtaggga cgtgtacaca gatgctgaag cagacactat tgtggagtcg ttactcgcca   9900
ttttccatgg aacctctatt gatgagaaag cagagatctt ttccttcttt aggacatttg   9960
gccaccccag cttagaggct gtcactgccg ccgacaaggt aagggcccat atgtatgcac  10020
```

-continued

```
aaaaggcaat aaagcttaag accctatacg agtgtcatgc agtttttgc actatcatca  10080
taaatgggta tagagagagg catggcggac agtggccccc ctgtgacttc cctgatcacg  10140
tgtgtctaga actaaggaac gctcaagggt ccaatacggc aatctcttat gaatgtgctg  10200
tagacaacta tacaagtttc ataggcttca agtttcggaa gtttatagaa ccacaactag  10260
atgaagatct cacaatatat atgaaagaca aagcactatc cccaggaag gaggcatggg  10320
actctgtata cccggatagt aatctgtact ataaagcccc agaatctgaa gagacccggc  10380
ggcttattga agtgttcata aatgatgaga atttcaaccc agaagaaatt atcaattatg  10440
tggagtcagg agattggttg aaagacgaga agttcaacat ctcgtacagt ctcaaagaga  10500
aagagatcaa gcaagagggt cgtctattcg caaaaatgac ttataagatg cgagccgtac  10560
aggtgctggc agagacacta ctggctaaag gaataggaga gctgttcagc gaaaatggga  10620
tggttaaagg agagatagac ctacttaaaa gattgactac tctttctgtc tcaggagtcc  10680
ccaggactga ttcagtgtac aataactcta aatcatcaga gaagagaaac gaaggcatga  10740
aaaagaagaa ctctgggggg tactgggacg aaaagaagag gtccagacat gaattcaagg  10800
caacagattc atcaacagac ggctatgaaa cgttaagttg cttcctcaca acagacctca  10860
agaaatactg cttaaactgg agatttgaaa gtactgcatt gtttggtcag agatgcaacg  10920
agatatttgg cttcaagacc ttctttaact ggatgcatcc agtccttgaa aggtgtacaa  10980
tatatgttgg ggatccttac tgtccagtcg ccgaccggat gcatcgacaa ctccaggatc  11040
atgcagactc tggcattttc atacataatc ctaggggggg catagaaggt tactgccaga  11100
agctgtggac cttaatctca atcagtgcaa tccacctagc agctgtgaga gtgggtgtca  11160
gggtctctgc aatggttcag ggtgacaatc aagctatagc cgtgacatca agagtacctg  11220
tagctcagac ttacaagcag aagaaaaatc atgtctataa ggagatcacc aaatattttg  11280
gtgctctaag acacgtcatg tttgatgtag ggcacgagct aaaattgaac gagaccatca  11340
ttagtagcaa gatgtttgtc tatagtaaaa gaatatacta tgatgggaag attttaccac  11400
agtgcctgaa agccttgacc aggtgtgtat tctggtccga gacactggta gatgaaaaca  11460
gatctgcttg ttcgaacatc tcaacatcca tagcaaaagc tatcgaaaat gggtattctc  11520
ctatactagg ctactgcatt gcgttgtata agacctgtca gcaggtgtgc atatcactag  11580
ggatgactat aaatccaact atcagcccga ccgtaagaga tcaatacttt aagggtaaga  11640
attggctgag atgtgcagtg ttgattccag caaatgttgg aggattcaac tacatgtcta  11700
catctagatg ctttgttaga aatattggag accccgcagt agcagcccta gctgatctca  11760
aaagattcat cagagcggat ctgttagaca agcaggtact atacagggtc atgaatcaag  11820
aacccggtga ctctagcttt ctagattggg cttcagaccc ttattcatgt aacctcccgc  11880
attctcagag tataactacg attataaaga atatcactgc tagatctgtg ctgcaggaat  11940
ccccgaatcc tctactgtct ggtctcttca ccgagactag tggagaagag gatctcaacc  12000
tggcctcgtt ccttatggac cggaaagtca tcctgccgag agtggctcat gagatcctgg  12060
gtaattcctt aactggagtt agggaggcga ttgcagggat gcttgatacg accaagtctc  12120
tagtgagatc cagcgttaag aaaggaggat tatcatatgg gatattgagg aggcttgtca  12180
attatgatct attgcagtac gagacactga ctagaactct caggaaaccg gtgaaagaca  12240
acatcgaata tgagtatatg tgttcagttg agctagctgt cggtctaagg cagaaaatgt  12300
ggatccacct aacttacggg agacccatac atgggctaga aacaccagac cctttagagc  12360
tcttgagggg aacatttatc gaaggttcag aggtgtgcaa gctttgcagg tctgagggag  12420
```

```
cagaccccat ctatacatgg ttctatctcc ctgacaatat agacctggac acgcttacaa  12480
acggatgtcc ggctataaga atcccctatt ttggatcagc cactgatgaa aggtcggaag  12540
cccaactcgg gtatgtaaga aatctaagca aacccgcaaa ggctgccatc cggatagcta  12600
tggtgtatac gtgggcctac gggactgatg agatatcgtg gatggaagcc gctcttatag  12660
cccaaacaag agctaatctg agcttagaga atctaaagct gctgactcct gtttcaacct  12720
ccactaatct atctcatagg ttgaaagata cggcaaccca gatgaagttc tctagtgcaa  12780
cactagtccg tgcaagtcgg ttcataacaa tatcaaatga taacatggca ctcaaagaag  12840
caggggagtc gaaggatact aatctcgtgt atcagcagat tatgctaact gggctaagct  12900
tgttcgagtt caatatgaga tataagaaag gttccttagg gaagccactg atattgcact  12960
tacatcttaa taacgggtgc tgtataatgg agtccccaca ggaggcgaat atcccccaa  13020
ggtccacatt agatttagag attacacaag agaacaataa attgatctat gatcctgatc  13080
cactcaagga tgtggacctt gagctattta gcaaggtcag agatgttgta catacagttg  13140
acatgactta ttggtcagat gatgaagtta tcagagcaac cagtatctgt actgcaatga  13200
cgatagctga tacaatgtct caattagata gagacaacct aaaagagatg atcgcgctag  13260
taaatgacga tgatgtcaac agcctgatta ctgagtttat ggtgattgat gttcctttat  13320
tttgctcaac gttcgggggt attctagtca atcagtttgc atactcactc tacggcttaa  13380
acatcagagg aagggaagaa atatggggac atgtagtccg gattcttaaa gatacctccc  13440
acgcagttct aaaagtctta tctaatgctc tatctcatcc caaaatcttc aaacgattct  13500
ggaatgcagg tgtcgtggaa cctgtgtatg ggcctaacct ctcaaatcag gacaagatac  13560
tcttggccct ctctgtctgt gaatattctg tggatctatt catgcacgat tggcaagggg  13620
gtgtaccgct tgagatcttt atctgtgaca atgacccaga tgtggccgac atgaggaggt  13680
cctctttctt ggcaagacat cttgcatacc tatgcagcgt ggcagagata tctagggatg  13740
ggccaagatt agaatcaatg aactctctag agaggctcga gtcactaaag agttacctgg  13800
aactcacatt tcttgatgac ccggtactga ggtacagtca gttgactggc ctagtcatca  13860
aagtattccc atctactttg acctatatcc ggaagtcatc tataaaagtg ttaaggacaa  13920
gaggtatagg agtccctgaa gtcttagaag attgggatcc cgaggcagat aatgcactgt  13980
tagatggtat cgcggcagaa atacaacaga atattccttt gggacatcag actagagccc  14040
ctttttgggg gttgagagta tccaagtcac aggtactgcg tctccggggg tacaaggaga  14100
tcacaagagg tgagataggc agatcaggcg ttggtctgac gttaccattc gatggaagat  14160
atctatctca ccagctgagg ctctttggca tcaacagtac tagctgcttg aaagcacttg  14220
aacttaccta cctattgagc cccttagttg acaaggataa agataggcta tatttagggg  14280
aaggagctgg ggccatgctt tcctgttatg acgctactct tggcccatgc atcaactatt  14340
ataactcagg ggtatactct tgtgatgtca atgggcagag agagttaaat atatatcctg  14400
ctgaggtggc actggtggga aagaaattaa acaatgttac tagtctgggt caaagagtta  14460
aagtgttatt caacgggaat cctggctcga catggattgg aaatgatgag tgtgaggctt  14520
tgatttggaa tgaattgcag aatagctcga taggcctagt ccactgtgac atggagggag  14580
gagatcataa ggatgatcaa gttgtactgc atgagcatta cagtgtaatc cggatcgcgt  14640
atctggtggg ggatcgagac gttgtgctta taagcaagat tgctcctagg ctgggcacgg  14700
attggaccag gcagctcagc ctatatctga gatactggga cgaggttaac ctaatagtgc  14760
```

```
ttaaaacatc taaccctgct tccacagaga tgtatctcct atcgaggcat cccaaatctg  14820

acattataga ggacagcaag acggtgttag ctagtctcct ccctttgtca aaagaagata  14880

gcatcaagat agaaaagtgg atcttaatag agaaggcaaa ggctcacgaa tgggttactc  14940

gggaattgag agaaggaagc tcttcatcag ggatgcttag accttaccat caagcactgc  15000

agacgtttgg ctttgaacca aacttgtata aattgagcag agatttcttg tccaccatga  15060

acatagctga tacacacaac tgcatgatag ctttcaacag ggttttgaag gatacaatct  15120

tcgaatgggc tagaataact gagtcagata aaaggcttaa actaactggt aagtatgacc  15180

tgtatcctgt gagagattca ggcaaattga agacagtttc tagaagactt gtgctatctt  15240

ggatatcttt atctatgtcc acaagattgg taactgggtc attccctgac cagaagtttg  15300

aagcaagact tcaattggga atagtttcat tatcatcccg tgaaatcagg aacctgaggg  15360

ttatcacaaa aactttatta gaccggtttg aggatattat acatagtata acgtacagat  15420

tcctcaccaa agaaataaag attttgatga agattttagg ggcagtcaag atgttcgggg  15480

ccaggcaaaa tgaatacacg accgtgattg atgatggatc actgggtgat atcgagccat  15540

atgacagctc gtaataatta gtccctatcg tgcagaacga tcgaagctcc gcggtacctg  15600

gaagtcttgg actgatccat atgacaatag taagaaaaac ttacaagaag acaagaaaat  15660

ttaaaagaat acatatctct taaactcttg tctggt                            15696


<210> SEQ ID NO 14
<211> LENGTH: 21
<212> TYPE: RNA
<213> ORGANISM: Artificial
<220> FEATURE:
<223> OTHER INFORMATION: Synthetic construct of siRNA:Sense strand

<400> SEQUENCE: 14

gguucagcau caaauaugaa g                                               21


<210> SEQ ID NO 15
<211> LENGTH: 21
<212> TYPE: RNA
<213> ORGANISM: Artificial
<220> FEATURE:
<223> OTHER INFORMATION: Synthetic construct of siRNA:Anti-sense strand

<400> SEQUENCE: 15

ucauauuuga ugcugaacca u                                               21


<210> SEQ ID NO 16
<211> LENGTH: 21
<212> TYPE: RNA
<213> ORGANISM: Artificial
<220> FEATURE:
<223> OTHER INFORMATION: Synthetic construct of siRNA:Sense strand

<400> SEQUENCE: 16

gguccagaca ugaauucaaa g                                               21


<210> SEQ ID NO 17
<211> LENGTH: 21
<212> TYPE: RNA
<213> ORGANISM: Artificial
<220> FEATURE:
<223> OTHER INFORMATION: Synthetic construct of siRNA:Anti-sense strand

<400> SEQUENCE: 17

uugaauucau gucuggacca u                                               21
```

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
ggaagcatcg aattctggga 20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
cggagcagca ttccaaggct 20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
tgagccgtct ttccaccagg 20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
acatggtctc cagactccac 20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
agcatccgac tgtaaagaat 20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
cctctccaca gttatagaag 20

<210> SEQ ID NO 24
<211> LENGTH: 20
<212> TYPE: DNA
<213> ORGANISM: Artificial
<220> FEATURE:

<223> OTHER INFORMATION: Primer

<400> SEQUENCE: 24
aagaccctaa gaggacgaag 20

<210> SEQ ID NO 25
<211> LENGTH: 25
<212> TYPE: DNA
<213> ORGANISM: Artificial
<220> FEATURE:
<223> OTHER INFORMATION: Primer

<400> SEQUENCE: 25
actcccatgg cgtaactcca tagtg 25

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
actgttgctg gggaatgg 18

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
ccaagttcaa agctgctgg 19

<210> SEQ ID NO 28
<211> LENGTH: 22
<212> TYPE: DNA
<213> ORGANISM: Artificial
<220> FEATURE:
<223> OTHER INFORMATION: Primer

<400> SEQUENCE: 28
ttctggcctc tgtgaagtag tg 22

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gtgaaaccat ggtgcagatg 20

<210> SEQ ID NO 30
<211> LENGTH: 24
<212> TYPE: DNA
<213> ORGANISM: Artificial
<220> FEATURE:
<223> OTHER INFORMATION: Primer

<400> SEQUENCE: 30
aggaatactg aatgtggact ttcc 24

<210> SEQ ID NO 31
<211> LENGTH: 23
<212> TYPE: DNA
<213> ORGANISM: Artificial
<220> FEATURE:
<223> OTHER INFORMATION: Primer

<400> SEQUENCE: 31
tcccttgatt aacagaagac ctg 23

<210> SEQ ID NO 32
<211> LENGTH: 39
<212> TYPE: DNA
<213> ORGANISM: Artificial
<220> FEATURE:
<223> OTHER INFORMATION: Primer

<400> SEQUENCE: 32
actagctagc ttagacgctg gatttttttc gggtagtgg 39

<210> SEQ ID NO 33
<211> LENGTH: 30
<212> TYPE: DNA
<213> ORGANISM: Artificial
<220> FEATURE:
<223> OTHER INFORMATION: Primer

<400> SEQUENCE: 33
gtccaccggt cttacgcaca agagttccgt 30

<210> SEQ ID NO 34
<211> LENGTH: 35
<212> TYPE: DNA
<213> ORGANISM: Artificial
<220> FEATURE:
<223> OTHER INFORMATION: Prmer

<400> SEQUENCE: 34
agtacctagg cgcatgtaca acatgatgga gacgg 35

<210> SEQ ID NO 35
<211> LENGTH: 33
<212> TYPE: DNA
<213> ORGANISM: Artificial
<220> FEATURE:
<223> OTHER INFORMATION: Primer

<400> SEQUENCE: 35
gtccgacgtc ctcacatgtg tgagaggggc agt 33

<210> SEQ ID NO 36
<211> LENGTH: 40
<212> TYPE: DNA
<213> ORGANISM: Artificial
<220> FEATURE:
<223> OTHER INFORMATION: Primer

<400> SEQUENCE: 36
actagctagc ggttccccat ggcgggacac ctggcttcgg 40

<210> SEQ ID NO 37
<211> LENGTH: 35
<212> TYPE: DNA
<213> ORGANISM: Artificial
<220> FEATURE:
<223> OTHER INFORMATION: Primer

<400> SEQUENCE: 37
ggtccacgcg ttcagtttga atgcatggga gagcc 35

<210> SEQ ID NO 38
<211> LENGTH: 15702
<212> TYPE: DNA
<213> ORGANISM: Artificial
<220> FEATURE:
<223> OTHER INFORMATION: Synthetic construct of full length genome cDNA of Sendai virus vector-version2

<400> SEQUENCE: 38
accaaacaag agaagaaaca tgtatggaat atataatgaa gttagacagg attttagggt 60
caaagtatcc accctgagga gcaggttcca gatccttttc tttgctgcca aagttcacga 120
tggccgggtt gttgagcacc ttcgatacat ttagctctag gaggagcgaa agtattaata 180
agtcgggagg aggtgctgtt atccccggcc agaggagcac agtctcagtg ttcatactag 240
gcccaagtgt gactgatgat gcagacaagt tattcattgc aacaaccttc ctagctcact 300
cattggacac agataagcag cactctcaga gaggagggtt cctcgtctct ctgcttgcca 360
tggcttacag tagtccagaa ttgtacttga caacaaacgg agtaaacgcc gatgtcaaat 420
atgtgatcta caacatagag aaagacccta agaggacgaa gacagacgga ttcattgtga 480
agacgagaga tatggaatat gagaggacca cagaatggct gtttggacct atggtcaaca 540
agagcccact cttccagggt caacgggatg ctgcagaccc tgacacactc cttcaaatct 600
atgggtatcc tgcatgccta ggagcaataa ttgtccaagt ctggattgtg ctggtgaagg 660
ccatcacaag cagcgccggc ttaaggaaag ggttcttcaa caggttagag gcgttcagac 720
aagacggcac cgtgaaaggt gccttagttt tcactgggga gacagttgag gggataggct 780
cggttatgag atctcagcaa agccttgtat ctctcatggt tgagaccctt gtgactatga 840
atactgcaag atctgatctc accacattag agaagaacat ccagatcgtt gggaactaca 900
tccgagatgc agggctggct tccttcatga acactattaa atatggggtg gagacaaaga 960
tggcagctct aacgttgtca aacctgaggc ccgatattaa taagcttaga agcctcatag 1020
acacctacct gtcaaaaggc cccagagctc cctttatctg tatcctcaag gaccctgttc 1080
atggtgaatt tgctccaggc aattatcctg cactatggag ttacgccatg ggagtcgccg 1140
tcgtacagaa caagtcaatg cagcagtacg tcacagggag gacatacctt gatatggaaa 1200
tgttcttact aggacaagcc gtggcaaagg atgctgaatc gaagatcagc agtgccttgg 1260
aagatgagtt aggagtgacg gatacagcca aggagaggct cagacatcat ctggcaaact 1320
tgtccggtgg ggatggtgct taccacaaac caacaggcgg tggtgcaatt gaggtagctc 1380
tagacaatgc cgatatcgac ctggaaacag aagctcatgc ggaccaggac gctaggggtt 1440
ggggtggaga tagtggtgaa agatgggcac gtcaggtgag tggtggccac tttgtcacac 1500
tacatggggc tgaacggtta gaggaggaaa ccaatgatga ggatgtatca gacatagaga 1560
gaagaatagc catgagactc gcagagagac ggcaagagga ttctgcaacc catggagatg 1620
aaggccgcaa taacggtgtt gatcacgaag aagatgacga tgccgcagca gcagctggga 1680
taggaggaat ctaggatcat acgaggcctc aaggtacttg atccgcagta agaaaaactt 1740
agggtgaaag ttcatccacc gatcggctca ggcaaggcca cacccaaccc caccgaccac 1800
acccagcagt cgagacagcc acggcttcgg ctacacttac cgcatggatc aagatgcctt 1860
cattcttaaa gaagattctg aagttgagag gaaggcgcca ggaggacgag agtcgctctc 1920

-continued ggatgttatc ggattcctcg atgctgtcct gtcgaatgaa ccaactgaca tcggagggga 1980
cagaagctgg ctccacaaca ccatcaacac tccccaagga ccaggctctg ctcatagagc 2040
caaaagtgag ggcgaaggag aagtctcaac accgtcgacc caagataatc gatcaggtga 2100
ggagagtaga gtctctggga gaacaagcaa gccagaggca gaagcacatg ctggaaacct 2160
tgataaacaa aatatacact gggcctttag gggaagaact ggtacaaact ctgtatctca 2220
ggatctggac gatggaggag actccggaat ccttgaaaat cctccaaatg agagaggata 2280
tccgagatca ggtattgaag atgaaaacag agagatggct gcgcaccctg ataagagggg 2340
agaagaccaa gctgaaggac ttccagaaga ggtacgagga ggtacatccc tacctgatga 2400
aggagaaggt ggagcaagta ataatggaag aagcatggag cctggcagct cacatagtgc 2460
aagagtaact ggggtcctgg tgattcctag ccccgaactt gaagaggctg tgctacggag 2520
gaacaaaaga agacctacca acagtgggtc caaacctctt actccagcaa ccgtgcctgg 2580
cacccggtcc ccaccgctga atcgttacaa cagcacaggg tcaccaccag gaaaaccccc 2640
atctacacag gatgagcaca tcaactctgg ggacaccccc gccgtcaggg tcaaagaccg 2700
gaaaccatca atagggactc gctctgtctc agattgtcca gccaacggcc gcccaatcca 2760
tccgggtata gagaccgact caacaaaaaa gggcatagga gagaacacat catctatgaa 2820
agatatggct acattgttga cgagtcttgg tgtaatccag tctgctcaag aattcgagtc 2880
atcccgagac gcgagttatg tgtttgcaag acgtgcccta aagtctgcaa actatgcaga 2940
gatgacattc aatgtatgcg gcctgatcct ttctgccgag aaatcttccg ctcgtaaggt 3000
agatgagaac aaacaactgc tcaaacagat ccaagagagc gtggaatcat tccgggatat 3060
ttacaagaga ttctctgagt atcagaaaga acagaactca ttgctgatgt ccaacctatc 3120
tacacttcat atcatcacag atagaggtgg caagactgac aacacagact cccttacaag 3180
gtccccctcc gtttttgcaa aatcaaaaga gaacaagact aaggctacca ggtttgaccc 3240
atctatggag accttagaag atatgaagta caaaccggac ctaatccgag aggatgaatt 3300
tagagatgag atccgcaacc cggtgtacca agagagggac acagaaccca gggcctcaaa 3360
cgcatcacgt ctcttcccct ccaaagagaa gcacacaatg cactctctca ggctcgtcat 3420
agagagcagt cccctaagca gagctgagaa agcagcatat gtgaaatcat tatccaagtg 3480
caagacagac caagaggtta aggcagtcat ggaactcgta gaagaggaca tagagtcact 3540
gaccaactag atcccgggtg aggcatccca ccatcctcag tcacagagag acccaatcta 3600
ccatcagcat cagccagtaa agattaagaa aaacttaggg tgaaagaaat ttcaccgcta 3660
gcacctaggt ctgacatggc tgtcagcgac gcgctgctcc catctttctc cacgttcgcg 3720
tctggcccgg cgggaaggga gaagacactg cgtcaagcag gtgccccgaa taaccgctgg 3780
cgggaggagc tctcccacat gaagcgactt cccccagtgc ttcccggccg ccccctatgac 3840 ctggcggcgg cgaccgtggc cacagacctg gagagcggcg gagccggtgc ggcttgcggc 3900
ggtagcaacc tggcgcccct acctcggaga gagaccgagg agttcaacga tctcctggac 3960
ctggacttta ttctctccaa ttcgctgacc catcctccgg agtcagtggc cgccaccgtg 4020
tcctcgtcag cgtcagcctc ctcttcgtcg tcgccgtcga gcagcggccc tgccagcgcg 4080
ccctccacct gcagcttcac ctatccgatc cgggccggga acgacccggg cgtggcgccg 4140
ggcggcacgg gcggaggcct cctctatggc agggagtccg ctccccctcc gacggctccc 4200
ttcaacctgg cggacatcaa cgacgtgagc ccctcgggcg gcttcgtggc cgagctcctg 4260
cggccagaat tggacccggt gtacattccg ccgcagcagc cgcagccgcc aggtggcggg 4320

-continued

```
ctgatgggca agttcgtgct gaaggcgtcg ctgagcgccc ctggcagcga gtacggcagc   4380
ccgtcggtca tcagcgtcag caaaggcagc cctgacggca gccacccggt ggtggtggcg   4440
ccctacaacg gcgggccgcc gcgcacgtgc cccaagatca agcaggaggc ggtctcttcg   4500
tgcacccact tgggcgctgg accccctctc agcaatggcc accggccggc tgcacacgac   4560
ttccccctgg ggcggcagct ccccagcagg actaccccga ccctgggtct tgaggaagtg   4620
ctgagcagca gggactgtca ccctgccctg ccgcttcctc ccggcttcca tccccacccg   4680
gggcccaatt acccatcctt cctgcccgat cagatgcagc cgcaagtccc gccgctccat   4740
taccaagagc tcatgccacc cggttcctgc atgccagagg agcccaagcc aaagaggga   4800
agacgatcgt ggccccggaa aaggaccgcc acccacactt gtgattacgc gggctgcggc   4860
aaaacctaca caaagagttc ccatctcaag gcacacctgc gaacccacac aggtgagaaa   4920
ccttaccact gtgactggga cggctgtgga tggaaattcg cccgctcaga tgaactgacc   4980
aggcactacc gtaaacacac ggggcaccgc ccgttccagt gccaaaaatg cgaccgagca   5040
ttttccaggt cggaccacct cgccttacac atgaagaggc atttttaaag acgtcgatta   5100
agaaaaactt agggtgaaag ttcatcgcgg ccgcttgcta gcggttcccc atggcgggac   5160
acctggcttc ggatttcgcc ttctcgcccc ctccaggtgg tggaggtgat gggccagggg   5220
ggccggagcc gggctgggtt gatcctcgga cctggctaag cttccaaggc cctcctggag   5280
ggccaggaat cgggccgggg gttgggccag gctctgaggt gtgggggatt cccccatgcc   5340
ccccgccgta tgagttctgt ggggggatgg cgtactgtgg gccccaggtt ggagtggggc   5400
tagtgcccca aggcggcttg gagacctctc agcctgaggg cgaagcagga gtcggggtgg   5460
agagcaactc cgatggggcc tccccggagc cctgcaccgt cacccctggt gccgtgaagc   5520
tggagaagga gaagctggag caaaacccgg aggagtccca ggacatcaaa gctctgcaga   5580
aagaactcga gcaatttgcc aagctcctga agcagaagag gatcaccctg ggatatacac   5640
aggccgatgt ggggctcacc ctgggggttc tatttgggaa ggtattcagc caaacgacca   5700
tctgccgctt tgaggctctg cagcttagct tcaagaacat gtgtaagctg cggcccttgc   5760
tgcagaagtg ggtggaggaa gctgacaaca atgaaaatct tcaggagata tgcaaagcag   5820
aaaccctcgt gcaggcccga aagagaaagc gaaccagtat cgagaaccga gtgagaggca   5880
acctggagaa tttgttcctg cagtgcccga aacccacact gcagcagatc agccacatcg   5940
cccagcagct tgggctcgag aaggatgtgg tccgagtgtg gttctgtaac cggcgccaga   6000
agggcaagcg atcaagcagc gactatgcac aacgagagga ttttgaggct gctgggtctc   6060
ctttctcagg gggaccagtg tcctttcctc tggccccagg gccccatttt ggtaccccag   6120
gctatgggag ccctcacttc actgcactgt actcctcggt ccctttccct gaggggggaag   6180
cctttccccc tgtctccgtc accactctgg gctctcccat gcattcaaac tgaacgcgtc   6240
agagacctgc aacaatgtct caagcagaca ccacctggca gtcggagcca ccgggtcact   6300
ccttgtctta aataagaaaa acttagggat aaagtccctt agatctagcc taggcgcatg   6360
tacaacatga tggagacgga gctgaagccg ccgggcccgc agcaaacttc ggggggcggc   6420
ggcggcaact ccaccgcggc ggcggccggc ggcaaccaga aaaacagccc ggaccgcgtc   6480
aagcggccca tgaatgcctt catggtgtgg tcccgcgggc agcggcgcaa gatggcccag   6540
gagaacccca agatgcacaa ctcggagatc agcaagcgcc tgggcgccga gtggaaactt   6600
ttgtcggaga cggagaagcg gccgttcatc gacgaggcta agcggctgcg agcgctgcac   6660
```

-continued

```
atgaaggagc acccggatta taaataccgg ccccggcgga aaaccaagac gctcatgaag   6720
aaggataagt acacgctgcc cggcgggctg ctggccccg gcggcaatag catggcgagc   6780
ggggtcgggg tgggcgccgg cctgggcgcg ggcgtgaacc agcgcatgga cagttacgcg   6840
cacatgaacg gctggagcaa cggcagctac agcatgatgc aggaccagct gggctacccg   6900
cagcacccgg gcctcaatgc gcacggcgca gcgcagatgc agcccatgca ccgctacgac   6960
gtgagcgccc tgcagtacaa ctccatgacc agctcgcaga cctacatgaa cggctcgccc   7020
acctacagca tgtcctactc gcagcagggc acccctggca tggctcttgg ctccatgggt   7080
tcggtggtca agtccgaggc cagctccagc ccccctgtgg ttacctcttc ctcccactcc   7140
agggcgccct gccaggccgg ggacctccgg gacatgatca gcatgtatct ccccggcgcc   7200
gaggtgccgg aacccgccgc ccccagcaga cttcacatgt cccagcacta ccagagcggc   7260
ccggtgcccg gcacggccat taacggcaca ctgcccctct cacacatgtg aggacgtcag   7320
atctgtatat aataagaaaa acttagggtg aaagtgaggt tgcgcggtat tttagctagc   7380
ttagacgctg gattttttttc gggtagtgga aaaccagcag cctcccgcga cgatgcccct   7440
caacgttagc ttcaccaaca ggaactatga cctcgactac gactcggtgc agccgtattt   7500
ctactgcgac gaggaggaga acttctacca gcagcagcag cagagcgagc tgcagccccc   7560
ggcgcccagc gaggatatct ggaagaaatt cgagctgctg cccaccccgc ccctgtcccc   7620
tagccgccgc tccgggctct gctcgccctc ctacgttgcg gtcacaccct tctcccttcg   7680
gggagacaac gacggcggtg gcgggagctt ctccacggcc gaccagctgg agatggtgac   7740
cgagctgctg ggaggagaca tggtgaacca gagtttcatc tgcgacccgg acgacgagac   7800
cttcatcaaa aacatcatca tccaggactg tatgtggagc ggcttctcgg ccgccgccaa   7860
gctcgtctca gagaagctgg cctcctacca ggctgcgcgc aaagacagcg gcagcccgaa   7920
ccccgcccgc ggccacagcg tctgctccac ctccagcttg tacctgcagg atctgagcgc   7980
cgccgcctca gagtgcatcg acccctcggt ggtcttcccc taccctctca acgacagcag   8040
ctcgcccaag tcctgcgcct cgcaagactc cagcgccttc tctccgtcct cggattctct   8100
gctctcctcg acggagtcct ccccgcaggg cagccccgag cccctggtgc tccatgagga   8160
gacaccgccc accaccagca gcgactctga ggaggaacaa gaagatgagg aagaaatcga   8220
tgttgtttct gtggaaaaga ggcaggctcc tggcaaaagg tcagagtctg gatcaccttc   8280
tgctggaggc cacagcaaac ctcctcacag cccactggtc ctcaagaggt gccacgtctc   8340
cacacatcag cacaactacg cagcgcctcc ctccactcgg aaggactatc ctgctgccaa   8400
gagggtcaag ttggacagtg tcagagtcct gagacagatc agcaacaacc gaaaatgcac   8460
cagccccagg tcctcggaca ccgaggagaa tgtcaagagg cgaacacaca acgtcttgga   8520
gcgccagagg aggaacgagc taaaacggag ctttttttgcc ctgcgtgacc agatcccgga   8580
gttggaaaac aatgaaaagg cccccaaggt agttatcctt aaaaaagcca cagcatacat   8640
cctgtccgtc caagcagagg agcaaaagct catttctgaa gaggacttgt tgcggaaacg   8700
acgagaacag ttgaaacaca aacttgaaca gctacggaac tcttgtgcgt aagaccggtg   8760
tcggctttgc tgacactaga gtcatctccg aacatccaca atatctctca gtctcttacg   8820
tctctcacag tattaagaaa aacccagggt gaatgggaag cttgccatag gtcatggatg   8880
ggcaggagtc ctcccaaaac ccttctgaca tactctatcc agaatgccac ctgaactctc   8940
ccatagtcag gggaagata gcacagttgc acgtcttgtt agatgtgaac cagccctaca   9000
gactaaagga cgacagcata ataaatatta caaagcacaa aattaggaac ggaggattgt   9060
```

-continued

```
cccctcgtca aattaagatc aggtctctgg gtaaggctct tcaacgcaca ataaaggatt   9120
tagaccgata cacctttgaa ccgtacccaa cctactctca ggaattactt aggcttgata   9180
taccagagat atgtgacaaa atccgatccg tcttcgcggt ctcggatcgg ctgaccaggg   9240
agttatctag tgggttccag gatctttggt tgaatatctt caagcaacta ggcaatatag   9300
aaggaagaga ggggtacgat ccgttgcagg atatcggcac catcccggag ataactgata   9360
aatacagcag gaatagatgg tataggccat tcctaacttg gttcagcatc aaatatgaca   9420
tgcggtggat gcagaagacc agaccggggg gacccctcga tacctctaat tcacataacc   9480
tcctagaatg caaatcatac actctagtaa catacggaga tcttatcatg atactgaaca   9540
agttgacatt gacagggtat atcctaaccc ctgagctggt cttgatgtat tgtgatgttg   9600
tagagggaag gtggaatatg tctgctgcag ggcatctaga taagaagtcc attgggataa   9660
caagcaaagg tgaggaatta tgggaactag tggattccct cttctcaagt cttggagagg   9720
aaatatacaa tgtcatcgca ctattggagc ccctatcact tgctctcata caactaaatg   9780
atccagttat acctctacgt ggggcattta tgaggcatgt gttgacagag ctacaggctg   9840
ttttaacaag tagggacgtg tacacagatg ctgaagcaga cactattgtg gagtcgttac   9900
tcgccatttt ccatggaacc tctattgatg agaaagcaga gatcttttcc ttctttagga   9960
catttggcca ccccagctta gaggctgtca ctgccgccga caaggtaagg gcccatatgt  10020
atgcacaaaa ggcaataaag cttaagaccc tatacgagtg tcatgcagtt ttttgcacta  10080
tcatcataaa tgggtataga gagaggcatg gcggacagtg gcccccctgt gacttccctg  10140
atcacgtgtg tctagaacta aggaacgctc aagggtccaa tacggcaatc tcttatgaat  10200
gtgctgtaga caactataca agtttcatag gcttcaagtt tcggaagttt atagaaccac  10260
aactagatga agatctcaca atatatatga aagacaaagc actatccccc aggaaggagg  10320
catgggactc tgtatacccg gatagtaatc tgtactataa agccccagaa tctgaagaga  10380
cccggcggct tattgaagtg ttcataaatg atgagaattt caacccagaa gaaattatca  10440
attatgtgga gtcaggagat tggttgaaag acgagaagtt caacatctcg tacagtctca  10500
aagagaaaga gatcaagcaa gagggtcgtc tattcgcaaa aatgacttat aagatgcgag  10560
ccgtacaggt gctggcagag acactactgg ctaaaggaat aggagagctg ttcagcgaaa  10620
atgggatggt taaaggagag atagacctac ttaaaagatt gactactctt tctgtctcag  10680
gagtccccag gactgattca gtgtacaata actctaaatc atcagagaag agaaacgaag  10740
gcatgaaaaa gaagaactct gggggggtact gggacgaaaa gaagaggtcc agacatgaat  10800
tcaaggcaac agattcatca acagacggct atgaaacgtt aagttgcttc ctcacaacag  10860
acctcaagaa atactgctta aactggagat ttgaaagtac tgcattgttt ggtcagagat  10920
gcaacgagat atttggcttc aagaccttct ttaactggat gcatccagtc cttgaaaggt  10980
gtacaatata tgttggggat ccttactgtc cagtcgccga ccggatgcat cgacaactcc  11040
aggatcatgc agactctggc attttcatac ataatcctag ggggggcata gaaggttact  11100
gccagaagct gtggacctta atctcaatca gtgcaatcca cctagcagct gtgagagtgg  11160
gtgtcagggt ctctgcaatg gttcagggtg acaatcaagc tatagccgtg acatcaagag  11220
tacctgtagc tcagacttac aagcagaaga aaaatcatgt ctataaggag atcaccaaat  11280
attttggtgc tctaagacac gtcatgtttg atgtagggca cgagctaaaa ttgaacgaga  11340
ccatcattag tagcaagatg tttgtctata gtaaaagaat atactatgat gggaagattt  11400
```

-continued tacccacagtg cctgaaagcc ttgaccaggt gtgtattctg gtccgagaca ctggtagatg 11460
aaaacagatc tgcttgttcg aacatctcaa catccatagc aaaagctatc gaaaatgggt 11520
attctcctat actaggctac tgcattgcgt tgtataagac ctgtcagcag gtgtgcatat 11580
cactagggat gactataaat ccaactatca gcccgaccgt aagagatcaa tactttaagg 11640
gtaagaattg gctgagatgt gcagtgttga ttccagcaaa tgttggagga ttcaactaca 11700
tgtctacatc tagatgcttt gttagaaata ttggagaccc cgcagtagca gccctagctg 11760
atctcaaaag attcatcaga gcggatctgt tagacaagca ggtactatac agggtcatga 11820
atcaagaacc cggtgactct agctttctag attgggcttc agacccttat tcatgtaacc 11880
tcccgcattc tcagagtata actacgatta taaagaatat cactgctaga tctgtgctgc 11940
aggaatcccc gaatcctcta ctgtctggtc tcttcaccga gactagtgga gaagaggatc 12000
tcaacctggc ctcgttcctt atggaccgga aagtcatcct gccgagagtg gctcatgaga 12060
tcctgggtaa ttccttaact ggagttaggg aggcgattgc agggatgctt gatacgacca 12120
agtctctagt gagatccagc gttaagaaag gaggattatc atatgggata ttgaggaggc 12180
ttgtcaatta tgatctattg cagtacgaga cactgactag aactctcagg aaaccggtga 12240
aagacaacat cgaatatgag tatatgtgtt cagttgagct agctgtcggt ctaaggcaga 12300
aaatgtggat ccacctaact tacgggagac ccatacatgg gctagaaaca ccagaccctt 12360
tagagctctt gaggggaaca tttatcgaag gttcagaggt gtgcaagctt tgcaggtctg 12420
agggagcaga ccccatctat acatggttct atctccctga caatatagac ctggacacgc 12480
ttacaaacgg atgtccggct ataagaatcc cctattttgg atcagccact gatgaaaggt 12540
cggaagccca actcgggtat gtaagaaatc taagcaaacc cgcaaaggct gccatccgga 12600
tagctatggt gtatacgtgg gcctacggga ctgatgagat atcgtggatg gaagccgctc 12660
ttatagccca aacaagagct aatctgagct tagagaatct aaagctgctg actcctgttt 12720
caacctccac taatctatct cataggttga aagatacggc aacccagatg aagttctcta 12780
gtgcaacact agtccgtgca agtcggttca taacaatatc aaatgataac atggcactca 12840
aagaagcagg ggagtcgaag gatactaatc tcgtgtatca gcagattatg ctaactgggc 12900
taagcttgtt cgagttcaat atgagatata agaaaggttc cttagggaag ccactgatat 12960
tgcacttaca tcttaataac gggtgctgta taatggagtc cccacaggag gcgaatatcc 13020
ccccaaggtc cacattagat ttagagatta cacaagagaa caataaattg atctatgatc 13080
ctgatccact caaggatgtg gaccttgagc tatttagcaa ggtcagagat gttgtacata 13140
cagttgacat gacttattgg tcagatgatg aagttatcag agcaaccagt atctgtactg 13200
caatgacgat agctgataca atgtctcaat tagatagaga caacctaaaa gagatgatcg 13260
cgctagtaaa tgacgatgat gtcaacagcc tgattactga gtttatggtg attgatgttc 13320
ctttattttg ctcaacgttc gggggtattc tagtcaatca gtttgcatac tcactctacg 13380
gcttaaacat cagaggaagg gaagaaatat ggggacatgt agtccggatt cttaaagata 13440
cctcccacgc agttctaaaa gtcttatcta atgctctatc tcatcccaaa atcttcaaac 13500
gattctggaa tgcaggtgtc gtggaacctg tgtatgggcc taacctctca aatcaggaca 13560
agatactctt ggccctctct gtctgtgaat attctgtgga tctattcatg cacgattggc 13620
aagggggtgt accgcttgag atctttatct gtgacaatga cccagatgtg gccgacatga 13680
ggaggtcctc tttcttggca agacatcttg catacctatg cagcgtggca gagatatcta 13740
gggatgggcc aagattagaa tcaatgaact ctctagagag gctcgagtca ctaaagagtt 13800

```
acctggaact cacatttctt gatgacccgg tactgaggta cagtcagttg actggcctag  13860

tcatcaaagt attcccatct actttgacct atatccggaa gtcatctata aaagtgttaa  13920

ggacaagagg tataggagtc cctgaagtct tagaagattg ggatcccgag gcagataatg  13980

cactgttaga tggtatcgcg gcagaaatac aacagaatat tcctttggga catcagacta  14040

gagccccttt ttgggggttg agagtatcca agtcacaggt actgcgtctc cgggggtaca  14100

aggagatcac aagaggtgag ataggcagat caggcgttgg tctgacgtta ccattcgatg  14160

gaagatatct atctcaccag ctgaggctct ttggcatcaa cagtactagc tgcttgaaag  14220

cacttgaact tacctaccta ttgagcccct tagttgacaa ggataaagat aggctatatt  14280

taggggaagg agctggggcc atgctttcct gttatgacgc tactcttggc ccatgcatca  14340

actattataa ctcaggggta tactcttgtg atgtcaatgg gcagagagag ttaaatatat  14400

atcctgctga ggtggcactg gtgggaaaga aattaaacaa tgttactagt ctgggtcaaa  14460

gagttaaagt gttattcaac gggaatcctg gctcgacatg gattggaaat gatgagtgtg  14520

aggctttgat ttggaatgaa ttgcagaata gctcgatagg cctagtccac tgtgacatgg  14580

agggaggaga tcataaggat gatcaagttg tactgcatga gcattacagt gtaatccgga  14640

tcgcgtatct ggtgggggat cgagacgttg tgcttataag caagattgct cctaggctgg  14700

gcacggattg gaccaggcag ctcagcctat atctgagata ctgggacgag gttaacctaa  14760

tagtgcttaa aacatctaac cctgcttcca cagagatgta tctcctatcg aggcatccca  14820

aatctgacat tatagaggac agcaagacgg tgttagctag tctcctccct ttgtcaaaag  14880

aagatagcat caagatagaa aagtggatct taatagagaa ggcaaaggct cacgaatggg  14940

ttactcggga attgagagaa ggaagctctt catcagggat gcttagacct taccatcaag  15000

cactgcagac gtttggcttt gaaccaaact tgtataaatt gagcagagat ttcttgtcca  15060

ccatgaacat agctgataca cacaactgca tgatagcttt caacagggtt ttgaaggata  15120

caatcttcga atgggctaga ataactgagt cagataaaag gcttaaacta actggtaagt  15180

atgacctgta tcctgtgaga gattcaggca aattgaagac agtttctaga agacttgtgc  15240

tatcttggat atctttatct atgtccacaa gattggtaac tgggtcattc cctgaccaga  15300

agtttgaagc aagacttcaa ttgggaatag tttcattatc atcccgtgaa atcaggaacc  15360

tgagggttat cacaaaaact ttattagacc ggtttgagga tattatacat agtataacgt  15420

acagattcct caccaaagaa ataaagattt tgatgaagat tttaggggca gtcaagatgt  15480

tcggggccag gcaaaatgaa tacacgaccg tgattgatga tggatcactg ggtgatatcg  15540

agccatatga cagctcgtaa taattagtcc ctatcgtgca gaacgatcga agctccgcgg  15600

tacctggaag tcttggactg atccatatga caatagtaag aaaaacttac aagaagacaa  15660

gaaaatttaa aagaatacat atctcttaaa ctcttgtctg gt                     15702
```

<210> SEQ ID NO 39
<211> LENGTH: 63
<212> TYPE: DNA
<213> ORGANISM: Artificial
<220> FEATURE:
<223> OTHER INFORMATION: Synthetic construct of oligo DNA for introducing target sequence of mir-302a

<400> SEQUENCE: 39

```
ccggttatca ccaaaacatg gaagcactta cgattcacca aaacatggaa gcacttaggt     60

acc                                                                 63
```

<210> SEQ ID NO 40
<211> LENGTH: 53
<212> TYPE: DNA
<213> ORGANISM: Artificial
<220> FEATURE:
<223> OTHER INFORMATION: Synthetic construct of Oligo DNA for introducing target sequence of mir-302a

<400> SEQUENCE: 40
taagtgcttc catgttttgg tgaatcgtaa gtgcttccat gttttggtga taa 53

<210> SEQ ID NO 41
<211> LENGTH: 51
<212> TYPE: DNA
<213> ORGANISM: Artificial
<220> FEATURE:
<223> OTHER INFORMATION: Synthetic construct of Oligo DNA for introducing target sequence of mir-302a

<400> SEQUENCE: 41
tcaccaaaac atggaagcac ttacgattca ccaaaacatg gaagcactta a 51

<210> SEQ ID NO 42
<211> LENGTH: 61
<212> TYPE: DNA
<213> ORGANISM: Artificial
<220> FEATURE:
<223> OTHER INFORMATION: Synthetic construct of Oligo DNA for introducing target sequence of mir-302a

<400> SEQUENCE: 42
ccggttaagt gcttccatgt tttggtgaat cgtaagtgct tccatgtttt ggtgaggtac 60
c 61

<210> SEQ ID NO 43
<211> LENGTH: 6576
<212> TYPE: DNA
<213> ORGANISM: Artificial
<220> FEATURE:
<223> OTHER INFORMATION: Synthetic construct pNK15(vector used to making Sendai virus vector having target sequence of mir-302a)

<400> SEQUENCE: 43
atcggcacca tcccggagat aactgataaa tacagcagga atagatggta taggccattc 60
ctaacttggt tcagcatcaa atatgacatg cggtggatgc agaagaccag accgggggga 120
cccctcgata cctctaattc acataacctc ctagaatgca aatcatacac tctagtaaca 180
tacggagatc ttatcatgat actgaacaag ttgacattga cagggtatat cctaacccct 240
gagctggtct tgatgtattg tgatgttgta gagggaaggt ggaatatgtc tgctgcaggg 300
catctagata agaagtccat tgggataaca agcaaaggtg aggaattatg ggaactagtg 360
gattccctct tctcaagtct tggagaggaa atatacaatg tcatcgcact attggagccc 420
ctatcacttg ctctcataca actaaatgat ccagttatac ctctacgtgg ggcatttatg 480
aggcatgtgt tgacagagct acaggctgtt ttaacaagta gggacgtgta cacagatgct 540
gaagcagaca ctattgtgga gtcgttactc gccattttcc atggaacctc tattgatgag 600
aaagcagaga tcttttcctt ctttaggaca tttggccacc ccagcttaga ggctgtcact 660
gccgccgaca aggtaagggc ccatatgtat gcacaaaagg caataaagct taagacccta 720
tacgagtgtc atgcagtttt ttgcactatc atcataaatg ggtatagaga gaggcatggc 780

-continued

```
ggacagtggc cccccctgtga cttccctgat cacgtgtgtc tagaactaag gaacgctcaa    840
gggtccaata cggcaatctc ttatgaatgt gctgtagaca actatacaag tttcataggc    900
ttcaagtttc ggaagtttat agaaccacaa ctagatgaag atctcacaat atatatgaaa    960
gacaaagcac tatcccccag gaaggaggca tgggactctg tatacccgga tagtaatctg   1020
tactataaag ccccagaatc tgaagagacc cggcggctta ttgaagtgtt cataaatgat   1080
gagaatttca acccagaaga aattatcaat tatgtggagt caggagattg gttgaaagac   1140
gagaagttca acatctcgta cagtctcaaa gagaaagaga tcaagcaaga gggtcgtcta   1200
ttcgcaaaaa tgacttataa gatgcgagcc gtacaggtgc tggcagagac actactggct   1260
aaaggaatag gagagctgtt cagcgaaaat gggatggtta aaggagagat agacctactt   1320
aaaagattga ctactctttc tgtctcagga gtccccagga ctgattcagt gtacaataac   1380
tctaaatcat cagagaagag aaacgaaggc atgaaaaaga agaactctgg ggggtactgg   1440
gacgaaaaga agaggtccag acatgaattc aaggcaacag attcatcaac agacggctat   1500
gaaacgttaa gttgcttcct cacaacagac ctcaagaaat actgcttaaa ctggagattt   1560
gaaagtactg cattgtttgg tcagagatgc aacgagatat ttggcttcaa gaccttcttt   1620
aactggatgc atccagtcct tgaaaggtgt acaatatatg ttggggatcc ttactgtcca   1680
gtcgccgacc ggatgcatcg acaactccag gatcatgcag actctggcat tttcatacat   1740
aatcctaggg ggggcataga aggttactgc cagaagctgt ggaccttaat ctcaatcagt   1800
gcaatccacc tagcagctgt gagagtgggt gtcagggtct ctgcaatggt tcagggtgac   1860
aatcaagcta tagccgtgac atcaagagta cctgtagctc agacttacaa gcagaagaaa   1920
aatcatgtct ataaggagat caccaaatat tttggtgctc taagacacgt catgtttgat   1980
gtagggcacg agctaaaatt gaacgagacc atcattagta gcaagatgtt tgtctatagt   2040
aaaagaatat actatgatgg gaagatttta ccacagtgcc tgaaagcctt gaccaggtgt   2100
gtattctggt ccgagacact ggtagatgaa aacagatctg cttgttcgaa catctcaaca   2160
tccatagcaa aagctatcga aaatgggtat tctcctatac taggctactg cattgcgttg   2220
tataagacct gtcagcaggt gtgcatatca ctagggatga ctataaatcc aactatcagc   2280
ccgaccgtaa gagatcaata ctttaagggt aagaattggc tgagatgtgc agtgttgatt   2340
ccagcaaatg ttggaggatt caactacatg tctacatcta gatgctttgt tagaaatatt   2400
ggagaccccg cagtagcagc cctagctgat ctcaaaagat tcatcagagc ggatctgtta   2460
gacaagcagg tactatacag ggtcatgaat caagaacccg gtgactctag ctttctagat   2520
tgggcttcag acccttattc atgtaacctc ccgcattctc agagtataac tacgattata   2580
aagaatatca ctgctagatc tgtgctgcag gaatccccga atcctctact gtctggtctc   2640
ttcaccgaga ctagtggaga agaggatctc aacctggcct cgttccttat ggaccggaaa   2700
gtcatcctgc cgagagtggc tcatgagatc ctgggtaatt ccttaactgg agttagggag   2760
gcgattgcag ggatgcttga tacgaccaag tctctagtga gatccagcgt taagaaagga   2820
ggattatcat atgggatatt gaggaggctt gtcaattatg atctattgca gtacgagaca   2880
ctgactagaa ctctcaggaa accggtgaaa gacaacatcg aatatgagta tatgtgttca   2940
gttgagctag ctgtcggtct aaggcagaaa atgtggatcc acctaactta cgggagaccc   3000
atacatgggc tagaaacacc agaccccttta gagctcttga ggggaacatt tatcgaaggt   3060
tcagaggtgt gcaagctttg caggtctgag ggagcagacc ccatctatac atggttctat   3120
ctccctgaca atatagacct ggacacgctt acaaacggat gtccggctat aagaatcccc   3180
```

```
tattttggat cagccactga tgaaaggtcg gaagcccaac tcgggtatgt aagaaatcta   3240
agcaaacccg caaaggctgc catccggata gctatggtgt atacgtgggc ctacgggact   3300
gatgagatat cgtggatgga agccgctctt atagcccaaa caagagctaa tctgagctta   3360
gagaatctaa agctgctgac tcctgtttca acctccacta atctatctca taggttgaaa   3420
gatacggcaa cccagatgaa gttctctagt gcaacactag tccgtgcaag tcggttcata   3480
acaatatcaa atgataacat ggcactcaaa gaagcagggg agtcgaagga tactaatctc   3540
gtgtatcagc agattatgct aactgggcta agcttgttcg agttcaatat gagatataag   3600
aaaggttcct tagggaagcc actgatattg cacttacatc ttaataacgg gtgctgtata   3660
atggagtccc cacaggaggc gaatatcccc ccaaggtcca cattagattt agagattaca   3720
caagagaaca ataaattgat ctatgatcct gatccactca aggatgtgga ccttgagcta   3780
tttagcaagg tcagagatgt tgtacataca gttgacatga cttattggtc agatgatgaa   3840
gttatcagag caaccagtat ctgtactgca atgacgatag ctgatacaat gtctcaatta   3900
gatagagaca acctaaaaga gatgatcgcg ctagtaaatg acgatgatgt caacagcctg   3960
attactgagt ttatggtgat tgatgttcct ttattttgct caacgttcgg gggtattcta   4020
gtcaatcagt ttgcatactc actctacggc ttaaacatca gaggaaggga agaaatatgg   4080
ggacatgtag tccggattct taaagatacc tcccacgcag ttctaaaagt cttatctaat   4140
gctctatctc atcccaaaat cttcaaacga ttctggaatg caggtgtcgt ggaacctgtg   4200
tatgggccta acctctcaaa tcaggacaag atactcttgg ccctctctgt ctgtgaatat   4260
tctgtggatc tattcatgca cgattggcaa gggggtgtac cgcttgagat ctttatctgt   4320
gacaatgacc cagatgtggc cgacatgagg aggtcctctt tcttggcaag acatcttgca   4380
tacctatgca gcgtggcaga gatatctagg gatgggccaa gattagaatc aatgaactct   4440
ctagagaggc tcgagtcact aaagagttac ctggaactca catttcttga tgacccggta   4500
ctgaggtaca gtcagttgac tggcctagtc atcaaagtat tcccatctac tttgacctat   4560
atccggaagt catctataaa agtgttaagg acaagaggta taggagtccc tgaagtctta   4620
gaagattggg atcccgaggc agataatgca ctgttagatg gtatcgcggc agaaatacaa   4680
cagaatattc ctttgggaca tcagactaga gccccttttt gggggttgag agtatccaag   4740
tcacaggtac tgcgtctccg ggggtacaag gagatcacaa gaggtgagat aggcagatca   4800
ggcgttggtc tgacgttacc attcgatgga agatatctat ctcaccagct gaggctcttt   4860
ggcatcaaca gtactagctg cttgaaagca cttgaactta cctacctatt gagcccctta   4920
gttgacaagg ataaagatag gctatattta ggggaaggag ctggggccat gctttcctgt   4980
tatgacgcta ctcttggccc atgcatcaac tattataact caggggtata ctcttgtgat   5040
gtcaatgggc agagagagtt aaatatatat cctgctgagg tggcactggt gggaaagaaa   5100
ttaaacaatg ttactagtct gggtcaaaga gttaaagtgt tattcaacgg gaatcctggc   5160
tcgacatgga ttggaaatga tgagtgtgag gctttgattt ggaatgaatt gcagaatagc   5220
tcgataggcc tagtccactg tgacatggag ggaggagatc ataaggatga tcaagttgta   5280
ctgcatgagc attacagtgt aatccggatc gcgtatctgg tgggggatcg agacgttgtg   5340
cttataagca agattgctcc taggctgggc acggattgga ccaggcagct cagcctatat   5400
ctgagatact gggacgaggt taacctaata gtgcttaaaa catctaaccc tgcttccaca   5460
gagatgtatc tcctatcgag gcatcccaaa tctgacatta tagaggacag caagacggtg   5520
```

ttagctagtc tcctcccttt gtcaaaagaa gatagcatca agatagaaaa gtggatctta 5580
atagagaagg caaaggctca cgaatgggtt actcgggaat tgagagaagg aagctcttca 5640
tcagggatgc ttagacctta ccatcaagca ctgcagacgt ttggctttga accaaacttg 5700
tataaattga gcagagattt cttgtccacc atgaacatag ctgatacaca caactgcatg 5760
atagctttca acagggtttt gaaggataca atcttcgaat gggctagaat aactgagtca 5820
gataaaaggc ttaaactaac tggtaagtat gacctgtatc ctgtgagaga ttcaggcaaa 5880
ttgaagacag tttctagaag acttgtgcta tcttggatat ctttatctat gtccacaaga 5940
ttggtaactg ggtcattccc tgaccagaag tttgaagcaa gacttcaatt gggaatagtt 6000
tcattatcat cccgtgaaat caggaacctg agggttatca caaaaacttt attagaccgg 6060
tttgaggata ttatacatag tataacgtac agattcctca ccaaagaaat aaagattttg 6120
atgaagattt taggggcagt caagatgttc ggggccaggc aaaatgaata cacgaccgtg 6180
attgatgatg gatcactggg tgatatcgag ccatatgaca gctcgtaata attagtccct 6240
atcgtgcaga acgatcgaag ctccgcggta cctggaagtc ttggactgat ccatatgaca 6300
atagtaagaa aaacttacaa gaagacaaga aaatttaaaa gaatacatat ctcttaaact 6360
cttgtctggt gtcctgtttc gaaaacgaaa cagagaacca gtaccagaga aacacacgtt 6420
gtggtatatt acctggttct cgagcaccac caccaccacc actgagatcc ggctgctaac 6480
aaagcccgaa aggaagctga gttggctgct gccaccgctg agcaataact agcataaccc 6540
cttggggcct ctaaacgggt cttgaggggt tttttg 6576

<210> SEQ ID NO 44
<211> LENGTH: 31
<212> TYPE: DNA
<213> ORGANISM: Artificial
<220> FEATURE:
<223> OTHER INFORMATION: Primer

<400> SEQUENCE: 44
gacagctcgt aatcccgggt ccctatcgtg c 31

<210> SEQ ID NO 45
<211> LENGTH: 31
<212> TYPE: DNA
<213> ORGANISM: Artificial
<220> FEATURE:
<223> OTHER INFORMATION: Primer

<400> SEQUENCE: 45
gcacgatagg gacccgggat tacgagctgt c 31

<210> SEQ ID NO 46
<211> LENGTH: 15810
<212> TYPE: DNA
<213> ORGANISM: Artificial
<220> FEATURE:
<223> OTHER INFORMATION: Synthetic construct (Full length genome cDNA of Sendai virus vector-version3)

<400> SEQUENCE: 46
accaaacaag agaagaaaca tgtatggaat atataatgaa gtttaagaaa aacttagggt 60
caaagtatcc accctgagga gcaggttcca gatccttttc tttgctgcca aagttcacga 120
tggccgggtt gttgagcacc ttcgatacat ttagctctag gaggagcgaa agtattaata 180
agtcgggagg aggtgctgtt atccccggcc agaggagcac agtctcagtg ttcatactag 240

-continued

```
gcccaagtgt gactgatgat gcagacaagt tattcattgc aacaaccttc ctagctcact    300
cattggacac agataagcag cactctcaga gaggagggtt cctcgtctct ctgcttgcca    360
tggcttacag tagtccagaa ttgtacttga caacaaacgg agtaaacgcc gatgtcaaat    420
atgtgatcta caacatagag aaagacccta agaggacgaa gacagacgga ttcattgtga    480
agacgagaga tatggaatat gagaggacca cagaatggct gtttggacct atggtcaaca    540
agagcccact cttccagggt caacgggatg ctgcagaccc tgacacactc cttcaaatct    600
atgggtatcc tgcatgccta ggagcaataa ttgtccaagt ctggattgtg ctggtgaagg    660
ccatcacaag cagcgccggc ttaaggaaag ggttcttcaa caggttagag gcgttcagac    720
aagacggcac cgtgaaaggt gccttagttt tcactgggga gacagttgag ggatagggct    780
cggttatgag atctcagcaa agccttgtat ctctcatggt tgagaccctt gtgactatga    840
atactgcaag atctgatctc accacattag agaagaacat ccagatcgtt gggaactaca    900
tccgagatgc agggctggct tccttcatga acactattaa atatggggtg gagacaaaga    960
tggcagctct aacgttgtca aacctgaggc ccgatattaa taagcttaga agcctcatag   1020
acacctacct gtcaaaaggc cccagagctc cctttatctg tatcctcaag gaccctgttc   1080
atggtgaatt tgctccaggc aattatcctg cactatggag ttacgccatg ggagtcgccg   1140
tcgtacagaa caagtcaatg cagcagtacg tcacagggag gacatacctt gatatggaaa   1200
tgttcttact aggacaagcc gtggcaaagg atgctgaatc gaagatcagc agtgccttgg   1260
aagatgagtt aggagtgacg gatacagcca aggagaggct cagacatcat ctggcaaact   1320
tgtccggtgg ggatggtgct taccacaaac caacaggcgg tggtgcaatt gaggtagctc   1380
tagacaatgc cgatatcgac ctggaaacag aagctcatgc ggaccaggac gctaggggtt   1440
ggggtggaga tagtggtgaa agatgggcac gtcaggtgag tggtggccac tttgtcacac   1500
tacatggggc tgaacggtta gaggaggaaa ccaatgatga ggatgtatca gacatagaga   1560
gaagaatagc catgagactc gcagagagac ggcaagagga ttctgcaacc catggagatg   1620
aaggccgcaa taacggtgtt gatcacgaag aagatgacga tgccgcagca gcagctggga   1680
taggaggaat ctaggatcat acgaggcctc aaggtacttg atccgcagta agaaaaactt   1740
agggtgaaag ttcatccacc gatcggctca ggcaaggcca cacccaaccc caccgaccac   1800
acccagcagt cgagacagcc acggcttcgg ctacacttac cgcatggatc aagatgcctt   1860
cattcttaaa gaagattctg aagttgagag gaaggcgcca ggaggacgag agtcgctctc   1920
ggatgttatc ggattcctcg atgctgtcct gtcgaatgaa ccaactgaca tcggagggga   1980
cagaagctgg ctccacaaca ccatcaacac tccccaagga ccaggctctg ctcatagagc   2040
caaaagtgag ggcgaaggag aagtctcaac accgtcgacc caagataatc gatcaggtga   2100
ggagagtaga gtctctggga gaacaagcaa gccagaggca gaagcacatg ctggaaacct   2160
tgataaacaa aatatacact gggcctttag ggaagaact ggtacaaact ctgtatctca    2220
ggatctggac gatggaggag actccggaat ccttgaaaat cctccaaatg agagaggata   2280
tccgagatca ggtattgaag atgaaaacag agagatggct gcgcaccctg ataagagggg   2340
agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
```

-continued

```
atctacacag gatgagcaca tcaactctgg ggacaccccc gccgtcaggg tcaaagaccg   2700
gaaaccatca atagggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
gatgacattc aatgtatgcg gcctgatcct ttctgccgag aaatcttccg ctcgtaaggt   3000
agatgagaac aaacaactgc tcaaacagat ccaagagagc gtggaatcat tccgggatat   3060
ttacaagaga ttctctgagt atcagaaaga acagaactca ttgctgatgt ccaacctatc   3120
tacacttcat atcatcacag atagaggtgg caagactgac aacacagact ccccttacaag  3180
gtccccctcc gtttttgcaa aatcaaaaga gaacaagact aaggctacca ggtttgaccc   3240
atctatggag accttagaag atatgaagta caaaccggac ctaatccgag aggatgaatt   3300
tagagatgag atccgcaacc cggtgtacca agagagggac acagaaccca gggcctcaaa   3360
cgcatcacgt ctcttcccct ccaaagagaa gcccacaatg cactctctca ggctcgtcat   3420
agagagcagt cccctaagca gagctgagaa agcagcatat gtgaaatcat tatccaagtg   3480
caagacagac caagaggtta aggcagtcat ggaactcgta gaagaggaca tagagtcact   3540
gaccaactag atcccgggtg aggcatccca ccatcctcag tcacagagag acccaatcta   3600
ccatcagcat cagccagtaa agattaagaa aaacttaggg tgaaagaaat ttcaccgcta   3660
gcttagacga tggatttttt tcgggtagtg gaaaaccagc agcctcccgc gacgatgccc   3720
ctcaacgtta gcttcaccaa caggaactat gacctcgact acgactcggt gcagccgtat   3780
ttctactgcg acgaggagga gaacttctac cagcagcagc agcagagcga gctgcagccc   3840
ccggcgccca gcgaggatat ctggaagaaa ttcgagctgc tgcccacccc gcccctgtcc   3900
cctagccgcc gctccgggct ctgctcgccc tcctacgttg cggtcacacc cttctccctt   3960
cggggagaca acgacggcgg tggcgggagc ttctccacgg ccgaccagct ggagatggtg   4020
accgagctgc tgggaggaga catggtgaac cagagtttca tctgcgaccc ggacgacgag   4080
accttcatca aaaacatcat catccaggac tgtatgtgga gcggcttctc ggccgccgcc   4140
aagctcgtct cagagaagct ggcctcctac caggctgcgc gcaaagacag cggcagcccg   4200
aaccccgccc gcggccacag cgtctgctcc acctccagct tgtacctgca ggatctgagc   4260
gccgccgcct cagagtgcat cgacccctcg gtggtcttcc cctaccctct caacgacagc   4320
agctcgccca agtcctgcgc ctcgcaagac tccagcgcct tctctccgtc ctcggattct   4380
ctgctctcct cgacggagtc ctccccgcag ggcagccccg agcccctggt gctccatgag   4440
gagacaccgc ccaccaccag cagcgactct gaggaggaac aagaagatga ggaagaaatc   4500
gatgttgttt ctgtggaaaa gaggcaggct cctggcaaaa ggtcagagtc tggatcacct   4560
tctgctggag gccacagcaa acctcctcac agcccactgg tcctcaagag gtgccacgtc   4620
tccacacatc agcacaacta cgcagcgcct ccctccactc ggaaggacta tcctgctgcc   4680
aagagggtca agttggacag tgtcagagtc ctgagacaga tcagcaacaa ccgaaaatgc   4740
accagcccca ggtcctcgga caccgaggag aatgtcaaga ggcgaacaca caacgtcttg   4800
gagcgccaga ggaggaacga gctaaaacgg agcttttttg ccctgcgtga ccagatcccg   4860
gagttggaaa acaatgaaaa ggcccccaag gtagttatcc ttaaaaaagc cacagcatac   4920
atcctgtccg tccaagcaga ggagcaaaag ctcatttctg aagaggactt gttgcggaaa   4980
```

-continued

```
cgacgagaac agttgaaaca caaacttgaa cagctacgga actcttgtgc gtaaggacgt   5040
cgattaagaa aaacttaggg tgaaagttca tcgcggccgc ttgctagcag tctgacatgg   5100
ctgtcagcga cgcgctgctc ccatctttct ccacgttcgc gtctggcccg gcgggaaggg   5160
agaagacact gcgtcaagca ggtgccccga ataaccgctg gcgggaggag ctctcccaca   5220
tgaagcgact tcccccagtg cttcccggcc gcccctatga cctggcggcg gcgaccgtgg   5280
ccacagacct ggagagcggc ggagccggtg cggcttgcgg cggtagcaac ctggcgcccc   5340
tacctcggag agagaccgag gagttcaacg atctcctgga cctggacttt attctctcca   5400
attcgctgac ccatcctccg gagtcagtgg ccgccaccgt gtcctcgtca gcgtcagcct   5460
cctcttcgtc gtcgccgtcg agcagcggcc ctgccagcgc gccctccacc tgcagcttca   5520
cctatccgat ccgggccggg aacgacccgg gcgtggcgcc gggcggcacg ggcggaggcc   5580
tcctctatgg cagggagtcc gctccccctc cgacggctcc cttcaacctg gcggacatca   5640
acgacgtgag cccctcgggc ggcttcgtgg ccgagctcct gcggccagaa ttggacccgg   5700
tgtacattcc gccgcagcag ccgcagccgc caggtggcgg gctgatgggc aagttcgtgc   5760
tgaaggcgtc gctgagcgcc cctggcagcg agtacggcag cccgtcggtc atcagcgtca   5820
gcaaaggcag ccctgacggc agccacccgg tggtggtggc gccctacaac ggcgggccgc   5880
cgcgcacgtg ccccaagatc aagcaggagg cggtctcttc gtgcacccac ttgggcgctg   5940
gacccccctct cagcaatggc caccggccgg ctgcacacga cttcccccctg ggcggcagc   6000
tccccagcag gactaccccg accctgggtc ttgaggaagt gctgagcagc agggactgtc   6060
accctgccct gccgcttcct cccggcttcc atccccaccc ggggcccaat tacccatcct   6120
tcctgcccga tcagatgcag ccgcaagtcc cgccgctcca ttaccaagag ctcatgccac   6180
ccggttcctg catgccagag gagcccaagc caaagagggg aagacgatcg tggccccgga   6240
aaaggaccgc cacccacact tgtgattacg cgggctgcgg caaaacctac acaaagagtt   6300
cccatctcaa ggcacacctg cgaacccaca caggtgagaa accttaccac tgtgactggg   6360
acggctgtgg atggaaattc gcccgctcag atgaactgac caggcactac cgtaaacaca   6420
cggggcaccg cccgttccag tgccaaaaat gcgaccgagc attttccagg tcggaccacc   6480
tcgccttaca catgaagagg catttttaaa cgcgtcagag acctgcaaca atgtctcaag   6540
cagacaccac ctggcagtcg gagccaccgg gtcactcctt gtcttaaata agaaaaactt   6600
agggataaag tcccttagat ctagcctagg ttccccatgg cgggacacct ggcttcggat   6660
ttcgccttct cgccccctcc aggtggtgga ggtgatgggc caggggggcc ggagccgggc   6720
tgggttgatc ctcggacctg gctaagcttc caaggccctc ctggagggcc aggaatcggg   6780
ccgggggttg ggccaggctc tgaggtgtgg gggattcccc catgcccccc gccgtatgag   6840
ttctgtgggg ggatggcgta ctgtgggccc caggttggag tggggctagt gccccaaggc   6900
ggcttggaga cctctcagcc tgagggcgaa gcaggagtcg gggtggagag caactccgat   6960
ggggcctccc cggagccctg caccgtcacc cctggtgccg tgaagctgga gaaggagaag   7020
ctggagcaaa acccggagga gtcccaggac atcaaagctc tgcagaaaga actcgagcaa   7080
tttgccaagc tcctgaagca gaagaggatc accctgggat atacacaggc cgatgtgggg   7140
ctcaccctgg gggttctatt tgggaaggta ttcagccaaa cgaccatctg ccgctttgag   7200
gctctgcagc ttagcttcaa gaacatgtgt aagctgcggc ccttgctgca gaagtgggtg   7260
gaggaagctg acaacaatga aaatcttcag gagatatgca aagcagaaac cctcgtgcag   7320
gcccgaaaga gaaagcgaac cagtatcgag aaccgagtga gaggcaacct ggagaatttg   7380
```

-continued

```
ttcctgcagt gcccgaaacc cacactgcag cagatcagcc acatcgccca gcagcttggg   7440
ctcgagaagg atgtggtccg agtgtggttc tgtaaccggc gccagaaggg caagcgatca   7500
agcagcgact atgcacaacg agaggatttt gaggctgctg ggtctccttt ctcaggggga   7560
ccagtgtcct ttcctctggc cccagggccc cattttggta ccccaggcta tgggagccct   7620
cacttcactg cactgtactc ctcggtccct ttccctgagg gggaagcctt tccccctgtc   7680
tccgtcacca ctctgggctc tcccatgcat tcaaactgag gacgtcagat ctgtatataa   7740
taagaaaaac ttagggtgaa agtgaggttg cgcggtattt tagctagccc gcatgtacaa   7800
catgatggag acggagctga agccgccggg cccgcagcaa acttcggggg gcggcggcgg   7860
caactccacc gcggcggcgg ccggcggcaa ccagaaaaac agcccggacc gcgtcaagcg   7920
gcccatgaat gccttcatgg tgtggtcccg cgggcagcgg cgcaagatgg cccaggagaa   7980
ccccaagatg cacaactcgg agatcagcaa gcgcctgggc gccgagtgga aacttttgtc   8040
ggagacggag aagcggccgt tcatcgacga ggctaagcgg ctgcgagcgc tgcacatgaa   8100
ggagcacccg gattataaat accggccccg gcggaaaacc aagacgctca tgaagaagga   8160
taagtacacg ctgcccggcg ggctgctggc ccccggcggc aatagcatgg cgagcggggt   8220
cggggtgggc gccggcctgg gcgcgggcgt gaaccagcgc atggacagtt acgcgcacat   8280
gaacggctgg agcaacggca gctacagcat gatgcaggac cagctgggct acccgcagca   8340
cccgggcctc aatgcgcacg gcgcagcgca gatgcagccc atgcaccgct acgacgtgag   8400
cgccctgcag tacaactcca tgaccagctc gcagacctac atgaacggct cgcccaccta   8460
cagcatgtcc tactcgcagc agggcacccc tggcatggct cttggctcca tgggttcggt   8520
ggtcaagtcc gaggccagct ccagcccccc tgtggttacc tcttcctccc actccagggc   8580
gccctgccag gccggggacc tccgggacat gatcagcatg tatctccccg gcgccgaggt   8640
gccggaaccc gccgccccca gcagacttca catgtcccag cactaccaga gcggcccggt   8700
gcccggcacg gccattaacg gcacactgcc cctctcacac atgtgagacc ggtgtcggct   8760
ttgctgacac tagagtcatc tccgaacatc cacaatatct ctcagtctct tacgtctctc   8820
acagtattaa gaaaaaccca gggtgaatgg gaagcttgcc ataggtcatg gatgggcagg   8880
agtcctccca aaacccttct gacatactct atccagaatg ccacctgaac tctcccatag   8940
tcagggggaa gatagcacag ttgcacgtct tgttagatgt gaaccagccc tacagactaa   9000
aggacgacag cataataaat attacaaagc acaaaattag gaacggagga ttgtcccctc   9060
gtcaaattaa gatcaggtct ctgggtaagg ctcttcaacg cacaataaag gatttagacc   9120
gatacacctt tgaaccgtac ccaacctact ctcaggaatt acttaggctt gatataccag   9180
agatatgtga caaaatccga tccgtcttcg cggtctcgga tcggctgacc agggagttat   9240
ctagtgggtt ccaggatctt tggttgaata tcttcaagca actaggcaat atagaaggaa   9300
gagaggggta cgatccgttg caggatatcg gcaccatccc ggagataact gataaataca   9360
gcaggaatag atggtatagg ccattcctaa cttggttcag catcaaatat gacatgcggt   9420
ggatgcagaa gaccagaccg gggggacccc tcgatacctc taattcacat aacctcctag   9480
aatgcaaatc atacactcta gtaacatacg gagatcttat catgatactg aacaagttga   9540
cattgacagg gtatatccta acccctgagc tggtcttgat gtattgtgat gttgtagagg   9600
gaaggtggaa tatgtctgct gcagggcatc tagataagaa gtccattggg ataacaagca   9660
aaggtgagga attatgggaa ctagtggatt ccctcttctc aagtcttgga gaggaaatat   9720
```

-continued

```
acaatgtcat cgcactattg gagcccctat cacttgctct catacaacta aatgatccag   9780
ttatacctct acgtggggca tttatgaggc atgtgttgac agagctacag gctgttttaa   9840
caagtaggga cgtgtacaca gatgctgaag cagacactat tgtggagtcg ttactcgcca   9900
ttttccatgg aacctctatt gatgagaaag cagagatctt ttccttcttt aggacatttg   9960
gccaccccag cttagaggct gtcactgccg ccgacaaggt aagggcccat atgtatgcac  10020
aaaaggcaat aaagcttaag accctatacg agtgtcatgc agtttttgc actatcatca  10080
taaatgggta tagagagagg catggcggac agtggccccc ctgtgacttc cctgatcacg  10140
tgtgtctaga actaaggaac gctcaagggt ccaatacggc aatctcttat gaatgtgctg  10200
tagacaacta tacaagtttc ataggcttca agtttcggaa gtttatagaa ccacaactag  10260
atgaagatct cacaatatat atgaaagaca aagcactatc ccccaggaag gaggcatggg  10320
actctgtata cccggatagt aatctgtact ataaagcccc agaatctgaa gagacccggc  10380
ggcttattga agtgttcata aatgatgaga atttcaaccc agaagaaatt atcaattatg  10440
tggagtcagg agattggttg aaagacgaga agttcaacat ctcgtacagt ctcaaagaga  10500
aagagatcaa gcaagagggt cgtctattcg caaaaatgac ttataagatg cgagccgtac  10560
aggtgctggc agagacacta ctggctaaag gaataggaga gctgttcagc gaaaatggga  10620
tggttaaagg agagatagac ctacttaaaa gattgactac tctttctgtc tcaggagtcc  10680
ccaggactga ttcagtgtac aataactcta aatcatcaga gaagagaaac gaaggcatga  10740
aaaagaagaa ctctgggggg tactgggacg aaaagaagag gtccagacat gaattcaagg  10800
caacagattc atcaacagac ggctatgaaa cgttaagttg cttcctcaca acagacctca  10860
agaaatactg cttaaactgg agatttgaaa gtactgcatt gtttggtcag agatgcaacg  10920
agatatttgg cttcaagacc ttctttaact ggatgcatcc agtccttgaa aggtgtacaa  10980
tatatgttgg ggatccttac tgtccagtcg ccgaccggat gcatcgacaa ctccaggatc  11040
atgcagactc tggcattttc atacataatc ctaggggggg catagaaggt tactgccaga  11100
agctgtggac cttaatctca atcagtgcaa tccacctagc agctgtgaga gtgggtgtca  11160
gggtctctgc aatggttcag ggtgacaatc aagctatagc cgtgacatca agagtacctg  11220
tagctcagac ttacaagcag aagaaaaatc atgtctataa ggagatcacc aaatattttg  11280
gtgctctaag acacgtcatg tttgatgtag ggcacgagct aaaattgaac gagaccatca  11340
ttagtagcaa gatgtttgtc tatagtaaaa gaatatacta tgatgggaag attttaccac  11400
agtgcctgaa agccttgacc aggtgtgtat tctggtccga gacactggta gatgaaaaca  11460
gatctgcttg ttcgaacatc tcaacatcca tagcaaaagc tatcgaaaat gggtattctc  11520
ctatactagg ctactgcatt gcgttgtata agacctgtca gcaggtgtgc atatcactag  11580
ggatgactat aaatccaact atcagcccga ccgtaagaga tcaatacttt aagggtaaga  11640
attggctgag atgtgcagtg ttgattccag caaatgttgg aggattcaac tacatgtcta  11700
catctagatg ctttgttaga aatattggag accccgcagt agcagcccta gctgatctca  11760
aaagattcat cagagcggat ctgttagaca agcaggtact atacagggtc atgaatcaag  11820
aacccggtga ctctagcttt ctagattggg cttcagaccc ttattcatgt aacctcccgc  11880
attctcagag tataactacg attataaaga atatcactgc tagatctgtg ctgcaggaat  11940
ccccgaatcc tctactgtct ggtctcttca ccgagactag tggagaagag gatctcaacc  12000
tggcctcgtt ccttatggac cggaaagtca tcctgccgag agtggctcat gagatcctgg  12060
gtaattcctt aactggagtt agggaggcga ttgcagggat gcttgatacg accaagtctc  12120
```

-continued

```
tagtgagatc cagcgttaag aaaggaggat tatcatatgg gatattgagg aggcttgtca  12180
attatgatct attgcagtac gagacactga ctagaactct caggaaaccg gtgaaagaca  12240
acatcgaata tgagtatatg tgttcagttg agctagctgt cggtctaagg cagaaaatgt  12300
ggatccacct aacttacggg agacccatac atgggctaga aacaccagac cctttagagc  12360
tcttgagggg aacatttatc gaaggttcag aggtgtgcaa gctttgcagg tctgagggag  12420
cagaccccat ctatacatgg ttctatctcc ctgacaatat agacctggac acgcttacaa  12480
acggatgtcc ggctataaga atcccctatt ttggatcagc cactgatgaa aggtcggaag  12540
cccaactcgg gtatgtaaga aatctaagca aacccgcaaa ggctgccatc cggatagcta  12600
tggtgtatac gtgggcctac gggactgatg agatatcgtg gatggaagcc gctcttatag  12660
cccaaacaag agctaatctg agcttagaga atctaaagct gctgactcct gtttcaacct  12720
ccactaatct atctcatagg ttgaaagata cggcaaccca gatgaagttc tctagtgcaa  12780
cactagtccg tgcaagtcgg ttcataacaa tatcaaatga taacatggca ctcaaagaag  12840
caggggagtc gaaggatact aatctcgtgt atcagcagat tatgctaact gggctaagct  12900
tgttcgagtt caatatgaga tataagaaag gttccttagg gaagccactg atattgcact  12960
tacatcttaa taacgggtgc tgtataatgg agtccccaca ggaggcgaat atcccccaa  13020
ggtccacatt agatttagag attacacaag agaacaataa attgatctat gatcctgatc  13080
cactcaagga tgtggacctt gagctattta gcaaggtcag agatgttgta catacagttg  13140
acatgactta ttggtcagat gatgaagtta tcagagcaac cagtatctgt actgcaatga  13200
cgatagctga tacaatgtct caattagata gagacaacct aaaagagatg atcgcgctag  13260
taaatgacga tgatgtcaac agcctgatta ctgagtttat ggtgattgat gttcctttat  13320
tttgctcaac gttcgggggt attctagtca atcagtttgc atactcactc tacggcttaa  13380
acatcagagg aagggaagaa atatggggac atgtagtccg gattcttaaa gatacctccc  13440
acgcagttct aaaagtctta tctaatgctc tatctcatcc caaaatcttc aaacgattct  13500
ggaatgcagg tgtcgtggaa cctgtgtatg ggcctaacct ctcaaatcag gacaagatac  13560
tcttggccct ctctgtctgt gaatattctg tggatctatt catgcacgat tggcaagggg  13620
gtgtaccgct tgagatcttt atctgtgaca atgacccaga tgtggccgac atgaggaggt  13680
cctctttctt ggcaagacat cttgcatacc tatgcagcgt ggcagagata tctagggatg  13740
ggccaagatt agaatcaatg aactctctag agaggctcga gtcactaaag agttacctgg  13800
aactcacatt tcttgatgac ccggtactga ggtacagtca gttgactggc ctagtcatca  13860
aagtattccc atctactttg acctatatcc ggaagtcatc tataaaagtg ttaaggacaa  13920
gaggtatagg agtccctgaa gtcttagaag attgggatcc cgaggcagat aatgcactgt  13980
tagatggtat cgcggcagaa atacaacaga atattccttt gggacatcag actagagccc  14040
ctttttgggg gttgagagta tccaagtcac aggtactgcg tctccggggg tacaaggaga  14100
tcacaagagg tgagataggc agatcaggcg ttggtctgac gttaccattc gatggaagat  14160
atctatctca ccagctgagg ctctttggca tcaacagtac tagctgcttg aaagcacttg  14220
aacttaccta cctattgagc cccttagttg acaaggataa agataggcta tatttagggg  14280
aaggagctgg ggccatgctt tcctgttatg acgctactct tggcccatgc atcaactatt  14340
ataactcagg ggtatactct tgtgatgtca atgggcagag agagttaaat atatatcctg  14400
ctgaggtggc actggtggga aagaaattaa acaatgttac tagtctgggt caaagagtta  14460
```

-continued aagtgttatt caacgggaat cctggctcga catggattgg aaatgatgag tgtgaggctt 14520
tgatttggaa tgaattgcag aatagctcga taggcctagt ccactgtgac atggagggag 14580
gagatcataa ggatgatcaa gttgtactgc atgagcatta cagtgtaatc cggatcgcgt 14640
atctggtggg ggatcgagac gttgtgctta taagcaagat tgctcctagg ctgggcacgg 14700
attggaccag gcagctcagc ctatatctga gatactggga cgaggttaac ctaatagtgc 14760
ttaaaacatc taaccctgct tccacagaga tgtatctcct atcgaggcat cccaaatctg 14820
acattataga ggacagcaag acggtgttag ctagtctcct ccctttgtca aaagaagata 14880
gcatcaagat agaaaagtgg atcttaatag agaaggcaaa ggctcacgaa tgggttactc 14940
gggaattgag agaaggaagc tcttcatcag ggatgcttag accttaccat caagcactgc 15000
agacgtttgg ctttgaacca aacttgtata aattgagcag agatttcttg tccaccatga 15060
acatagctga tacacacaac tgcatgatag ctttcaacag ggttttgaag gatacaatct 15120
tcgaatgggc tagaataact gagtcagata aaaggcttaa actaactggt aagtatgacc 15180
tgtatcctgt gagagattca ggcaaattga agacagtttc tagaagactt gtgctatctt 15240
ggatatcttt atctatgtcc acaagattgg taactgggtc attccctgac cagaagtttg 15300
aagcaagact tcaattggga atagtttcat tatcatcccg tgaaatcagg aacctgaggg 15360
ttatcacaaa aactttatta gaccggtttg aggatattat acatagtata acgtacagat 15420
tcctcaccaa agaaataaag attttgatga agattttagg ggcagtcaag atgttcgggg 15480
ccaggcaaaa tgaatacacg accgtgattg atgatggatc actgggtgat atcgagccat 15540
atgacagctc gtaataccgg ttatcaccaa aacatggaag cacttacgat tcaccaaaac 15600
atggaagcac ttaggtacct caccaaaaca tggaagcact tacgattcac caaaacatgg 15660
aagcacttaa ccggttccct atcgtgcaga acgatcgaag ctccgcggta cctggaagtc 15720
ttggactgat ccatatgaca atagtaagaa aaacttacaa gaagacaaga aaatttaaaa 15780
gaatacatat ctcttaaact cttgtctggt 15810

<210> SEQ ID NO 47
<211> LENGTH: 15816
<212> TYPE: DNA
<213> ORGANISM: Artificial
<220> FEATURE:
<223> OTHER INFORMATION: Synthetic construct (cDNA complementary to full length genome of Sendai virus vector-version4 for continuous expression of hOct4, hSox2, hKlf4 and hc-Myc)

<400> SEQUENCE: 47
accaaacaag agaagaaaca tgtatggaat atataatgaa gttagacagg attttagggt 60
caaagtatcc accctgagga gcaggttcca gatccttttc tttgctgcca aagttcacga 120
tggccgggtt gttgagcacc ttcgatacat ttagctctag gaggagcgaa agtattaata 180
agtcgggagg aggtgctgtt atccccggcc agaggagcac agtctcagtg ttcatactag 240
gcccaagtgt gactgatgat gcagacaagt tattcattgc aacaaccttc ctagctcact 300
cattggacac agataagcag cactctcaga gaggagggtt cctcgtctct ctgcttgcca 360
tggcttacag tagtccagaa ttgtacttga caacaaacgg agtaaacgcc gatgtcaaat 420
atgtgatcta caacatagag aaagacccta agaggacgaa gacagacgga ttcattgtga 480
agacgagaga tatggaatat gagaggacca cagaatggct gtttggacct atggtcaaca 540
agagcccact cttccagggt caacgggatg ctgcagaccc tgacacactc cttcaaatct 600
atgggtatcc tgcatgccta ggagcaataa ttgtccaagt ctggattgtg ctggtgaagg 660

```
ccatcacaag cagcgccggc ttaaggaaag ggttcttcaa caggttagag gcgttcagac    720
aagacggcac cgtgaaaggt gccttagttt tcactgggga gacagttgag gggataggct    780
cggttatgag atctcagcaa agccttgtat ctctcatggt tgagaccctt gtgactatga    840
atactgcaag atctgatctc accacattag agaagaacat ccagatcgtt gggaactaca    900
tccgagatgc agggctggct tccttcatga acactattaa atatggggtg gagacaaaga    960
tggcagctct aacgttgtca aacctgaggc ccgatattaa taagcttaga agcctcatag   1020
acacctacct gtcaaaaggc cccagagctc cctttatctg tatcctcaag gaccctgttc   1080
atggtgaatt tgctccaggc aattatcctg cactatggag ttacgccatg ggagtcgccg   1140
tcgtacagaa caagtcaatg cagcagtacg tcacagggag gacatacctt gatatggaaa   1200
tgttcttact aggacaagcc gtggcaaagg atgctgaatc gaagatcagc agtgccttgg   1260
aagatgagtt aggagtgacg gatacagcca aggagaggct cagacatcat ctggcaaact   1320
tgtccggtgg ggatggtgct taccacaaac caacaggcgg tggtgcaatt gaggtagctc   1380
tagacaatgc cgatatcgac ctggaaacag aagctcatgc ggaccaggac gctaggggtt   1440
ggggtggaga tagtggtgaa agatgggcac gtcaggtgag tggtggccac tttgtcacac   1500
tacatggggc tgaacggtta gaggaggaaa ccaatgatga ggatgtatca gacatagaga   1560
gaagaatagc catgagactc gcagagagac ggcaagagga ttctgcaacc catggagatg   1620
aaggccgcaa taacggtgtt gatcacgaag aagatgacga tgccgcagca gcagctggga   1680
taggaggaat ctaggatcat acgaggcctc aaggtacttg atccgcagta agaaaaactt   1740
agggtgaaag ttcatccacc gatcggctca ggcaaggcca cacccaaccc caccgaccac   1800
acccagcagt cgagacagcc acggcttcgg ctacacttac cgcatggatc aagatgcctt   1860
cattcttaaa gaagattctg aagttgagag gaaggcgcca ggaggacgag agtcgctctc   1920
ggatgttatc ggattcctcg atgctgtcct gtcgaatgaa ccaactgaca tcggaggga    1980
cagaagctgg ctccacaaca ccatcaacac tccccaagga ccaggctctg ctcatagagc   2040
caaaagtgag ggcgaaggag aagtctcaac accgtcgacc caagataatc gatcaggtga   2100
ggagagtaga gtctctggga gaacaagcaa gccagaggca gaagcacatg ctggaaacct   2160
tgataaacaa aatatacact gggcctttag ggaagaact ggtacaaact ctgtatctca    2220
ggatctggac gatggaggag actccggaat ccttgaaaat cctccaaatg agagaggata   2280
tccgagatca ggtattgaag atgaaaacag agagatggct gcgcaccctg ataagagggg   2340
agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
atctacacag gatgagcaca tcaactctgg ggacaccccc gccgtcaggg tcaaagaccg   2700
gaaaccatca atagggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
gatgacattc aatgtatgcg gcctgatcct ttctgccgag aaatcttccg ctcgtaaggt   3000
```

-continued

```
agatgagaac aaacaactgc tcaaacagat ccaagagagc gtggaatcat tccgggatat   3060
ttacaagaga ttctctgagt atcagaaaga acagaactca ttgctgatgt ccaacctatc   3120
tacacttcat atcatcacag atagaggtgg caagactgac aacacagact cccttacaag   3180
gtccccctcc gtttttgcaa aatcaaaaga gaacaagact aaggctacca ggtttgaccc   3240
atctatggag accttagaag atatgaagta caaaccggac ctaatccgag aggatgaatt   3300
tagagatgag atccgcaacc cggtgtacca agagagggac acagaaccca gggcctcaaa   3360
cgcatcacgt ctcttcccct ccaaagagaa gcacacaatg cactctctca ggctcgtcat   3420
agagagcagt cccctaagca gagctgagaa agcagcatat gtgaaatcat tatccaagtg   3480
caagacagac caagaggtta aggcagtcat ggaactcgta gaagaggaca tagagtcact   3540
gaccaactag atcccgggtg aggcatccca ccatcctcag tcacagagag acccaatcta   3600
ccatcagcat cagccagtaa agattaagaa aaacttaggg tgaaagaaat ttcaccgcta   3660
gcacctaggt ctgacatggc tgtcagcgac gcgctgctcc catctttctc cacgttcgcg   3720
tctggcccgg cgggaaggga gaagacactg cgtcaagcag gtgccccgaa taaccgctgg   3780
cgggaggagc tctcccacat gaagcgactt cccccagtgc ttcccggccg cccctatgac   3840
ctggcggcgg cgaccgtggc cacagacctg gagagcggcg gagccggtgc ggcttgcggc   3900
ggtagcaacc tggcgcccct acctcggaga gagaccgagg agttcaacga tctcctggac   3960
ctggacttta ttctctccaa ttcgctgacc catcctccgg agtcagtggc cgccaccgtg   4020
tcctcgtcag cgtcagcctc ctcttcgtcg tcgccgtcga gcagcggccc tgccagcgcg   4080
ccctccacct gcagcttcac ctatccgatc cgggccggga acgacccggg cgtggcgccg   4140
ggcggcacgg gcggaggcct cctctatggc agggagtccg ctccccctcc gacggctccc   4200
ttcaacctgg cggacatcaa cgacgtgagc cccctcgggcg gcttcgtggc cgagctcctg   4260
cggccagaat tggacccggt gtacattccg ccgcagcagc cgcagccgcc aggtggcggg   4320
ctgatgggca agttcgtgct gaaggcgtcg ctgagcgccc ctggcagcga gtacggcagc   4380
ccgtcggtca tcagcgtcag caaaggcagc cctgacggca gccacccggt ggtggtggcg   4440
ccctacaacg gcgggccgcc gcgcacgtgc cccaagatca agcaggaggc ggtctcttcg   4500
tgcacccact tgggcgctgg acccccctctc agcaatggcc accggccggc tgcacacgac   4560
ttcccccctgg ggcggcagct ccccagcagg actaccccga ccctgggtct tgaggaagtg   4620
ctgagcagca gggactgtca ccctgccctg ccgcttcctc ccggcttcca tccccacccg   4680
gggcccaatt acccatcctt cctgcccgat cagatgcagc cgcaagtccc gccgctccat   4740
taccaagagc tcatgccacc cggttcctgc atgccagagg agcccaagcc aaagaggggga   4800
agacgatcgt ggccccggaa aaggaccgcc acccacactt gtgattacgc gggctgcggc   4860
aaaacctaca caaagagttc ccatctcaag gcacacctgc gaacccacac aggtgagaaa   4920
ccttaccact gtgactggga cggctgtgga tggaaattcg cccgctcaga tgaactgacc   4980
aggcactacc gtaaacacac ggggcaccgc ccgttccagt gccaaaaatg cgaccgagca   5040
ttttccaggt cggaccacct cgccttacac atgaagaggc atttttaaag acgtcgatta   5100
agaaaaactt agggtgaaag ttcatcgcgg ccgcttgcta gcggttcccc atggcgggac   5160
acctggcttc ggatttcgcc ttctcgcccc ctccaggtgg tggaggtgat gggccagggg   5220
ggccggagcc gggctgggtt gatcctcgga cctggctaag cttccaaggc cctcctggag   5280
ggccaggaat cgggccgggg gttgggccag gctctgaggt gtgggggatt cccccatgcc   5340
ccccgccgta tgagttctgt ggggggatgg cgtactgtgg gccccaggtt ggagtggggc   5400
```

-continued

```
tagtgcccca aggcggcttg gagacctctc agcctgaggg cgaagcagga gtcggggtgg   5460
agagcaactc cgatggggcc tccccggagc cctgcaccgt cacccctggt gccgtgaagc   5520
tggagaagga gaagctggag caaaacccgg aggagtccca ggacatcaaa gctctgcaga   5580
aagaactcga gcaatttgcc aagctcctga agcagaagag gatcaccctg ggatatacac   5640
aggccgatgt ggggctcacc ctgggggttc tatttgggaa ggtattcagc caaacgacca   5700
tctgccgctt tgaggctctg cagcttagct tcaagaacat gtgtaagctg cggcccttgc   5760
tgcagaagtg ggtggaggaa gctgacaaca atgaaaatct tcaggagata tgcaaagcag   5820
aaaccctcgt gcaggcccga aagagaaagc gaaccagtat cgagaaccga gtgagaggca   5880
acctggagaa tttgttcctg cagtgcccga aacccacact gcagcagatc agccacatcg   5940
cccagcagct tgggctcgag aaggatgtgg tccgagtgtg gttctgtaac cggcgccaga   6000
agggcaagcg atcaagcagc gactatgcac aacgagagga ttttgaggct gctgggtctc   6060
ctttctcagg gggaccagtg tcctttcctc tggccccagg gccccatttt ggtaccccag   6120
gctatgggag ccctcacttc actgcactgt actcctcggt ccctttccct gagggggaag   6180
cctttccccc tgtctccgtc accactctgg gctctcccat gcattcaaac tgaacgcgtc   6240
agagacctgc aacaatgtct caagcagaca ccacctggca gtcggagcca ccgggtcact   6300
ccttgtctta aataagaaaa acttagggat aaagtccctt agatctagcc taggcgcatg   6360
tacaacatga tggagacgga gctgaagccg ccgggcccgc agcaaacttc gggggggcggc   6420
ggcggcaact ccaccgcggc ggcggccggc ggcaaccaga aaaacagccc ggaccgcgtc   6480
aagcggccca tgaatgcctt catggtgtgg tcccgcgggc agcggcgcaa gatggcccag   6540
gagaacccca agatgcacaa ctcggagatc agcaagcgcc tgggcgccga gtggaaactt   6600
ttgtcggaga cggagaagcg gccgttcatc gacgaggcta agcggctgcg agcgctgcac   6660
atgaaggagc acccggatta taaataccgg ccccggcgga aaaccaagac gctcatgaag   6720
aaggataagt acacgctgcc cggcgggctg ctggcccccg gcggcaatag catggcgagc   6780
ggggtcgggg tgggcgccgg cctgggcgcg ggcgtgaacc agcgcatgga cagttacgcg   6840
cacatgaacg gctggagcaa cggcagctac agcatgatgc aggaccagct gggctacccg   6900
cagcacccgg gcctcaatgc gcacggcgca gcgcagatgc agcccatgca ccgctacgac   6960
gtgagcgccc tgcagtacaa ctccatgacc agctcgcaga cctacatgaa cggctcgccc   7020
acctacagca tgtcctactc gcagcagggc acccctggca tggctcttgg ctccatgggt   7080
tcggtggtca agtccgaggc cagctccagc ccccctgtgg ttacctcttc ctcccactcc   7140
agggcgccct gccaggccgg ggacctccgg gacatgatca gcatgtatct ccccggcgcc   7200
gaggtgccgg aacccgccgc ccccagcaga cttcacatgt cccagcacta ccagagcggc   7260
ccggtgcccg gcacggccat taacggcaca ctgcccctct cacacatgtg aggacgtcag   7320
atctgtatat aataagaaaa acttagggtg aaagtgaggt tgcgcggtat tttagctagc   7380
ttagacgctg gatttttttc gggtagtgga aaaccagcag cctcccgcga cgatgcccct   7440
caacgttagc ttcaccaaca ggaactatga cctcgactac gactcggtgc agccgtattt   7500
ctactgcgac gaggaggaga acttctacca gcagcagcag cagagcgagc tgcagccccc   7560
ggcgcccagc gaggatatct ggaagaaatt cgagctgctg cccaccccgc ccctgtcccc   7620
tagccgccgc tccgggctct gctcgccctc ctacgttgcg gtcacaccct tctcccttcg   7680
gggagacaac gacggcggtg gcgggagctt ctccacggcc gaccagctgg agatggtgac   7740
```

-continued

```
cgagctgctg ggaggagaca tggtgaacca gagtttcatc tgcgacccgg acgacgagac   7800
cttcatcaaa aacatcatca tccaggactg tatgtggagc ggcttctcgg ccgccgccaa   7860
gctcgtctca gagaagctgg cctcctacca ggctgcgcgc aaagacagcg gcagcccgaa   7920
ccccgcccgc ggccacagcg tctgctccac ctccagcttg tacctgcagg atctgagcgc   7980
cgccgcctca gagtgcatcg acccctcggt ggtcttcccc taccctctca acgacagcag   8040
ctcgcccaag tcctgcgcct cgcaagactc cagcgccttc tctccgtcct cggattctct   8100
gctctcctcg acggagtcct ccccgcaggg cagccccgag cccctggtgc tccatgagga   8160
gacaccgccc accaccagca gcgactctga ggaggaacaa gaagatgagg aagaaatcga   8220
tgttgtttct gtggaaaaga ggcaggctcc tggcaaaagg tcagagtctg gatcaccttc   8280
tgctggaggc cacagcaaac ctcctcacag cccactggtc ctcaagaggt gccacgtctc   8340
cacacatcag cacaactacg cagcgcctcc ctccactcgg aaggactatc ctgctgccaa   8400
gagggtcaag ttggacagtg tcagagtcct gagacagatc agcaacaacc gaaaatgcac   8460
cagccccagg tcctcggaca ccgaggagaa tgtcaagagg cgaacacaca acgtcttgga   8520
gcgccagagg aggaacgagc taaaacggag ctttttgcc ctgcgtgacc agatcccgga   8580
gttggaaaac aatgaaaagg cccccaaggt agttatcctt aaaaaagcca cagcatacat   8640
cctgtccgtc caagcagagg agcaaaagct catttctgaa gaggacttgt tgcggaaacg   8700
acgagaacag ttgaaacaca aacttgaaca gctacggaac tcttgtgcgt aagaccggtg   8760
tcggctttgc tgacactaga gtcatctccg aacatccaca atatctctca gtctcttacg   8820
tctctcacag tattaagaaa aacccagggt gaatgggaag cttgccatag gtcatggatg   8880
ggcaggagtc ctcccaaaac ccttctgaca tactctatcc agaatgccac ctgaactctc   8940
ccatagtcag gggggaagata gcacagttgc acgtcttgtt agatgtgaac cagccctaca   9000
gactaaagga cgacagcata ataaatatta caaagcacaa aattaggaac ggaggattgt   9060
cccctcgtca aattaagatc aggtctctgg gtaaggctct tcaacgcaca ataaaggatt   9120
tagaccgata cacctttgaa ccgtacccaa cctactctca ggaattactt aggcttgata   9180
taccagagat atgtgacaaa atccgatccg tcttcgcggt ctcggatcgg ctgaccaggg   9240
agttatctag tgggttccag gatctttggt tgaatatctt caagcaacta ggcaatatag   9300
aaggaagaga ggggtacgat ccgttgcagg atatcggcac catcccggag ataactgata   9360
aatacagcag gaatagatgg tataggccat tcctaacttg gttcagcatc aaatatgaca   9420
tgcggtggat gcagaagacc agaccggggg gacccctcga tacctctaat tcacataacc   9480
tcctagaatg caaatcatac actctagtaa catacggaga tcttatcatg atactgaaca   9540
agttgacatt gacagggtat atcctaaccc ctgagctggt cttgatgtat tgtgatgttg   9600
tagagggaag gtggaatatg tctgctgcag ggcatctaga taagaagtcc attgggataa   9660
caagcaaagg tgaggaatta tgggaactag tggattccct cttctcaagt cttggagagg   9720
aaatatacaa tgtcatcgca ctattggagc ccctatcact tgctctcata caactaaatg   9780
atccagttat acctctacgt ggggcattta tgaggcatgt gttgacagag ctacaggctg   9840
ttttaacaag tagggacgtg tacacagatg ctgaagcaga cactattgtg gagtcgttac   9900
tcgccatttt ccatggaacc tctattgatg agaaagcaga gatcttttcc ttctttagga   9960
catttggcca ccccagctta gaggctgtca ctgccgccga caaggtaagg gcccatatgt  10020
atgcacaaaa ggcaataaag cttaagaccc tatacgagtg tcatgcagtt ttttgcacta  10080
tcatcataaa tgggtataga gagaggcatg gcggacagtg gccccccctgt gacttccctg  10140
```

atcacgtgtg tctagaacta aggaacgctc aagggtccaa tacggcaatc tcttatgaat 10200
gtgctgtaga caactataca agtttcatag gcttcaagtt tcggaagttt atagaaccac 10260
aactagatga agatctcaca atatatatga aagacaaagc actatccccc aggaaggagg 10320
catgggactc tgtataccccg gatagtaatc tgtactataa agccccagaa tctgaagaga 10380
cccggcggct tattgaagtg ttcataaatg atgagaattt caacccagaa gaaattatca 10440
attatgtgga gtcaggagat tggttgaaag acgagaagtt caacatctcg tacagtctca 10500
aagagaaaga gatcaagcaa gagggtcgtc tattcgcaaa aatgacttat aagatgcgag 10560
ccgtacaggt gctggcagag acactactgg ctaaaggaat aggagagctg ttcagcgaaa 10620
atgggatggt taaaggagag atagacctac ttaaaagatt gactactctt tctgtctcag 10680
gagtccccag gactgattca gtgtacaata actctaaatc atcagagaag agaaacgaag 10740
gcatgaaaaa gaagaactct ggggggtact gggacgaaaa gaagaggtcc agacatgaat 10800
tcaaggcaac agattcatca acagacggct atgaaacgtt aagttgcttc ctcacaacag 10860
acctcaagaa atactgctta aactggagat ttgaaagtac tgcattgttt ggtcagagat 10920
gcaacgagat atttggcttc aagaccttct ttaactggat gcatccagtc cttgaaaggt 10980
gtacaatata tgttggggat ccttactgtc cagtcgccga ccggatgcat cgacaactcc 11040
aggatcatgc agactctggc attttcatac ataatcctag ggggggcata gaaggttact 11100
gccagaagct gtggacctta atctcaatca gtgcaatcca cctagcagct gtgagagtgg 11160
gtgtcagggt ctctgcaatg gttcagggtg acaatcaagc tatagccgtg acatcaagag 11220
tacctgtagc tcagacttac aagcagaaga aaaatcatgt ctataaggag atcaccaaat 11280
attttggtgc tctaagacac gtcatgtttg atgtagggca cgagctaaaa ttgaacgaga 11340
ccatcattag tagcaagatg tttgtctata gtaaaagaat atactatgat gggaagattt 11400
taccacagtg cctgaaagcc ttgaccaggt gtgtattctg gtccgagaca ctggtagatg 11460
aaaacagatc tgcttgttcg aacatctcaa catccatagc aaaagctatc gaaaatgggt 11520
attctcctat actaggctac tgcattgcgt tgtataagac ctgtcagcag gtgtgcatat 11580
cactagggat gactataaat ccaactatca gcccgaccgt aagagatcaa tactttaagg 11640
gtaagaattg gctgagatgt gcagtgttga ttccagcaaa tgttggagga ttcaactaca 11700
tgtctacatc tagatgcttt gttagaaata ttggagaccc cgcagtagca gccctagctg 11760
atctcaaaag attcatcaga gcggatctgt tagacaagca ggtactatac agggtcatga 11820
atcaagaacc cggtgactct agctttctag attgggcttc agacccttat tcatgtaacc 11880
tcccgcattc tcagagtata actacgatta taaagaatat cactgctaga tctgtgctgc 11940
aggaatcccc gaatcctcta ctgtctggtc tcttcaccga gactagtgga gaagaggatc 12000
tcaacctggc ctcgttcctt atggaccgga aagtcatcct gccgagagtg gctcatgaga 12060
tcctgggtaa ttccttaact ggagttaggg aggcgattgc agggatgctt gatacgacca 12120
agtctctagt gagatccagc gttaagaaag gaggattatc atatgggata ttgaggaggc 12180
ttgtcaatta tgatctattg cagtacgaga cactgactag aactctcagg aaaccggtga 12240
aagacaacat cgaatatgag tatatgtgtt cagttgagct agctgtcggt ctaaggcaga 12300
aaatgtggat ccacctaact tacgggagac ccatacatgg gctagaaaca ccagaccctt 12360
tagagctctt gaggggaaca tttatcgaag gttcagaggt gtgcaagctt tgcaggtctg 12420
agggagcaga ccccatctat acatggttct atctccctga caatatagac ctggacacgc 12480

-continued

```
ttacaaacgg atgtccggct ataagaatcc cctattttgg atcagccact gatgaaaggt  12540
cggaagccca actcgggtat gtaagaaatc taagcaaacc cgcaaaggct gccatccgga  12600
tagctatggt gtatacgtgg gcctacggga ctgatgagat atcgtggatg gaagccgctc  12660
ttatagccca aacaagagct aatctgagct tagagaatct aaagctgctg actcctgttt  12720
caacctccac taatctatct cataggttga aagatacggc aacccagatg aagttctcta  12780
gtgcaacact agtccgtgca agtcggttca taacaatatc aaatgataac atggcactca  12840
aagaagcagg ggagtcgaag gatactaatc tcgtgtatca gcagattatg ctaactgggc  12900
taagcttgtt cgagttcaat atgagatata agaaaggttc cttagggaag ccactgatat  12960
tgcacttaca tcttaataac gggtgctgta taatggagtc cccacaggag gcgaatatcc  13020
ccccaaggtc cacattagat ttagagatta cacaagagaa caataaattg atctatgatc  13080
ctgatccact caaggatgtg gaccttgagc tatttagcaa ggtcagagat gttgtacata  13140
cagttgacat gacttattgg tcagatgatg aagttatcag agcaaccagt atctgtactg  13200
caatgacgat agctgataca atgtctcaat tagatagaga caacctaaaa gagatgatcg  13260
cgctagtaaa tgacgatgat gtcaacagcc tgattactga gtttatggtg attgatgttc  13320
ctttattttg ctcaacgttc gggggtattc tagtcaatca gtttgcatac tcactctacg  13380
gcttaaacat cagaggaagg gaagaaatat ggggacatgt agtccggatt cttaaagata  13440
cctcccacgc agttctaaaa gtcttatcta atgctctatc tcatcccaaa atcttcaaac  13500
gattctggaa tgcaggtgtc gtggaacctg tgtatgggcc taacctctca aatcaggaca  13560
agatactctt ggccctctct gtctgtgaat attctgtgga tctattcatg cacgattggc  13620
aaggggggtgt accgcttgag atctttatct gtgacaatga cccagatgtg gccgacatga  13680
ggaggtcctc tttcttggca agacatcttg catacctatg cagcgtggca gagatatcta  13740
gggatgggcc aagattagaa tcaatgaact ctctagagag gctcgagtca ctaaagagtt  13800
acctggaact cacatttctt gatgacccgg tactgaggta cagtcagttg actggcctag  13860
tcatcaaagt attcccatct actttgacct atatccggaa gtcatctata aaagtgttaa  13920
ggacaagagg tataggagtc cctgaagtct tagaagattg ggatcccgag gcagataatg  13980
cactgttaga tggtatcgcg gcagaaatac aacagaatat tcctttggga catcagacta  14040
gagccccttt ttgggggttg agagtatcca agtcacaggt actgcgtctc cgggggtaca  14100
aggagatcac aagaggtgag ataggcagat caggcgttgg tctgacgtta ccattcgatg  14160
gaagatatct atctcaccag ctgaggctct ttggcatcaa cagtactagc tgcttgaaag  14220
cacttgaact tacctaccta ttgagcccct tagttgacaa ggataaagat aggctatatt  14280
taggggaagg agctggggcc atgctttcct gttatgacgc tactcttggc ccatgcatca  14340
actattataa ctcaggggta tactcttgtg atgtcaatgg gcagagagag ttaaatatat  14400
atcctgctga ggtggcactg gtgggaaaga aattaaacaa tgttactagt ctgggtcaaa  14460
gagttaaagt gttattcaac gggaatcctg gctcgacatg gattggaaat gatgagtgtg  14520
aggctttgat ttggaatgaa ttgcagaata gctcgatagg cctagtccac tgtgacatgg  14580
agggaggaga tcataaggat gatcaagttg tactgcatga gcattacagt gtaatccgga  14640
tcgcgtatct ggtgggggat cgagacgttg tgcttataag caagattgct cctaggctgg  14700
gcacggattg gaccaggcag ctcagcctat atctgagata ctgggacgag gttaacctaa  14760
tagtgcttaa aacatctaac cctgcttcca cagagatgta tctcctatcg aggcatccca  14820
aatctgacat tatagaggac agcaagacgg tgttagctag tctcctccct ttgtcaaaag  14880
```

-continued

```
aagatagcat caagatagaa aagtggatct taatagagaa ggcaaaggct cacgaatggg  14940

ttactcggga attgagagaa ggaagctctt catcagggat gcttagacct taccatcaag  15000

cactgcagac gtttggcttt gaaccaaact tgtataaatt gagcagagat ttcttgtcca  15060

ccatgaacat agctgataca cacaactgca tgatagcttt caacagggtt ttgaaggata  15120

caatcttcga atgggctaga ataactgagt cagataaaag gcttaaacta actggtaagt  15180

atgacctgta tcctgtgaga gattcaggca aattgaagac agtttctaga agacttgtgc  15240

tatcttggat atctttatct atgtccacaa gattggtaac tgggtcattc cctgaccaga  15300

agtttgaagc aagacttcaa ttgggaatag tttcattatc atcccgtgaa atcaggaacc  15360

tgagggttat cacaaaaact ttattagacc ggtttgagga tattatacat agtataacgt  15420

acagattcct caccaaagaa ataaagattt tgatgaagat tttaggggca gtcaagatgt  15480

tcggggccag gcaaaatgaa tacacgaccg tgattgatga tggatcactg ggtgatatcg  15540

agccatatga cagctcgtaa taccggttat caccaaaaca tggaagcact tacgattcac  15600

caaaacatgg aagcacttag gtacctcacc aaaacatgga agcacttacg attcaccaaa  15660

acatggaagc acttaaccgg ttccctatcg tgcagaacga tcgaagctcc gcggtacctg  15720

gaagtcttgg actgatccat atgacaatag taagaaaaac ttacaagaag acaagaaaat  15780

ttaaaagaat acatatctct taaactcttg tctggt                            15816
```